United States Patent
Schmahl et al.

(10) Patent No.: US 12,041,918 B2
(45) Date of Patent: Jul. 23, 2024

(54) PRODUCTION OF FERTILE XY FEMALE ANIMALS BY SILENCING OF GENES ON THE Y CHROMOSOME

(71) Applicant: Regeneron Pharmaceuticals, Inc., Tarrytown, NY (US)

(72) Inventors: Jennifer Schmahl, Mount Vernon, NY (US); David Frendewey, New York, NY (US); Junko Kuno, Holmes, NY (US); Chia-Jen Siao, New York, NY (US); Gustavo Droguett, New City, NY (US); Yu Bai, Scarsdale, NY (US); Wojtek Auerbach, Ridgewood, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 635 days.

(21) Appl. No.: 17/119,076

(22) Filed: Dec. 11, 2020

(65) Prior Publication Data
US 2021/0112788 A1    Apr. 22, 2021

Related U.S. Application Data

(62) Division of application No. 15/268,452, filed on Sep. 16, 2016, now Pat. No. 10,893,666.

(60) Provisional application No. 62/219,927, filed on Sep. 17, 2015.

(51) Int. Cl.
| | |
|---|---|
| *A01K 67/0271* | (2024.01) |
| *C12N 5/0735* | (2010.01) |
| *C12Q 1/6876* | (2018.01) |
| *G01N 33/50* | (2006.01) |

(52) U.S. Cl.
CPC ........ *A01K 67/0271* (2013.01); *C12N 5/0606* (2013.01); *C12Q 1/6876* (2013.01); *G01N 33/5073* (2013.01); *A01K 2207/12* (2013.01); *A01K 2207/35* (2013.01); *A01K 2227/105* (2013.01); *A01K 2267/02* (2013.01); *C12Q 2600/136* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,294,754 B2 | 11/2007 | Poueymirou et al. | |
| 7,576,259 B2 | 8/2009 | Poueymirou et al. | |
| 7,659,442 B2 | 2/2010 | Poueymirou et al. | |
| 9,149,026 B2 | 10/2015 | Auerbach et al. | |
| 9,398,762 B2 | 7/2016 | Auerbach et al. | |
| 9,655,351 B2 | 5/2017 | Auerbach et al. | |
| 9,885,058 B2 | 2/2018 | Auerbach et al. | |
| 9,902,971 B2 | 2/2018 | Frendewey et al. | |
| 10,793,874 B2 | 10/2020 | Frendewey et al. | |
| 10,893,666 B2 | 1/2021 | Schmahl et al. | |
| 2003/0204862 A1 | 10/2003 | Kuehn et al. | |
| 2005/0216966 A1 | 9/2005 | Nagao | |
| 2007/0155013 A1 | 7/2007 | Akaike et al. | |
| 2007/0245424 A1 | 10/2007 | Nagao et al. | |
| 2008/0124801 A1 | 5/2008 | Mee et al. | |
| 2011/0307968 A1* | 12/2011 | Auerbach | C12N 15/873 800/21 |
| 2015/0067901 A1 | 3/2015 | Auerbach et al. | |
| 2015/0376651 A1 | 12/2015 | Frendewey et al. | |
| 2016/0046960 A1 | 2/2016 | Frendewey et al. | |
| 2016/0108369 A1 | 4/2016 | Kuno et al. | |
| 2016/0295841 A1 | 10/2016 | Auerbach et al. | |
| 2017/0218399 A1 | 8/2017 | Auerbach et al. | |

(Continued)

FOREIGN PATENT DOCUMENTS

| | | |
|---|---|---|
| CN | 1387401 A | 12/2002 |
| CN | 102355814 A | 2/2012 |

(Continued)

OTHER PUBLICATIONS

Chung et al., Cell Stem Cell, 2:113-117 (Year: 2008).*
Xu Gene expression Patterns, 6, 146-155 (Year: 2006).*
Werner et al Biology of Sex Differences, 8, 26, 1-18 (Year: 2017).*
Jangravi et al J. Proteome Res. 12:6-22 (Year: 2013).*
Sharova et al Developmental Biology 307 446-459) (Year: 2007).*
/Xu et al.PLoS ONE, 7(7), e40481, 1-7, (Year: 2012).*

(Continued)

*Primary Examiner* — Anoop K Singh
(74) *Attorney, Agent, or Firm* — Alston & Bird LLP

(57) ABSTRACT

Methods and compositions are provided for generating F0 fertile XY female animals. The methods and compositions involve making XY pluripotent or totipotent animal cells, in vitro cell cultures, or embryos that are capable of producing a fertile female XY animal in an F0 generation. Such cells, embryos, and animals can be made by silencing a region of the Y chromosome. Optionally, the cells can also be cultured in feminizing medium such as a low-osmolality medium and/or can be modified to decrease the level and/or activity of an Sry protein. Methods and compositions are also provided for silencing a region of the Y chromosome in an XY pluripotent or totipotent animal cell, or in vitro cell cultures, embryos, or animals derived therefrom, by maintaining an XY pluripotent or totipotent animal cell in a feminizing medium. Methods and compositions are also provided for maintaining a population of XY pluripotent or totipotent animal cells in a feminizing medium and selecting cells or clones having increased capabilities for producing a fertile female XY animal in an F0 generation. Methods and compositions are also provided for screening for compounds with feminizing activity or for optimizing concentrations of components in feminizing media.

18 Claims, 21 Drawing Sheets
Specification includes a Sequence Listing.

(56) References Cited

U.S. PATENT DOCUMENTS

| | | |
|---|---|---|
| 2018/0251784 A1 | 9/2018 | Frendewey et al. |
| 2021/0024953 A1 | 1/2021 | Frendewey et al. |

FOREIGN PATENT DOCUMENTS

| | | | |
|---|---|---|---|
| EP | 1516924 A1 | 3/2005 | |
| WO | WO 1997/041209 A1 | 11/1997 | |
| WO | WO 2000/077046 A1 | 12/2000 | |
| WO | WO 2001/045500 A1 | 6/2001 | |
| WO | WO 2008/017704 A1 | 2/2008 | |
| WO | WO 2009/037337 A1 | 3/2009 | |
| WO | WO 2011/044684 A1 | 4/2011 | |
| WO | WO 2011/156723 A1 | 12/2011 | |
| WO | WO 2012/022634 A1 | 2/2012 | |
| WO | WO 2015/200805 A2 | 12/2015 | |
| WO | WO-2015200805 A2 * | 12/2015 | ......... A01K 67/0275 |
| WO | WO 2016/061374 A1 | 4/2016 | |

OTHER PUBLICATIONS

Nef et al Developmental Biology 287 361-377 (Year: 2005).*
Kuno et al Transgenic Res. Aug. 3, 1-11 (Year: 2014).*
"129S6 INBRED," Taconic Biosciences, Inc. Web Site (2016). [Retrieved from the Internet Oct. 17, 2016: <URL: http://www.taconic.com/mouse-model/129s6>].
"Black 6 (B6NTac) INBRED," Taconic Biosciences, Inc. Web Site (2016). [Retrieved from the Internet Oct. 17, 2016: <URL: http://www.taconic.com/mouse-model/black-6-b6ntac>].
"Mouse Strain 129 Substrain Nomenclature", Mouse Genome Informatics Web Site (2016). [Retrieved from the Internet Oct. 17, 2016: <URL: http://www.informatics.jax.org/mgihome/nomen/strain_129.shtml>].
Affara, "The role of the Y chromosome in male infertility," Expert Rev. Mol. Med., vol. 2001, pp. 1-16, 2001.
Alton et al., "The behavior of the X- and Y-chromosomes in the oocyte during meiotic prophase in the B6.Y(TIR) sex-reversed mouse ovary," Reproduction, vol. 135(2), pp. 241-252, 2008.
Auerbach et al., "Establishment and chimera analysis of 129/SvEv- and C57BL/6-derived mouse embryonic stem cell lines," Biotechniques, vol. 29(5), pp. 1024-1028, 1030, 1032, Nov. 2000.
Bassing et al., "Increased ionizing radiation sensitivity and genomic instability in the absence of histone H2AX," Proc. Natl. Acad. Sci. U.S.A., vol. 99(12), pp. 8173-8178, 2002.
Bernart, et al., "Frozen storage of Ham's F-10 medium for human in-vitro fertilization," Human Reproduction, 5:610-612 (1990).
Bronson et al., "High incidence of XXY and XYY males among the offspring of female chimeras from embryonic cells," Proc. Natl. Acad. Sci. USA, Apr. 1995, vol. 92:3120-3123.
Certificate of Analysis for KNOCKOUT™ DMEM, Life Technologies, Catalog No. 10829, Lot No. 1677060, May 21, 2015.
Chan, "Integrating Transcriptomics and Proteomics," G & P Magazine, vol. 6, No. 3, pp. 20-26 (Apr. 2006).
Chen, W., et al., "Formation of germline chimeras from murine embryonic stem cell lines," 1999, Acta Genetica Sinica, 26(2):126-134 English Abstract.
Cheng, et al., "Improved generation of C57BL/6J mouse embryonic stem cells in a defined serum-free media," Genesis, Jun. 2004, vol. 39(2):100-104.
Cheung, et al., "Natural variation in human gene expression assessed in lymphoblastoid cells," Nature Genetics, vol. 33, pp. 422-425, (Mar. 2003).
Chung, et al., "Human Embryonic Stem Cell Lines Generated without Embryo Destruction", Cell Stem Cell 2, pp. 113-117 (Feb. 2008).
Colvin et al., "Male-to-Female Sex Reversal in Mice Lacking Fibroblast Growth Factor 9," Cell, Mar. 23, 2001, vol. 104:875-889.
D'Aiuto et al., "Large-scale generation of human iPSC-derived neural stem cells/early neural progenitor cells and their neuronal differentiation," Organogenesis, vol. 10(4), pp. 365-377, Oct. 2, 2014.
Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.
Dulbecco, et al., "Plaque production by the polyoma virus," Virology, vol. 8(3):396-7 (Jul. 1959).
Fan et al., "107 Genetic Inactivation of the Sry Gene in Argali Wild and Romney Domestic Sheep with CRISPR/Cas Systems for Producing Sex-Reversed Female Animals," Reproduction Fertility and Development, vol. 26(1), p. 167, Dec. 5, 2013.
Frendewey, "VelociGene: Large-scale Modification of Rodent Genomes," Wellcome Trust Advanced Course: Genetic Engineering of Mammalian Stem Cells, Feb. 20, 2015.
Frendewey, "VelociGene: Large-scale Modification of Rodent Genomes," Wellcome Trust Advanced Course: Genetic Engineering of Mammalian Stem Cells, Mar. 13, 2014.
Gueler et al., "AZFa protein DDX3Y is differentially expressed in human male germ cells during development and in testicular tumours: new evidence for phenotypic plasticity of germ cells," Human Reproduction, vol. 27(6), pp. 1547-1555, 2012.
Hirano et al., "Human and Mouse Induced Pluripotent Stem Cells Are Differentially Reprogrammed in Response to Kinase Inhibitors," Stem Cells and Development, vol. 21(8), pp. 1287-1298, May 20, 2012.
Hoekstra et al., "Multiple origins of XY female mice (genus *Akodon*): phylogenetic and chromosomal evidence," Proc. R. Soc. Lond. B, Sep. 22, 2000, vol. 267(1455):1825-31.
Jangravi, et al., "A Fresh Look at the Male-specific Region of the Human Y Chromosome," J. Proteome Res., 12(1):6-22, (2013).
Kallos, et al., "Inoculation and Growth Conditions for High-Cell-Density Expansion of Mammalian Neural Stem Cells in Suspension Bioreactors," Bioengineering, 63:473-483 (1999).
Kashimada et al., "Sry: the master switch in mammalian sex determination," Development, vol. 137(23), pp. 3921-3930, Dec. 2, 2010.
Kato et al., "Production of Sry knockout mouse using TALEN via oocyte injection," Scientific Reports, vol. 3, p. 3136, 2013 (published Nov. 5, 2013).
Kuno et al., "Generation of fertile and fecund F0 XY female mice from XY ES cells," Transgenic Res, vol. 24, pp. 19-29, 2015.
Li, et al., "Non-equivalence of cloned and clonal mice, Current Biology," R756-R757, vol. 15, No. 18 (Sep. 19, 2005).
Lovell-Badge et al., "XY female mice resulting from a heritable mutation in the primary testis-determining Tdy," Development, Jul. 1, 1990, vol. 109:635-646.
Mazeyrat et al., "The mouse Y chromosome interval necessary for spermatogonial proliferation is gene dense with syntenic homology to the human AZFa region," Hum. Mol. Genet., vol. 7(11), pp. 1713-1724, 1998.
Novus Biologicals, LLC, "Novus Biologicals launches new v6.5 Mouse embryonic stem cells," Jun. 18, 2010 [Retrieved from the Internet Mar. 29, 2016: <http://www.novusbio.com/about/press-release/novus-biologicals-launches-new-v65-mouse-embryonic-stem-cells>].
PCT International Preliminary Report on Patentability for application PCT/US2016/052345 mailed Mar. 29, 2018.
PCT International Search Report and Written Opinion of the International Searching Authority for application PCT/US2016/052345 mailed Feb. 8, 2017.
PCT Invitation to Pay Additional Fees PCT/US2016/052345 mailed Dec. 5, 2016.
Porkka, et al., "Cloning and Characterization of a Novel Six-Transmembrane Protein STEAP2, Expressed in Normal and Malignant Prostate," Lab. Invest., 82:1573-1582 (2002).
Poueymirou et al., "F0 generation mice fully derived from gene-targeted embryonic stem cells allowing immediate analysis," Nature Biotechnology, Epub Dec. 24, 2006, vol. 25(1):91-99.
Rideout et al., "Generation of mice from wild-type and targeted ES cells by nuclear cloning," Nat. Genet., vol. 24(2), pp. 109-110, Feb. 2000.
Sargent et al., "The critical region of overlap defining the AZFa male infertility interval of proximal Yq contains three transcribed sequences," J. Med. Genet., vol. 36(9), pp. 670-677, 1999.

(56) References Cited

OTHER PUBLICATIONS

Sharova et al., "Global gene expression profiling reveals similarities and differences among mouse pluripotent stem cells of different origins and strains," Developmental Biology, vol. 307), pp. 446-459, 2007.
Sim, et al., "Defective calmodulin-mediated nuclear transport of the sex-determining region of the Y chromosome (SRY) in XY sex reversal," Mol. Endocrinol. 19(7):1884-1892, (2005).
Song, Z., et al., "Formation of Mouse Chimeras from Early Embryonic Pluripotential Stein Cell," 1993, Acta Genetica Sinica, 20(6): 499-503 English Abstract.
Tang, et al., "A mouse knockout library for secreted and transmembrane proteins," Nature Biotechnology, 28:749-755 (2010).
Tong, Y., et al., "Establishment of a High Germline Competent CS7BL | 6J ES Cell Line," 1999, Acta Genetica Sinica, 26(5): 468-473 English Abstract.
Turinetto et al., "High Basal γH2AX Levels Sustain Self-Renewal of Mouse Embryonic and Induced Pluripotent Stem Cells," Stem Cells, vol. 30(7), pp. 1414-1423, 2012.
Turner, "Meiotic sex chromosome inactivation," Development vol. 134(1), pp. 1823-1831, 2007.
U.S. Appl. No. 15/268,452 Advisory Action and Interview Summary mailed Jul. 17, 2019.
U.S. Appl. No. 15/268,452, Final Office Action mailed Jun. 25, 2020.
U.S. Appl. No. 15/268,452, Non-Final Office Action mailed Oct. 9, 2018.
U.S. Appl. No. 15/268,452, Non-Final Office Action mailed Dec. 12, 2019.
U.S. Appl. No. 15/268,452, Notice of Allowance and Interview Summary mailed Sep. 30, 2020.
U.S. Appl. No. 15/268,452, Requirement for Restriction/Election mailed Apr. 27, 2018.
U.S. Appl. No. 15/268,452, Final Office Action mailed Apr. 17, 2019.
Vakilian et al., "DDX3Y, a Male-Specific Region of Y Chromosome Gene, May Modulate Neuronal Differentiation," Journal of Proteome Research, vol. 14, pp. 3474-3483, 2015.
Vernet et al., "The expression of Y-linked Zfy2 in XY mouse oocytes leads to frequent meiosis 2 defects, a high incidence of subsequent early cleavage stage arrest and infertility," Development, vol. 141, pp. 855-866, 2014 (published Feb. 2014).
Wang et al., "TALEN-mediated editing of the mouse Y chromosome," Nature Biotechnology, vol. 31(6), p. 530-532, 2013 (epub May 12, 2013).
Ward et al., "The 5T4 oncofoetal antigen is an early differentiation marker of mouse ES cells and its absence is a means to assess pluripotency," The Journal of Cell Science, vol. 116:4533-4542 (Nov. 15, 2003).
Werner, et al., "Sex chromosomes drive gene expression and regulatory dimorphisms in mouse embryonic stem cells," Biology of Sex Differences, 8:28, (2017).
Xu et al., "Sexually dimorphic expression of the X-linked gene Eif2s3x mRNA but not protein in mouse brain," Gene Expression Patterns, vol. 6, pp. 146-155, 2006.
Xu, et al., "The Presence of the Y-Chromosome, Not the Absence of the Second X-Chromosome, Alters the mRNA Levels Stored in the Fully Grown XY Mouse Oocyte," PLoS ONE, vol. 7(7):e40481, (2012).

* cited by examiner

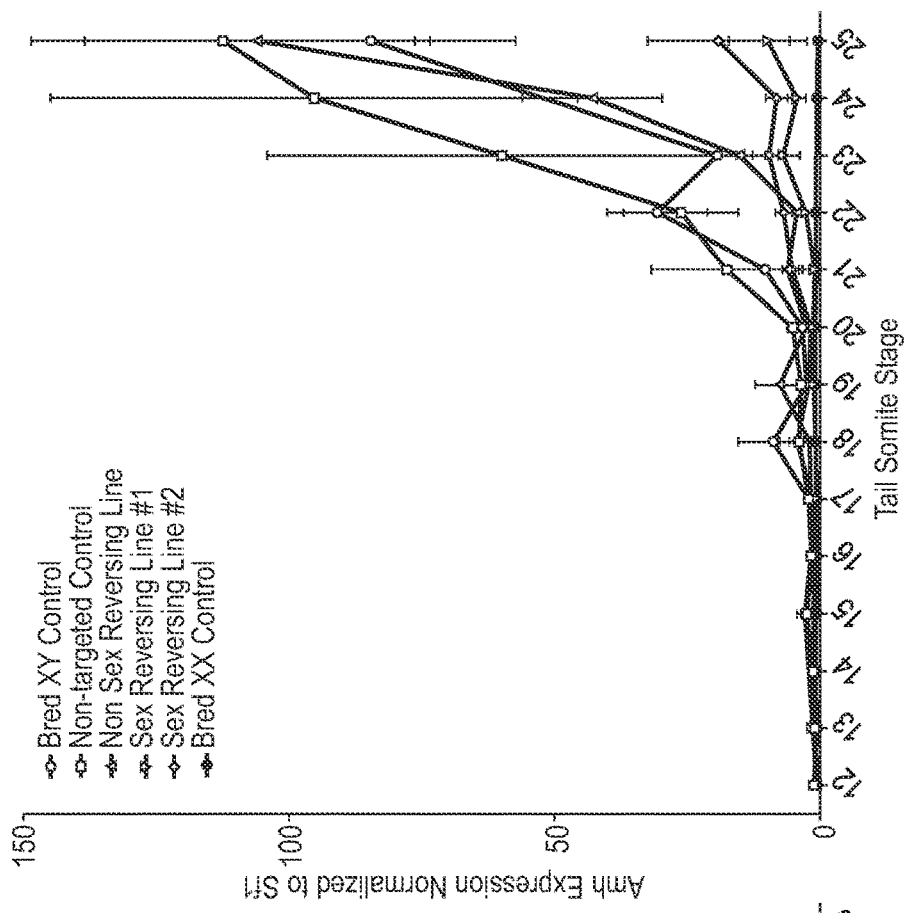
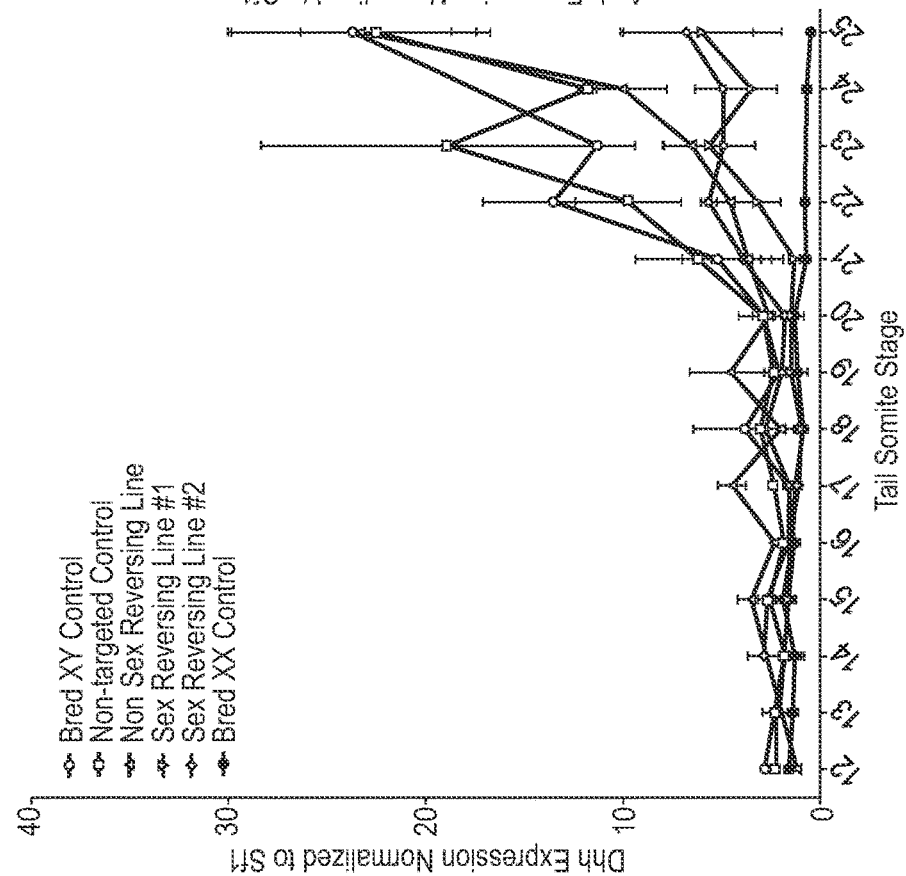

PRODUCTION OF FERTILE XY FEMALE ANIMALS BY SILENCING OF GENES ON THE Y CHROMOSOME

CROSS-REFERENCE TO RELATED APPLICATIONS

This application is a divisional of U.S. application Ser. No. 15/268,452, filed Sep. 16, 2016, which claims the benefit of U.S. Application No. 62/219,927, filed Sep. 17, 2015, each of which is herein incorporated by reference in its entirety for all purposes.

REFERENCE TO A SEQUENCE LISTING SUBMITTED AS A TEXT FILE VIA EFS WEB

The Sequence Listing written in file 552351SEQLIST.txt is 9.20 kb, was created on Dec. 9, 2020, and is hereby incorporated by reference.

BACKGROUND

The creation of genetically modified mice carrying targeted mutations is usually accomplished with XY ES cell lines derived from male embryos. Injection of the ES cells into blastocyst stage embryos, which can be either male or female, followed by uterine transfer to a surrogate mother results in the birth of chimeric F0 generation pups that have genetic contributions from both the host embryo and the ES cells. A hallmark of success in this type of experiment is a distortion of the sex ratio in the F0 mice in favor of males as a result of the colonization by the XY ES cells of the developing genital ridge of XX female embryos and conversion to the male state. Male chimeras with a strong ES cell-derived coat color contribution are likely to produce sperm carrying the targeted mutation and are therefore considered good candidates to transmit the ES cell genome to their progeny. Although female chimeras can rarely achieve germline transmission with poor efficiency, they are expected to have poor ES cell contribution and are not normally bred to establish mutant mouse lines.

To accelerate the production of genetically modified mice, we developed the VELOCIMOUSE® method in which ES cells injected into 8-cell stage embryos are converted into fully ES-cell-derived F0 generation mice (Poueymirou et al. (2007) *Nat. Biotech.* 25(1):91-99). As the VELOCIMOUSE® method eliminates chimeras, all VELOCIMICE® share the genotype of the ES cells from which they were derived. XY ES cells would be expected to produce exclusively male VELOCIMICE®. Although sex reversal has been reported in XY mice, such mice are often infertile or having very low fertility.

Most genetic modifications are carried out by targeting the XY ES cells to create a modification of one of two existing alleles, with the resulting donor mouse ES cell being heterozygous for the genetic modification. However, it is often desirable to obtain a mouse that is homozygous for the genetic modification. Because essentially no fully ES cell-derived female mice are born in the F0 generation that comprise the modification, the F0 male is typically bred to a female (e.g., a matched inbred female) to generate a litter in which at least one female (an F1 female) might be heterozygous for the genetic modification. The heterozygous F1 female is then intercrossed with an F1 heterozygous male to obtain a homozygous progeny. Such breeding requirements represent costly and time-consuming steps.

SUMMARY

Methods and compositions are provided for making donor non-human mammalian XY pluripotent cells capable of producing F0 XY non-human mammal progeny comprising a fertile, phenotypically female XY non-human mammal. In one aspect, the invention provide methods for screening a target compound for feminizing activity in non-human mammalian XY pluripotent cells, comprising: (a) culturing a first population and a second population of non-human mammalian XY pluripotent cells in a medium comprising a base medium and supplements suitable for maintaining the pluripotency of the non-human mammalian XY pluripotent cells, wherein the first population is cultured in the presence of a target compound and the second population is cultured in the absence of the target compound; and (b) assaying one or more of the non-human mammalian XY pluripotent cells in each of the first and second populations of non-human mammalian XY pluripotent cells for expression and/or activity of one or more of Ddx3y, Uty, and Eif2s3y, whereby feminizing activity is identified by a decrease in the expression and/or activity of the one or more of Ddx3y, Uty, and Eif2s3y in the one or more non-human mammalian XY pluripotent cells from the first population compared to the one or more non-human mammalian XY pluripotent cells from the second population. Optionally, such methods further comprise: (c) selecting a donor non-human mammalian XY pluripotent cell from the first population for producing a fertile, phenotypically female XY non-human mammal in an F0 generation based on the expression and/or activity of the one or more of Ddx3y, Uty, and Eif2s3y, wherein the proportion of the fertile, phenotypically female XY non-human mammals in the F0 generation is inversely related to the expression and/or activity of the one or more of Ddx3y, Uty, and Eif2s3y. Optionally, such methods further comprise: (d) introducing the donor non-human mammalian XY pluripotent cell into a host embryo; (e) introducing the host embryo from step (d) into a recipient female non-human mammal and gestating the host embryo; and (f) obtaining F0 XY non-human mammal progeny comprising a phenotypically female XY non-human mammal, wherein upon attaining sexual maturity the F0 phenotypically female XY non-human mammal is fertile or is fertile and fecund.

In some such methods, the assaying in step (b) detects expression of the one or more of Ddx3y, Uty, and Eif2s3y at the mRNA level. In some such methods, the assaying in step (b) detects expression of the one or more of Ddx3y, Uty, and Eif2s3y at the protein level.

In some methods, the feminizing activity is identified in step (b) by a lack of expression and/or activity of the one or more of Ddx3y, Uty, and Eif2s3y in the one or more non-human mammalian XY pluripotent cells from the first population. In some methods, the feminizing activity is identified in step (b) by a decrease in the expression and/or activity of Ddx3y, Uty, and Eif2s3y in the one or more non-human mammalian XY pluripotent cells from the first population compared to the one or more non-human mammalian XY pluripotent cells from the second population. In some methods, the feminizing activity is identified in step (b) by a lack of expression and/or activity of Ddx3y, Uty, and Eif2s3y in the one or more non-human mammalian XY pluripotent cells from the first population.

In some methods, the donor non-human mammalian XY pluripotent cell in step (c) has decreased expression and/or activity of the one or more of Ddx3y, Uty, and Eif2s3y relative to a control non-human mammalian XY pluripotent cell that has been cultured in a medium that is sufficient for maintaining the pluripotency of the control non-human mammalian XY pluripotent cell but does not alter the cell's capacity to give rise to fertile female progeny. In some methods, the donor non-human mammalian XY pluripotent cell in step (c) has decreased expression and/or activity of the one or more of Ddx3y, Uty, and Eif2s3y relative to a control non-human mammalian XY pluripotent cell from the second population. In some methods, the donor non-human mammalian XY pluripotent cell in step (c) has decreased expression and/or activity of Ddx3y, Uty, and Eif2s3y relative to the control non-human mammalian XY pluripotent cell. In some methods, step (b) comprises assaying at least two of the non-human mammalian XY pluripotent cells in the first population for expression and/or activity of one or more of Ddx3y, Uty, and Eif2s3y, and step (c) comprises selecting as the donor non-human mammalian XY pluripotent cell the assayed cell in step (b) having the lowest expression and/or activity of the one or more of Ddx3y, Uty, and Eif2s3y relative to the other assayed cells. In some methods, the donor non-human mammalian XY pluripotent cell in step (c) lacks expression and/or activity of the one or more of Ddx3y, Uty, and Eif2s3y. In some methods, the donor non-human mammalian XY pluripotent cell in step (c) lacks expression and/or activity of Ddx3y, Uty, and Eif2s3y.

In some methods, the first population is cultured in the presence of the target compound for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to assaying step (b).

In some methods, the pluripotent cell is an embryonic stem (ES) cell. Optionally, the pluripotent cell is a VGF1 mouse ES cell.

In some methods, in the absence of the target compound the medium in step (a) is sufficient for maintaining the pluripotency of the non-human mammalian XY pluripotent cells but does not alter the cells' capacity to give rise to fertile female progeny.

In some methods, in the absence of the target compound the medium in step (a) is a low-osmolality medium that has an osmolality from about 200 mOsm/kg to less than about 329 mOsm/kg. Optionally, the low-osmolality medium has one or more of the following properties: (I) the low-osmolality medium has an osmolality of from about 218 mOsm/kg to about 322 mOsm/kg; (II) the low-osmolality medium has an osmolality of 218 mOsm/kg; (III) the low-osmolality medium has a conductivity of about 11 mS/cm to about 13 mS/cm; (IV) the base medium comprises a salt of an alkaline metal and a halide in a concentration of about 50 mM to about 110 mM; (V) the base medium comprises sodium chloride in a concentration of about 50 mM to about 110 mM; (VI) the base medium comprises a carbonic acid salt in a concentration of about 17 mM to about 30 mM; (VII) the base medium comprises sodium bicarbonate in a concentration of about 13 mM to about 25 mM; (VIII) the base medium has a total alkaline metal halide salt and carbonic acid salt concentration of about 85 mM to about 130 mM; (IX) the base medium comprises sodium chloride in a concentration of 87±5 mM, and the low-osmolality medium has an osmolality of 261±26 mOsm/kg; (X) the base medium comprises a salt of an alkaline metal and a halide in a concentration of about 50 mM to about 110 mM and a carbonic acid salt in a concentration of about 17 mM to about 30 mM, and the low-osmolality medium has an osmolality of about 200 mOsm/kg to about 329 mOsm/kg; and (XI) the low-osmolality medium has an osmolality of 218 mOsm/kg, and the base medium comprises sodium chloride in a concentration of 50 mM to 110 mM and sodium bicarbonate in a concentration of 13 mM to 25 mM. Optionally, the base medium comprises a carbonic acid salt in a concentration of about 18 mM to about 44 mM. Optionally, the base medium comprises a salt of an alkaline metal and a halide in a concentration of about 50 mM to about 110 mM. Optionally, the carbonic acid salt is sodium bicarbonate, the salt of the alkaline metal and the halide is sodium chloride, and the low-osmolality medium has an osmolality of from about 216 mOsm/kg to about 322 mOsm/kg. Optionally, the base medium comprises sodium chloride in a concentration of about 3 mg/mL and sodium bicarbonate in a concentration of about 2.2 mg/mL, and the low-osmolality medium has an osmolality of about 216 mOsm/kg.

In some methods, the non-human mammal is a rodent. Optionally, the rodent is a rat or a mouse. In some methods, the rodent is a mouse that comprises a C57BL/6 strain. Optionally, the Y chromosome is from the C57BL/6 strain. In some methods, the rodent is a mouse that comprises a 129 strain. Optionally, the Y chromosome is from a 129 strain. Optionally, the Y chromosome is from a BALB/c strain. In some methods, the mouse does not comprise a 129 strain. In some methods, the Y chromosome is not from a 129 strain. In some methods, the rodent is a mouse that comprises a C57BL/6 strain and a 129 strain.

In some methods, the pluripotent cell comprises a targeted genetic modification in a target genomic locus. Optionally, the targeted genetic modification comprises an insertion, a deletion, a knockout, a knockin, a point mutation, or a combination thereof.

Some methods further comprise: (g) breeding the F0 XY fertile female non-human mammal to produce progeny. Optionally, at least 5%, at least 10%, at least 20%, at least 30%, at least 40%, at least 50%, at least 60%, at least 70%, at least 80%, at least 90%, at least 95%, or all of the XY progeny are phenotypically male and fertile. Optionally, none of the XY progeny are phenotypically female. Optionally, all of the XY progeny are phenotypically male and fertile. Optionally, the breeding comprises crossing the F0 XY fertile female non-human mammal with a cohort F0 XY male non-human mammal, wherein the F0 XY fertile female non-human mammal and the F0 XY male non-human mammal each is heterozygous for a genetic modification, and obtaining an F1 progeny non-human mammal that is homozygous for the genetic modification.

In some methods, the host embryo is a pre-morula stage embryo, and step (d) further comprises culturing the host embryo to the blastocyst stage.

In some methods, wherein the non-human mammalian XY pluripotent cell is cultured in the presence of the target compound for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into the host embryo.

In some methods, at least 5%, at least 10%, at least 20%, at least 30%, at least 40%, at least 50%, at least 60%, at least 70%, at least 80%, at least 90%, or at least 95% of the F0 XY progeny are phenotypically female XY non-human mammals that are fertile upon attaining sexual maturity. Optionally, the percentage of the F0 XY progeny that are fertile, phenotypically female XY animals is higher for F0 XY progeny derived from a non-human mammalian XY pluripotent cell having decreased expression and/or activity of the one or more of Ddx3y, Uty, and Eif2s3y when compared to F0 XY progeny derived from a non-human mammalian XY pluripotent cell having higher expression and/or activity of the one or more of Ddx3y, Uty, and Eif2s3y.

In some methods, all of the F0 females derived from the donor non-human mammalian XY pluripotent cell have an XY genotype.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are fertile. Optionally, the percentage of the F0 XY females that are fertile is higher for F0 XY progeny derived from a non-human mammalian XY pluripotent cell having decreased expression and/or activity of the one or more of Ddx3y, Uty, and Eif2s3y when compared to F0 XY progeny derived from a non-human mammalian XY pluripotent cell having higher expression and/or activity of the one or more of Ddx3y, Uty, and Eif2s3y.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing litters having at least 2, 3, 4, 5, 6, 7, 8, 9, or 10 pups. Optionally, the average litter size produced by F0 XY females or fertile F0 XY females is higher for F0 XY females or fertile F0 XY females derived from a non-human mammalian XY pluripotent cell having decreased expression and/or activity of the one or more of Ddx3y, Uty, and Eif2s3y when compared to F0 XY females or fertile F0 XY females derived from a non-human mammalian XY pluripotent cell having higher expression and/or activity of the one or more of Ddx3y, Uty, and Eif2s3y.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing at least 2, 3, 4, 5, 6, 7, 8, 9, or 10 litters in their lifetimes. Optionally, the average number of lifetime litters produced by F0 XY females or fertile F0 XY females is higher for F0 XY females or fertile F0 XY females derived from a non-human mammalian XY pluripotent cell having decreased expression and/or activity of the one or more of Ddx3y, Uty, and Eif2s3y when compared to F0 XY females or fertile F0 XY females derived from a non-human mammalian XY pluripotent cell having higher expression and/or activity of the one or more of Ddx3y, Uty, and Eif2s3y.

In some methods, the average number of lifetime offspring produced by F0 XY females or fertile F0 XY females is higher for F0 XY females or fertile F0 XY females derived from a non-human mammalian XY pluripotent cell having decreased expression and/or activity of the one or more of Ddx3y, Uty, and Eif2s3y when compared to F0 XY females or fertile F0 XY females derived from a non-human mammalian XY pluripotent cell having higher expression and/or activity of the one or more of Ddx3y, Uty, and Eif2s3y.

In another aspect, the invention provides methods for making a donor non-human mammalian XY pluripotent cell, comprising: (a) culturing a population of non-human mammalian XY pluripotent cells in a low-osmolality medium comprising a base medium and supplements suitable for maintaining the pluripotency of the non-human mammalian XY pluripotent cells, wherein the low-osmolality medium has an osmolality from about 200 mOsm/kg to less than about 329 mOsm/kg; (b) assaying one or more of the non-human mammalian XY pluripotent cells in the population of non-human mammalian XY pluripotent cells for expression and/or activity of one or more of Ddx3y, Uty, and Eif2s3y; and (c) selecting a donor non-human mammalian XY pluripotent cell for producing a fertile, phenotypically female XY non-human mammal in an F0 generation based on the expression and/or activity of the one or more of Ddx3y, Uty, and Eif2s3y, wherein the proportion of the fertile, phenotypically female XY non-human mammals in the F0 generation is inversely related to the expression and/or activity of the one or more of Ddx3y, Uty, and Eif2s3y.

In some such methods, the assaying in step (b) detects expression of the one or more of Ddx3y, Uty, and Eif2s3y at the mRNA level. In some such methods, the assaying in step (b) detects expression of the one or more of Ddx3y, Uty, and Eif2s3y at the protein level.

In some methods, the donor non-human mammalian XY pluripotent cell is selected based on decreased expression and/or activity of the one or more of Ddx3y, Uty, and Eif2s3y relative to a control non-human mammalian XY pluripotent cell that has been cultured in a medium that is sufficient for maintaining the pluripotency of the control non-human mammalian XY pluripotent cell but does not alter the cell's capacity to give rise to fertile female progeny. In some methods, the donor non-human mammalian XY pluripotent cell has decreased expression and/or activity of Ddx3y, Uty, and Eif2s3y relative to the control non-human mammalian XY pluripotent cell. In some methods, step (b) comprises assaying at least two of the non-human mammalian XY pluripotent cells in the population of non-human mammalian XY pluripotent cells for expression and/or activity of one or more of Ddx3y, Uty, and Eif2s3y, and step (c) comprises selecting as the donor non-human mammalian XY pluripotent cell the assayed cell in step (b) having the lowest expression and/or activity of the one or more of Ddx3y, Uty, and Eif2s3y relative to the other assayed cells. In some methods, the donor non-human mammalian XY pluripotent cell lacks expression and/or activity of the one or more of Ddx3y, Uty, and Eif2s3y. In some methods, the donor non-human mammalian XY pluripotent cell lacks expression and/or activity of Ddx3y, Uty, and Eif2s3y.

In some methods, the non-human mammalian XY pluripotent cell is cultured in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to assaying step (b).

In some methods, the pluripotent cell is an embryonic stem (ES) cell. Optionally, the pluripotent cell is a VGF1 mouse ES cell.

In some methods, the low-osmolality medium has one or more of the following properties: (I) the low-osmolality medium has an osmolality of from about 218 mOsm/kg to about 322 mOsm/kg; (II) the low-osmolality medium has an osmolality of 218 mOsm/kg; (III) the low-osmolality medium has a conductivity of about 11 mS/cm to about 13 mS/cm; (IV) the base medium comprises a salt of an alkaline metal and a halide in a concentration of about 50 mM to about 110 mM; (V) the base medium comprises sodium chloride in a concentration of about 50 mM to about 110 mM; (VI) the base medium comprises a carbonic acid salt in a concentration of about 17 mM to about 30 mM; (VII) the base medium comprises sodium bicarbonate in a concentration of about 13 mM to about 25 mM; (VIII) the base medium has a total alkaline metal halide salt and carbonic acid salt concentration of about 85 mM to about 130 mM; (IX) the base medium comprises sodium chloride in a concentration of 87±5 mM, and the low-osmolality medium has an osmolality of 261±26 mOsm/kg; (X) the base medium comprises a salt of an alkaline metal and a halide in a concentration of about 50 mM to about 110 mM and a carbonic acid salt in a concentration of about 17 mM to about 30 mM, and the low-osmolality medium has an osmolality of about 200 mOsm/kg to about 329 mOsm/kg; and (XI) the low-osmolality medium has an osmolality of 218 mOsm/kg, and the base medium comprises sodium chloride in a concentration of 50 mM to 110 mM and sodium bicarbonate in a concentration of 13 mM to 25 mM. Optionally, the base medium comprises a carbonic acid salt in a concentration of about 18 mM to about 44 mM. Optionally, the base medium comprises a salt of an alkaline metal and a halide in a concentration of about 50 mM to about 110 mM. Optionally, the carbonic acid salt is sodium bicarbonate, the salt of the alkaline metal and the halide is sodium chloride, and the low-osmolality medium has an osmolality of from about 216 mOsm/kg to about 322 mOsm/kg. Optionally, the base medium comprises sodium chloride in a concentration of about 3 mg/mL and sodium bicarbonate in a concentration of about 2.2 mg/mL, and the low-osmolality medium has an osmolality of about 216 mOsm/kg.

In some methods, the non-human mammal is a rodent. Optionally, the rodent is a rat or a mouse. In some methods, the rodent is a mouse that comprises a C57BL/6 strain. Optionally, the Y chromosome is from the C57BL/6 strain. In some methods, the rodent is a mouse that comprises a 129 strain. Optionally, the Y chromosome is from a 129 strain. Optionally, the Y chromosome is from a BALB/c strain. In some methods, the mouse does not comprise a 129 strain. In some methods, the Y chromosome is not from a 129 strain. In some methods, the rodent is a mouse that comprises a C57BL/6 strain and a 129 strain.

In some methods, the pluripotent cell comprises a targeted genetic modification in a target genomic locus. Optionally, the targeted genetic modification comprises an insertion, a deletion, a knockout, a knockin, a point mutation, or a combination thereof.

Some methods further comprise: (d) introducing the donor non-human mammalian XY pluripotent cell into a host embryo; (e) introducing the host embryo from step (d) into a recipient female non-human mammal and gestating the host embryo; and (f) obtaining F0 XY non-human mammal progeny comprising a phenotypically female XY non-human mammal, wherein upon attaining sexual maturity the F0 phenotypically female XY non-human mammal is fertile or is fertile and fecund. Some methods further comprise: (g) breeding the F0 XY fertile female non-human mammal to produce progeny. Optionally, at least 5%, at least 10%, at least 20%, at least 30%, at least 40%, at least 50%, at least 60%, at least 70%, at least 80%, at least 90%, at least 95%, or all of the XY progeny are phenotypically male and fertile. Optionally, none of the XY progeny are phenotypically female. Optionally, all of the XY progeny are phenotypically male and fertile. Optionally, the breeding comprises crossing the F0 XY fertile female non-human mammal with a cohort F0 XY male non-human mammal, wherein the F0 XY fertile female non-human mammal and the F0 XY male non-human mammal each is heterozygous for a genetic modification, and obtaining an F1 progeny non-human mammal that is homozygous for the genetic modification.

In some methods, the host embryo is a pre-morula stage embryo, and step (d) further comprises culturing the host embryo to the blastocyst stage.

In some methods, the non-human mammalian XY pluripotent cell is cultured in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into the host embryo.

In some methods, at least 5%, at least 10%, at least 20%, at least 30%, at least 40%, at least 50%, at least 60%, at least 70%, at least 80%, at least 90%, or at least 95% of the F0 XY progeny are phenotypically female XY non-human mammals that are fertile upon attaining sexual maturity. Optionally, the percentage of the F0 XY progeny that are fertile, phenotypically female XY animals is higher for F0 XY progeny derived from a non-human mammalian XY pluripotent cell having decreased expression and/or activity of the one or more of Ddx3y, Uty, and Eif2s3y when compared to F0 XY progeny derived from a non-human mammalian XY pluripotent cell having higher expression and/or activity of the one or more of Ddx3y, Uty, and Eif2s3y.

In some methods, all of the F0 females derived from the donor non-human mammalian XY pluripotent cell have an XY genotype.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are fertile. Optionally, the percentage of the F0 XY females that are fertile is higher for F0 XY progeny derived from a non-human mammalian XY pluripotent cell having decreased expression and/or activity of the one or more of Ddx3y, Uty, and Eif2s3y when compared to F0 XY progeny derived from a non-human mammalian XY pluripotent cell having higher expression and/or activity of the one or more of Ddx3y, Uty, and Eif2s3y.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing litters having at least 2, 3, 4, 5, 6, 7, 8, 9, or 10 pups. Optionally, the average litter size produced by F0 XY females or fertile F0 XY females is higher for F0 XY females or fertile F0 XY females derived from a non-human mammalian XY pluripotent cell having decreased expression and/or activity of the one or more of Ddx3y, Uty, and Eif2s3y when compared to F0 XY females or fertile F0 XY females derived from a non-human mammalian XY pluripotent cell having higher expression and/or activity of the one or more of Ddx3y, Uty, and Eif2s3y.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing at least 2, 3, 4, 5, 6, 7, 8, 9, or 10 litters in their lifetimes. Optionally, the average number of lifetime litters produced by F0 XY females or fertile F0 XY females is higher for F0 XY females or fertile F0 XY females derived from a non-human mammalian XY pluripotent cell having decreased expression and/or activity of the one or more of Ddx3y, Uty, and Eif2s3y when compared to F0 XY females or fertile F0 XY females derived from a non-human mammalian XY pluripotent cell having higher expression and/or activity of the one or more of Ddx3y, Uty, and Eif2s3y.

In some methods, the average number of lifetime offspring produced by F0 XY females or fertile F0 XY females is higher for F0 XY females or fertile F0 XY females derived from a non-human mammalian XY pluripotent cell having decreased expression and/or activity of the one or more of Ddx3y, Uty, and Eif2s3y when compared to F0 XY females or fertile F0 XY females derived from a non-human mammalian XY pluripotent cell having higher expression and/or activity of the one or more of Ddx3y, Uty, and Eif2s3y.

In another aspect, the invention provides a kit comprising: (a) a detection reagent for detecting expression and/or activity levels of one or more of Ddx3y, Uty, and Eif2s3y in a non-human mammalian XY pluripotent cell; and (b) instructions for using the detection reagents and correlating detection with predicted propensity of the non-human mammalian XY pluripotent cell for producing fertile, phenotypically female XY non-human mammals in an F0 generation. Optionally, the detection reagent comprises one or more primer sets and/or one or more probes for detecting expression of the one or more of Ddx3y, Uty, and Eif2s3y.

In another aspect, the invention provides methods for optimizing the concentration of a target medium component in a feminizing medium, comprising: (a) culturing a first population and a second population of non-human mammalian XY pluripotent cells in a medium comprising a base medium and supplements suitable for maintaining the pluripotency of the non-human mammalian XY pluripotent cells, wherein the first population is cultured in the presence of a first concentration of the target medium component and the second population is cultured in the presence of a second concentration of the target medium component that is different from the first concentration; (b) assaying one or more of the non-human mammalian XY pluripotent cells in each of the first and second populations of non-human mammalian XY pluripotent cells for expression and/or activity of one or more of Ddx3y, Uty, and Eif2s3y; and (c) selecting the first concentration if the expression and/or activity of the one or more of Ddx3y, Uty, and Eif2s3y is decreased in the one or more non-human mammalian XY pluripotent cells from the first population compared to the one or more non-human mammalian XY pluripotent cells from the second population. Some such methods further comprise: (d) selecting a donor non-human mammalian XY pluripotent cell from the first population for producing a fertile, phenotypically female XY non-human mammal in an F0 generation based on the expression and/or activity of the one or more of Ddx3y, Uty, and Eif2s3y, wherein the proportion of the fertile, phenotypically female XY non-human mammals in the F0 generation is inversely related to the expression and/or activity of the one or more of Ddx3y, Uty, and Eif2s3y. Some such methods further comprise: (e) introducing the donor non-human mammalian XY pluripotent cell into a host embryo; (f) introducing the host embryo from step (e) into a recipient female non-human mammal and gestating the host embryo; and (g) obtaining F0 XY non-human mammal progeny comprising a phenotypically female XY non-human mammal, wherein upon attaining sexual maturity the F0 phenotypically female XY non-human mammal is fertile or is fertile and fecund.

In some methods, the assaying in step (b) detects expression of the one or more of Ddx3y, Uty, and Eif2s3y at the mRNA level. In some methods, the assaying in step (b) detects expression of the one or more of Ddx3y, Uty, and Eif2s3y at the protein level.

In some methods, the first concentration is selected in step (c) if the one or more non-human mammalian XY pluripotent cells from the first population lack expression and/or activity of the one or more of Ddx3y, Uty, and Eif2s3y. In some methods, the first concentration is selected in step (c) if the one or more non-human mammalian XY pluripotent cells from the first population have decreased expression and/or activity of Ddx3y, Uty, and Eif2s3y compared to the one or more non-human mammalian XY pluripotent cells from the second population. In some methods, the first concentration is selected in step (c) if the one or more non-human mammalian XY pluripotent cells from the first population lack expression and/or activity of Ddx3y, Uty, and Eif2s3y.

In some methods, the donor non-human mammalian XY pluripotent cell in step (c) has decreased expression and/or activity of the one or more of Ddx3y, Uty, and Eif2s3y relative to a control non-human mammalian XY pluripotent cell that has been cultured in a medium that is sufficient for maintaining the pluripotency of the control non-human mammalian XY pluripotent cell but does not alter the cell's capacity to give rise to fertile female progeny. In some methods, the donor non-human mammalian XY pluripotent cell in step (c) has decreased expression and/or activity of the one or more of Ddx3y, Uty, and Eif2s3y relative to a control non-human mammalian XY pluripotent cell from the second population. In some methods, the donor non-human mammalian XY pluripotent cell has decreased expression and/or activity of Ddx3y, Uty, and Eif2s3y relative to the control non-human mammalian XY pluripotent cell. In some methods, step (b) comprises assaying at least two of the non-human mammalian XY pluripotent cells in the first population of non-human mammalian XY pluripotent cells for expression and/or activity of one or more of Ddx3y, Uty, and Eif2s3y, and step (d) comprises selecting as the donor non-human mammalian XY pluripotent cell the assayed cell from step (b) having the lowest expression and/or activity of the one or more of Ddx3y, Uty, and Eif2s3y relative to the other assayed cells. In some methods, the donor non-human mammalian XY pluripotent cell lacks expression and/or activity of the one or more of Ddx3y, Uty, and Eif2s3y. In some methods, the donor non-human mammalian XY pluripotent cell lacks expression and/or activity of Ddx3y, Uty, and Eif2s3y.

In some methods, the first and second populations are cultured in the presence of the target medium component for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to assaying step (b).

In some methods, the pluripotent cell is an embryonic stem (ES) cell. Optionally, the pluripotent cell is a VGF1 mouse ES cell.

In some methods, the medium in step (a) is a low-osmolality medium having an osmolality from about 200 mOsm/kg to less than about 329 mOsm/kg. Optionally, the low-osmolality medium has one or more of the following properties: (I) the low-osmolality medium has an osmolality of from about 218 mOsm/kg to about 322 mOsm/kg; (II) the low-osmolality medium has an osmolality of 218 mOsm/kg; (III) the low-osmolality medium has a conductivity of about 11 mS/cm to about 13 mS/cm; (IV) the base medium comprises a salt of an alkaline metal and a halide in a concentration of about 50 mM to about 110 mM; (V) the base medium comprises sodium chloride in a concentration of about 50 mM to about 110 mM; (VI) the base medium comprises a carbonic acid salt in a concentration of about 17 mM to about 30 mM; (VII) the base medium comprises sodium bicarbonate in a concentration of about 13 mM to about 25 mM; (VIII) the base medium has a total alkaline metal halide salt and carbonic acid salt concentration of about 85 mM to about 130 mM; (IX) the base medium comprises sodium chloride in a concentration of 87±5 mM, and the low-osmolality medium has an osmolality of 261±26 mOsm/kg; (X) the base medium comprises a salt of an alkaline metal and a halide in a concentration of about 50 mM to about 110 mM and a carbonic acid salt in a concentration of about 17 mM to about 30 mM, and the low-osmolality medium has an osmolality of about 200 mOsm/kg to about 329 mOsm/kg; and (XI) the low-osmolality medium has an osmolality of 218 mOsm/kg, and the base medium comprises sodium chloride in a concentration of 50 mM to 110 mM and sodium bicarbonate in a concentration of 13 mM to 25 mM. Optionally, the base medium comprises a carbonic acid salt in a concentration of about 18 mM to about 44 mM. Optionally, the base medium comprises a salt of an alkaline metal and a halide in a concentration of about 50 mM to about 110 mM. Optionally, the carbonic acid salt is sodium bicarbonate, the salt of the alkaline metal and the halide is sodium chloride, and the low-osmolality medium has an osmolality of from about 216 mOsm/kg to about 322 mOsm/kg. Optionally, the base medium comprises sodium chloride in a concentration of about 3 mg/mL and sodium bicarbonate in a concentration of about 2.2 mg/mL, and the low-osmolality medium has an osmolality of about 216 mOsm/kg.

In some methods, the non-human mammal is a rodent. Optionally, the rodent is a rat or a mouse. In some methods, the rodent is a mouse that comprises a C57BL/6 strain. Optionally, the Y chromosome is from the C57BL/6 strain. In some methods, the rodent is a mouse that comprises a 129 strain. Optionally, the Y chromosome is from a 129 strain. Optionally, the Y chromosome is from a BALB/c strain. In some methods, the mouse does not comprise a 129 strain. In some methods, the Y chromosome is not from a 129 strain. In some methods, the rodent is a mouse that comprises a C57BL/6 strain and a 129 strain.

In some methods, the pluripotent cell comprises a targeted genetic modification in a target genomic locus. Optionally, the targeted genetic modification comprises an insertion, a deletion, a knockout, a knockin, a point mutation, or a combination thereof.

Some methods further comprise: (h) breeding the F0 XY fertile female non-human mammal to produce progeny. Optionally, at least 5%, at least 10%, at least 20%, at least 30%, at least 40%, at least 50%, at least 60%, at least 70%, at least 80%, at least 90%, at least 95%, or all of the XY progeny are phenotypically male and fertile. Optionally, none of the XY progeny are phenotypically female. Optionally, all of the XY progeny are phenotypically male and fertile. Optionally, the breeding comprises crossing the F0 XY fertile female non-human mammal with a cohort F0 XY male non-human mammal, wherein the F0 XY fertile female non-human mammal and the F0 XY male non-human mammal each is heterozygous for a genetic modification, and obtaining an F1 progeny non-human mammal that is homozygous for the genetic modification.

In some methods, the host embryo is a pre-morula stage embryo, and step (e) further comprises culturing the host embryo to the blastocyst stage.

In some methods, the non-human mammalian XY pluripotent cell is cultured in the presence of the target medium component for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into the host embryo.

In some methods, at least 5%, at least 10%, at least 20%, at least 30%, at least 40%, at least 50%, at least 60%, at least 70%, at least 80%, at least 90%, or at least 95% of the F0 XY progeny are phenotypically female XY non-human mammals that are fertile upon attaining sexual maturity. Optionally, the percentage of the F0 XY progeny that are fertile, phenotypically female XY animals is higher for F0 XY progeny derived from a non-human mammalian XY pluripotent cell having decreased expression and/or activity of the one or more of Ddx3y, Uty, and Eif2s3y when compared to F0 XY progeny derived from a non-human mammalian XY pluripotent cell having higher expression and/or activity of the one or more of Ddx3y, Uty, and Eif2s3y.

In some methods, all of the F0 females derived from the donor non-human mammalian XY pluripotent cell have an XY genotype.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are fertile. Optionally, the percentage of the F0 XY females that are fertile is higher for F0 XY progeny derived from a non-human mammalian XY pluripotent cell having decreased expression and/or activity of the one or more of Ddx3y, Uty, and Eif2s3y when compared to F0 XY progeny derived from a non-human mammalian XY pluripotent cell having higher expression and/or activity of the one or more of Ddx3y, Uty, and Eif2s3y.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing litters having at least 2, 3, 4, 5, 6, 7, 8, 9, or 10 pups. Optionally, the average litter size produced by F0 XY females or fertile F0 XY females is higher for F0 XY females or fertile F0 XY females derived from a non-human mammalian XY pluripotent cell having decreased expression and/or activity of the one or more of Ddx3y, Uty, and Eif2s3y when compared to F0 XY females or fertile F0 XY females derived from a non-human mammalian XY pluripotent cell having higher expression and/or activity of the one or more of Ddx3y, Uty, and Eif2s3y.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing at least 2, 3, 4, 5, 6, 7, 8, 9, or 10 litters in their lifetimes. Optionally, the average number of lifetime litters produced by F0 XY females or fertile F0 XY females is higher for F0 XY females or fertile F0 XY females derived from a non-human mammalian XY pluripotent cell having decreased expression and/or activity of the one or more of Ddx3y, Uty, and Eif2s3y when compared to F0 XY females or fertile F0 XY females derived from a non-human mammalian XY pluripotent cell having higher expression and/or activity of the one or more of Ddx3y, Uty, and Eif2s3y.

In some methods, the average number of lifetime offspring produced by F0 XY females or fertile F0 XY females is higher for F0 XY females or fertile F0 XY females derived from a non-human mammalian XY pluripotent cell having decreased expression and/or activity of the one or more of Ddx3y, Uty, and Eif2s3y when compared to F0 XY females or fertile F0 XY females derived from a non-human mammalian XY pluripotent cell having higher expression and/or activity of the one or more of Ddx3y, Uty, and Eif2s3y.

In one aspect, the invention provides methods for making a donor non-human mammalian XY pluripotent cell, comprising: modifying a non-human mammalian XY pluripotent cell to silence a region of the Y chromosome and produce the donor non-human mammalian XY pluripotent cell, wherein the silencing is achieved by a means other than maintaining the non-human mammalian XY pluripotent cell in a low-osmolality medium comprising a base medium comprising an osmolality from about 200 mOsm/kg to less than about 329 mOsm/kg, and wherein the donor non-human mammalian XY pluripotent cell is capable of producing F0 XY non-human mammal progeny comprising a fertile, phenotypically female XY non-human mammal. Optionally, the pluripotent cell is an embryonic stem (ES) cell.

In some methods, the region comprises all or part of the small arm of the Y chromosome. In some methods, the region excludes one or more of the Rbmy cluster, Zfy2, and Sry. In some methods, the region comprises all or part of a section of the Y chromosome corresponding to the Sxr$^a$ region and/or the Sxr$^b$ region of the mouse Y chromosome. In some methods, the region comprises all or part of a section of the Y chromosome corresponding to one or more of deletion interval 1, deletion interval 2, and deletion interval 3 on the mouse Y chromosome. In some methods, the region comprises all or part of a section of the Y chromosome corresponding to deletion interval 2 on the mouse Y chromosome. In some methods, the region comprises a portion of the Y chromosome telomeric of Kdm5d or centromeric of Usp9y. In some methods, the region is telomeric of Zfy2, Sry, or the Rbmy cluster. In some methods, the region is telomeric of the Zfy2 gene.

In some methods, the silencing decreases the level and/or activity of a protein encoded by a gene located on the region of the small arm of the Y chromosome. In some methods, the level and/or activity of one or more of Ddx3y, Uty, and Eif2s3y is decreased. Optionally, the level and/or activity of one or more of Ddx3y, Uty, and Eif2s3y is eliminated. In some methods, the level and/or activity of one or more of Sry and Zfy2 is decreased. Optionally, the level and/or activity of one or more of Sry and Zfy2 is eliminated.

In some methods, the silencing is permanent. In some methods, the silencing is achieved by one or more of the following: (1) a targeted genetic modification; (2) deletion or disruption of the region; (3) RNA interference or antisense inhibition of mRNAs transcribed from one or more genes within the region; (4) directed degradation of proteins encoded by one or more genes within the region; (5) heterochromatin-mediated silencing; (6) increasing levels of the phosphorylated form of histone variant γH2AX on the Y chromosome; and (7) decreasing transcription of one or more genes within the region. Optionally, the region is deleted or disrupted with a targeted nuclease. Optionally, the nuclease is a zinc finger nuclease (ZFN), a Transcription Activator-Like Effector Nuclease (TALEN), a meganuclease, or a Clustered Regularly Interspaced Short Palindromic Repeats (CRISPR)-associated (Cas) protein and a guide RNA (gRNA).

In some methods, the silencing occurs during at least one of the following times: (1) after the donor non-human mammalian XY pluripotent cell is introduced into a host embryo; (2) after the host embryo comprising the donor non-human mammalian XY pluripotent cell is introduced into a recipient female non-human mammal; (3) during embryonic development when the male sex determination program is engaged; (4) during embryonic development up to at least a developmental stage corresponding to E11-E12 in mice; (5) during embryonic development up to at least a developmental stage corresponding to E17-E19 in mice; (6) throughout embryonic development; (7) throughout the period of oogenesis; (8) during meiotic prophase in oocyte development; (9) during the first two cell divisions after the oocyte is fertilized; and (10) in oocytes post-ovulation through the first two cell divisions post-fertilization. In some methods, the sex reversal is capable of being transmitted to F1 progeny.

In some methods, the non-human mammalian XY pluripotent cell is not cultured in a low-osmolality medium comprising a base medium comprising an osmolality from about 200 mOsm/kg to less than about 329 mOsm/kg. Other methods further comprise culturing the non-human mammalian XY pluripotent cell in a medium comprising a base medium and supplements suitable for maintaining the non-human mammalian XY pluripotent cell in culture, wherein the medium is a low-osmolality medium comprising a base medium comprising an osmolality from about 200 mOsm/kg to less than about 329 mOsm/kg. In some methods, the region includes one or more of the Rbmy cluster, Zfy2, and Sry, and wherein the non-human mammalian XY pluripotent cell is cultured in a medium comprising a base medium and supplements suitable for maintaining the non-human mammalian XY pluripotent cell in culture, wherein the medium is a low-osmolality medium comprising a base medium comprising an osmolality from about 200 mOsm/kg to less than about 329 mOsm/kg. Optionally, the low-osmolality medium comprises a base medium comprising one or more of the following: (1) an osmolality of from about 218 mOsm/kg to about 322 mOsm/Kg; (2) an osmolality of 218 mOsm/kg; (3) a conductivity of about 11 mS/cm to about 13 mS/cm; (4) a salt of an alkaline metal and a halide in a concentration of about 50 mM to about 110 mM; (5) a sodium chloride concentration of about 50 mM to about 110 mM; (6) a carbonic acid salt concentration of about 17 mM to about 30 mM; (7) a sodium bicarbonate concentration of about 13 mM to about 25 mM; (8) a total alkaline metal halide salt and carbonic acid salt concentration of about 85 mM to about 130 mM; (9) a sodium chloride concentration of 87±5 mM and an osmolality of 261±26 mOsm/kg; (10) a salt of an alkaline metal and a halide in a concentration of about 50 mM to about 110 mM, a carbonic acid salt in a concentration of about 17 mM to about 30 mM, and an osmolality of about 200 mOsm/kg to about 329 mOsm/kg; and (11) an osmolality of 218 mOsm/kg, a sodium chloride concentration of 50 mM to 110 mM, and a sodium bicarbonate concentration of 13 mM to 25 mM. Optionally, the non-human mammalian XY pluripotent cell is maintained in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into a host embryo.

In some methods, the non-human mammal is a rodent. Optionally, the rodent is a rat or a mouse. In some methods, the rodent is a mouse that comprises a C57BL/6 strain. Optionally, the Y chromosome is from a C57BL/6 strain. In some methods, the rodent is a mouse that comprises a 129 strain. Optionally, the Y chromosome is from a 129 strain. In some methods, the mouse does not comprise a 129 strain. In some methods, the Y chromosome is not from a 129 strain. In some methods, the rodent is a mouse that comprises a C57BL/6 strain and a 129 strain. Optionally, the pluripotent cell is a VGF1 mouse ES cell.

In some methods, the pluripotent cell comprises a targeted genetic modification in a target genomic locus. Optionally, wherein the targeted genetic modification comprises an insertion, a deletion, a knockout, a knockin, a point mutation, or a combination thereof.

In some methods, the region includes Zfy2, and the non-human mammalian XY pluripotent cell further comprises a modification that decreases the level and/or activity of an Sry protein. Optionally, the non-human mammal is a mouse that comprises a C57BL/6 strain, the non-human mammal is a mouse that does not comprise a 129 strain, the non-human mammal is a mouse, wherein the Y chromosome is from a C57BL/6 strain, or the non-human mammal is a mouse, wherein the Y chromosome is not from a 129 strain. Optionally, such methods further comprise culturing the non-human mammalian XY pluripotent cell in a medium comprising a base medium and supplements suitable for maintaining the non-human mammalian XY pluripotent cell in culture, wherein the medium is a low-osmolality medium comprising a base medium comprising an osmolality from about 200 mOsm/kg to less than about 329 mOsm/kg.

The invention also provides in vitro cultures comprising donor non-human mammalian XY pluripotent cells produced by any of the above methods for making a donor non-human mammalian XY pluripotent cell.

The invention also provides methods for generating an embryo, comprising introducing a donor non-human mammalian XY pluripotent cell produced by any of the above methods into a host embryo, wherein the host embryo is capable of producing a fertile, phenotypically female XY non-human mammal in an F0 generation.

The invention also provides modified non-human mammalian embryos produced by the above methods for generating an embryo. The invention also provides modified non-human mammalian embryos comprising a cell having in its genome a modification that silences a region of the Y chromosome.

The invention also provides methods for making a fertile, phenotypically female XY non-human mammal in an F0 generation, comprising: (a) introducing into a host embryo the donor non-human mammalian XY pluripotent cell produced by any of the above methods for making a donor non-human mammalian XY pluripotent cell; (b) introducing the host embryo from step (a) into a recipient female non-human mammal and gestating the host embryo; and (c) obtaining F0 XY non-human mammal progeny comprising a phenotypically female XY non-human mammal, wherein upon attaining sexual maturity the F0 phenotypically female XY non-human mammal is fertile. Alternatively, methods are provided for making a fertile, phenotypically female XY non-human mammal in an F0 generation, comprising: (a) introducing a modified embryo into a recipient female non-human mammal and gestating the embryo, wherein the embryo is produced by the above methods; and (b) obtaining F0 XY non-human mammal progeny comprising a phenotypically female XY non-human mammal, wherein upon attaining sexual maturity the F0 phenotypically female XY non-human mammal is fertile.

In some methods, at least 5%, at least 10%, at least 20%, at least 30%, at least 40%, at least 50%, at least 60%, at least 70%, at least 80%, at least 90%, or at least 95% of the F0 XY progeny are phenotypically female XY non-human mammals that are fertile upon attaining sexual maturity. In some methods, all of the F0 females derived from the donor non-human mammalian XY pluripotent cell have an XY genotype. In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are fertile. In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing litters having at least 2, 3, 4, 5, 6, 7, 8, 9, or 10 pups. In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing at least 2, 3, 4, 5, 6, 7, 8, 9, or 10 litters in their lifetimes.

The invention also provides fertile, phenotypically female XY non-human mammal produced by any of the above methods for making a fertile, phenotypically female XY non-human mammal in an F0 generation.

The invention also provides methods of producing a transgenic non-human mammal homozygous for a targeted genetic modification in a target genomic locus in the F1 generation, comprising: (a) crossing an F0 XY fertile female produced by the above methods with an F0 XY male non-human mammal, wherein the F0 XY fertile female non-human mammal and the F0 XY male non-human mammal are each heterozygous for the targeted genetic modification; and (b) obtaining an F1 progeny non-human mammal that is homozygous for the targeted genetic modification. Optionally, the F0 XY male is a cohort clonal sibling derived from the same pluripotent cell clone as the F0 XY fertile female.

The invention also provides methods for making a fertile, phenotypically female XY non-human mammal in an F0 generation, comprising: (a) generating a donor non-human mammalian XY pluripotent cell by modifying a non-human mammalian XY pluripotent cell to silence a region of the Y chromosome comprising a portion of the Y chromosome outside of the Sry gene, wherein the donor non-human mammalian XY pluripotent cell further comprises a modification that decreases the level and/or activity of a Sry protein; (b) introducing the donor non-human mammalian XY pluripotent cell into a host embryo; (c) introducing the host embryo of step (b) into a recipient female non-human mammal and gestating the host embryo; and (d) obtaining F0 XY non-human mammal progeny comprising a phenotypically female XY non-human mammal, wherein upon attaining sexual maturity the F0 phenotypically female XY non-human mammal is fertile. Optionally, the pluripotent cell is an embryonic stem cell.

In some methods, the region comprises all or part of the small arm of the Y chromosome; excludes one or more of the Rbmy cluster, Zfy2, and Sry; comprises all or part of a section of the Y chromosome corresponding to the $Sxr^a$ region and/or the $Sxr^b$ region of the mouse Y chromosome; comprises all or part of a section of the Y chromosome corresponding to one or more of deletion interval 1, deletion interval 2, and deletion interval 3 on the mouse Y chromosome; comprises a portion of the Y chromosome telomeric of Kdm5d or centromeric of Usp9y; or is telomeric of Zfy2, Sry, or the Rbmy cluster.

In some methods, the silencing decreases the level and/or activity of a protein encoded by a gene located in the region. Optionally, the level and/or activity of one or more of Ddx3y, Uty, and Eif2s3y is decreased; the level and/or activity of one or more of Ddx3y, Uty, and Eif2s3y is eliminated; the level and/or activity of one or more of Sry and Zfy2 is decreased; or the level and/or activity of one or more of Sry and Zfy2 is eliminated. In some methods, the silencing is permanent.

In some methods, the silencing is achieved by one or more of the following: (1) a targeted genetic modification; (2) deletion or disruption of the region; (3) RNA interference or antisense inhibition of mRNAs transcribed from one or more genes within the region; (4) directed degradation of proteins encoded by one or more genes within the region; (5) heterochromatin-mediated silencing; (6) increasing levels of the phosphorylated form of histone variant γH2AX on the Y chromosome; and (7) decreasing transcription of one or more genes within the region. Optionally, the region is deleted or disrupted with a targeted nuclease. Optionally, the nuclease is a zinc finger nuclease (ZFN), a Transcription Activator-Like Effector Nuclease (TALEN), a meganuclease, or a Clustered Regularly Interspaced Short Palindromic Repeats (CRISPR)-associated (Cas) protein and a guide RNA (gRNA).

In some methods, the silencing occurs during at least one of the following times: (1) after the donor non-human mammalian XY pluripotent cell is introduced into a host embryo; (2) after the host embryo comprising the donor non-human mammalian XY pluripotent cell is introduced into a recipient female non-human mammal; (3) during embryonic development when the male sex determination program is engaged; (4) during embryonic development up to at least a developmental stage corresponding to E11-E12 in mice; (5) during embryonic development up to at least a developmental stage corresponding to E17-E19 in mice; (6) throughout embryonic development; (7) throughout the period of oogenesis; (8) during meiotic prophase in oocyte development; (9) during the first two cell divisions after the oocyte is fertilized; and (10) in oocytes post-ovulation through the first two cell divisions post-fertilization. In some methods, the sex reversal is capable of being transmitted to F1 progeny.

In some methods, the non-human mammalian XY pluripotent cell is not cultured in a low-osmolality medium comprising a base medium comprising an osmolality from about 200 mOsm/kg to less than about 329 mOsm/kg. Other methods further comprise culturing the non-human mammalian XY pluripotent cell in a medium comprising a base medium and supplements suitable for maintaining the non-human mammalian XY pluripotent cell in culture, wherein the medium is a low-osmolality medium comprising a base medium comprising an osmolality from about 200 mOsm/kg to less than about 329 mOsm/kg. Optionally, the low-osmolality medium comprises a base medium comprising one or more of the following: (1) an osmolality of from about 218 mOsm/kg to about 322 mOsm/Kg; (2) an osmolality of 218 mOsm/kg; (3) a conductivity of about 11 mS/cm to about 13 mS/cm; (4) a salt of an alkaline metal and a halide in a concentration of about 50 mM to about 110 mM; (5) a sodium chloride concentration of about 50 mM to about 110 mM; (6) a carbonic acid salt concentration of about 17 mM to about 30 mM; (7) a sodium bicarbonate concentration of about 13 mM to about 25 mM; (8) a total alkaline metal halide salt and carbonic acid salt concentration of about 85 mM to about 130 mM; (9) a sodium chloride concentration of 87±5 mM and an osmolality of 261±26 mOsm/kg; (10) a salt of an alkaline metal and a halide in a concentration of about 50 mM to about 110 mM, a carbonic acid salt in a concentration of about 17 mM to about 30 mM, and an osmolality of about 200 mOsm/kg to about 329 mOsm/kg; and (11) an osmolality of 218 mOsm/kg, a sodium chloride concentration of 50 mM to 110 mM, and a sodium bicarbonate concentration of 13 mM to 25 mM. Optionally, the non-human mammalian XY pluripotent cell is maintained in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into a host embryo.

In some methods, the non-human mammal is a rodent, a rat, or a mouse. Optionally, the mouse comprises a C57BL/6 strain; the mouse comprises a 129 strain; the mouse does not comprise a 129 strain; the mouse comprises a C57BL/6 strain and a 129 strain; the non-human mammal is a mouse, wherein the Y chromosome is from a C57BL/6 strain; the non-human mammal is a mouse, wherein the Y chromosome is from a 129 strain; the non-human mammal is a mouse, wherein the Y chromosome is not from a 129 strain; or the non-human mammal is a mouse, and the pluripotent cell is a VGF1 mouse ES cell.

In some methods, the pluripotent cell comprises a targeted genetic modification in a target genomic locus. Optionally, wherein the targeted genetic modification comprises an insertion, a deletion, a knockout, a knockin, a point mutation, or a combination thereof.

In some methods, the region includes Zfy2. Optionally, the non-human mammal is a mouse that comprises a C57BL/6 strain, the non-human mammal is a mouse that does not comprise a 129 strain, the non-human mammal is a mouse, wherein the Y chromosome is from a C57BL/6 strain, or the non-human mammal is a mouse, wherein the Y chromosome is not from a 129 strain. Optionally, such methods further comprise culturing the non-human mammalian XY pluripotent cell in a medium comprising a base medium and supplements suitable for maintaining the non-human mammalian XY pluripotent cell in culture, wherein the medium is a low-osmolality medium comprising a base medium comprising an osmolality from about 200 mOsm/kg to less than about 329 mOsm/kg.

In some methods, at least 5%, at least 10%, at least 20%, at least 30%, at least 40%, at least 50%, at least 60%, at least 70%, at least 80%, at least 90%, at least 95%, at least 98%, or at least 99% of the F0 XY progeny are phenotypically female XY non-human mammals that are fertile upon attaining sexual maturity. Optionally, the percentage of the F0 XY progeny that are fertile, phenotypically female XY non-human mammals is greater than the percentage of fertile, phenotypically female XY non-human mammals derived from a non-human mammalian XY pluripotent cell that does not comprise silencing of a region of the Y chromosome comprising a portion of the Y chromosome outside of the Sry gene.

In some methods, all of the F0 females derived from the donor non-human mammalian XY pluripotent cell have an XY genotype.

In some methods, at least 5%, at least 10%, at least 20%, at least 30%, at least 40%, at least 50%, at least 60%, at least 70%, at least 80%, at least 90%, at least 95%, at least 98%, or at least 99% of the F0 XY females derived from the donor non-human mammalian XY pluripotent cell are fertile. Optionally, the percentage of F0 XY females derived from the donor non-human mammalian XY pluripotent cell that are fertile is greater than the percentage of fertile F0 XY females derived from a non-human mammalian XY pluripotent cell that does not comprise silencing of a region of the Y chromosome comprising a portion of the Y chromosome outside of the Sry gene.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing litters having at least 2, 3, 4, 5, 6, 7, 8, 9, or 10 pups. Optionally, the average litter size produced by the F0 XY females derived from the donor non-human mammalian XY pluripotent cell is greater than the average litter size produced by F0 XY females derived from a non-human mammalian XY pluripotent cell that does not comprise silencing of a region of the Y chromosome comprising a portion of the Y chromosome outside of Sry gene.

In some methods, at least 5%, at least 10%, at least 20%, at least 30%, at least 40%, at least 50%, at least 60%, at least 70%, at least 80%, at least 90%, or at least 95% of the F0 females derived from the donor non-human mammalian XY pluripotent cell are capable of producing at least 2, 3, 4, 5, 6, 7, 8, 9, or 10 litters in their lifetimes. Optionally, the average number of litters produced by the F0 XY females derived from the donor non-human mammalian XY pluripotent cell is greater than the average number of litters produced by F0 XY females derived from a non-human mammalian XY pluripotent cell that does not comprise silencing of a region of the Y chromosome comprising a portion of the Y chromosome outside of Sry gene. Optionally, the average number of lifetime offspring produced by the F0 XY females derived from the donor non-human mammalian XY pluripotent cell is greater than the average number of lifetime offspring produced by F0 XY females derived from a non-human mammalian XY pluripotent cell that does not comprise silencing of a region of the Y chromosome comprising a portion of the Y chromosome outside of Sry gene.

The invention also provides methods for making a fertile, phenotypically female XY non-human mammal in an F0 generation, comprising: (a) generating a donor non-human mammalian XY pluripotent cell by modifying a non-human mammalian XY pluripotent cell to silence a region of the Y chromosome, wherein the non-human mammalian XY pluripotent cell is maintained in a low-osmolality medium but the silencing is achieved by a means other than or in addition to maintaining the non-human mammalian XY pluripotent cell in the low-osmolality medium, wherein the low-osmolality medium comprises a base medium and supplements suitable for maintaining the non-human mammalian XY pluripotent cell in culture, wherein the base medium comprises an osmolality from about 200 mOsm/kg to less than about 329 mOsm/kg; (b) introducing the donor non-human mammalian XY pluripotent cell into a host embryo; (c) introducing the host embryo of step (b) into a recipient female non-human mammal and gestating the host embryo; and (d) obtaining F0 XY non-human mammal progeny comprising a phenotypically female XY non-human mammal, wherein upon attaining sexual maturity the F0 phenotypically female XY non-human mammal is fertile. Optionally, the pluripotent cell is an embryonic stem (ES) cell.

In some methods, the region comprises all or part of the small arm of the Y chromosome; excludes one or more of the Rbmy cluster, Zfy2, and Sry; comprises all or part of a section of the Y chromosome corresponding to the Sxr$^a$ region and/or the Sxr$^b$ region of the mouse Y chromosome; comprises all or part of a section of the Y chromosome corresponding to one or more of deletion interval 1, deletion interval 2, and deletion interval 3 on the mouse Y chromosome; comprises a portion of the Y chromosome telomeric of Kdm5d or centromeric of Usp9y; or is telomeric of Zfy2, Sry, or the Rbmy cluster.

In some methods, the silencing decreases the level and/or activity of a protein encoded by a gene located in the region. Optionally, the level and/or activity of one or more of Ddx3y, Uty, and Eif2s3y is decreased; the level and/or activity of one or more of Ddx3y, Uty, and Eif2s3y is eliminated; the level and/or activity of one or more of Sry and Zfy2 is decreased; or the level and/or activity of one or more of Sry and Zfy2 is eliminated. In some methods, the silencing is permanent.

In some methods, the silencing is achieved by one or more of the following: (1) a targeted genetic modification; (2) deletion or disruption of the region; (3) RNA interference or antisense inhibition of mRNAs transcribed from one or more genes within the region; (4) directed degradation of proteins encoded by one or more genes within the region; (5) heterochromatin-mediated silencing; (6) increasing levels of the phosphorylated form of histone variant γH2AX on the Y chromosome; and (7) decreasing transcription of one or more genes within the region. Optionally, the region is deleted or disrupted with a targeted nuclease. Optionally, the nuclease is a zinc finger nuclease (ZFN), a Transcription Activator-Like Effector Nuclease (TALEN), a meganuclease, or a Clustered Regularly Interspaced Short Palindromic Repeats (CRISPR)-associated (Cas) protein and a guide RNA (gRNA).

In some methods, the silencing occurs during at least one of the following times: (1) after the donor non-human mammalian XY pluripotent cell is introduced into a host embryo; (2) after the host embryo comprising the donor non-human mammalian XY pluripotent cell is introduced into a recipient female non-human mammal; (3) during embryonic development when the male sex determination program is engaged; (4) during embryonic development up to at least a developmental stage corresponding to E11-E12 in mice; (5) during embryonic development up to at least a developmental stage corresponding to E17-E19 in mice; (6) throughout embryonic development; (7) throughout the period of oogenesis; (8) during meiotic prophase in oocyte development; (9) during the first two cell divisions after the oocyte is fertilized; and (10) in oocytes post-ovulation through the first two cell divisions post-fertilization. In some methods, the sex reversal is capable of being transmitted to F1 progeny.

In some methods, the low-osmolality medium comprises a base medium comprising one or more of the following: (1) an osmolality of from about 218 mOsm/kg to about 322 mOsm/Kg; (2) an osmolality of 218 mOsm/kg; (3) a conductivity of about 11 mS/cm to about 13 mS/cm; (4) a salt of an alkaline metal and a halide in a concentration of about 50 mM to about 110 mM; (5) a sodium chloride concentration of about 50 mM to about 110 mM; (6) a carbonic acid salt concentration of about 17 mM to about 30 mM; (7) a sodium bicarbonate concentration of about 13 mM to about 25 mM; (8) a total alkaline metal halide salt and carbonic acid salt concentration of about 85 mM to about 130 mM; (9) a sodium chloride concentration of 87±5 mM and an osmolality of 261±26 mOsm/kg; (10) a salt of an alkaline metal and a halide in a concentration of about 50 mM to about 110 mM, a carbonic acid salt in a concentration of about 17 mM to about 30 mM, and an osmolality of about 200 mOsm/kg to about 329 mOsm/kg; and (11) an osmolality of 218 mOsm/kg, a sodium chloride concentration of 50 mM to 110 mM, and a sodium bicarbonate concentration of 13 mM to 25 mM. Optionally, the non-human mammalian XY pluripotent cell is maintained in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into a host embryo.

In some methods, the non-human mammal is a rodent, a rat, or a mouse. Optionally, the mouse comprises a C57BL/6 strain; the mouse comprises a 129 strain; the mouse does not comprise a 129 strain; the mouse comprises a C57BL/6 strain and a 129 strain; the non-human mammal is a mouse, wherein the Y chromosome is from a C57BL/6 strain; the non-human mammal is a mouse, wherein the Y chromosome is from a 129 strain; the non-human mammal is a mouse, wherein the Y chromosome is not from a 129 strain; or the non-human mammal is a mouse, and the pluripotent cell is a VGF1 mouse ES cell.

In some methods, the pluripotent cell comprises a targeted genetic modification in a target genomic locus. Optionally, wherein the targeted genetic modification comprises an insertion, a deletion, a knockout, a knockin, a point mutation, or a combination thereof.

In some methods, the region includes Zfy2, and the non-human mammalian XY pluripotent cell further comprises a modification that decreases the level and/or activity of an Sry protein.

In some methods, at least 5%, at least 10%, at least 20%, at least 30%, at least 40%, at least 50%, at least 60%, at least 70%, at least 80%, at least 90%, at least 95%, at least 98%, or at least 99% of the F0 XY progeny are phenotypically female XY non-human mammals that are fertile upon attaining sexual maturity. Optionally, the percentage of the F0 XY progeny that are fertile, phenotypically female XY non-human mammals is greater than the percentage of fertile, phenotypically female XY non-human mammals derived from a non-human mammalian XY pluripotent cell that does not comprise silencing of a region of the Y chromosome.

In some methods, all of the F0 females derived from the donor non-human mammalian XY pluripotent cell have an XY genotype.

In some methods, at least 5%, at least 10%, at least 20%, at least 30%, at least 40%, at least 50%, at least 60%, at least 70%, at least 80%, at least 90%, at least 95%, at least 98%, or at least 99% of the F0 XY females derived from the donor non-human mammalian XY pluripotent cell are fertile. Optionally, the percentage of F0 XY females derived from the donor non-human mammalian XY pluripotent cell that are fertile is greater than the percentage of fertile F0 XY females derived from a non-human mammalian XY pluripotent cell that does not comprise silencing of a region of the Y chromosome.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing litters having at least 2, 3, 4, 5, 6, 7, 8, 9, or 10 pups. Optionally, the average litter size produced by the F0 XY females derived from the donor non-human mammalian XY pluripotent cell is greater than the average litter size produced by F0 XY females derived from a non-human mammalian XY pluripotent cell that does not comprise silencing of a region of the Y chromosome.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing at least 2, 3, 4, 5, 6, 7, 8, 9, or 10 litters in their lifetimes. Optionally, the average number of litters produced by the F0 XY females derived from the donor non-human mammalian XY pluripotent cell is greater than the average number of litters produced by F0 XY females derived from a non-human mammalian XY pluripotent cell that does not comprise silencing of a region of the Y chromosome. Optionally, the average number of lifetime offspring produced by the F0 XY females derived from the donor non-human mammalian XY pluripotent cell is greater than the average number of lifetime offspring produced by F0 XY females derived from a non-human mammalian XY pluripotent cell that does not comprise silencing of a region of the Y chromosome.

The invention also provides methods for silencing a region of the Y chromosome in a non-human mammalian XY pluripotent cell, comprising: (a) maintaining a non-human mammalian XY pluripotent cell in a medium comprising a base medium and supplements suitable for growing the non-human mammalian XY pluripotent cell in culture with maintenance of pluripotency, wherein the base medium comprises an osmolality from about 200 mOsm/kg to less than about 329 mOsm/kg; and (b) assaying the non-human mammalian XY pluripotent cell to identify silencing of the region of the Y chromosome. Optionally, the pluripotent cell is an embryonic stem (ES) cell.

In some methods, the low-osmolality medium comprises a base medium comprising one or more of the following: (1) an osmolality of from about 218 mOsm/kg to about 322 mOsm/Kg; (2) an osmolality of 218 mOsm/kg; (3) a conductivity of about 11 mS/cm to about 13 mS/cm; (4) a salt of an alkaline metal and a halide in a concentration of about 50 mM to about 110 mM; (5) a sodium chloride concentration of about 50 mM to about 110 mM; (6) a carbonic acid salt concentration of about 17 mM to about 30 mM; (7) a sodium bicarbonate concentration of about 13 mM to about 25 mM; (8) a total alkaline metal halide salt and carbonic acid salt concentration of about 85 mM to about 130 mM; (9) a sodium chloride concentration of 87±5 mM and an osmolality of 261±26 mOsm/kg; (10) a salt of an alkaline metal and a halide in a concentration of about 50 mM to about 110 mM, a carbonic acid salt in a concentration of about 17 mM to about 30 mM, and an osmolality of about 200 mOsm/kg to about 329 mOsm/kg; and (11) an osmolality of 218 mOsm/kg, a sodium chloride concentration of 50 mM to 110 mM, and a sodium bicarbonate concentration of 13 mM to 25 mM. Optionally, the non-human mammalian XY pluripotent cell is maintained in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to assaying.

In some methods, the region comprises all or part of the small arm of the Y chromosome; excludes one or more of the Rbmy cluster, Zfy2, and Sry; comprises all or part of a section of the Y chromosome corresponding to the $Sxr^a$ region and/or the $Sxr^b$ region of mouse the Y chromosome; comprises all or part of a section of the Y chromosome corresponding to one or more of deletion interval 1, deletion interval 2, and deletion interval 3 on the mouse Y chromosome; comprises a portion of the Y chromosome telomeric of Kdm5d or centromeric of Usp9y; or is telomeric of Zfy2, Sry, or the Rbmy cluster.

In some methods, the silencing decreases the level and/or activity of a protein encoded by a gene located in the region. Optionally, the level and/or activity of one or more of Ddx3y, Uty, and Eif2s3y is decreased; the level and/or activity of one or more of Ddx3y, Uty, and Eif2s3y is eliminated; the level and/or activity of one or more of Sry and Zfy2 is decreased; or the level and/or activity of one or more of Sry and Zfy2 is eliminated.

Some such methods further comprise: (b) introducing the non-human mammalian XY pluripotent cell into a host embryo; and (c) introducing the host embryo from step (b) into a recipient female non-human mammal and gestating the host embryo. Optionally, the non-human mammalian XY pluripotent cell is maintained in the medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into a host embryo.

The invention also provides methods for making a donor non-human mammalian XY pluripotent cell, comprising: (a) maintaining a population of one or more non-human mammalian XY pluripotent cells in a low-osmolality medium comprising a base medium and supplements suitable for maintaining the non-human mammalian XY pluripotent cell in culture, wherein the base medium comprises an osmolality from about 200 mOsm/kg to less than about 329 mOsm/kg; (b) assaying the one or more non-human mammalian XY pluripotent cells for expression and/or activity of one or more of Ddx3y, Uty, and Eif2s3y; and (c) selecting a donor non-human mammalian XY pluripotent cell having a decreased expression and/or activity of one or more of Ddx3y, Uty, and Eif2s3y, wherein the donor non-human mammalian XY pluripotent cell is capable of producing a fertile, phenotypically female XY non-human mammal in an F0 generation. Optionally, the non-human mammalian XY pluripotent cell is maintained in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to assaying step (b). Optionally, the pluripotent cell is an embryonic stem (ES) cell.

In some methods, the low-osmolality medium comprises a base medium comprising one or more of the following: (1) an osmolality of from about 218 mOsm/kg to about 322 mOsm/Kg; (2) an osmolality of 218 mOsm/kg; (3) a conductivity of about 11 mS/cm to about 13 mS/cm; (4) a salt of an alkaline metal and a halide in a concentration of about 50 mM to about 110 mM; (5) a sodium chloride concentration of about 50 mM to about 110 mM; (6) a carbonic acid salt concentration of about 17 mM to about 30 mM; (7) a sodium bicarbonate concentration of about 13 mM to about 25 mM; (8) a total alkaline metal halide salt and carbonic acid salt concentration of about 85 mM to about 130 mM; (9) a sodium chloride concentration of 87±5 mM and an osmolality of 261±26 mOsm/kg; (10) a salt of an alkaline metal and a halide in a concentration of about 50 mM to about 110 mM, a carbonic acid salt in a concentration of about 17 mM to about 30 mM, and an osmolality of about 200 mOsm/kg to about 329 mOsm/kg; and (11) an osmolality of 218 mOsm/kg, a sodium chloride concentration of 50 mM to 110 mM, and a sodium bicarbonate concentration of 13 mM to 25 mM. Optionally, the non-human mammalian XY pluripotent cell is maintained in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to assaying.

In some methods, the donor non-human mammalian XY pluripotent cell has decreased expression and/or activity of Ddx3y, Uty, and Eif2s3y. In some methods, the donor non-human mammalian XY pluripotent cell lacks expression and/or activity of one or more of Ddx3y, Uty, and Eif2s3y. In some methods, the donor non-human mammalian XY pluripotent cell lacks expression and/or activity of Ddx3y, Uty, and Eif2s3y.

In some methods, the non-human mammal is a rodent. Optionally, the rodent is a rat or a mouse. In some methods, the rodent is a mouse that comprises a C57BL/6 strain. Optionally, the Y chromosome is from a C57BL/6 strain. In some methods, the rodent is a mouse that comprises a 129 strain. Optionally, the Y chromosome is from a 129 strain. In some methods, the mouse does not comprise a 129 strain. In some methods, the Y chromosome is not from a 129 strain. In some methods, the rodent is a mouse that comprises a C57BL/6 strain and a 129 strain. Optionally, the pluripotent cell is a VGF1 mouse ES cell.

In some methods, the pluripotent cell comprises a targeted genetic modification in a target genomic locus. Optionally, wherein the targeted genetic modification comprises an insertion, a deletion, a knockout, a knockin, a point mutation, or a combination thereof.

The invention also provides methods of generating an embryo, comprising introducing into a host embryo a donor non-human mammalian XY pluripotent cell having a decreased expression and/or activity of one or more of Ddx3y, Uty, and Eif2s3y produced by the above methods for making a donor non-human mammalian XY pluripotent cell, wherein the host embryo is capable of producing a fertile, phenotypically female XY non-human mammal in an F0 generation.

The invention also provides methods for making a fertile, phenotypically female XY non-human mammal in an F0 generation, comprising: (a) introducing into a host embryo a donor non-human mammalian XY pluripotent cell having a decreased expression and/or activity of one or more of Ddx3y, Uty, and Eif2s3y produced by the above methods for making a donor non-human mammalian XY pluripotent cell; (b) introducing the host embryo from step (a) into a recipient female non-human mammal and gestating the host embryo; and (c) obtaining F0 XY non-human mammal progeny comprising a phenotypically female XY non-human mammal, wherein upon attaining sexual maturity the F0 phenotypically female XY non-human mammal is fertile. Alternatively, methods are provided for making a fertile, phenotypically female XY non-human mammal in an F0 generation, comprising: (a) introducing an embryo into a recipient female non-human mammal and gestating the embryo, wherein the embryo is produced by the above methods and comprises a cell having a decreased expression and/or activity of one or more of Ddx3y, Uty, and Eif2s3y; and (b) obtaining F0 XY non-human mammal progeny comprising a phenotypically female XY non-human mammal, wherein upon attaining sexual maturity the F0 phenotypically female XY non-human mammal is fertile. Optionally, the host embryo is a pre-morula stage embryo. Optionally, the method further comprises culturing the host embryo to the blastocyst stage.

In some methods, the non-human mammalian XY pluripotent cell is maintained in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into the host embryo.

In some methods, at least 5%, at least 10%, at least 20%, at least 30%, at least 40%, at least 50%, at least 60%, at least 70%, at least 80%, at least 90%, or at least 95% of the F0 XY progeny are phenotypically female XY non-human mammals that are fertile upon attaining sexual maturity. In some methods, the percentage of the F0 XY progeny that are fertile, phenotypically female XY animals is higher for F0 XY progeny derived from a non-human mammalian XY pluripotent cell having decreased expression and/or activity of one or more of Ddx3y, Uty, and Eif2s3y when compared to F0 XY progeny derived from a non-human mammalian XY pluripotent cell having higher expression and/or activity of one or more of Ddx3y, Uty, and Eif2s3y.

In some methods, all of the F0 females derived from the donor non-human mammalian XY pluripotent cell have an XY genotype.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are fertile. In some methods, the percentage of the F0 XY females that are fertile is higher for F0 XY progeny derived from a non-human mammalian XY pluripotent cell having decreased expression and/or activity of one or more of Ddx3y, Uty, and Eif2s3y when compared to F0 XY progeny derived from a non-human mammalian XY pluripotent cell having higher expression and/or activity of one or more of Ddx3y, Uty, and Eif2s3y.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing litters having at least 2, 3, 4, 5, 6, 7, 8, 9, or 10 pups. In some methods, the average litter size produced by F0 XY females or fertile F0 XY females is higher for F0 XY females or fertile F0 XY females derived from a non-human mammalian XY pluripotent cell having decreased expression and/or activity of one or more of Ddx3y, Uty, and Eif2s3y when compared to F0 XY females or fertile F0 XY females derived from a non-human mammalian XY pluripotent cell having higher expression and/or activity of one or more of Ddx3y, Uty, and Eif2s3y.

In some methods, at least 5%, at least 10%, at least 20%, at least 30%, at least 40%, at least 50%, at least 60%, at least 70%, at least 80%, at least 90%, or at least 95% of the F0 XY females derived from the donor non-human mammalian XY pluripotent cell are capable of producing at least 2, 3, 4, 5, 6, 7, 8, 9, or 10 litters in their lifetimes. In some methods, the average number of lifetime litters produced by F0 XY females or fertile F0 XY females is higher for F0 XY females or fertile F0 XY females derived from a non-human mammalian XY pluripotent cell having decreased expression and/or activity of one or more of Ddx3y, Uty, and Eif2s3y when compared to F0 XY females or fertile F0 XY females derived from a non-human mammalian XY pluripotent cell having higher expression and/or activity of one or more of Ddx3y, Uty, and Eif2s3y. In some methods, the average number of lifetime offspring produced by F0 XY females or fertile F0 XY females is higher for F0 XY females or fertile F0 XY females derived from a non-human mammalian XY pluripotent cell having decreased expression and/or activity of one or more of Ddx3y, Uty, and Eif2s3y when compared to F0 XY females or fertile F0 XY females derived from a non-human mammalian XY pluripotent cell having higher expression and/or activity of one or more of Ddx3y, Uty, and Eif2s3y.

The invention also provides kits comprising: (a) a detection reagent for detecting expression and/or activity levels of one or more of Ddx3y, Uty, and Eif2s3y in a non-human mammalian XY pluripotent cell; and (b) instructions for using the detection reagents and correlating detection with predicted propensity of the non-human mammalian XY pluripotent cell for producing fertile, phenotypically female XY non-human mammals in an F0 generation.

BRIEF DESCRIPTION OF THE FIGURES

FIG. 11A shows relative expression levels of Sox9 and FIG. 11B shows relative expression levels of Fgf9 in genital ridges dissected from embryos derived from two sex-reversing XY ES cell clones cultured in KO-DMEM. The developmental stages of the embryos analyzed ranged from 12 to 25 tail somites (ts). Four controls were used: XY mouse embryos generated via breeding; XX mouse embryos generated via breeding; XY mouse embryos from non-targeted ES cells; and XY mouse embryos from a line that does not sex-reverse in KO-DMEM. The x-axis shows the ts stage, and the y-axis shows Sox9 expression measured by TAQMAN® reverse transcription-coupled quantitative polymerase chain reaction (RT-qPCR) of mRNA normalized to that of the Sf1 reference gene.

FIG. 12A-B show relative expression levels during the stages of sex determination of markers of male gonad development. FIG. 11A shows relative expression levels of Dhh and FIG. 11B shows relative expression levels of Amh in genital ridges dissected from embryos derived from two sex-reversing XY ES cell clones cultured in KO-DMEM. The developmental stages of the embryos analyzed ranged from 12 to 25 tail somites (ts). Four controls were used: XY mouse embryos generated via breeding; XX mouse embryos generated via breeding; XY mouse embryos from non-targeted ES cells; and XY mouse embryos from a line that does not sex-reverse in KO-DMEM. The x-axis shows the ts stage, and the y-axis shows Sox9 expression measured by TAQMAN® reverse transcription-coupled quantitative polymerase chain reaction (RT-qPCR) of mRNA normalized to that of the Sf1 reference gene.

FIG. 13 shows relative expression levels of Fox12 in genital ridges dissected from embryos derived from two sex-reversing XY ES cell clones cultured in KO-DMEM. The developmental stages of the embryos analyzed ranged from 12 to 25 tail somites (ts). Two controls were used: XY mouse embryos generated via breeding; and XX mouse embryos generated via breeding. The x-axis shows the ts stage, and the y-axis shows Sox9 expression measured by TAQMAN® reverse transcription-coupled quantitative polymerase chain reaction (RT-qPCR) of mRNA normalized to that of the Sf1 reference gene.

DEFINITIONS

Figure 1:
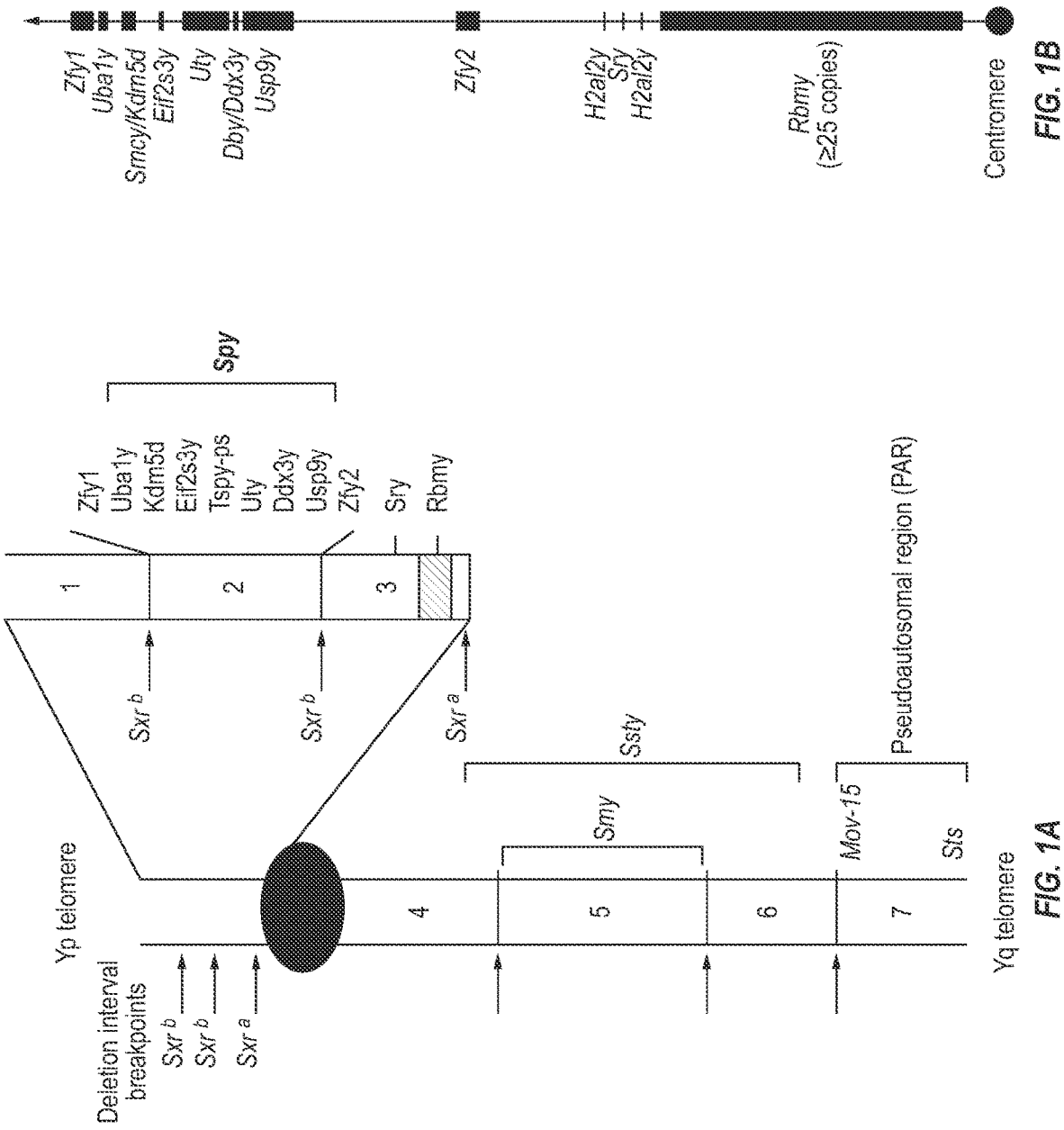
FIG. 1A provides a schematic of the mouse Y chromosome, including deletion intervals 1-7, the $Sxr^a$ and $Sxr^b$ regions, and genes mapped to the $Sxr^b$ deletion.
FIG. 1B provides a schematic of the short arm (Yp) of the mouse Y chromosome.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "wild type" includes entities having a structure and/or activity as found in a normal (as contrasted with mutant, diseased, altered, or so forth) state or context. Wild type gene and polypeptides often exist in multiple different forms (e.g., alleles).

"Fertility" and "fertile" refer to the ability of a female animal to breed, get pregnant, and deliver live-born offspring. An animal need only produce one live-born offspring to be considered fertile.

"Fecundity" and "fecund" refer to the quality of fertility. Fecundity can be a quantitative measure, such as the total number of live offspring born in the lifetime of an animal or in a defined experimental time frame. The number and frequency of litters and the number of offspring per litter are also measures of fecundity. An animal can be fertile but not very fecund (e.g., only one or a few small litters).

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The singular forms of the articles "a," "an," and "the" include plural references unless the context clearly dictates otherwise. For example, the term "a Cas protein" or "at least one Cas protein" can include a plurality of Cas proteins, including mixtures thereof.

Statistically significant means $p \leq 0.05$.

DETAILED DESCRIPTION

I. Overview

Methods and compositions are provided for generating F0 fertile XY female animals. The methods and compositions involve making XY pluripotent or totipotent animal cells, in vitro cell cultures, or embryos that are capable of producing a fertile female XY animal in an F0 generation. Such cells (and embryos and animals derived from them) can be made by culturing XY pluripotent or totipotent cells in a feminizing medium and assessing expression and/or activity of one or more of Ddx3y, Uty, and Eif2s3y. The propensity of animal XY pluripotent or totipotent cell clones to produce fertile, phenotypically female XY animals in an F0 generation is inversely correlated with the expression or activity of Ddx3y, Uty, and Eif2s3y in those clones. Alternatively, such cells (and embryos and animals derived from them) can be made by silencing a region of the Y chromosome. Optionally, the cells can also be cultured in feminizing medium and/or can be modified to decrease the level and/or activity of an Sry protein. Methods and compositions are also provided for silencing a region of the Y chromosome in an XY pluripotent or totipotent animal cell (or in vitro cell cultures, embryos, or animals derived therefrom) by maintaining an XY pluripotent or totipotent animal cell in a feminizing medium such as a low-osmolality medium. Methods and compositions are also provided for maintaining a population of XY pluripotent or totipotent animal cells in a feminizing medium and selecting cells or clones having increased capabilities for producing a fertile female XY animal in an F0 generation. Methods and compositions are also provided for screening for compounds with feminizing activity or for optimizing concentrations of components in a feminizing medium through assessment of expression and/or activity of one or more of Ddx3y, Uty, and Eif2s3y, whose expression and/or activity in XY pluripotent or totipotent cells is inversely correlated with the propensity of animal XY pluripotent or totipotent cell clones to produce fertile, phenotypically female XY animals in an F0 generation.

The majority of ES cell lines for making non-human mammals (e.g., mice) have a male XY genotype. Because of the dominance of the Y chromosome in mammalian sex determination, when XY ES cells are introduced into a host embryo and gestated, what nearly always result in the first generation (F0) is phenotypically male animals that are chimeras containing cells derived from the male donor ES cell (XY) and cells derived from the host embryo, which can be either male (XY) or female (XX). To the extent that phenotypic females are observed in the F0 generation, these typically arise from the introduction of XY ES cells into a female XX embryo that results in a chimera whose ES cell contribution is insufficient to masculinize the embryonic genital ridge. In most cases such female chimeras do not produce oocytes derived from the XY ES cells and, therefore, are not capable of transmitting the ES cell genome to the next generation.

Using the VELOCIMOUSE® method (see, e.g., U.S. Pat. Nos. 7,659,442; 7,576,259; and 7,294,754; and Poueymirou et al. (2007) *Nat. Biotech.* 25(1):91-99; each of which is herein incorporated by reference in its entirety for all purposes), it is possible to obtain F0 generation mice that are fully derived from a donor ES cell. Under normal circumstances and standard experimental conditions, XY donor ES cells produce only phenotypically male fully ES cell-derived mice, while ES cells that are XX or XO (XY ES cells that have lost the Y chromosome) produce only phenotypically female fully ES cell-derived mice. To produce mice with homozygous targeted mutations from the male and female fully ES cell-derived mice requires two subsequent generations of breeding to first produce the F1 generation heterozygous male and females that when intercrossed have the potential to produce homozygous progeny in the F2 generation.

Phenotypically female mice with an XY genotype can arise as the result of specific mutations. See, e.g., Lovell-Badge et al. (1990) *Development* 109:635-646; see also Colvin et al. (2001) *Cell* 104(6):875-889. However, such XY female mice are often sterile or have very limited fertility.

WO 2011/156723 (herein incorporated by reference in its entirety for all purposes) provides methods and compositions which employ a feminizing culture medium (e.g., low-osmolality medium or low-salt medium as disclosed elsewhere herein) for maintaining XY donor cells in culture such that after introduction of the XY donor cells into a host embryo and gestation in a suitable host, fertile XY female animals can be produced in the F0 population. Such compositions find use in making F1 progeny that are homozygous for a given targeted genetic modification at a target genomic locus.

The instant application provides methods for making a phenotypically female fertile XY non-human mammal (e.g., mouse) from an XY donor cell (e.g., an XY donor cell derived from a phenotypically male mouse) and a suitable host embryo. The method comprises making such a non-human mammal in the F0 generation, which allows for forming a breeding pair (a male F0 and a female F0) in the F0 generation. This is particularly useful where the donor cell comprises a heterozygous genetic modification, and a non-human mammal homozygous for the genetic modification is desired. Although this disclosure illustrates the invention in the context of making phenotypically female fertile XY mice from donor mouse XY ES cells, the methods and compositions described herein may be applied to make phenotypically female XY fertile non-human mammals from any suitable non-human mammalian cell (e.g., an induced pluripotent stem (iPS) cell, an ES cell, or a pluripotent cell) and any suitable non-human mammalian embryo.

The instant application provides methods and compositions that employ XY donor cells having a modification that silences a region of the Y chromosome to promote the production of anatomically normal, fertile, and fecund, XY F0 females. Such methods and compositions allow for making a fertile female XY non-human animal in an F0 generation. The methods and compositions can be further employed in combination with a modification that decreases the level and/or activity of the Sry protein in combination and/or culturing in the feminizing culture medium (e.g., low-osmolality medium) disclosed elsewhere herein to significantly increase the percentage of fertile female XY progeny in the F0 generation. These phenotypically female fertile XY non-human mammals include non-human mammals that exhibit sufficient phenotypically female characteristics to ovulate and to gestate an embryo upon fertilization of an ovum produced by ovulation in the animal, including to gestate an embryo to term and give birth to a live-born animal.

Methods for the efficient male to female sex conversion are valuable to the domestic animal industry. For example, female calves are much more valuable to the dairy cattle industry than males. The same is true for poultry. For breeding purposes, whether it be cattle or hogs or sheep, it is preferred to breed many females to only a few bulls, boars, or rams. Thus, the various methods provided herein find use in various commercially important breeding industries.

II. Methods and Compositions for Making a Fertile XY Animal in an F0 Generation

A. Methods of Making XY Pluripotent or Totipotent Cells Capable of Producing Fertile XY Female in F0 Generation Phenotypically female animals (e.g., mice) with an XY genotype can be generated as the result of specific mutations. See, e.g., Lovell-Badge et al. (1990) *Development* 109:635-646; see also Colvin et al. (2001) *Cell* 104(6):875-889. However, such XY female animals are often sterile or, if fertile, have very poor fecundity. To be most useful in the context of generating animals homozygous for a targeted genetic modification at a target genomic locus, both sex reversal and fertility need to be achieved in the XY female. Through the methods and compositions provided herein, XY pluripotent or totipotent animal cells or embryos can be made that are capable of producing a fertile female XY in an F0 generation. Such cells (and in vitro cell cultures, embryos, and animals derived from them) can be made by silencing a region of the Y chromosome. Optionally, the cells can also be cultured in feminizing medium and/or can be modified to decrease the level and/or activity of an Sry protein.

i. Silencing of a Region of the Y Chromosome

Methods and compositions are provided for modifying XY animal cells (e.g., XY pluripotent or totipotent cells such as XY ES cells) to silence a region of the Y chromosome, thereby converting some of the cells to donor XY pluripotent or totipotent cells with the potential to develop into fertile female animals, such that the cells can be implanted into a recipient embryo and give rise to a fertile female progeny. Thus, the donor XY pluripotent or totipotent cells are capable of producing F0 XY progeny comprising a fertile, phenotypically female animal.

The region silenced can be any part of the Y chromosome, such as a region comprising all or part of the small arm of the Y chromosome or a region that is silenced by treating with a feminizing medium as disclosed elsewhere herein. The silencing could also affect other parts of the Y chromosome (e.g., the long arm (Yq)), particularly parts that carry genes required for male fertility and spermatogenesis. For example, the region can comprise all or part of the $Sxr^a$ region (e.g., a portion containing the Sry gene), and/or the region can comprise all or part of the $Sxr^b$ region (e.g., a portion containing the Zfy2 gene) of the mouse Y chromosome (see FIG. 1A) or a corresponding region of Y chromosomes from other species (e.g., the AZFa, AZFb, or AZFc regions of the human Y chromosome). For example, the region can comprise parts or all of both the $Sxr^a$ and $Sxr^b$ regions. The boundaries of the $Sxr^b$ region, for example, are Zfy1 and Zfy2 (see FIG. 1A and Mazeyrat et al. (1998) *Human Molecular Genetics* 7(11):1713-1724, incorporated by reference in its entirety for all purposes). Corresponding regions from other animal species include regions having one or more genes that are orthologous or homologous to genes in the region on the mouse Y chromosome. For example, the AZFa region of the human region corresponds with the $Sxr^b$ region of the mouse Y chromosome in that each region contains Uty, Dby (Ddx3y), and Dffry (Usp9y). See, e.g., Affara (2001) *Expert Rev. Mol. Med.*, Jan. 3, 2001: 1-16; Mazeyrat et al. (1998) *Human Molecular Genetics* 7(11); 1713-1724; and Sargent et al. (1999) *J. Med. Genet.* 36:370-377, each of which is incorporated by reference in its entirety for all purposes. The region can also comprise all or part of the Smy region or the Spy region (see FIG. 1A and Affara (2001) *Expert Rev. Mol. Med.*, Jan. 3, 2001: 1-16). Likewise, the region can comprise all or part of one or more of deletion interval 1, deletion interval 2, deletion interval 3, deletion interval 4, deletion interval 5, deletion interval 6, and deletion interval 7 of the mouse Y chromosome or corresponding regions of Y chromosomes from other animal species (see, e.g., FIG. 1A and Affara (2001) *Expert Rev. Mol. Med.*, Jan. 3, 2001: 1-16). For example, the region can comprise all or part of one or more of deletion interval 1, deletion interval 2, and deletion interval 3 of the mouse Y chromosome or corresponding regions of Y chromosomes from other animal species (see, e.g., FIG. 1A). In one example, the region can comprise deletion interval 2 and deletion interval 3, or part of deletion interval 2 and part of deletion interval 3.

The region can include one or more of the following: the Rbmy cluster, H2al2y, Sry, Zfy2, Usp9y, Ddx3y, Uty, Tspy-ps, Eif2s3y, Kdm5d, Ubaly, or Zfy1 (see Table A). The region can be telomeric to the Rbmy cluster or can be centromeric or telomeric to H2al2y, Sry, Zfy2, Usp9y, Ddx3y, Uty, Tspy-ps, Eif2s3y, Kdm5d, Ubaly, or Zfy1. For example, the region can comprise a portion of the Y chromosome telomeric of Kdm5d or centromeric of Uspy9y, or the region can be telomeric of Zfy2, Sry, or the Rbmy cluster. The region can exclude one or more of the Rbmy cluster, H2al2y, Sry, Zfy2, Usp9y, Ddx3y, Uty, Tspy-ps, Eif2s3y, Kdm5d, Ubaly, or Zfy1. For example, the region can exclude one or more of the Rbmy cluster, Zfy2, and Sry. Likewise, the region can include a portion of the Y chromosome outside of one or more of the Rbmy cluster, H2al2y, Sry, Zfy2, Usp9y, Ddx3y, Uty, Tspy-ps, Eif2s3y, Kdm5d, Ubaly, or Zfy11. For example, the region can comprise a portion of the Y chromosome outside of one or more of the Rbmy cluster, Zfy2, and Sry.

TABLE A

Genes on Mouse Chromosome Arm Yp

| SYMBOL | NAME | MGI ID | ENTREZ ID |
|---|---|---|---|
| Rbmy | RNA binding motif protein, Y chromosome | 104732 | 19657 |
| Gm16501 (H2al2y) | Predicted Gene 16501 | 3710623 | 100042840 |
| Sry | Sex determining region of chromosome Y | 98660 | 21674 |
| Zfy2 | Zinc finger protein 2, Y linked | 99213 | 22768 |
| Usp9y | Ubiquitin specific peptidase 9, Y chromosome | 1313274 | 107868 |
| Ddx3y | DEAD box polypeptide 3, Y-linked | 1349406 | 26900 |
| Uty | Ubiquitously transcribed tetratricopeptide repeat gene, Y chromosome | 894810 | 22290 |
| Tspy-ps | Testis specific protein-Y encoded, pseudogene | 1201688 | 22109 |
| Eif2s3y | Eukaryotic translation initiation factor 2, subunit 3, structural gene Y-linked | 1349430 | 26908 |
| Kdm5d | Lysine-specific demethylase 5D | 99780 | 20592 |
| Uba1y | Ubiquitin-activating enzyme, chromosome Y | 98891 | 22202 |
| Zfy1 | Zinc finger protein 1, Y linked | 99212 | 22767 |

The silencing can decrease the level and/or activity of a protein encoded by a gene located on the Y chromosome. For example, the level and/or activity of one or more of the proteins encoded by the Rbmy cluster, H2al2y, Sry, Zfy2, Usp9y, Ddx3y, Uty, Tspy-ps, Eif2s3y, Kdm5d, Uba1y, or Zfy1 can be decreased. Alternatively, the silencing can result in elimination of expression of a gene located on the Y chromosome (i.e., the gene is not expressed or the cell lacks detectable expression of the gene). In some methods, for example, one or more of one or more of the Rbmy cluster, H2al2y, Sry, Zfy2, Usp9y, Ddx3y, Uty, Tspy-ps, Eif2s3y, Kdm5d, Uba1y, or Zfy1 are not expressed upon silencing. In some methods, the level and/or activity of one or more of the proteins encoded by Ddx3y, Eif2s3y, Uty, Zfy2, and Sry is decreased, or one or more of Ddx3y, Eif2s3y, Uty, Zfy2, and Sry are not expressed.

Silencing of a region can include, for example, removal of the region from the genome, decreasing expression of one or more genes within the region is reduced, or decreasing the activity of one or more proteins or RNAs encoded by genes within the region. A decrease in expression or activity in a subject cell can include any statistically significant reduction in expression or activity levels when compared to an appropriate control cell. In general, the expression or activity is decreased if the expression or activity is statistically lower than the expression or activity in an appropriate control cell that has not been modified to silence a region of the Y chromosome. Such a decrease includes a reduction of at least 1%, 5%, 10%, 20%, 30%, 40%, 50%, 60%, 70%, 80%, 90%, 95%, 99%, or greater relative to a control cell that has not been modified to silence a region of the Y chromosome. Statistical significance means $p \leq 0.05$. A decrease in expression or activity can occur via any mechanism at any stage. For example, a decrease in expression could occur via modifications made directly or indirectly to the region or via events or regulation that occurs during transcription, post-transcription, during translation, or post-translation.

In some cases, genes within a silenced region are not expressed (e.g., expression is eliminated or the cell lacks detectable expression of the gene). A gene is not expressed when transcription of the gene is not carried out or when there are no detectable levels of the products of a gene (e.g., mRNA or protein) by common techniques known in the art. The expression level of a polypeptide may be measured directly, for example, by assaying for the level of the polypeptide in the cell or organism (e.g., Western blot analysis, FACS analysis, ELISA), or indirectly, for example, by measuring the activity of the polypeptide. In other instances, reduced expression and/or activity of a gene can be measured using methods that include, for example, Southern blot analysis, DNA sequencing, PCR analysis, Northern blot analysis, quantitative RT-PCR analysis, Next Generation Sequencing (NGS), microarray analysis, or phenotypic analysis.

A "subject cell" is one in which a genetic alteration, such as a genetic modification disclosed herein has been effected, or is a cell which is descended from a cell so altered and which comprises the alteration. A "control" or "control cell" provides a reference point for measuring changes in phenotype of the subject cell. A control cell can be as closely matched as possible with the cell with reduced levels and/or activity of the protein except it lacks the genetic modification or mutation resulting in the reduced levels or activity (for example, the respective cells can originate from the same cell line). In other instances, the control cell may comprise, for example: (a) a wild-type cell (i.e., of the same genotype as the starting material for the genetic alteration which resulted in the subject cell); (b) a cell of the same genotype as the starting material but which has been genetically modified with a null construct (i.e., with a construct which has no known effect on the trait of interest, such as a construct comprising a marker gene); (c) a cell which is a non-genetically modified progeny of a subject cell (i.e., the control cell and the subject cell originate from the same cell line); (d) a cell genetically identical to the subject cell but which is not exposed to conditions or stimuli that would alter the protein levels and/or activity levels; or (e) the subject cell itself, under conditions in which the genetic modification does not result in an alteration in expression of the protein levels and/or activity levels.

The silencing can be a permanent genetic change or transient. A permanent genetic change can be, for example, a change that remains without an additional step being taken to reverse it (e.g., through an additional modification), whereas a transient change can be a change that lasts for only a certain amount of time, even if no additional steps are taken to reverse it (e.g., silencing achieved by culturing in feminizing medium). In some methods, the silencing is achieved by a means other than maintaining the XY pluripotent or totipotent cell in a feminizing medium disclosed elsewhere herein (e.g., a low-osmolality medium comprising a base medium comprising an osmolality from about 200 mOsm/kg to less than about 329 mOsm/kg). In other methods, the silencing is achieved by culturing the XY pluripotent or totipotent cell in a feminizing medium disclosed elsewhere herein (e.g., a low-osmolality medium having an osmolality from about 200 mOsm/kg to less than about 329 mOsm/kg or a low-osmolality medium comprising a base medium that has an osmolality from about 200 mOsm/kg to less than about 329 mOsm/kg). For example, the silencing can be achieved by one or more of the following: (1) a targeted genetic modification such as deletion or disruption of the region; (2) RNA interference or antisense inhibition of mRNAs transcribed from one or more genes within the region; (3) directed degradation or inhibition of proteins encoded by one or more genes within the region; (4) heterochromatin-mediated silencing or altering heterochromatin formation in one or more locations on the Y chromosome; (5) increasing levels of the phosphorylated form of histone variant γH2AX on the Y chromosome; or (6) decreasing transcription of one or more genes within the region. Targeted genetic modifications and methods of producing them are disclosed elsewhere herein. Silencing can also be achieved using inhibitory nucleic acids such as short interfering nucleic acids (e.g., short interfering RNA (siRNA), double-stranded RNA (dsRNA), micro-RNA (miRNA), and short hairpin RNA (shRNA)) or antisense oligonucleotides specific for a gene transcript. Silencing can also be achieved through use of inhibitors of proteins encoded by one or more genes within the region or their upstream regulation by post-translational modification via, for example, phosphorylation, ubiquitylation, and sumoylation. Altering heterochromatin formation on the Y chromosome can also result in silencing. For example, deletion of a first region of the Y chromosome could bring a second region closer to the heterochromatin domain of the centromere and result in silencing of the second region. Increasing levels of the phosphorylated form of histone variant γH2AX on the Y chromosome can also result in silencing of a region of the Y chromosome. Phosphorylated histone γH2AX is known to be associated with transcriptional repression, and is associated with transcriptional repression of the X and Y chromosomes in the XY sex body during meiotic prophase. See, e.g., Alton et al. (2008) *Reproduction* 135:241-252. Decreasing transcription of one or more genes within the region can also result in silencing of the region of the Y chromosome. Repressing transcription of one or more genes can be accomplished, for example, using DNA-binding proteins fused to transcriptional repressor domains or epigenetic modification domains (see, e.g., WO 2014/089290, herein incorporated by reference in its entirety for all purposes).

A decreased level and/or activity of a protein can be achieved by a targeted genetic modification to the gene encoding the protein or to a genomic locus that affects or regulates levels or activity of the protein. Such targeted modifications can include, for example, additions of one or more nucleotides, deletions of one or more nucleotides, substitutions of one or more nucleotides, a knockout of a polynucleotide of interest or a portion thereof, a knock-in of a polynucleotide of interest or a portion thereof, a replacement of an endogenous nucleic acid sequence with a heterologous nucleic acid sequence, or a combination thereof. For example, at least 1, 2, 3, 4, 5, 7, 8, 9, 10 or more nucleotides can be changed to form the targeted genomic modification. Various methods can be used to generate a targeted genetic modification. See, e.g., Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes. In addition, the various methods described herein can be used to introduce targeted genetic modification to the gene encoding the protein or other genomic loci.

Various methods for making targeted genetic modifications that decrease the level and/or the activity of the protein can be used and are disclosed elsewhere herein.

The targeted genetic modification of the gene encoding the protein or of any other target genomic locus can occur while the cell (e.g., ES cell) is being maintained in the feminizing medium (e.g., low-osmolality medium) disclosed elsewhere herein (e.g., a medium that promotes the development of XY F0 fertile females). Conversely, the cell can be cultured in a medium that is not the feminizing medium disclosed herein (e.g., not a low-osmolality medium comprising a base medium comprising an osmolality from about 200 mOsm/kg to less than about 329 mOsm/kg). Alternatively, the targeted genetic modification of the gene or other target genomic locus can occur while the cell is being maintained in different culture medium, and subsequently transferring to the feminizing culture medium (e.g., low-osmolality) disclosed herein.

The activity and/or level of the protein can also be reduced or eliminated by introducing into the cell a polynucleotide that inhibits the level or activity of the protein. The polynucleotide may inhibit the expression of the protein directly, by preventing translation of the Sry messenger RNA, or indirectly, by encoding a polypeptide that inhibits the transcription of the gene encoding the protein. Alternatively, the activity of the protein is reduced or eliminated by introducing into the cell a sequence encoding a polypeptide that inhibits the activity of the protein.

The level and/or activity of the protein can also be regulated through use of a conditional allele that reduces the activity and/or level of the protein. A conditional allele includes a modified gene encoding the protein designed to have the decreased level and/or activity of the protein at a desired developmental time and/or within a desired tissue of interest. Reduced level and/or activity can be compared with a control cell lacking the modification giving rise to the conditional allele, or in the case of reduced activity at a desired developmental time with preceding and/or following times, or in the case of a desired tissue, with a mean activity of all tissues. For example, the conditional allele can comprise a conditional null allele of gene encoding the protein that can be switched off at a desired developmental time point and/or in specific tissues. Such a conditional allele can be used to create fertile XY females derived from any gene-targeted clone. As described elsewhere herein, such a method enables the creation of a desired homozygous genetic modification in the F1 generation. Such methods provide a quick look at the phenotype without having to breed to the F2 generation.

A conditional allele can also be a multifunctional allele as described in US 2011/0104799, which is incorporated by reference in its entirety for all purposes. For example, such a conditional allele can comprise: (a) an actuating sequence in sense orientation with respect to transcription of a target gene, and a drug selection cassette (DSC) in sense or antisense orientation; (b) in antisense orientation a nucleotide sequence of interest (NSI) and a conditional by inversion module (COIN), which utilizes an exon-splitting intron and an invertible genetrap-like module (see, e.g., US 2011/0104799, which is incorporated by reference in its entirety for all purposes); and (c) recombinable units that recombine upon exposure to a first recombinase to form a conditional allele that (i) lacks the actuating sequence and the DSC, and (ii) contains the NSI in sense orientation and the COIN in antisense orientation.

The conditional allele of the gene encoding the protein can be generated in any cell type, and is not limited to an XY pluripotent or totipotent cell. Such cells types along with non-limiting methods to target a genomic locus on the Y chromosome are discussed in further detail elsewhere herein.

The silencing can occur when the XY pluripotent or totipotent cell is being cultured, after the donor XY pluripotent or totipotent cell is introduced into a host embryo, or after the host embryo comprising the donor XY pluripotent or totipotent cell is introduced into a recipient female animal. The silencing can also occur during different stages of embryonic development or throughout embryonic development. In some cases, the silencing continues after birth. For example, after an oocyte is fertilized, some silencing can be maintained through the first two cell divisions. The sex reversal caused by the silencing can also be capable of being transmitted to F1 progeny. Some examples of periods in which the silencing occur include one or more of the following: (1) during embryonic development when the male sex determination program is engaged; (2) during embryonic development up to at least a developmental stage corresponding to E11-E12 in mice (e.g., developmental stages important for sex determination or sex reversal); (3) during embryonic development up to at least a development stage corresponding to E17-E19 in mice (e.g., developmental stages important for fertility in embryonic oocytes); (4) throughout the period of oogenesis; (5) during meiotic prophase in oocyte development, which initiates in the embryo just before birth; (6) after the oocyte is fertilized (e.g., during its first two cell divisions); or (7) in oocytes post-ovulation through the first two cell divisions post-fertilization.

ii. Culturing and Maintaining in Feminizing Medium

The culture media employed in the various methods and compositions that promote XY fertile females in the F0 generation is such that it maintains the pluripotent or totipotent cells (e.g., ES cells, iPS cells, XY ES cells, XY iPS cells, etc.). The terms "maintain," "maintaining," and "maintenance" refer to the stable preservation of at least one or more of the characteristics or phenotypes of pluripotent or totipotent cells described herein (including ES cells or iPS cells). Such phenotypes can include maintaining pluripotency or totipotency, cell morphology, gene expression profiles, and the other functional characteristics of the cells. The terms "maintain," "maintaining" and "maintenance" can also encompass the propagation of cells or an increase in the number of cells being cultured. The terms further contemplate culture conditions that permit the cells to remain pluripotent, while the cells may or may not continue to divide and increase in number. The cells can be cultured in various concentrations of carbon dioxide. In one example, the cells are cultured in 5% carbon dioxide.

The XY pluripotent or totipotent cells having the modification that silences a region of the Y chromosome can be maintained by culturing in any base medium known in the art (e.g., DMEM) that is suitable for use (with added supplements) in growing or maintaining the pluripotent or totipotent cells (e.g., ES cells, iPS cells, XY ES cells, XY iPS cells, etc.) in culture. Such cultured XY pluripotent or totipotent cells (e.g., ES cells) have the potential to develop into fertile female animals due to the silencing of a region of the Y chromosome and retain pluripotency or totipotency, such that the cells can be implanted into a recipient embryo and give rise to a fertile female progeny.

1. Feminizing Medium

Silencing of a region of the Y chromosome can be achieved by culturing or maintaining XY pluripotent or totipotent cells in a feminizing medium as further defined below. Likewise, XY pluripotent or totipotent cells having a further modification that silences a region of the Y chromosome can also be maintained by culturing in a feminizing medium as further defined below. By culturing the cells for sufficient time in the medium, the cells can be converted to XY pluripotent or totipotent cells having the potential to develop into fertile female animals, such that the cells can be implanted to a recipient embryo and give rise to a fertile female progeny. WO 2011/156723 and Kuno et al. (2015) *Transgenic Res.* 24(1):19-29 (each of which is herein incorporated by reference in its entirety for all purposes) provide methods and compositions which employ such a feminizing culture medium (e.g., low-osmolality medium or low-salt medium as disclosed elsewhere herein) for maintaining XY donor cells in culture such that after introduction of the XY donor cells into a host embryo and gestation in a suitable host, fertile XY female animals can be produced in the F0 population. In some such methods, the propensity of a particular XY pluripotent or totipotent cell clone for producing fertile XY female animals can be from 0% to 60%, and these feminizing effects cannot be reversed by re-growing the clones in control non-feminizing medium. Such F0 XY females can have a normal female external and internal anatomy, can be fully donor-cell-derived with no host embryo contribution and no chimerism, can have one X and one Y chromosome in all tissues including sex organs, and can have a normal XY male karyotype with no visible chromosome aberrations. F0 XY females derived from XY pluripotent or totipotent cells cultured in feminizing medium can have fertility and fecundity comparable to XX females. For example, in some such methods, the F0 XY females have a fertility of 60-70% compared with approximately 90% for F1 XX female controls. In some such methods, there is no difference in fecundity between F0 XY females and F1 XX females in a 9-month breeding test.

Culturing in a feminizing medium can result in repression or silencing of Y chromosome genes (see Example 1). For example, a region of the Y chromosome can be silenced, such as all or part of the short arm of the Y chromosome. Although an understanding of mechanism is not required for practice, the silencing on the short arm of the Y chromosome can extend to the key regulator of the male sex determination pathway, the Sry gene, which fails to express sufficiently at the correct time from E11-E12 during mouse embryonic development, resulting in expression of the female sex determination program in the bipotential genital ridge (see Example 1 and FIG. 2A-D). Other genes such as Ddx3y and Eif2s3y can also fail to express (see Example 1 and FIGS. 3 and 4). From then on, the sex-reversed embryo can develop to birth (F0 generation) as a female and then grow into a normal, fertile female mouse despite its XY genotype. In some methods, the feminizing medium-induced Y chromosome silencing is not a permanent genetic change and does not persist into the F1 generation (i.e., no XY females are found among the F1 progeny of the F0 XY females).

Although an understanding of mechanism is not required for practice, altering chromatin and/or increasing levels of the phosphorylated form of histone variant γH2AX on the Y chromosome could contribute to the silencing. Phosphorylated histone γH2AX is known to be associated with transcriptional repression, and is associated with transcriptional repression of the X and Y chromosomes in the XY sex body during meiotic prophase. See, e.g., Alton et al. (2008) *Reproduction* 135:241-252.

In some cases, the initial feminizing medium-induced silencing of the Y chromosome in XY pluripotent or totipotent cells is not complete throughout all cells of a clone, so some embryos injected with cells from the clone will develop into normal males. These F0 males can be bred with their genetically identical sex-reversed female clonal siblings to produce homozygous genetically modified mice in the first (F1) generation, thereby eliminating the time and cost of the additional generation (F2) of breeding that would normally be required to produce homozygous mice.

Feminizing media can promote the development of XY F0 fertile females. Thus, culturing in such a medium can increase the percentage of F0 XY progeny that are phenotypically female XY animals that are fertile upon attaining sexual maturity, the percentage of F0 XY females that are fertile, or the percentage of F0 XY females capable of producing normal numbers of litters, sizes of litters, and lifetime offspring (e.g., compared to wild type female animals) when compared to XY pluripotent or totipotent cells cultured in an appropriate control medium (such as, for example, one based on DMEM) or when compared to XY pluripotent or totipotent cell clones that lack the capability or have reduced capability to produce XY female mice notwithstanding their being cultured in feminizing medium.

The XY pluripotent or totipotent cells can further comprise at least one additional targeted genetic modification to a target genomic locus. In methods comprising modifying at least one additional target genomic locus, the XY pluripotent or totipotent cells can be cultured in the feminizing medium for the entire targeting process—e.g., electroporation, selection of drug resistant colonies, screening for targeted mutations, expansion, and cryopreservation—or for only one or more parts of the entire targeting process. Likewise, the cells can be cultured in the feminizing medium before and/or during and/or after the targeting process.

A "base medium" or "base media" includes, for example, a base medium known in the art (e.g., DMEM) that is suitable for use (with added supplements) in growing or maintaining the pluripotent or totipotent cells (e.g., ES cells, iPS cells, XY ES cells, XY iPS cells, etc.) in culture. A base medium that promotes making a fertile XY female (i.e., "feminizing medium" (e.g., "low-salt medium" or "low-osmolality medium")) differs from base media typically used to maintain ES cells in culture. For purposes of discussing base media in general, a base medium that does not promote making fertile XY females is described in this section and in Table 1 as "DMEM" (e.g., typical DMEM media). For purposes of discussing a base medium that promotes making fertile XY females, the phrase "feminizing medium" (e.g., "low-salt medium," "low-salt DMEM," "low-osmolality medium," or "low-osmolality DMEM") is used. Differences between base media typically used to maintain pluripotent or totipotent cells in culture (e.g., DMEM) and base media that promote making fertile XY females (e.g., "feminizing medium" such as a "low-salt DMEM") are articulated herein. The phrase "low-salt medium" is used for convenience; suitable DMEM for making fertile XY females exhibits characteristics not limited to "low-salt," but includes those described herein. For example, the DMEM shown in Table 1 can be made suitable for making fertile XY females by altering the sodium chloride and/or sodium bicarbonate concentrations as provided for herein, which will also result in a different osmolality and a different conductivity as compared with the DMEM shown in Table 1. An example of base medium is Dulbecco's Modified Eagle's Medium (DMEM) in various forms (e.g., Invitrogen DMEM, Cat. No. 1 1971-025; Table 1). A suitable low-salt DMEM is available commercially as KO-DMEM™ (Invitrogen Cat. No. 10829-018). Base medium is typically supplemented with a number of supplements known in the art when used to maintain cells in culture for use as donor cells. Such supplements are indicated as "supplements" or "+ supplements" in this disclosure.

TABLE 1

DMEM Base Media for Maintaining or Culturing Pluripotent and Totipotent Cells.

| Component | Mg/L | mM |
|---|---|---|
| Glycine | 30 | 0.4 |
| L-Arginine•HCl | 84 | 0.398 |
| L-Cystine•2HCl | 63 | 0.201 |
| L-Glutamine | 584 | 4 |
| L-Histidine•HCl•H2O | 42 | 0.2 |
| L-Isoleucine | 105 | 0.802 |
| L-Leucine | 105 | 0.802 |
| L-Lysine•HCl | 146 | 0.798 |
| L-Methionine | 30 | 0.201 |
| L-Phenylalanine | 66 | 0.4 |
| L-Serine | 42 | 0.4 |
| L-Threonine | 95 | 0.798 |
| L-Tryptophan | 16 | 0.0784 |
| L-Tyrosine disodium salt dihydrate | 104 | 0.398 |
| L-Valine | 94 | 0.803 |
| Choline chloride | 4 | 0.0286 |
| D-Calcium pantothenate | 4 | $8.39 \times 10^{-3}$ |
| Folic Acid | 4 | $9.07 \times 10^{-3}$ |
| Niacinamide | 4 | 0.0328 |
| Pyridoxine•HCl | 4 | 0.0196 |
| Riboflavin | 0.4 | $1.06 \times 10^{-3}$ |
| Thiamine•HCl | 4 | 0.0119 |
| i-Inositol | 7.2 | 0.04 |
| Calcium Chloride (CaCl$_2$) (anhydrous) | 200 | 1.8 |
| Ferric Nitrate (Fe(NO$_3$)$_3$•9H$_2$O) | 0.1 | $2.48 \times 10^{-4}$ |
| Magnesium Sulfate (MgSO$_4$) (anhyd.) | 97.67 | 0.814 |
| Potassium Chloride (KCl) | 400 | 5.33 |
| D-Glucose (Dextrose) | 4500 | 25 |
| Phenol Red | 15 | 0.0399 |
| NaCl/NaHCO$_3$ Content of DMEM | | |
| Sodium Bicarbonate (NaHCO$_3$) | 3700 | 44.05 |
| Sodium Chloride (NaCl) | 6400 | 110.34 |
| NaCl/NaHCO$_3$ Content of Low-Salt DMEM | | |
| Sodium Bicarbonate (NaHCO$_3$) | <3700 | <44.05 |
| Sodium Chloride (NaCl) | <6400 | <110.34 |

"Supplements" or the phrase "+ supplements" include elements added to base medium for growing or maintaining pluripotent or totipotent cells (e.g., XY ES cell or XY iPS cells) in culture (e.g., for maintaining pluripotency or totipotency of donor cells in culture). For example, media supplements suitable for growing or maintaining pluripotent or totipotent cells in culture include, but are not limited to, fetal bovine serum (FBS), glutamine, antibiotic(s), penicillin and streptomycin (e.g., penstrep), pyruvate salts (e.g., sodium pyruvate), nonessential amino acids (e.g., MEM NEAA), 2-mercaptoethanol, and Leukemia Inhibitory Factor (LIF).

In some methods, the base medium comprises one or more supplements suitable for maintaining pluripotent or totipotent cells in culture, including for example, XY ES cells or XY iPS cells having a reduced capacity to contribute to the male sex determination developmental program after injection into an embryo and intrauterine transfer to a surrogate mother mouse. For some cell lines, the medium is Wnt-conditioned media, e.g., Wnt-3a conditioned media For example, the base medium can comprise one or more of the following supplements: FBS (90 ml FBS/0.5 L base medium), glutamine (2.4 mmoles/0.5 L base medium), sodium pyruvate (0.6 mmoles/0.5 L base medium), nonessential amino acids (<0.1 mmol/0.5 L base medium), 2-mercaptoethanol, LIF, and one or more antibiotics. One example of a medium for maintaining pluripotent or totipotent cells in culture, including for example, XY ES cells or XY iPS cells having a reduced capacity to contribute to the male sex determination developmental program after injection into an embryo and intrauterine transfer to a surrogate mother mouse, comprises about 500 ml of base medium in which the following supplements are added: about 90 ml FBS (e.g., Hyclone FBS Cat. No. SH30070.03), about 2.4 millimoles of glutamine (e.g., about 12 ml of a 200 mM glutamine solution, e.g., Invitrogen Cat. No. 25030-081, penicillin: streptomycin (e.g., 60,000 units of Penicillin G sodium and 60 mg of streptomycin sulfate, with about 51 mg of NaCl; e.g., about 6 ml. of Invitrogen pennstrep, Cat. No. 15140-122), about 0.6 millimoles of sodium pyruvate (e.g., 6 ml. of 100 mM sodium pyruvate, Invitrogen Cat. No. 1 1360-070), about 0.06 millimoles of nonessential amino acids (e.g., about 6 ml. of MEM NEAA, e.g., MEM NEAA from Invitrogen Cat. No. 1 1 140-050), about 1.2 ml. 2-mercaptoethanol, and about 1.2 micrograms of LIF (e.g., about 120 microliters of a 106 units/mL LIF preparation; e.g., about 120 microliters of Millipore ESGRO™-LIF, Cat. No. ESG1 107). When composing base media for maintaining XY pluripotent or totipotent cells (e.g., XY ES or XY iPS cells) for making fertile XY females, typically the same supplements in about the same amounts are employed, but the composition of the base medium will differ (from DMEM, e.g., from the medium described in Table 1) and the difference(s) correspond to the difference(s) taught herein.

Other characteristics of the feminizing medium that can be altered include osmolality, conductivity, salt concentration, concentration of salt of an alkaline metal and a halide, concentration of carbonic acid salt, total alkaline metal halide salt and carbonic acid salt concentration, and molar ratio of a salt of an alkaline metal and halide and a salt of carbonic acid. For example, the base medium can be a low-salt medium (e.g., low-salt DMEM having an NaCl concentration of 85-130 mM (about 5.0 to 7.6 mg/mL)), a low-osmolality medium (e.g., low-osmolality DMEM having an osmolality of 250-310 mOsm/kg or 218-322 mOsm/kg), or a low-conductivity medium (e.g., low-conductivity DMEM having a conductivity of 11-13 mS/cm).

The osmolality of the base medium or a medium comprising the base medium and supplements can be, for example, no more than about 320, 310, 300, 290, 280, 275, 270, 260, 250, 240, 230, 220, 210, or 200 mOsm/kg. Alternatively, the osmolality of the base medium or a medium comprising the base medium and supplements can be, for example, no more than about 340 mOsm/kg or 330 mOsm/kg. Optionally, the base medium has an osmolality of no more than about 340, 330, 320, 310, 300, 290, 280, 275, 270, 260, 250, 240, 230, 220, 210, or 200 mOsm/kg, wherein the osmolality does not change by more than 1%, 2%, 3%, 4%, 5%, 10%, 15%, 20%, or 25% upon addition of supplements suitable for maintaining the pluripotency or totipotency of non-human animal XY pluripotent or totipotent cells to the base medium. For example, the base medium or the medium comprising the base medium and supplements can comprise an osmolality of about 200-329, 218-322, 240-320, 250-310, 275-295, or 260-300 mOsm/kg. Optionally, the base medium has an osmolality of about 200-329, 218-322, 240-320, 250-310, 275-295, or 260-300 mOsm/kg, wherein the osmolality does not change by more than 1%, 2%, 3%, 4%, 5%, 10%, 15%, 20%, or 25% upon addition of supplements suitable for maintaining the pluripotency or totipotency of non-human animal XY pluripotent or totipotent cells to the base medium. Alternatively, the base medium or the medium comprising the base medium and supplements can comprise an osmolality of about 214, about 216, about 200-322, about 200-340, about 200-292, about 214-322, about 216-322, about 218-322, about 214-332, about 216-332, or about 218-332 mOsm/kg. Optionally, the base medium has an osmolality of about 214, about 216, about 200-322, about 200-340, about 200-292, about 214-322, about 216-322, about 218-322, about 214-332, about 216-332, or about 218-332 mOsm/kg, wherein the osmolality does not change by more than 1%, 2%, 3%, 4%, 5%, 10%, 15%, 20%, or 25% upon addition of supplements suitable for maintaining the pluripotency or totipotency of non-human animal XY pluripotent or totipotent cells to the base medium. For example, the base medium or the medium comprising the base medium and the supplements can comprise an osmolality of about 270 mOsm/kg or 218 mOsm/kg. Alternatively, the osmolality can be 218±22 mOsm/kg, 261±26 mOsm/kg, 294±29 mOsm/kg, or 322±32 mOsm/kg. Alternatively, the osmolality can be about 216 or 214 mOsm/kg or 216±22 mOsm/kg or 214±22 mOsm/kg. Optionally, the base medium has an osmolality of about 270 mOsm/kg, about 218 mOsm/kg, 216 mOsm/kg, 214 mOsm/kg, 218±22 mOsm/kg, 261±26 mOsm/kg, 294±29 mOsm/kg, 322±32 mOsm/kg, 216±22 mOsm/kg, or 214±22 mOsm/kg wherein the osmolality does not change by more than 1%, 2%, 3%, 4%, 5%, 10%, 15%, 20%, or 25% upon addition of supplements suitable for maintaining the pluripotency or totipotency of non-human animal XY pluripotent or totipotent cells to the base medium.

The conductivity of the base medium or a medium comprising the base medium and supplements can be, for example, no more than about 10.0, 10.5, 11.0, 11.5, 12.0, 12.5, 13.0, 13.5, or 14.0 mS/cm. For example, the base medium or a medium comprising the base medium and supplements can exhibit a conductivity of no more than about 10-14 mS/cm, about 11-13 mS/cm, or about 12-13 mS/cm.

The pH of the base medium or a medium comprising the base medium and supplements can be, for example, from about 6.9 to about 7.5, about 6.98 to about 7.41, about 7.0 to about 7.4, about 7.05 to about 7.35, about 7.1 to about 7.3, about 7.15 to about 7.25, about 7.18 to about 7.22, about 7.19 to about 7.23, or about 7.2 to about 7.22, or the pH can be about 7.21, about 7.17, about 7.38, about 6.99, about 6.98, about 7.40, about 7.41, about 7.34, or about 7.37.

Some media exhibit a concentration of a salt of an alkaline metal and a halide, such as NaCl. The concentration of a salt of an alkaline metal and a halide in the base medium or a medium comprising the base medium and supplements can be, for example, no more than about 100, 90, 80, 70, 60, or 50 mM. For example, for NaCl, the concentration in the base medium or a medium comprising the medium and supplements can be, for example, no more than about 5.8, 5.3, 4.7, 4.1, 3.5, or 2.9 mg/mL. For example, the base medium or a medium comprising the base medium and supplements can comprise a concentration of a salt of an alkaline metal and halide of about 50-110, 60-105, 70-95, 80-90, 90, or 85 mM. For example, for NaCl, the concentration in the base medium or a medium comprising the medium and supplements can be, for example, about 2.9-6.4, 3.5-6.1, 4.1-5.6, 4.7-5.3, 5.3, or 5.0 mg/mL. Alternatively, the concentration of a salt of an alkaline metal and halide can be 50±5 mM, 87±5 mM, 110±5 mM, about 3 mg/mL, about 5.1 mg/mL, or about 6.4 mg/mL.

Some media exhibit a concentration of a salt of carbonic acid (carbonate), such as a sodium salt (e.g., sodium bicarbonate). The concentration of a salt of carbonic acid in the base medium or a medium comprising the base medium and supplements can be, for example, no more than 45, 40, 35, 30, 25, or 20 mM. For example, for sodium bicarbonate, the concentration in the base medium or a medium comprising the base medium and supplements can be, for example, no more than 3.8, 3.4, 2.9, 2.5, 2.1, or 1.7 mg/mL. For example, the base medium or a medium comprising the base medium and supplements can comprise a concentration of carbonic acid salt in the base medium of about 10-40, 18-44, 17-30, 18-26, 13-25, 20-30, 25-26, 18, or 26 mM. For example, for sodium bicarbonate, the concentration in the base medium or a medium comprising the base medium and supplements can be, for example, about 0.8-3.4, 1.5-3.7, 1.4-2.5, 1.5-2.2, 1.1-2.1, 1.7-2.5, 2.1-2.2, 1.5, or 2.2 mg/mL. Alternatively, the concentration of carbonic acid salt can be 18±5 mM, 26±5 mM, about 1.5 mg/mL, or about 2.2 mg/mL.

The sum of the concentration of the salt of the alkaline metal and halide and the salt of carbonic acid in the base medium or a medium comprising the base medium and supplements can be, for example, no more than 140, 130, 120, 110, 100, 90, or 80 mM. For example, the base medium or a medium comprising the base medium and supplements can comprise a sum concentration of a salt of an alkaline metal and halide and a salt of carbonic acid of about 80-140, 85-130, 90-120, 95-120, 100-120, or 115 mM.

The molar ratio of the salt of the alkaline metal and halide and the salt of carbonic acid in the base medium or a medium comprising the base medium and supplements can be, for example, higher than 2.5. For example, the base medium or a medium comprising the base medium and supplements can comprise a molar ratio of a salt of an alkaline metal and halide and a salt of carbonic acid of about 2.6-4.0, 2.8-3.8, 3.0-3.6, 3.2-3.4, 3.3-3.5, or 3.4.

One example of a feminizing medium (e.g., low-osmolality medium) is a medium comprising a base medium comprising one or more of the following characteristics: (a) an osmolality from about 200 mOsm/kg to less than about 329 mOsm/kg; (b) a conductivity of about 11 mS/cm to about 13 mS/cm; (c) a salt of an alkaline metal and a halide in a concentration of about 50 mM to about 110 mM; (d) a carbonic acid salt concentration of about 17 mM to about 30 mM; and (e) a total alkaline metal halide salt and carbonic acid salt concentration of about 85 mM to about 130 mM. Alternatively, the medium comprising the base medium and supplements can have the osmolality from about 200 mOsm/kg to less than about 329 mOsm/kg or the conductivity of about 11 mS/cm to about 13 mS/cm.

Another example of a feminizing medium (e.g., low-osmolality medium) is a medium comprising a base medium comprising one or more of the following characteristics: (a) a salt of an alkaline metal and a halide in a concentration of about 50 mM to about 110 mM; (b) a carbonic acid salt in a concentration of about 17 mM to about 30 mM; and (c) an osmolality of about 200 mOsm/kg to about 329 mOsm/kg. For example, the base medium can comprise NaCl in a concentration of about 2.9-6.4 mg/mL and/or can comprise sodium bicarbonate in a concentration of about 1.4-2.5 mg/mL. Alternatively, the medium comprising the base medium and supplements can have the osmolality of about 200 mOsm/kg to about 329 mOsm/kg.

Another example of a feminizing medium (e.g., low-osmolality medium) is a medium comprising a base medium comprising one or more of the following characteristics: (a) a salt of an alkaline metal and a halide (e.g., NaCl) in a concentration of about 50 mM to about 110 mM; (b) a carbonic acid salt (e.g., NaHCO$_3$) in a concentration of about 18 mM to about 44 mM or about 18 mM to about 26 mM; and (c) an osmolality of about 218 mOsm/kg to about 322 mOsm/kg. For example, the base medium can comprise NaCl in a concentration of about 2.9-6.4 mg/mL and/or can comprise sodium bicarbonate in a concentration of about 1.5-3.7 mg/mL or 1.5-2.2 mg/mL. Alternatively, the medium comprising the base medium and supplements can have the osmolality of about 218 mOsm/kg to about 322 mOsm/kg.

Another example of a feminizing medium (e.g., low-osmolality medium) is a medium comprising a base medium comprising one or more of the following characteristics: (a) an osmolality of about 250-310 mOsm/kg; (b) a conductivity of about 11-13 mS/cm; (c) an alkaline metal and halide salt in a concentration of about 60-105 mM; (d) a carbonic acid salt concentration of about 20-30 mM; and (e) a total alkaline metal halide salt and carbonic acid salt concentration of no more than about 85-130 mM. Alternatively, the medium comprising the base medium and supplements can have the osmolality of about 250-310 mOsm/kg.

Another example of a feminizing medium (e.g., low-osmolality medium) is a medium comprising a base medium comprising a conductivity of about 12-13 mS/cm and an osmolality of about 260-300 mOsm/kg. Alternatively, a medium comprising the base medium and supplements can have the conductivity of about 12-13 mS/cm and the osmolality of about 260-300 mOsm/kg. Optionally, the base medium further comprises sodium chloride at a concentration of about 70-95 mM (i.e., about 4.1-5.6 mg/mL) or about 90 mM NaCl (i.e., about 5.3 mg/mL). Optionally, the base medium further comprises sodium bicarbonate at a concentration of less than about 35 mM (i.e., about 2.9 mg/mL) or about 20-30 mM (i.e., about 1.7-2.5 mg/mL).

Another example of a feminizing medium (e.g., low-osmolality medium) is a medium comprising a base medium comprising an osmolality of about 250-310 mOsm/kg and a concentration of a salt of an alkaline metal and a halide of about 60-105 mM. Alternatively, a medium comprising the base medium and supplements can have the osmolality of about 250-310 mOsm/kg. For example, the base medium can comprise about 3.5-6.1 mg/mL NaCl with an osmolality of about 250-310 mOsm/kg, or the base medium can comprise about 3.5-6.1 mg/mL NaCl, and the medium comprising the base medium and supplements has an osmolality of about 250-310 mOsm/kg. Optionally, the base medium comprises a concentration of a salt of carbonic acid of about 20-30 mM. For example, the base medium can comprise about 1.7-2.5 mg/mL sodium bicarbonate. Optionally, the sum of the concentrations of the salt of an alkaline metal and halide and the salt of carbonic acid is about 80-140 mM. Optionally, the conductivity of the base medium is about 12-13 mS/cm. Alternatively, the conductivity of the medium comprising the base medium and supplements is about 12-13 mS/cm.

Another example of a feminizing medium (e.g., low-osmolality medium) is a medium comprising a base medium comprising about 50±5 mM NaCl and about 26±5 mM carbonate (e.g., sodium bicarbonate), with an osmolality of about 218±22 mOsm/kg. Alternatively, a medium comprising the base medium and supplements can have the osmolality of about 218±22 mOsm/kg. For example, the medium can comprise a base medium comprising about 2.6-3.2 mg/mL NaCl and about 1.8-2.6 mg/mL sodium bicarbonate, and the base medium or the medium comprising the base medium and supplements can have an osmolality of about 218±22 mOsm/kg. For example, the base medium can comprise about 3 mg/mL NaCl and about 2.2 mg/mL sodium bicarbonate, with an osmolality of about 218 mOsm/kg. Alternatively, the medium comprising the base medium and supplements can have the osmolality of about 218 mOsm/kg.

Another example of a feminizing medium (e.g., low-osmolality medium) is a medium comprising a base medium comprising about 87±5 mM NaCl and about 18±5 mM carbonate (e.g., sodium bicarbonate), with an osmolality of about 261±26 mOsm/kg. Alternatively, a medium comprising the base medium and supplements can have the osmolality of about 261±26 mOsm/kg. For example, the base medium can comprise about 4.8-5.4 mg/mL NaCl and about 1.1-1.9 mg/mL sodium bicarbonate, and the base medium or the medium comprising the base medium and supplements can have an osmolality of about 261±26 mOsm/kg. For example, the base medium can comprise about 5.1 mg/mL NaCl and about 1.5 mg/mL sodium bicarbonate, with an osmolality of about 261 mOsm/kg. Alternatively, the medium comprising the base medium and supplements can have the osmolality of about 261 mOsm/kg. Optionally, the base medium can further comprise 4.5 mg/mL glucose.

Another example of a feminizing medium (e.g., low-osmolality medium) is a medium comprising a base medium comprising about 110±5 mM NaCl and about 18±5 mM carbonate (e.g., sodium bicarbonate), with an osmolality of about 294±29 mOsm/kg. Alternatively, a medium comprising the base medium and supplements can have the osmolality of about 294±29 mOsm/kg. For example, the base medium can comprise about 6.1-6.7 mg/mL NaCl and about 1.1-1.9 mg/mL sodium bicarbonate, and the base medium or the medium comprising the base medium and supplements can have an osmolality of about 294±29 mOsm/kg. For example, the base medium can comprise about 6.4 mg/mL NaCl and about 1.5 mg/mL sodium bicarbonate, with an osmolality of about 294 mOsm/kg. Alternatively, the medium comprising the base medium and supplements can have the osmolality of about 294 mOsm/kg. Optionally, the base medium can further comprise 4.5 mg/mL glucose.

Another example of a feminizing medium (e.g., low-osmolality medium) is a medium comprising a base medium comprising about 87±5 mM NaCl and about 26±5 mM carbonate (e.g., sodium bicarbonate), with an osmolality of about 270±27 mOsm/kg. Alternatively, a medium comprising the base medium and supplements can have the osmolality of about 270±27 mOsm/kg. For example, the medium can comprise a base medium comprising about 4.8-5.4 mg/mL NaCl and about 1.8-2.6 mg/mL sodium bicarbonate, and the base medium or the medium comprising the base medium and supplements can have an osmolality of about 270±27 mOsm/kg. For example, the base medium can comprise about 5.1 mg/mL NaCl and about 2.2 mg/mL sodium bicarbonate, with an osmolality of about 270 mOsm/kg. Alternatively, the medium comprising the base medium and supplements can have the osmolality of about 270 mOsm/kg. As another example, the base medium can comprise about 5.1 mg/mL NaCl and about 2.2 mg/mL sodium bicarbonate, and the base medium or the medium comprising the base medium and supplements can have an osmolality of about 275 mOsm/kg. As another example, the base medium can comprise about 5.1 mg/mL NaCl and about 2.2 mg/mL sodium bicarbonate, and the base medium or the medium comprising the base medium and supplements can have an osmolality of about 268 mOsm/kg. As another example, the base medium can comprise about 5.1 mg/mL NaCl and about 2.2 mg/mL sodium bicarbonate, and the base medium or the medium comprising the base medium and supplements can have an osmolality of about 280 mOsm/kg. Optionally, the base medium can further comprise 4.5 mg/mL glucose.

Another example of a feminizing medium (e.g., low-osmolality medium) is a medium comprising a base medium comprising about 87±5 mM NaCl, about 26±5 mM carbonate (e.g., sodium bicarbonate), and about 86±5 mM glucose, with an osmolality of about 322±32 mOsm/kg. Alternatively, a medium comprising the base medium and supplements can have the osmolality of about 322±32 mOsm/kg. For example, the medium can comprise a base medium comprising about 4.8-5.4 mg/mL NaCl and about 1.8-2.6 mg/mL sodium bicarbonate, and the base medium or the medium comprising the base medium and supplements can have an osmolality of about 322±32 mOsm/kg. For example, the base medium can comprise about 5.1 mg/mL NaCl, about 2.2 mg/mL sodium bicarbonate, and about 15.5 mg/mL glucose, with an osmolality of about 322 mOsm/kg. Alternatively, the medium comprising the base medium and supplements can have the osmolality of about 322 mOsm/kg.

Another example of a feminizing medium (e.g., low-osmolality medium) is a medium comprising a base medium comprising 50±5 mM NaCl and 26±5 mM carbonate, with an osmolality of 218±22 mOsm/kg. Alternatively, a medium comprising the base medium and supplements can have the osmolality of about 218±22 mOsm/kg. For example, the medium can comprise a base medium comprising about 2.6-3.2 mg/mL NaCl and about 1.8-2.6 mg/mL sodium bicarbonate, and the base medium or the medium comprising the base medium and supplements can have an osmolality of 218±22 mOsm/kg. For example, the base medium can comprise about 3 mg/mL NaCl and about 2.2 mg/mL sodium bicarbonate, with an osmolality of about 218 mOsm/kg. Alternatively, the medium comprising the base medium and supplements can have the osmolality of about 218 mOsm/kg. Alternatively, the base medium can comprise about 3 mg/mL NaCl and about 2.2 mg/mL sodium bicarbonate, and the base medium or the medium comprising the base medium and supplements can have an osmolality of about 216 mOsm/kg. Alternatively, the base medium can comprise about 3 mg/mL NaCl and about 2.2 mg/mL sodium bicarbonate, and the base medium or the medium comprising the base medium and supplements can have an osmolality of about 214 mOsm/kg. Optionally, the base medium can further comprise 4.5 mg/mL glucose.

Another example of a feminizing medium (e.g., low-osmolality medium) is a medium comprising a base medium comprising about 50±5 mM NaCl and about 44±5 mM carbonate (e.g., sodium bicarbonate), and the base medium or the medium comprising the base medium and supplements can have an osmolality of about 238±24 mOsm/kg. For example, the medium can comprise a base medium comprising about 2.6-3.2 mg/mL NaCl and about 3.3-4.1 mg/mL sodium bicarbonate, and the base medium or the medium comprising the base medium and supplements can have an osmolality of about 238±24 mOsm/kg. For example, the base medium can comprise about 3 mg/mL NaCl and about 3.7 mg/mL sodium bicarbonate, and the base medium or the medium comprising the base medium and supplements can have an osmolality of about 238 mOsm/kg. Optionally, the base medium can further comprise 4.5 mg/mL glucose.

Another example of a feminizing medium (e.g., low-osmolality medium) is a medium comprising a base medium comprising about 87±5 mM NaCl and about 44±5 mM carbonate (e.g., sodium bicarbonate), and the base medium or the medium comprising the base medium and supplements can have an osmolality of about 288±29 mOsm/kg. For example, the medium can comprise a base medium comprising about 4.8-5.4 mg/mL NaCl and about 3.3-4.1 mg/mL sodium bicarbonate, and the base medium or the medium comprising the base medium and supplements can have an osmolality of about 288±29 mOsm/kg. For example, the base medium can comprise about 5.1 mg/mL NaCl and about 3.7 mg/mL sodium bicarbonate, and the base medium or the medium comprising the base medium and supplements can have an osmolality of about 288 mOsm/kg. Optionally, the base medium can further comprise 4.5 mg/mL glucose.

Another example of a feminizing medium (e.g., low-osmolality medium) is a medium comprising a base medium comprising about 3 mg/mL NaCl and about 1.5 mg/mL sodium bicarbonate, and the base medium or the medium comprising the base medium and supplements can have an osmolality of about 203 mOsm/kg.

Another example of a feminizing medium (e.g., low-osmolality medium) is a medium comprising a base medium comprising about 44 mM sodium bicarbonate (i.e., about 3.7 mg/mL), and the base medium or the medium comprising the base medium and supplements can have an osmolality of about 290 mOsm/kg. Another example of a feminizing medium (e.g., low-osmolality medium) is a medium comprising a base medium comprising about 26 mM (i.e., about 2.2 mg/mL) sodium bicarbonate, and the base medium or the medium comprising the base medium and supplements can have an osmolality of about 264 mOsm/kg. Another example of a feminizing medium (e.g., low-osmolality medium) is a medium comprising a base medium comprising about 18 mM (i.e., about 1.5 mg/mL) sodium bicarbonate, and the base medium or the medium comprising the base medium and supplements can have an osmolality of about 292 mOsm/kg. Another example of a feminizing medium (e.g., low-osmolality medium) is a medium comprising a base medium comprising about 18 mM (i.e., about 1.5 mg/mL) sodium bicarbonate, and the base medium or the medium comprising the base medium and supplements can have an osmolality of about 251 mOsm/kg.

Other media that can be used include high glucose DMEM medium (LifeTech) with NaHCO$_3$ concentrations as disclosed herein (e.g., about 44 mM, 26 mM or 18 mM) and supplemented with 0.1 mM nonessential amino acids, 1 mM sodium pyruvate, 0.1 mM 2-mercaptoethanol, 2 mM L-glutamine, 50 ug/ml each penicillin and streptomycin (LifeTech), 15% FBS (Hyclone), and 2000 U/ml LIF (Millipore).

Other examples of feminizing media (e.g., low-osmolality media) are described in WO 2011/156723, US 2011/0307968, and US 2015/0067901, each of which is herein incorporated by reference in its entirety for all purposes. Yet other examples of feminizing media are described in Kuno et al. (2015) *Transgenic Res.* 24(1):19-29, herein incorporated by reference in its entirety for all purposes.

2. Selecting XY Pluripotent or Totipotent Cells or Clones with Enhanced Capacity for Producing Fertile XY Female Animals Methods and compositions are provided for determining the propensity of an animal XY pluripotent or totipotent cell or clone for producing fertile, phenotypically female XY animals in an F0 generation. The propensity of animal XY pluripotent or totipotent cell clones to produce fertile, phenotypically female XY animals in an F0 generation is inversely correlated with the expression or activity of Ddx3y, Uty, and Eif2s3y in those clones. Loss of expression of one or more of these genes in animal XY pluripotent or totipotent cells (e.g., XY ES cells) can predict which cell clones will produce XY female animals in an F0 generation: the more silencing of Ddx3y, Uty, and Eif2s3y that is observed, the higher the propensity of the XY ES cell clone to produce fertile, phenotypically female XY animals in an F0 generation (see, e.g., Example 3). Likewise, loss of activity or decreased expression and/or activity of one or more of these genes in animal XY pluripotent or totipotent cells (e.g., XY ES cells) can predict which cell clones will produce XY female animals in an F0 generation: the lower the expression of Ddx3y, Uty, and Eif2s3y that is observed, the higher the propensity of the XY ES cell clone to produce fertile, phenotypically female XY animals in an F0 generation (see, e.g., Example 3). In other words, expression and/or activity of one or more of these genes can be a surrogate marker for predicting XY female production.

This information can be used to select animal XY pluripotent or totipotent cells having a high propensity for producing fertile, phenotypically female XY animals in an F0 generation. For example, when a population of one or more animal XY pluripotent or totipotent cells (e.g., ES cells) is maintained in a feminizing medium (e.g., low-osmolality medium), such a method can comprise assaying one or more animal XY pluripotent or totipotent cells for expression and/or activity of one or more of Ddx3y, Uty, and Eif2s3y, and selecting a donor animal XY pluripotent or totipotent cell having decreased expression and/or activity of one or more of Ddx3y, Uty, and Eif2s3y, wherein the donor animal XY pluripotent or totipotent cell is capable of producing a fertile, phenotypically female XY animal in an F0 generation. For example, such a donor animal XY pluripotent or totipotent cell can have decreased expression and/or activity of Ddx3y, of Uty, of Eif2s3y, of Ddx3y and Uty, of Ddx3y and Eif2s3y, of Uty and Eif2s3y, or of Ddx3y, Uty, and Eif2s3y.

The donor animal XY pluripotent or totipotent cell can then be introduced into a host embryo, wherein the host embryo is capable of producing a fertile phenotypically female XY animal in an F0 generation. For example, the host embryo can be a pre-morula stage embryo, and the host embryo can be cultured to the blastocyst stage upon introduction of the donor animal XY pluripotent or totipotent cell. Animals, embryos, methods for introducing donor XY pluripotent or totipotent cells into embryos, and methods of producing F0 animals are disclosed elsewhere herein.

Feminizing medium (e.g., a base medium and supplements suitable for maintaining animal XY pluripotent or totipotent cells in culture, wherein base medium comprises an osmolality from about 200 mOsm/kg to less than about 329 mOsm/kg) and methods for maintaining cells in such medium are disclosed elsewhere herein.

The animal XY pluripotent or totipotent cell can be maintained in the medium for various amounts of time prior to the assaying step and/or prior introduction into a host embryo. For example, the animal XY pluripotent or totipotent cell can be maintained in the feminizing medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to the assaying step and/or introduction into the host embryo. Alternatively, the animal XY pluripotent or totipotent cell can be maintained in the feminizing medium for no more than 1 day, 2 days, 3 days, 4 days, 5 days, 6 days, 7 days, 8 days, 9 days, 10 days, 11 days, 12 days, 13 days, 2 weeks, 3 weeks, or 4 weeks prior to the assaying step and/or introduction into the host embryo. In some methods, the XY pluripotent or totipotent cell is cultured or maintained in the feminizing medium until injection of the cell into an embryo. In other methods, the embryo into which the XY pluripotent or totipotent cell was injected is cultured or maintained in the feminizing medium until being transferred to a surrogate mother.

The assaying step can comprise assaying the clone itself and determining a level of expression or activity for one or more of Ddx3y, Uty, and Eif2s3y. Alternatively, the assaying step can comprise assaying several subclones derived from the clone and determining, for example, the percentage of subclones having reduced expression and/or activity or lacking expression and/or activity of one or more of Ddx3y, Uty, and Eif2s3y. Alternatively, the assaying step can comprise assaying several subclones derived from the clone and determining the comparative expression and/or activity of one or more of Ddx3y, Uty, and Eif2s3y among the subclones. Expression and/or activity of one or more of Ddx3y, Uty, and Eif2s3y can be decreased, or the expression and/or activity of all of Ddx3y, Uty, and Eif2s3y can be decreased. Alternatively, the donor animal XY pluripotent or totipotent cell lacks expression and/or activity of one or more of Ddx3y, Uty, and Eif2s3y or lacks expression and/or activity of all of Ddx3y, Uty, and Eif2s3y. For example, there can be a lack of detectable expression of all of Ddx3y, Uty, and Eif2s3y.

Expression can be assessed at the protein level or the mRNA level. The expression level of a polypeptide may be measured directly, for example, by assaying for the level of the polypeptide in the cell or organism (e.g., Western blot analysis, FACS analysis, ELISA), or indirectly, for example, by measuring the activity of the polypeptide. In other instances, reduced expression and/or activity of a gene can be measured using methods that include, for example, Southern blot analysis, DNA sequencing, PCR analysis, Northern blot analysis, quantitative RT-PCR analysis, Next Generation Sequencing (NGS), microarray analysis, or phenotypic analysis. For example, expression of a gene can be assessed by measuring mRNA levels by RT-PCR, RNA-seq, digital PCR, or any other suitable method for measure mRNA levels. As one example, RNA levels can be measured by RT-PCR relative to a control gene, such as B2m. In some cases, for example, the ΔCt between the control gene (e.g., B2m) and the target gene can be at least 2, at least 4, at least 6, or at least 8. Likewise, in some cases, there will be no detectable RNA for the target gene after 30, 31, 32, 33, 34, 35, 36, 37, 38, 39, or 40 cycles.

Optionally, when measuring expression levels of the mRNA or polypeptide, a control experiment can be done to confirm the presence of the Y chromosome. For example, a TAQMAN® copy number assay can be done to confirm the presence of one copy of the Y chromosome by using probes to different genomic sequences on the Y chromosome. Such assays are designed to measure copy number variation within the genome.

A decrease in expression or activity of a gene or the protein it encodes in a subject cell, embryo, or animal can include any statistically significant reduction in expression or activity levels when compared to an appropriate control cell, embryo, or animal or population of control cells, embryos, or animals. In general, the expression or activity is decreased if the expression or activity is statistically lower than the expression or activity in an appropriate control cell, embryo, or animal derived therefrom (e.g., an animal XY pluripotent cell) that has been cultured in an appropriate control medium that is not a feminizing medium, an animal XY pluripotent cell that historically produces entirely male mice, notwithstanding its being cultured in feminizing medium). Such a decrease includes a reduction of at least 1%, 5%, 10%, 20%, 30%, 40%, 50%, 60%, 70%, 80%, 90%, 95%, 99%, or greater relative to a control cell. Statistical significance means $p \leq 0.05$. A decrease in expression or activity can occur via any mechanism at any stage. For example, a decrease in expression could occur via events or regulation that occurs during transcription, post-transcription, during translation, or post-translation.

A "subject cell" is one that has been cultured in feminizing medium (e.g., low-osmolality medium) or is a cell which is descended from a cell cultured in feminizing medium. A "control" or "control cell" provides a reference point for measuring changes in phenotype of the subject cell. A control cell is preferably as closely matched as possible with the subject cell (for example, the respective cells can originate from the same cell line or the same clone or can have the same genotype) except it was either not cultured in feminizing medium or lacks the capability or has reduced capability to produce XY female mice notwithstanding its being cultured in feminizing medium. For example, the control cell may comprise: (a) a cell of the same genotype or that originates from the same cell line or clone as the subject cell but which has been cultured in an appropriate control medium that is not a feminizing medium (e.g., DMEM or another type of medium that is sufficient for maintaining pluripotency or totipotency of an animal XY pluripotent or totipotent cell but does not alter the cell by giving it the capacity to give rise to fertile female progeny); (b) an animal XY pluripotent or totipotent cell genetically identical to the subject cell or derived from the same cell line or clone but which is not genetically altered or exposed to conditions or stimuli that would give it the potential to generate fertile female XY animals; and (c) an animal XY pluripotent and totipotent cell that is cultured in feminizing medium (e.g., low-osmolality medium) but historically produces entirely male animals notwithstanding its being cultured in feminizing medium.

In some experiments, a population animal XY pluripotent or totipotent cells (e.g., ES cells) or clones is maintained in a feminizing medium (e.g., low-osmolality medium), and two or more of the cells or clones are assayed for expression and/or activity of one or more of Ddx3y, Uty, and Eif2s3y. The cell or clone with the lowest expression and/or activity of the one or more of Ddx3y, Uty, and Eif2s3y can then be selected to be a donor animal XY pluripotent or totipotent cell or clone, wherein the donor animal XY pluripotent or totipotent cell is capable of producing a fertile, phenotypically female XY animal in an F0 generation.

Selecting a donor animal XY pluripotent or totipotent cell having decreased expression and/or activity of one or more of Ddx3y, Uty, and Eif2s3y can result in higher percentages of F0 progeny that are phenotypically female XY animals, higher percentages of F0 progeny that are phenotypically female XY animals that are fertile, higher percentages of F0 XY progeny that are phenotypically female XY animals that are fertile, higher percentages of F0 XY females that are fertile, higher average numbers of lifetime litters for F0 XY females or fertile F0 XY females, and higher average litter sizes for F0 XY females or fertile F0 XY females. Such F0 progeny can be produced from the donor XY pluripotent or totipotent animal cells following introduction of the cells into a host embryo and gestation of the host embryo using the methods disclosed elsewhere herein.

The increase can be any statistically significant increase when compared to the appropriate control. For example, the increase can be at least 1.1-fold, 1.2-fold, 1.3-fold, 1.4-fold, 1.5-fold, 1.6-fold, 1.7-fold, 1.8-fold, 1.9-fold, 2-fold, 2.5- fold, 3-fold, 3.5-fold, 4-fold, 4.5-fold, or 5-fold when compared to the appropriate control.

For example, the percentage of F0 progeny or F0 XY progeny that are phenotypically female XY animals can be increased by selecting a donor animal XY pluripotent or totipotent cell having decreased expression and/or activity of one or more of Ddx3y, Uty, and Eif2s3y. In some methods, the percentage of the F0 progeny or F0 XY progeny that are phenotypically female XY animals is higher for F0 progeny derived from donor XY pluripotent or totipotent animal cells having decreased expression and/or activity of one or more of Ddx3y, Uty, and Eif2s3y when compared to F0 progeny derived from XY pluripotent or totipotent animal cells having higher expression and/or activity of one or more of Ddx3y, Uty, and Eif2s3y.

The percentage of F0 progeny or F0 XY progeny that are fertile, phenotypically female XY animals can also be increased by selecting a donor animal XY pluripotent or totipotent cell having decreased expression and/or activity of one or more of Ddx3y, Uty, and Eif2s3y. In some methods, the percentage of the F0 progeny or F0 XY progeny that are fertile, phenotypically female XY animals is higher for F0 progeny derived from donor XY pluripotent or totipotent animal cells having decreased expression and/or activity of one or more of Ddx3y, Uty, and Eif2s3y when compared to F0 progeny derived from XY pluripotent or totipotent animal cells having higher expression and/or activity of one or more of Ddx3y, Uty, and Eif2s3y.

The percentage of F0 XY females that are fertile can also be increased by selecting a donor animal XY pluripotent or totipotent cell having decreased expression and/or activity of one or more of Ddx3y, Uty, and Eif2s3y. In some methods, the percentage of the F0 XY females that are fertile is higher for F0 XY progeny derived from donor XY pluripotent or totipotent animal cells having decreased expression and/or activity of one or more of Ddx3y, Uty, and Eif2s3y when compared to F0 XY progeny derived from XY pluripotent or totipotent animal cells having higher expression and/or activity of one or more of Ddx3y, Uty, and Eif2s3y.

The percentage of F0 XY females that are capable of producing normal numbers of litters and/or normal litter sizes (e.g., compared to wild type female animals) can also be increased by selecting a donor animal XY pluripotent or totipotent cell having decreased expression and/or activity of one or more of Ddx3y, Uty, and Eif2s3y. In some methods, the percentage of the F0 XY females that are capable of producing normal numbers of litters and/or normal litter sizes is higher for F0 XY progeny derived from donor XY pluripotent or totipotent animal cells having decreased expression and/or activity of one or more of Ddx3y, Uty, and Eif2s3y when compared to F0 XY progeny derived from XY pluripotent or totipotent animal cells having higher expression and/or activity of one or more of Ddx3y, Uty, and Eif2s3y.

The average litter size produced by F0 XY females or fertile F0 XY females can also be increased by selecting a donor animal XY pluripotent or totipotent cell having decreased expression and/or activity of one or more of Ddx3y, Uty, and Eif2s3y. In some methods, the average litter size produced by F0 XY females or fertile F0 XY females is higher for F0 XY females or fertile F0 XY females derived from donor XY pluripotent or totipotent animal cells having decreased expression and/or activity of one or more of Ddx3y, Uty, and Eif2s3y when compared to F0 XY females or fertile F0 XY females derived from XY pluripotent or totipotent animal cells having higher expression and/or activity of one or more of Ddx3y, Uty, and Eif2s3y.

The average number of lifetime litters produced by F0 XY females or fertile F0 XY females can also be increased by selecting a donor animal XY pluripotent or totipotent cell having decreased expression and/or activity of one or more of Ddx3y, Uty, and Eif2s3y. In some methods, the average number of lifetime litters produced by F0 XY females or fertile F0 XY females is higher for F0 XY females or fertile F0 XY females derived from donor XY pluripotent or totipotent animal cells having decreased expression and/or activity of one or more of Ddx3y, Uty, and Eif2s3y when compared to F0 XY females or fertile F0 XY females derived from XY pluripotent or totipotent animal cells having higher expression and/or activity of one or more of Ddx3y, Uty, and Eif2s3y.

The average number of lifetime offspring produced by F0 XY females or fertile F0 XY females can also be increased by selecting a donor animal XY pluripotent or totipotent cell having decreased expression and/or activity of one or more of Ddx3y, Uty, and Eif2s3y. In some methods, the average number of lifetime offspring produced by F0 XY females or fertile F0 XY females is higher for F0 XY females or fertile F0 XY females derived from donor XY pluripotent or totipotent animal cells having decreased expression and/or activity of one or more of Ddx3y, Uty, and Eif2s3y when compared to F0 XY females or fertile F0 XY females derived from XY pluripotent or totipotent animal cells having higher expression and/or activity of one or more of Ddx3y, Uty, and Eif2s3y.

Also provided are kits for determining the propensity of an animal XY pluripotent or totipotent cell or clone for producing fertile, phenotypically female XY animals in an F0 generation. Such kits can comprise, for example, a detection reagent for one or more of Ddx3y, Uty, and Eif2s3y. The detection reagent can measure expression and/or activity levels of one or more of Ddx3y, Uty, and Eif2s3y. For example, the detection reagent can be used for detecting the level of mRNA or protein expression from one or more of Ddx3y, Uty, and Eif2s3y in an animal pluripotent or totipotent cell. Such a detection reagent can comprise one or more primer sets and/or one or more probes for detecting expression of one or more of Ddx3y, Uty, and Eif2s3y in an animal pluripotent or totipotent cell.

Such kits can also include a label. Kits typically contain labeling providing directions for use of the kit. Labeling generally refers to any written or recorded material that is attached to, or otherwise accompanies, a kit at any time during its manufacture, transport, sale, or use. For example, the term labeling includes advertising leaflets and brochures, packaging materials, instructions, audio or video cassettes, computer discs, as well as writing imprinted directly on kits.

Such kits can further comprise instructions for using the detection reagents and correlating detection with predicted propensity of an animal XY pluripotent or totipotent cell or clone for producing fertile, phenotypically female XY animals in an F0 generation.

iii. Modification that Decreases the Level and/or Activity of an Sry Protein

XY pluripotent or totipotent cells having the modification that silences a region of the Y chromosome can further comprise a genetic modification that results in a decreased level and/or activity of the Sry protein to convert some of the cells to XY pluripotent or totipotent cells with the potential to develop into fertile female animals, such that the cells can be implanted into a recipient embryo and give rise to a fertile female progeny. Likewise, XY pluripotent or totipotent cells cultured in feminizing media as disclosed elsewhere herein can comprise a genetic modification that results in a decreased level and/or activity of the Sry protein or can be such that they do not comprise a genetic modification that results in a decreased level and/or activity of the Sry protein. The "Sex Determining Region Y" protein or the "Sry" protein is a transcription factor that is a member of the high mobility group (HMG)-box family of DNA-binding proteins. Sry is the testis-determining factor that initiates male sex determination. The sequence of the Sry protein from a variety of organisms is known, including from mouse (Accession No. Q05738); rat (GenBank: CAA61882.1) human (Accession No. Q05066); cat (Accession No. Q67C50), and horse (Accession No. P36389), each of which is herein incorporated by reference in its entirety for all purposes.

Methods for making phenotypically female XY animals in an F0 generation through modifying XY pluripotent or totipotent cells to decrease the level and/or activity of an Sry protein are disclosed in WO 2015/200805 and US 2015/0376651, each of which is incorporated by reference in its entirety for all purposes. In some genetic backgrounds (e.g., using VGB6 mouse ES cell line, which has a Y chromosome from a C57BL/6 strain), modifying an ES cell to decrease the level and/or activity of Sry and using such cells to generate F0 mice results in phenotypically female F0 XY mice, but all of the mice are infertile or sterile. This infertility or very limited fertility has been reported by others as well. See, e.g., Kato et al. (2013) *Scientific Reports* 3:3136 and Vernet et al. (2014) *Development* 141:855-866. In other genetic backgrounds (e.g., using VGF1 mouse ES cell line, which has a Y chromosome from a 129 strain), however, modifying the ES cell to decrease the level and/or activity of Sry and using such cells to generate F0 mice results in phenotypically female F0 XY mice, most of which are fertile. By further culturing these VGF1 cells in a feminizing medium as disclosed herein, an even higher percentage of the phenotypically female F0 XY mice can be fertile. See WO 2015/200805 and US 2015/0376651, each of which is incorporated by reference in its entirety for all purposes.

Modifying the XY pluripotent or totipotent cells to comprise not only a genetic modification that results in a decreased level and/or activity of the Sry protein but also silencing of an additional region of the Y chromosome can promote the development of XY F0 fertile females (e.g., by increasing XY F0 female production and/or by further increasing the fertility and/or fecundity of XY F0 females). Such a combination of modifications can increase the percentage of F0 XY progeny that are phenotypically female XY animals that are fertile upon attaining sexual maturity, the percentage of F0 XY females that are fertile, or the percentage of F0 XY females capable of producing normal numbers of litters and sizes of litters (e.g., compared to wild type female animals) when compared to XY pluripotent or totipotent cells without a genetic modification that results in a decreased level and/or activity of the Sry protein.

In general, the level and/or activity of the Sry protein is decreased if the protein level and/or the activity level of the Sry protein is statistically lower than the protein level of Sry in an appropriate control cell that has not been genetically modified or mutagenized to inhibit the expression and/or activity of the Sry protein. For example, the concentration and/or activity of the Sry protein is decreased by at least 1%, 5%, 10%, 20%, 30%, 40%, 50%, 60%, 70%, 80%, 90%, 95%, 99%, or greater relative to a control cell which has not been modified to have the decreased level and/or activity of the Sry protein.

A "subject cell" is one in which a genetic alteration, such as a genetic modification disclosed herein has been effected, or is a cell which is descended from a cell so altered and which comprises the alteration. A "control" or "control cell" provides a reference point for measuring changes in phenotype of the subject cell. A control cell can be as closely matched as possible with the cell with reduced Sry activity except it lacks the genetic modification or mutation resulting in the reduced activity (for example, the respective cells can originate from the same cell line). In other instances, the control cell may comprise, for example: (a) a wild-type cell (i.e., of the same genotype as the starting material for the genetic alteration which resulted in the subject cell); (b) a cell of the same genotype as the starting material but which has been genetically modified with a null construct (i.e., with a construct which has no known effect on the trait of interest, such as a construct comprising a marker gene); (c) a cell which is a non-genetically modified progeny of a subject cell (i.e., the control cell and the subject cell originate from the same cell line); (d) a cell genetically identical to the subject cell but which is not exposed to conditions or stimuli that would alter Sry protein levels and/or activity levels; or (e) the subject cell itself, under conditions in which the genetic modification does not result in an alteration in expression of Sry protein levels and/or activity levels.

The expression level of the Sry polypeptide may be measured directly, for example, by assaying for the level of the Sry polypeptide in the cell or organism, or indirectly, for example, by measuring the activity of the Sry polypeptide. Various methods for determining the activity of the Sry protein are known. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

In other instances, cells having a targeted genetic modification that reduces the activity and/or level of the Sry polypeptide are selected using methods that include, for example, Southern blot analysis, DNA sequencing, PCR analysis, Northern blot analysis, quantitative RT-PCR analysis, Next Generation Sequencing (NGS), microarray analysis, or phenotypic analysis.

A decreased level and/or activity of the Sry protein can be achieved by a targeted genetic modification to the Sry gene or to a genomic locus that affects or regulates levels or activity of the Sry protein. Such targeted modifications can include, for example, additions of one or more nucleotides, deletions of one or more nucleotides, substitutions of one or more nucleotides, a knockout of a polynucleotide of interest or a portion thereof, a knock-in of a polynucleotide of interest or a portion thereof, a replacement of an endogenous nucleic acid sequence with a heterologous nucleic acid sequence, or a combination thereof. For example, at least 1, 2, 3, 4, 5, 7, 8, 9, 10 or more nucleotides can be changed to form the targeted genomic modification. Various methods can be used to generate a targeted genetic modification. See, e.g., Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes. In addition, the various methods described herein can be used to introduce targeted genetic modification to the Sry gene or other genomic loci.

Various methods for making targeted genetic modifications that decrease the level and/or the activity of the Sry protein can be used and are disclosed elsewhere herein.

The targeted genetic modification of the Sry gene or of any other target genomic locus can occur while the cell (e.g., ES cell) is being maintained in a feminizing culture medium (e.g., low-osmolality medium) disclosed elsewhere herein (e.g., a medium that promotes the development of XY F0 fertile females). Alternatively, the targeted genetic modification of the Sry gene or other target genomic locus can occur while the cell is being maintained in different culture medium, and optionally subsequently transferred to the feminizing culture medium (e.g., low-osmolality medium) disclosed elsewhere herein (e.g., a medium that promotes the development of XY F0 fertile females).

The activity and/or level of the Sry polypeptide can also be reduced or eliminated by introducing into the cell a polynucleotide that inhibits the level or activity of the Sry polypeptide. The polynucleotide may inhibit the expression of the Sry polypeptide directly, by preventing translation of the Sry messenger RNA, or indirectly, by encoding a polypeptide that inhibits the transcription of the gene encoding an Sry protein. Alternatively, the activity of Sry polypeptide is reduced or eliminated by introducing into the cell a sequence encoding a polypeptide that inhibits the activity of the Sry polypeptide.

The level and/or activity of the Sry protein can also be regulated through use of a conditional Sry allele that reduces the activity and/or level of the Sry protein. A "conditional Sry allele" includes a modified Sry gene designed to have the decreased level and/or activity of the Sry protein at a desired developmental time and/or within a desired tissue of interest. Reduced level and/or activity can be compared with a control cell lacking the modification giving rise to the conditional allele, or in the case of reduced activity at a desired developmental time with preceding and/or following times, or in the case of a desired tissue, with a mean activity of all tissues. For example, the conditional Sry allele can comprise a conditional null allele of Sry that can be switched off at a desired developmental time point and/or in specific tissues. Such a conditional allele can be used to create fertile XY females derived from any gene-targeted clone. As described elsewhere herein, such a method enables the creation of a desired homozygous genetic modification in the F1 generation. Such methods provide a quick look at the phenotype without having to breed to the F2 generation.

A conditional Sry allele can also be a multifunctional allele as described in US 2011/0104799, which is incorporated by reference in its entirety for all purposes. For example, such a conditional allele can comprise: (a) an actuating sequence in sense orientation with respect to transcription of a target gene, and a drug selection cassette (DSC) in sense or antisense orientation; (b) in antisense orientation a nucleotide sequence of interest (NSI) and a conditional by inversion module (COIN), which utilizes an exon-splitting intron and an invertible genetrap-like module (see, e.g., US 2011/0104799, which is incorporated by reference in its entirety for all purposes); and (c) recombinable units that recombine upon exposure to a first recombinase to form a conditional allele that (i) lacks the actuating sequence and the DSC, and (ii) contains the NSI in sense orientation and the COIN in antisense orientation.

The conditional allele of the Sry gene can be generated in any cell type, and is not limited to an XY pluripotent or totipotent cell. Such cells types along with non-limiting methods to target a genomic locus on the Y chromosome are discussed in further detail elsewhere herein.

iv. Combinations

The methods and compositions provided for modifying XY pluripotent or totipotent animal cells to silence a region of the Y chromosome can be combined with methods involving culturing the XY pluripotent or totipotent animal cells in a feminizing medium (e.g., a low-osmolality medium) and/or methods involving modifying the XY pluripotent or totipotent animal cells to decrease the level and/or activity of an Sry protein. Likewise, the methods involving culturing XY pluripotent or totipotent animal cells in a feminizing medium (e.g., a low-osmolality medium) can be combined with the methods and compositions provided for modifying XY pluripotent or totipotent animal cells to silence a region of the Y chromosome and/or methods involving modifying the XY pluripotent or totipotent animal cells to decrease the level and/or activity of an Sry protein. The XY pluripotent or totipotent cells can further comprise at least one additional targeted genetic modification to a target genomic locus.

In methods in which the XY pluripotent or totipotent cells are cultured in feminizing medium, the cells can be cultured in the feminizing medium for the entire silencing process or for only one or more parts of the entire silencing process. That is, in methods in which the XY pluripotent or totipotent cells are cultured in feminizing medium and in which a region of the Y chromosome is silenced by another silencing process, the cells can be cultured in the feminizing medium for the entire silencing process or for only one or more parts of the entire silencing process. Likewise, the cells can be cultured in the feminizing medium before and/or during and/or after the silencing process. In methods which further comprise both maintaining the cells in feminizing medium and decreasing the level and/or activity of an Sry protein, the cells can be cultured in the feminizing medium for the entire process of decreasing the level and/or activity of the Sry protein or for only one or more parts of the process. Likewise, the cells can be cultured in the feminizing medium before and/or during and/or after the process of decreasing the level and/or activity of the Sry protein.

In some such combinations with methods involving culturing the XY pluripotent or totipotent cells in a feminizing medium, the XY pluripotent or totipotent cell can be maintained in the feminizing medium (e.g., low-osmolality medium) but the silencing of a region of the Y chromosome is achieved by a means other than or in addition to maintaining the cell in the feminizing medium. In some such combinations with methods involving modifying the XY pluripotent or totipotent cell to decrease the level and/or activity of an Sry protein, the silencing of a region of the Y chromosome can be silencing of a region comprising a portion of the Y chromosome outside of the Sry gene.

In one example, the Sry gene is silenced in addition to one or more additional genes on the Y chromosome. Although an understanding of mechanism is not required for practice, silencing of Sry can enhance sex reversal in such XY embryos (e.g., due to silencing in gonad somatic cells at ~11.0 dpc), and silencing of one or more other genes on the Y chromosome can enhance the fertility and/or fecundity of XY females produced from the sex reversed XY embryos (e.g., due to silencing in oocytes at ~18.5 dpc and beyond). For example, both the Zfy2 and the Sry genes can be silenced (e.g., in a mouse XY ES cell from a C57BL strain, a C57BL/6 strain, or a strain other than 129, or with a Y chromosome from a C57BL strain, a C57BL/6 strain, or a strain other than 129), and the XY pluripotent or totipotent animal cell is optionally cultured in a feminizing medium (e.g., low-osmolality medium) disclosed herein. In some methods, silencing of Sry can enhance sex reversal in XY embryos (e.g., due to silencing in gonad somatic cells at ~11.0 dpc), and silencing of Zfy12 can enhance the fertility and/or fecundity of XY females (e.g., due to silencing in oocytes at ~18.5 dpc and beyond).

Such combinations can result in higher percentages of F0 progeny that are phenotypically female XY animals, higher percentages of F0 progeny that are phenotypically female XY animals that are fertile, higher percentages of F0 XY progeny that are phenotypically female XY animals that are fertile, higher percentages of F0 XY females that are fertile, higher average numbers of lifetime litters for F0 XY females or fertile F0 XY females, and higher average litter sizes for F0 XY females or fertile F0 XY females. Such F0 progeny can be produced from the donor XY pluripotent or totipotent animal cells following introduction of the cells into a host embryo and gestation of the host embryo using the methods disclosed elsewhere herein.

The increase can be any statistically significant increase when compared to the appropriate control. For example, the increase can be at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, or 5-fold when compared to the appropriate control.

For example, the percentage of F0 progeny or F0 XY progeny that are phenotypically female XY animals can be increased by using the combinations disclosed herein. In some methods, the percentage of the F0 progeny or F0 XY progeny that are phenotypically female XY animals is higher for F0 progeny derived from donor XY pluripotent or totipotent animal cells modified to silence a region of the Y chromosome and further modified to decrease the level and/or activity of an Sry protein when compared to F0 progeny derived from XY pluripotent or totipotent animal cells that are not modified to decrease the level and/or activity of an Sry protein. Likewise, in some methods, the percentage of the F0 progeny or F0 XY progeny that are phenotypically female XY animals is higher for F0 progeny derived from donor XY pluripotent or totipotent animal cells modified to silence a region of the Y chromosome and further modified to decrease the level and/or activity of an Sry protein when compared to F0 progeny derived from XY pluripotent or totipotent animal cells that are not modified to silence a region of the Y chromosome.

In some methods, the percentage of the F0 progeny or F0 XY progeny that are phenotypically female XY animals is higher for F0 progeny derived from donor XY pluripotent or totipotent animal cells modified to silence a region of the Y chromosome and cultured in a feminizing medium when compared to F0 progeny derived from XY pluripotent or totipotent animal cells that are cultured in an appropriate control medium (e.g., one based on DMEM). Likewise, in some methods, the percentage of the F0 progeny or F0 XY progeny that are phenotypically female XY animals is higher for F0 progeny derived from donor XY pluripotent or totipotent animal cells modified to silence a region of the Y chromosome and cultured in feminizing medium when compared to F0 progeny derived from XY pluripotent or totipotent animal cells that are not modified to silence a region of the Y chromosome.

The percentage of F0 progeny or F0 XY progeny that are fertile, phenotypically female XY animals can also be increased by using the combinations disclosed herein. In some methods, the percentage of the F0 progeny or F0 XY progeny that are fertile, phenotypically female XY animals is higher for F0 progeny derived from donor XY pluripotent or totipotent animal cells modified to silence a region of the Y chromosome and further modified to decrease the level and/or activity of an Sry protein when compared to F0 progeny derived from XY pluripotent or totipotent animal cells that are not modified to decrease the level and/or activity of an Sry protein. Likewise, in some methods, the percentage of the F0 progeny or F0 XY progeny that are fertile, phenotypically female XY animals is higher for F0 progeny derived from donor XY pluripotent or totipotent animal cells modified to silence a region of the Y chromosome and further modified to decrease the level and/or activity of an Sry protein when compared to F0 progeny derived from XY pluripotent or totipotent animal cells that are not modified to silence a region of the Y chromosome.

In some methods, the percentage of the F0 progeny or F0 XY progeny that are fertile, phenotypically female XY animals is higher for F0 progeny derived from donor XY pluripotent or totipotent animal cells modified to silence a region of the Y chromosome and cultured in a feminizing medium when compared to F0 progeny derived from XY pluripotent or totipotent animal cells that are cultured in an appropriate control medium (e.g., one based on DMEM). Likewise, in some methods, the percentage of the F0 progeny or F0 XY progeny that are fertile, phenotypically female XY animals is higher for F0 progeny derived from donor XY pluripotent or totipotent animal cells modified to silence a region of the Y chromosome and cultured in feminizing medium when compared to F0 progeny derived from XY pluripotent or totipotent animal cells that are not modified to silence a region of the Y chromosome.

The percentage of F0 XY females that are fertile can also be increased by using the combinations disclosed herein. In some methods, the percentage of the F0 XY females that are fertile is higher for F0 XY progeny derived from donor XY pluripotent or totipotent animal cells modified to silence a region of the Y chromosome and further modified to decrease the level and/or activity of an Sry protein when compared to F0 XY progeny derived from XY pluripotent or totipotent animal cells that are not modified to decrease the level and/or activity of an Sry protein. Likewise, in some methods, the percentage of the F0 XY females that are fertile is higher for F0 XY progeny derived from donor XY pluripotent or totipotent animal cells modified to silence a region of the Y chromosome and further modified to decrease the level and/or activity of an Sry protein when compared to F0 XY progeny derived from XY pluripotent or totipotent animal cells that are not modified to silence a region of the Y chromosome.

In some methods, the percentage of the F0 XY females that are fertile is higher for F0 XY progeny derived from donor XY pluripotent or totipotent animal cells modified to silence a region of the Y chromosome and cultured in a feminizing medium when compared to F0 XY progeny derived from XY pluripotent or totipotent animal cells that are cultured in an appropriate control medium (e.g., one based on DMEM). Likewise, in some methods, the percentage of the F0 XY females that are fertile is higher for F0 XY progeny derived from donor XY pluripotent or totipotent animal cells modified to silence a region of the Y chromosome and cultured in feminizing medium when compared to F0 XY progeny derived from XY pluripotent or totipotent animal cells that are not modified to silence a region of the Y chromosome.

The percentage of F0 XY females that are capable of producing normal numbers of litters and/or normal litter sizes (e.g., compared to wild type female animals) can also be increased by using the combinations disclosed herein. In some methods, the percentage of the F0 XY females that are capable of producing normal numbers of litters and/or normal litter sizes is higher for F0 XY progeny derived from donor XY pluripotent or totipotent animal cells modified to silence a region of the Y chromosome and further modified to decrease the level and/or activity of an Sry protein when compared to F0 XY progeny derived from XY pluripotent or totipotent animal cells that are not modified to decrease the level and/or activity of an Sry protein. Likewise, in some methods, the percentage of the F0 XY females that are capable of producing normal numbers of litters and/or normal litter sizes is higher for F0 XY progeny derived from donor XY pluripotent or totipotent animal cells modified to silence a region of the Y chromosome and further modified to decrease the level and/or activity of an Sry protein when compared to F0 XY progeny derived from XY pluripotent or totipotent animal cells that are not modified to silence a region of the Y chromosome.

In some methods, the percentage of the F0 XY females that are capable of producing normal numbers of litters and/or normal litter sizes is higher for F0 XY progeny derived from donor XY pluripotent or totipotent animal cells modified to silence a region of the Y chromosome and cultured in a feminizing medium when compared to F0 XY progeny derived from XY pluripotent or totipotent animal cells that are cultured in an appropriate control medium (e.g., one based on DMEM). Likewise, in some methods, the percentage of the F0 XY females that are capable of producing normal numbers of litters and/or normal litter sizes is higher for F0 XY progeny derived from donor XY pluripotent or totipotent animal cells modified to silence a region of the Y chromosome and cultured in feminizing medium when compared to F0 XY progeny derived from XY pluripotent or totipotent animal cells that are not modified to silence a region of the Y chromosome.

The average litter size produced by F0 XY females or fertile F0 XY females can also be increased by using the combinations disclosed herein. In some methods, the average litter size produced by F0 XY females or fertile F0 XY females is higher for F0 XY females or fertile F0 XY females derived from donor XY pluripotent or totipotent animal cells modified to silence a region of the Y chromosome and further modified to decrease the level and/or activity of an Sry protein when compared to F0 XY females or fertile F0 XY females derived from XY pluripotent or totipotent animal cells that are not modified to decrease the level and/or activity of an Sry protein. Likewise, in some methods, the average litter size produced by F0 XY females or fertile F0 XY females is higher for F0 XY females or fertile F0 XY females derived from donor XY pluripotent or totipotent animal cells modified to silence a region of the Y chromosome and further modified to decrease the level and/or activity of an Sry protein when compared to F0 XY females or fertile F0 XY females derived from XY pluripotent or totipotent animal cells that are not modified to silence a region of the Y chromosome.

In some methods, the average litter size produced by F0 XY females or fertile F0 XY females is higher for F0 XY females or fertile F0 XY females derived from donor XY pluripotent or totipotent animal cells modified to silence a region of the Y chromosome and cultured in a feminizing medium when compared to F0 XY females or fertile F0 XY females derived from XY pluripotent or totipotent animal cells that are cultured in an appropriate control medium (e.g., one based on DMEM). Likewise, in some methods, the average litter size produced by F0 XY females or fertile F0 XY females is higher for F0 XY females or fertile F0 XY females derived from donor XY pluripotent or totipotent animal cells modified to silence a region of the Y chromosome and cultured in feminizing medium when compared to F0 XY females or fertile F0 XY females derived from XY pluripotent or totipotent animal cells that are not modified to silence a region of the Y chromosome.

The average number of lifetime litters produced by F0 XY females or fertile F0 XY females can also be increased by using the combinations disclosed herein. In some methods, the average number of lifetime litters produced by F0 XY females or fertile F0 XY females is higher for F0 XY females or fertile F0 XY females derived from donor XY pluripotent or totipotent animal cells modified to silence a region of the Y chromosome and further modified to decrease the level and/or activity of an Sry protein when compared to F0 XY females or fertile F0 XY females derived from XY pluripotent or totipotent animal cells that are not modified to decrease the level and/or activity of an Sry protein. Likewise, in some methods, the average number of lifetime litters produced by F0 XY females or fertile F0 XY females is higher for F0 XY females or fertile F0 XY females derived from donor XY pluripotent or totipotent animal cells modified to silence a region of the Y chromosome and further modified to decrease the level and/or activity of an Sry protein when compared to F0 XY females or fertile F0 XY females derived from XY pluripotent or totipotent animal cells that are not modified to silence a region of the Y chromosome.

In some methods, the average number of lifetime litters produced by F0 XY females or fertile F0 XY females is higher for F0 XY females or fertile F0 XY females derived from donor XY pluripotent or totipotent animal cells modified to silence a region of the Y chromosome and cultured in a feminizing medium when compared to F0 XY females or fertile F0 XY females derived from XY pluripotent or totipotent animal cells that are cultured in an appropriate control medium (e.g., one based on DMEM). Likewise, in some methods, the average number of lifetime litters produced by F0 XY females or fertile F0 XY females is higher for F0 XY females or fertile F0 XY females derived from donor XY pluripotent or totipotent animal cells modified to silence a region of the Y chromosome and cultured in feminizing medium when compared to F0 XY females or fertile F0 XY females derived from XY pluripotent or totipotent animal cells that are not modified to silence a region of the Y chromosome.

The average number of lifetime offspring produced by F0 XY females or fertile F0 XY females can also be increased by using the combinations disclosed herein. In some methods, the average number of lifetime offspring produced by F0 XY females or fertile F0 XY females is higher for F0 XY females or fertile F0 XY females derived from donor XY pluripotent or totipotent animal cells modified to silence a region of the Y chromosome and further modified to decrease the level and/or activity of an Sry protein when compared to F0 XY females or fertile F0 XY females derived from XY pluripotent or totipotent animal cells that are not modified to decrease the level and/or activity of an Sry protein. Likewise, in some methods, the average number of lifetime offspring produced by F0 XY females or fertile F0 XY females is higher for F0 XY females or fertile F0 XY females derived from donor XY pluripotent or totipotent animal cells modified to silence a region of the Y chromosome and further modified to decrease the level and/or activity of an Sry protein when compared to F0 XY females or fertile F0 XY females derived from XY pluripotent or totipotent animal cells that are not modified to silence a region of the Y chromosome.

In some methods, the average number of lifetime offspring produced by F0 XY females or fertile F0 XY females is higher for F0 XY females or fertile F0 XY females derived from donor XY pluripotent or totipotent animal cells modified to silence a region of the Y chromosome and cultured in a feminizing medium when compared to F0 XY females or fertile F0 XY females derived from XY pluripotent or totipotent animal cells that are cultured in an appropriate control medium (e.g., one based on DMEM). Likewise, in some methods, the average number of lifetime offspring produced by F0 XY females or fertile F0 XY females is higher for F0 XY females or fertile F0 XY females derived from donor XY pluripotent or totipotent animal cells modified to silence a region of the Y chromosome and cultured in feminizing medium when compared to F0 XY females or fertile F0 XY females derived from XY pluripotent or totipotent animal cells that are not modified to silence a region of the Y chromosome.

B. In Vitro Cell Cultures and Methods of Culturing and Maintaining a Pluripotent or Totipotent Cell in Culture Further provided are in vitro cell cultures comprising the donor XY pluripotent or totipotent cell modified to silence a region of the Y chromosome. Also provided are in vitro cell cultures comprising the donor XY pluripotent or totipotent cultured in a feminizing medium as disclosed elsewhere herein. Also provided are methods and compositions for maintaining or culturing such cells. The cells can further comprise a modification that decreases the level and/or activity of the Sry protein. Likewise, the XY pluripotent or totipotent cells can further comprise at least one additional targeted genetic modification to a target genomic locus.

A method for maintaining or culturing an XY pluripotent or totipotent cell in an in vitro culture is provided, wherein the cell is maintained in an in vitro culture in the presence of feminizing media as described herein. Likewise, a method for maintaining or culturing an XY pluripotent or totipotent cell in an in vitro culture is provided, wherein the cell comprises a modification that silences a region of the Y chromosome and the cell is maintained in an in vitro culture under conditions described herein. Such methods of maintaining or culturing an XY pluripotent or totipotent cell in an in vitro culture is such as to promote an increase in the number XY F0 fertile female animals upon the introduction of the non-human animal XY ES cells into a host embryo and following gestation of the host embryos.

While any medium disclosed herein can be employed for such maintaining or culturing methods, one non-limiting example includes culturing in a medium comprising a base medium and supplements suitable for maintaining or culturing the XY pluripotent or totipotent cell in culture. For example, the medium can comprise a feminizing medium as disclosed elsewhere herein (e.g., a low-osmolality medium in which the base medium or the medium comprising the base medium and the supplements exhibits an osmolality from about 200 mOsm/kg to less than about 329 mOsm/kg).

The period of time in which the XY pluripotent or totipotent cell is maintained in the feminizing medium can vary. For example, the XY pluripotent or totipotent cell can be maintained in the medium for a period of about or at least 1, 2, 3, 4, 5, 6, 7, 8, 9, 10, 11, 12, or 13 days, or 2 weeks, 3 weeks, or 4 weeks prior to introduction into a host embryo (e.g., is maintained in the medium for about or at least 3 days, about or at least 1 week, or for about or at least 2-4 weeks prior to introduction into the host embryo). Likewise, the XY pluripotent or totipotent cell can be maintained in the medium for a period of no more than 1, 2, 3, 4, 5, 6, 7, 8, 9, 10, 11, 12, or 13 days, or 2 weeks, 3 weeks, or 4 weeks prior to introduction into a host embryo. Alternatively, the XY pluripotent or totipotent cell can be maintained (e.g., frozen) in a feminizing medium (e.g., that promotes XY fertile F0 females) and can then be thawed in and maintained in a feminizing medium (e.g., that promotes XY fertile F0 females) for at least 1, 2, 3, 4, or more days before the XY pluripotent or totipotent cell is introduced into the host embryo. Likewise, the XY pluripotent or totipotent cell can be maintained (e.g., frozen) in a feminizing medium (e.g., that promotes XY fertile F0 females) and can then be thawed in and maintained in a feminizing medium (e.g., that promotes XY fertile F0 females) for no more than 1, 2, 3, 4, or more days before the XY pluripotent or totipotent cell is introduced into the host embryo. For example, the XY pluripotent or totipotent cell can be passaged at least once in a feminizing medium, after which the cell is frozen in a feminizing medium, after which the cell is thawed in a feminizing medium and grown for about or at least 1, 2, 3, 4, 5, 6, 7, 8, 9, 10, 11, 12, or 13 days, or 2 weeks, 3 weeks, or 4 weeks prior to introduction into a host embryo. Alternatively, the XY pluripotent or totipotent cell can be passaged at least once in a feminizing medium, after which the cell is frozen in a feminizing medium, after which the cell is thawed in a feminizing medium and grown for no more than 1, 2, 3, 4, 5, 6, 7, 8, 9, 10, 11, 12, or 13 days, or 2 weeks, 3 weeks, or 4 weeks prior to introduction into a host embryo.

In some methods, the XY pluripotent or totipotent cell is cultured or maintained in the feminizing medium until injection of the cell into an embryo. In other methods, the embryo into which the XY pluripotent or totipotent cell was injected is cultured or maintained in the feminizing medium until being transferred to a surrogate mother.

C. Embryos Capable of Producing Fertile XY Female in F0 Generation

Further provided is an F0 embryo comprising an inner cell mass having at least one heterologous donor pluripotent or totipotent XY cell modified to silence a region of the Y chromosome. Likewise, further provided is an F0 embryo comprising an inner cell mass having at least one heterologous donor pluripotent or totipotent XY cell that was cultured or maintained in a feminizing medium as disclosed elsewhere herein. The heterologous donor pluripotent or totipotent XY cell can be produced by the methods disclosed herein. The heterologous donor pluripotent or totipotent XY cell can further comprise a modification that decreases the level and/or activity of the Sry protein. Likewise, the heterologous donor pluripotent or totipotent XY cell can further comprise at least one additional targeted genetic modification to a target genomic locus.

Such embryos can be produced by introducing a donor XY pluripotent or totipotent animal cell into a host embryo. For example, the embryo can be a pre-morula stage embryo, and the embryo can be cultured to the blastocyst stage following introduction of the donor XY pluripotent or totipotent cell. In methods in which the donor animal XY pluripotent or totipotent cell is cultured in feminizing medium (e.g., low-osmolality medium), the animal XY pluripotent or totipotent cell can be maintained in the feminizing medium for any period of time prior to being introduced into the host embryo. For example, the animal XY pluripotent or totipotent cell can be maintained in the feminizing medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into the host embryo. Alternatively, the animal XY pluripotent or totipotent cell can be maintained in the feminizing medium for no more than 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into the host embryo.

In some F0 embryos, the heterologous donor pluripotent or totipotent XY cell and/or the host embryo are not from one or more of the following: *Akodon* spp., *Myopus* spp., *Microtus* spp., *Talpa* spp. Likewise, in some methods, the heterologous donor pluripotent or totipotent XY cell and/or the host embryo are not from any species of which a normal wild-type characteristic is XY female fertility. In some methods in which the heterologous donor pluripotent or totipotent cell and/or host embryo comprises an additional genetic modification, the genetic modification is not an XYY or XXY, a Tdy-negative (i.e., Sry-negative) sex reversal, Tdy-positive sex reversal, an X0 modification, an aneuploidy, an Fgf9$^{-/-}$ genotype, or a Sox9 modification.

D. Methods of Generating F0 Fertile XY Females and F1 Progeny

The various methods and compositions employing the XY pluripotent or totipotent cells having a modification comprising silencing of a region of the Y chromosome can be used to generate fertile F0 XY female animals that optionally comprise an additional targeted genetic modification to a target genomic locus. Likewise, the various methods and compositions employing the XY pluripotent or totipotent cells cultured or maintained in a feminizing medium as disclosed elsewhere herein can be used to generate fertile F0 XY female animals that optionally comprise an additional targeted genetic modification to a target genomic locus. For example, an F0 XY female animal produced by the methods disclosed herein can be fertile when crossed to a wild type animal to generate an F1 generation.

i. Methods of Making a Fertile Female XY Animal in an F0 Generation

Methods and compositions are provided for making a fertile female XY animal in an F0 generation. Also provided are the resulting fertile, phenotypically female XY animals produced by such methods. Methods for making a fertile, phenotypically female XY animal in an F0 generation can comprise (a) introducing any of the modified donor XY pluripotent or totipotent cells disclosed elsewhere herein (i.e., donor XY pluripotent or totipotent cells that are capable of producing fertile XY females in an F0 generation) into a host embryo; (b) introducing the host embryo from step (a) into a recipient female animal and gestating the host embryo; and (c) obtaining F0 XY animal progeny comprising a phenotypically female XY animal, wherein upon attaining sexual maturity the F0 phenotypically female XY animal is fertile. Other methods for making a fertile, phenotypically female XY animal in an F0 generation can comprise (a) introducing any of the modified embryos disclosed elsewhere herein into a recipient female animal and gestating the embryo; and (b) obtaining F0 XY animal progeny comprising a phenotypically female XY animal, wherein upon attaining sexual maturity the F0 phenotypically female XY animal is fertile.

Cells that have been implanted into an embryo can be referred to as "donor cells," and embryos that have received the cells can be referred to as "host embryos." In some methods, the donor XY pluripotent or totipotent cell or the host embryo can comprise at least one additional targeted genetic modification to a target genomic locus. For example, the XY pluripotent or totipotent cell employed can comprise (1) a modification to silence a region of the Y chromosome and (2) one or more additional targeted genetic modifications to one or more target genomic loci. Such modifications are disclosed in detail elsewhere herein. As outlined elsewhere herein, at least 1, 2, 3, 4, 5, 6, 7, 8, 9, 10, or more additional targeted genetic modifications can be made in the XY pluripotent or totipotent cell. In such instances, the F0 fertile female XY animal can comprise one or more of these additional targeted genetic modifications. Animals bearing a genetically modified genomic locus can be identified via modification of allele (MOA) assay as described herein.

The donor XY pluripotent or totipotent cell can be from the same strain as the host embryo or from a different strain as the host embryo. Likewise, the surrogate mother can be from the same strain as the donor XY pluripotent or totipotent cell and/or the host embryo, or the surrogate mother can be from a strain that is different from the strain of the donor XY pluripotent or totipotent cell and/or the host embryo.

The genotype of the XY pluripotent or totipotent cell can be the same as the genotype of the host embryo or different. For example, the XY donor cell can be implanted into an XX host embryo.

A variety of host embryos can be employed. The XY donor cells can be implanted, for example, into a 2-cell stage, 4-cell stage, 8-cell stage, 16-cell stage, 32-cell stage, or 64-cell stage host embryo. For example, the XY pluripotent or totipotent cells can be introduced into a pre-morula stage embryo (e.g., an 8-cell stage embryo) from a corresponding organism. See, e.g., U.S. Pat. Nos. 7,576,259; 7,659,442; 7,294,754; and US 2008-0078000 A1, each of which is herein incorporated by reference in its entireties. Likewise, the host embryo can be, for example, a blastocyst, a pre-blastocyst embryo, a pre-morula stage, a morula stage, an uncompacted morula stage, or a compacted morula stage. Alternatively, the host embryo can be a morula-stage host embryo that is aggregated. In the case of mice, the host embryo stage can be, for example, a Theiler Stage 1 (TS1), a TS2, a TS3, a TS4, a TS5, or a TS6 embryo (e.g., selected from TS1, TS2, TS3, and TS4), with reference to the Theiler stages described in Theiler (1989) "The House Mouse: Atlas of Mouse Development," Springer-Verlag, New York. In methods in which the host embryo comprises a zona pellucida, the donor cell (e.g., and XY ES cell) can be introduced into the host embryo through a hole in the zona pellucida. Zone-less embryos can also be used.

In some methods, the donor pluripotent or totipotent cell and/or the host embryo are not from one or more of the following: *Akodon* spp., *Myopus* spp., *Microtus* spp., *Talpa* spp. Likewise, in some methods, the donor cell and/or the host embryo are not from any species of which a normal wild-type characteristic is XY female fertility. In some methods in which the donor cell and/or host embryo comprises an additional genetic modification, the genetic modification is not an XYY or XXY, a Tdy-negative (i.e., Sry-negative) sex reversal, Tdy-positive sex reversal, an X0 modification, an aneuploidy, an Fgf9$^{-/-}$ genotype, or a Sox9 modification.

Nuclear transfer techniques can also be used to generate the animals. Briefly, methods for nuclear transfer can include the steps of: (1) enucleating an oocyte; (2) isolating a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods oocytes are generally retrieved from deceased animals, although they may be isolated also from either oviducts and/or ovaries of live animals. Oocytes can be matured in a variety of medium known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell is usually by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium well known to those of ordinary skill in the art and then transferred to the womb of an animal. See, e.g., US 2008/0092249; WO 1999/005266 A2; US 2004/0177390; WO 2008/017234 A1; and U.S. Pat. No. 7,612,250, each of which is herein incorporated by reference in its entirety for all purposes.

The host embryo comprising the donor XY pluripotent or totipotent cell can be incubated until the blastocyst stage and then implanted into a surrogate mother to produce an F0 animal. The host embryo can then be gestated in the surrogate mother.

In some methods, the host embryo comprising the donor XY pluripotent or totipotent cells can be maintained in a feminizing medium (e.g., low-osmolality medium or low-salt base medium) that promotes the development of XY fertile female ES cells for one, two, three, or four or more days prior to implantation in a suitable host. Alternatively, the host embryo comprising the donor XY pluripotent or totipotent cells can be maintained in a feminizing medium (e.g., low-osmolality medium or low-salt base medium) that promotes the development of XY fertile female ES cells for at least one, two, three, or four or more days or no more than one, two, three, or four or more days prior to implantation in a suitable host. Such methods provide can promote the generation of an F0 fertile female animal.

In some methods, upon introduction of the donor non-human animal XY pluripotent or totipotent cells (e.g., an XY ES cell or an XY iPS cell) into a host embryo and gestation of the host embryo, at least 5%, 10%, 20%, 30%, 40%, 50%, 60%, 70%, 75%, 80% 85%, 90%, 91%, 92%, 93%, 94%, 95%, 96%, 97%, 98%, 99% or all of the F0 progeny or F0 XY progeny are phenotypically female XY animals.

The fertility and fecundity of the F0 XY female animals produced by these methods can be comparable to wild type XX female animals. In some methods, upon introduction of the donor non-human animal XY pluripotent or totipotent cells (e.g., an XY ES cell or an XY iPS cell) into a host embryo and gestation of the host embryo, at least 5%, 10%, 20%, 30%, 40%, 50%, 60%, 70%, 75%, 80% 85%, 90%, 91%, 92%, 93%, 94%, 95%, 96%, 97%, 98%, 99% or all of the F0 progeny are phenotypically female XY animals that are fertile upon attaining sexual maturity.

In some methods, at least 5%, 10%, 20%, 30%, 40%, 50%, 60%, 70%, 75%, 80%, 85%, 90%, 91%, 92%, 93%, 94%, 95%, 96%, 97%, 98%, 99%, or all of the F0 XY progeny are phenotypically female XY animals that are fertile upon attaining sexual maturity.

In some methods, at least 5%, 10%, 20%, 30%, 40%, 50%, 60%, 70%, 75%, 80%, 85%, 90%, 91%, 92%, 93%, 94%, 95%, 96%, 97%, 98%, 99%, or all of the F0 females derived from the donor XY pluripotent or totipotent cell have an XY genotype.

In some methods, at least 5%, 10%, 20%, 30%, 40%, 50%, 60%, 70%, 75%, 80%, 85%, 90%, 91%, 92%, 93%, 94%, 95%, 96%, 97%, 98%, 99%, or all of the F0 females derived from the donor XY pluripotent or totipotent cell are fertile.

In some methods, at least 5%, 10%, 20%, 30%, 40%, 50%, 60%, 70%, 75%, 80%, 85%, 90%, 91%, 92%, 93%, 94%, 95%, 96%, 97%, 98%, 99%, or all of the F0 females derived from the donor XY pluripotent or totipotent cell are capable of producing a number of litters and/or a number of pups per litter and/or a lifetime number of offspring that is comparable to wild type XX female mice. In some methods, an F0 fertile XY female non-human animal can produce 1, 2, 3, 4, 5, 6, 7, 8, 9, or 10 litters during its lifetime (e.g., 2-6 litters). In some methods, at least 5%, 10%, 20%, 30%, 40%, 50%, 60%, 70%, 75%, 80%, 85%, 90%, 91%, 92%, 93%, 94%, 95%, 96%, 97%, 98%, 99%, or all of the F0 females derived from the donor XY pluripotent or totipotent cell are capable of producing 1, 2, 3, 4, 5, 6, 7, 8, 9, or 10 litters in their lifetimes (e.g., 2-6 litters). In some methods, an F0 fertile XY female non-human animal can produce at least 1, 2, 3, 4, 5, 6, 7, 8, 9, or 10 offspring (i.e., pups) per litter (e.g., 4-6 offspring per litter). In some methods, at least 5%, 10%, 20%, 30%, 40%, 50%, 60%, 70%, 75%, 80%, 85%, 90%, 91%, 92%, 93%, 94%, 95%, 96%, 97%, 98%, 99%, or all of the F0 females derived from the donor XY pluripotent or totipotent cell are capable of producing litters having at least 1, 2, 3, 4, 5, 6, 7, 8, 9, or 10 offspring (i.e., pups) per litter (e.g., 4-6 offspring per litter). For example, an F0 fertile XY female non-human animal can produce 2-6 litters, wherein each litter has at least 2, 3, 4, 5, or 6 offspring. In some methods, at least about 5%, 10%, 15%, 20%, 25%, 30%, 35%, 40%, 45%, 50%, 60%, 70%, 80%, 85%, 90%, 95% or 100% of the offspring are XY fertile female offspring (e.g., 15%-25% of the offspring are XY fertile female offspring).

In other embodiments, the F0 progeny produced from such methods are about 3%, about 10% or more, or about 63% or more derived from the donor XY pluripotent or totipotent cell.

The methods and compositions provided herein allow for at least 1%, 3%, 5%, 10%, 15%, 20%, 25%, 30%, 35%, 40%, 45%, 50%, 55%, 60%, 65%, 70%, 75% or more of the F0 animals to have a targeted genetic modification (e.g., a targeted genetic modification resulting in silencing of a region of the Y chromosome and/or a targeted genetic modification to another target genomic locus) to transmit the genetic modification to the F1 progeny.

In some methods, one or more F0 generation female XY non-human animals (e.g., at least 5%, 10%, 20%, 30%, 40%, 50%, 60%, 70%, 75%, 80%, 85%, 90%, 91%, 92%, 93%, 94%, 95%, 96%, 97%, 98%, 99%, or all of the F0 generate female XY non-human animals) are at least 90%, 92%, 94%, 96%, 98%, 99%, or 99.8% derived from the donor XY pluripotent or totipotent cell. For example, one or more F0 female XY non-human animals can have a coat color that is 100% derived from the donor XY pluripotent or totipotent cell. The contribution of a host embryo cell to the non-human female XY animal in the F0 generation can be determined, for example, by a quantitative assay that is capable of detecting 1 cell in 2,000 (0.05%), and no tissue of the female XY animal is positive for host embryo cell contribution.

ii. Methods of Breeding the Fertile Female XY F0 Generation

In some methods, the resulting fertile XY female F0 generation derived from the XY pluripotent or totipotent cells (i.e., the XY ES cell or XY iPS cell) having the genetic modification silencing a region of the Y chromosome is crossed to an animal to obtain F1 generation offspring. The F0 generation female XY non-human animal can be at least 20%, at least 30%, at least 40%, at least 50%, at least 60%, at least 70%, at least 80%, at least 90%, at least 92%, at least 94%, at least 96%, at least 98%, at least 99%, at least 99.5%, or fully derived from a donor XY pluripotent or totipotent cell (e.g., XY ES cell).

Likewise, the resulting fertile XY female F0 generation derived from the XY pluripotent or totipotent cells from any other method disclosed herein (e.g., through use of low-osmolality medium or other feminizing medium as disclosed elsewhere herein) can be crossed to an animal to obtain F1 generation offspring. The F0 generation female XY non-human animal can be at least 20%, at least 30%, at least 40%, at least 50%, at least 60%, at least 70%, at least 80%, at least 90%, at least 92%, at least 94%, at least 96%, at least 98%, at least 99%, at least 99.5%, or fully derived from a donor XY pluripotent or totipotent cell (e.g., XY ES cell). The progeny (e.g., F1 progeny and/or any or all other generations of progeny) can be such that at least 5%, at least 10%, at least 20%, at least 30%, at least 40%, at least 50%, at least 60%, at least 70%, at least 80%, at least 90%, at least 95%, or all of the XY progeny have a normal male phenotype or have a normal male phenotype and are fertile. In some cases, less than 20%, less than 15%, less than 10%, less than 5%, less than 1%, or none of the XY progeny (e.g., F1 progeny and/or any or all other generations of progeny) are phenotypically female. In some cases, all of the XY progeny (e.g., F1 progeny and/or any or all other generations of progeny) have a normal male phenotype or have a normal male phenotype and are fertile. In some cases, at least 5%, at least 10%, at least 20%, at least 30%, at least 40%, at least 50%, at least 60%, at least 70%, at least 80%, at least 90%, at least 95%, or all of the progeny have the expected sex phenotype (i.e., male or female) based on genotype (i.e., XY or XX).

The non-human animal to which the F0 generation female XY non-human animal can be bred can be a male XY non-human animal that is also at least 20%, at least 30%, at least 40%, at least 50%, at least 60%, at least 70%, at least 80%, at least 90%, at least 92%, at least 94%, at least 96%, at least 98%, at least 99%, at least 99.5%, or fully derived from the donor XY pluripotent or totipotent cell (e.g., XY ES cell). For example, the F0 female XY non-human animal and/or the male XY non-human animal can have a coat color that is 100% derived from the donor XY pluripotent or totipotent cell. The breeding pair used to obtain F1 generation offspring can each be fully derived from the donor XY pluripotent or totipotent cell (e.g., ES cell or iPS cell) in the same F0 generation. For example, the F0 XY male can be a cohort clonal sibling derived from the same XY pluripotent or totipotent cell (e.g., XY ES cell) clone as the F0 XY fertile female. The F1 generation progeny can then comprise a genome completely derived from the donor ES cell. In some cases, the frequency of crosses of F0 generation male and F0 generation female mice that give rise to fully ES cell-derived mice is 100%.

The F1 progeny can be genotyped using specific primers and/or probes to determine if the targeted genetic modification comprising the silencing of a region of the Y chromosome is present. If additional targeted genetic modifications were present in the F0 generation (e.g., a modification that decreases the level and/or activity of an Sry protein, or one or more additional targeted genetic modifications to a target genomic locus), the F1 progeny can be genotyped using specific primers and/or probes that determine if such modifications are present. An appropriate F1 progeny for a desired use can then be identified. For example, F1 progeny lacking the genetic modification comprising silencing of a region of the Y chromosome can be selected, or F1 progeny lacking the genetic modification comprising silencing of a region of the Y but comprising at least one additional targeted genetic modification to a target genomic locus can be selected. Following genotyping with specific primers and/or probes, F1 animals that are heterozygous for the additional targeted genetic modification to a target genomic locus and lacking the genetic modification comprising silencing of a region of the Y chromosome can be crossed to one another. Such a cross produces an F2 progeny that is homozygous for the genetically modified genomic locus of interest and does not comprise the genetic modification to silence a region of the Y chromosome.

Further provided is a method of producing a transgenic non-human animal homozygous for a targeted genetic modification to a target genomic locus in the F1 generation. The method comprises (a) crossing an F0 XY fertile female non-human animal having a modification comprising silencing of a region of the Y chromosome with a F0 XY male non-human animal, wherein the F0 XY fertile female non-human animal and the F0 XY male non-human animal are each heterozygous for the targeted genetic modification to the target genomic locus, and (b) obtaining an F1 progeny that is homozygous for the targeted genetic modification to the target genomic locus. In some methods, the F0 XY male is a cohort clonal sibling derived from the same pluripotent or totipotent cell clone as the F0 XY fertile female. For example, the F1 progeny can be selected to be homozygous for the targeted genetic modification to the target genomic locus but to lack the modification silencing a region of the Y chromosome. If the F0 XY fertile female further comprises a modification that decreases the level and/or activity of an Sry protein, the F1 progeny can be selected to be homozygous for the targeted genetic modification to the target genomic locus but to lack one or both of the modification silencing a region of the Y chromosome and the modification that decreases the level and/or activity of an Sry protein.

E. Methods for Making Targeted Genetic Modifications

Various methods and compositions for making targeted genetic modifications (e.g., that silence a region of the Y chromosome, that decrease the level and/or activity of an Sry protein, or that modify any additional target genomic locus as disclosed elsewhere herein) can be used. One means of making a targeted genetic modification is through recombination, which includes any process of exchange of genetic information between two polynucleotides. Recombination in response to double-strand breaks (DSBs) occurs principally through two conserved DNA repair pathways: non-homologous end joining (NHEJ) and homologous recombination (HR). See Kasparek & Humphrey (2011) *Seminars in Cell & Dev. Biol.* 22:886-897, hereby incorporated by reference in its entirety for all purposes. NHEJ includes the repair of double-strand breaks in a nucleic acid by direct ligation of the break ends to one another without the need for a homologous template. Ligation of non-contiguous sequences by NHEJ can often result in deletions, insertions, or translocations near the site of the double-strand break. Such systems find use, for example, in generating targeted loss of function genetic modifications.

Recombination can also occur via homology directed repair (HDR) or homologous recombination (HR). HDR or HR includes a form of nucleic acid repair that can require nucleotide sequence homology, uses a "donor" molecule to template repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. Non-limiting methods for generating such targeted genetic modification are discussed in detail elsewhere herein, including, for example, the use of targeting plasmids, small targeting vectors (smallTVECs), or large targeting vectors. See also Wang et al. (2013) Cell 153:910-918; Mandalos et al. (2012) PLOS ONE 7:e45768:1-9; and Wang et al. (2013) Nat Biotechnol. 31:530-532, each of which is herein incorporated by reference in its entirety for all purposes.

Methods for making targeted genetic modifications can comprise, for example, the use of a targeting vector (e.g., a smallTVEC or an LTVEC), either alone or in combination with one or more nucleases as described elsewhere herein. See, e.g., US 2015/0159175, US 2015/0159174, US 2014/0310828, US 2014/0309487, and US 2013-0309670, each of which is herein incorporated by reference in its entirety for all purposes. Likewise, methods for making targeted genetic modifications can comprise the use of one or more nucleases either alone or in combination with a targeting vector.

For example, methods are provided for modifying a target genomic locus (e.g., on the Y chromosome) in a cell, comprising: (a) introducing into the cell one or more nuclease agents that induces one or more nicks or double-strand breaks at a recognition site at or near the target genomic locus; and (b) identifying at least one cell comprising in its genome a modification at the target genomic locus.

Other methods for modifying a target genomic locus in a cell comprise: (a) introducing into the cell a targeting vector comprising an insert polynucleotide flanked by 5' and 3' homology arms corresponding to 5' and 3' target sites; and (b) identifying at least one cell comprising in its genome the insert polynucleotide integrated at the target genomic locus.

Other methods for modifying a target genomic locus in a cell comprise: (a) introducing into the cell: (i) a nuclease agent, wherein the nuclease agent induces a nick or double-strand break at a recognition site within the target genomic locus; and (ii) a targeting vector comprising an insert nucleic acid flanked by 5' and 3' homology arms corresponding to 5' and 3' target sites located in sufficient proximity to the recognition site; and (c) identifying at least one cell comprising a modification (e.g., integration of the insert nucleic acid) at the target genomic locus.

The targeted genetic modification that silences a region of the Y chromosome and any other targeted genetic modification (e.g., a modification that decreases the level and/or activity of an Sry protein, or a targeted genetic modification to any target genomic locus) can occur while the pluripotent or totipotent XY cell is being maintained in the feminizing medium (e.g., low-osmolality medium) disclosed elsewhere herein (e.g. a medium that promotes the development of XY F0 fertile females). Alternatively, the targeted genetic modification that silences a region of the Y chromosome and/or the targeted genetic modification of any other target genomic locus can occur while the pluripotent or totipotent XY cell is being maintained in different culture media. Optionally, the cell can subsequently be transferred to the feminizing culture medium (e.g., low-osmolality medium) disclosed elsewhere herein (e.g. a medium that promotes the development of XY F0 fertile females).

The targeted genetic modification that silences a region of the Y chromosome and any other targeted genetic modification (e.g., a modification that decreases the level and/or activity of an Sry protein, or a targeted genetic modification to any other target genomic locus) can be introduced simultaneously or sequentially.

i. Nuclease Agents

Any nuclease agent that induces a nick or double-strand break into a desired recognition site can be used in the methods and compositions disclosed herein. A naturally occurring or native nuclease agent can be employed, or a modified or engineered nuclease agent (e.g., a nuclease that is engineered (modified or derived) from its native form to specifically recognize and induce a nick or double-strand break in the desired recognition site) can be employed.

One type of nuclease agent is a Transcription Activator-Like Effector Nuclease (TALEN). TAL effector nucleases are created by fusing a native or engineered transcription activator-like (TAL) effector, or functional part thereof, to the catalytic domain of an endonuclease, such as, for example, FokI. See WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. (2010) doi: 10.1093/nar/gkq704; and Miller et al. (2011) Nature Biotechnology 29:143-148, each of which is herein incorporated by reference in its entirety for all purposes. Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety for all purposes.

Another type of nuclease agent is a zinc-finger nuclease (ZFN). In some ZFNs, each monomer of the ZFN comprises 3 or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US20060246567; US20080182332; US20020081614; US20030021776; WO/2002/057308A2; US20130123484; US20100291048; WO/2011/017293A2; and Gaj et al. (2013) Trends in Biotechnology, 31(7):397-405, each of which is herein incorporated by reference in its entirety for all purposes.

Another type of nuclease agent is a meganuclease. Meganucleases have been classified into four families based on conserved sequence motifs, the families are the LAGLI-DADG, GIY-YIG, H-N-H, and His-Cys box families. These motifs participate in the coordination of metal ions and hydrolysis of phosphodiester bonds. Meganucleases are notable for their long recognition sites, and for tolerating some sequence polymorphisms in their DNA substrates. Meganuclease domains, structure and function are known. See, e.g., Guhan and Muniyappa (2003) Crit Rev Biochem Mol Biol 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764.

Nuclease agents can further comprise restriction endonucleases, which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example, in the REBASE database (webpage at rebase.neb.com; Roberts et al., (2003) *Nucleic Acids Res* 31:418-20); Roberts et al., (2003) *Nucleic Acids Res* 31:1805-12; and Belfort et al., (2002) in *Mobile DNA II*, pp. 761-783, Eds. Craigie et al., (ASM Press, Washington, DC), each of which is herein incorporated by reference in its entirety for all purposes.

Nuclease agents can further comprise Clustered Regularly Interspersed Short Palindromic Repeats (CRISPR)/CRISPR-associated (Cas) systems or components of such systems. CRISPR/Cas systems include transcripts and other elements involved in the expression of, or directing the activity of, Cas genes. CRISPR/Cas systems utilize CRISPR complexes (comprising a guide RNA (gRNA) complexed with a Cas protein) for site-directed cleavage of nucleic acids. See, e.g., WO/2013/176772A1, WO/2014/065596A1, WO/2014/089290A1, WO/2014/093622A2, WO/2014/099750A2, WO/2013142578A1, WO 2014/131833A1, US 2015/0159175, US 2015/0159174, US 2014/0310828, and US 2014/0309487, each of which is herein incorporated by reference in its entirety for all purposes.

Cas proteins, such as Cas9, generally comprise at least one RNA recognition or binding domain that interacts with guide RNAs (gRNAs), and one or more nuclease domains. Cas proteins can also be fusion proteins, for example, to regulate transcription or expression of a gene. For example, a Cas protein can be fused to a cleavage domain, an epigenetic modification domain, a transcriptional activation domain, or a transcriptional repressor domain. See WO 2014/089290, incorporated herein by reference in its entirety for all purposes. Examples of the Cas9 family members are described in WO 2014/131833, herein incorporated by reference in its entirety for all purposes.

A "guide RNA" or "gRNA" includes an RNA molecule that binds to a Cas protein and targets the Cas protein to a specific location within a target DNA. Guide RNAs can comprise two segments: a "DNA-targeting segment" and a "protein-binding segment." Some gRNAs comprise two separate RNA molecules: (1) an "activator-RNA" ("trans-acting CRISPR RNA" or "tracrRNA" or "scaffold"); and (2) a "targeter-RNA" ("CRISPR RNA" or "targeter-RNA" or "crRNA" or "crRNA repeat"). A crRNA comprises both the DNA-targeting segment (single-stranded) of the gRNA and a stretch of nucleotides that forms one half of the dsRNA duplex of the protein-binding segment of the gRNA. A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

Other gRNAs are a single RNA molecule (single RNA polynucleotide), which can also be called a "single-molecule gRNA," a "single-guide RNA," or an "sgRNA." See, e.g., WO/2013/176772A1, WO/2014/065596A1, WO/2014/089290A1, WO/2014/093622A2, WO/2014/099750A2, WO/2013142578A1, and WO 2014/131833A1, each of which is herein incorporated by reference in its entirety for all purposes. The terms "guide RNA" and "gRNA" include both double-molecule gRNAs and single-molecule gRNAs.

The crRNA and the corresponding tracrRNA hybridize to form a gRNA. The crRNA additionally provides the single-stranded DNA-targeting segment that hybridizes to a CRISPR RNA recognition sequence in a target DNA. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes. Site-specific cleavage of target DNA by Cas9 can occur at locations determined by both (i) base-pairing complementarity between the gRNA and the target DNA and (ii) a short motif, called the protospacer adjacent motif (PAM), in the target DNA. The PAM can flank the CRISPR RNA recognition sequence.

ii. Targeting Vectors

Targeting vectors can be employed to introduce a nucleic acid insert into a genomic target locus and comprise the nucleic acid insert and homology arms that flank the nucleic acid insert. Targeting vectors can be in linear form or in circular form, and can be single-stranded or double-stranded. For ease of reference, the homology arms are referred to herein as 5' and 3' (i.e., upstream and downstream) homology arms. This terminology relates to the relative position of the homology arms to the nucleic acid insert within the targeting vector. The 5' and 3' homology arms correspond to regions within the targeted locus, which are referred to herein as "5' target sequence" and "3' target sequence," respectively.

Nucleic acid inserts include segments of DNA to be integrated at genomic target loci. Integration of a nucleic acid insert at a target locus can result in addition of a nucleic acid sequence of interest to the target locus, deletion of a nucleic acid sequence of interest at the target locus, and/or replacement of a nucleic acid sequence of interest at the target locus. Moreover, the nucleic acid insert or the corresponding nucleic acid at the target locus being replaced can be of any desired length, including, for example, between about 10 nucleotides to about 500 kb in length or more.

Nucleic acid inserts can comprise a polynucleotide encoding a selection marker, a reporter gene, or one or more expression cassettes or deletion cassettes. A given cassette can comprise a nucleotide sequence of interest, a nucleic acid encoding a selection marker, and/or a reporter gene, along with various regulatory components that influence expression.

The insert nucleic acid can comprise a nucleic acid flanked with site-specific recombination target sequences (e.g., loxP, lox511, lox2272, lox66, lox71, loxM2, lox5171, FRT, FRT11, FRT71, attp, att, FRT, rox). The entire insert nucleic acid can be flanked by such site-specific recombination target sequences, or any region or individual polynucleotide of interest within the insert nucleic acid can be flanked by such sites. For example, the site-specific recombination sites can flank a polynucleotide encoding a selection marker and/or a reporter gene contained within the insert nucleic acid. Following integration of the insert nucleic acid at a targeted locus, the sequences between the site-specific recombination sites can be removed.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found on the targeting vector can be any degree of sequence identity that allows for homologous recombination to occur. Moreover, a corresponding region of homology between the homology arm and the corresponding target sequence can be of any length that is sufficient to promote homologous recombination at the cleaved recognition site. For example, a given homology arm and/or corresponding target sequence can comprise corresponding regions of homology that are, for example, about 5 kb to about 300 kb in length or more such that the homology arm has sufficient homology to undergo homologous recombination with the corresponding target sequences within the genome of the cell.

Nuclease agents (e.g., CRISPR/Cas systems) can be employed in combination with targeting vectors to aid in the modification of a target locus. Such nuclease agents may promote homologous recombination between the targeting vector and the target locus. When nuclease agents are employed in combination with a targeting vector, the targeting vector can comprise 5' and 3' homology arms corresponding to 5' and 3' target sequences located in sufficient proximity to a nuclease cleavage site so as to promote the occurrence of a homologous recombination event between the target sequences and the homology arms upon a nick or double-strand break at the nuclease cleavage site. The target sequences within the targeted locus that correspond to the 5' and 3' homology arms of the targeting vector are "located in sufficient proximity" to a nuclease cleavage site if the distance is such as to promote the occurrence of a homologous recombination event between the 5' and 3' target sequences and the homology arms upon a nick or double-strand break at the recognition site.

Combined use of the targeting vector (including, for example, a large targeting vector (LTVEC) or a small targeting vector (smallTVEC)) with a nuclease agent can result in an increased targeting efficiency compared to use of the targeting vector alone.

1. Small Targeting Vectors (SmallTVECs)

Some methods utilize a small targeting vector or smallTVEC. Examples of using smallTVECs to make targeted genetic modifications to the Y chromosome are disclosed, for example, in WO 2015/200805 and US 2015/0376651, each of which is incorporated by reference in its entirety for all purposes. A "smallTVEC" includes a targeting vector that comprises short homology arms. The length of a homology arm on a smallTVEC can be, for example from about 400 bp to about 1000 bp. A homology arm of a smallTVEC can be of any length that is sufficient to promote a homologous recombination event with a corresponding target site, including for example, from about 400 bp to about 500 bp, from about 500 bp to about 600 bp, from about 600 bp to about 700 bp, from about 700 bp to about 800 bp, from about 800 bp to about 900 bp, or from about 900 bp to about 1000 bp. A preferred length of a homology arm on a smallTVEC is from about 700 bp to about 800 bp. The sum total of the 5' and 3' homology arms of a smallTVEC can be, for example, about 0.5 kb to about 10 kb. In such methods, the short length of the homology arms can increase the targeting efficiency as compared to a targeting vector with longer homology arms. Due to the nature of the Y chromosome which has highly repetitive sequences, the short arms of the smallTVECs can allow for highly specific targeting on the Y chromosome.

2. Large Targeting Vectors (LTVECs)

Some targeting vectors are "large targeting vectors" or "LTVECs," which includes targeting vectors that comprise homology arms that correspond to and are derived from nucleic acid sequences larger than those typically used by other approaches intended to perform homologous recombination in cells. Examples of generating targeted genetic modifications using LTVECs are disclosed, for example, in WO 2015/088643, US 2015/0159175, US 2015/0159174, US 2014/0310828, US 2014/0309487, and US 2013-0309670, each of which is herein incorporated by reference in its entirety for all purposes. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein).

Examples of LTVECs include vectors derived from a bacterial artificial chromosome (BAC), a human artificial chromosome, or a yeast artificial chromosome (YAC). Non-limiting examples of LTVECs and methods for making them are described, e.g., in U.S. Pat. Nos. 6,586,251; 6,596,541; 7,105,348; and WO 2002/036789, each of which is herein incorporated by reference in its entirety for all purposes. LTVECs can be in linear form or in circular form.

LTVECs can be of any length, including, for example, at least 10 kb or from about 50 kb to about 400 kb or greater. The size of an LTVEC can be too large to enable screening of targeting events by conventional assays, e.g., southern blotting and long-range (e.g., 1 kb to 5 kb) PCR. The sum total of the 5' homology arm and the 3' homology arm can be, for example, at least 10 kb (each homology arm can range, for example, from about 5 kb to about 200 kb). The LTVEC and nucleic acid insert can be designed to allow for a deletion at the target locus of a length, for example, from about 5 kb to about 3 Mb (e.g., about 500 kb or greater). Likewise, the LTVEC and nucleic acid insert can be designed to allow for an insertion into the target locus of an exogenous nucleic acid sequence of a length, for example, ranging from about 5 kb to about 400 kb or greater.

iii. Introducing Components into Cells

Various methods and compositions are provided herein to allow for introduction of a nucleic acid into a cell. In some cases, the system employed for introducing the nucleic acid allows for the targeted integration at a specific genomic locus. Such systems employ a variety of components and for ease of reference, the term "targeted genomic integration system" generically includes all the components required for an integration event (e.g., one or more of nuclease agents, nuclease cleavage sites, insert DNA polynucleotides, targeting vectors, target genomic loci, and polynucleotides of interest).

The methods provided herein can comprise introducing into a cell one or more polynucleotides or polypeptide constructs comprising one or more components of a targeted genomic integration system. "Introducing" includes presenting to the cell the sequence (polypeptide or polynucleotide) in such a manner that the sequence gains access to the interior of the cell. The methods provided herein do not depend on a particular method for introducing a nucleic acid or protein into the cell, only that the nucleic acid or protein gains access to the interior of a least one cell. Methods for introducing nucleic acids and proteins into various cell types are known in the art and include, for example, stable transfection methods, transient transfection methods, and virus-mediated methods.

Transfection protocols as well as protocols for introducing polypeptides or polynucleotide sequences into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc Natl Acad Sci USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

In some cases, the introduction of nucleic acids or proteins into a cell is mediated by electroporation, by intracytoplasmic injection, by viral infection, by adenovirus, by lentivirus, by retrovirus, by transfection, by lipid-mediated transfection, or by Nucleofection™.

The introduction of nucleic acids or proteins into the cell can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

When both nuclease agents and targeting vectors (e.g., LTVECs) are introduced into the cell, they can be introduced simultaneously. Alternatively, the nuclease agent can be introduced separately from the targeting vector. For example, the nuclease agent can be introduced prior to the introduction of the targeting vector, or it can be introduced following introduction of the targeting vector.

iv. Types of Modifications

Various types of targeted genetic modifications can be used to silence a region of the Y chromosome (e.g., via deletion or disruption of a region of the Y chromosome). For example, a decreased level and/or activity of a protein can be achieved by a targeted genetic modification to the gene encoding the protein or to a genomic locus that affects or regulates levels or activity of the protein. Such targeted modifications can include, for example, additions of one or more nucleotides, deletions of one or more nucleotides, substitutions of one or more nucleotides, a point mutation, a knockout of a polynucleotide of interest or a portion thereof, a knock-in of a polynucleotide of interest or a portion thereof, a replacement of an endogenous nucleic acid sequence with a heterologous, exogenous, or orthologous nucleic acid sequence, a domain swap, an exon swap, an intron swap, a regulatory sequence swap, a gene swap, or a combination thereof. For example, at least 1, 2, 3, 4, 5, 7, 8, 9, 10 or more nucleotides can be changed to form the targeted genomic modification. The deletions, insertions, or replacements can be of any size, as disclosed elsewhere herein. Various methods can be used to generate a targeted genetic modification. See, e.g., Wang et al. (2013) *Cell* 153:910-918; Mandalos et al. (2012) *PLOS ONE* 7:e45768: 1-9; and Wang et al. (2013) *Nat Biotechnol.* 31:530-532, each of which is herein incorporated by reference in its entirety for all purposes.

A deletion on the Y chromosome can be a deletion of any nucleic acid sequence, such as a gene that is associated with fertility/infertility or with sex development. The deletion on the Y chromosome can comprise a deletion of multiple genes. For example, 1, 2, 3, 4, 5, 6, 7, 8, 9, 10 or more genes can be deleted. If two nuclease agents are used, the sequence between their corresponding recognition sites can be deleted. The deletion can range, for example, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, from about 700 kb to about 800 kb, from about 800 kb to about 900 kb, from about 900 kb to about 1 Mb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb. For example, the deletion can be greater than 500 kb, from about 500 kb to about 600 kb, or about 500 kb.

Likewise, a disruption of the Y chromosome can be a disruption of any nucleic acid sequence, such as a gene that is associated with fertility/infertility or with sex development. The disruption of the Y chromosome can comprise a disruption of multiple genes. For example, 1, 2, 3, 4, 5, 6, 7, 8, 9, 10 or more genes can be disrupted. Disruption of the endogenous nucleic acid sequence can result, for example, when a double-strand break created by a nuclease is repaired by non-homologous end joining (NHEJ)-mediated DNA repair, which generates a mutant allele comprising an insertion or a deletion of a nucleic acid sequence and thereby causes disruption of that genomic locus. Examples of disruption include alteration of a regulatory element (e.g., promoter or enhancer), a missense mutation, a nonsense mutation, a frame-shift mutation, a truncation mutation, a null mutation, or an insertion or deletion of small number of nucleotides (e.g., causing a frameshift mutation). Disruption can result in inactivation (i.e., loss of function) or loss of the allele.

v. Identifying Cells with Targeted Modification

Various methods can be used to identify cells having a targeted modification, such as a deletion or an insertion. Such methods can comprise identifying one cell having the targeted modification at a target locus (e.g., between first and second CRISPR RNA recognition sequences). Screening can be done to identify such cells with modified genomic loci.

The screening step can comprise a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), Invader Probes®, MMP assays, TAQMAN® Molecular Beacon, or Eclipse™ probe technology (see, e.g., US2005/ 0144655, which is incorporated by reference herein in its entirety for all purposes).

F. Cells and Animals

The animals in the above methods and compositions (e.g., cells, embryos) can include any animal, including mammals, fishes, and birds. Mammals include, for example, humans, non-human mammals, non-human primates (e.g., monkeys, marmosets, rhesus monkeys, and apes), rodents (e.g., mice, rats, hamsters, and guinea pigs), livestock or agricultural mammals (e.g., goats, bulls, deer, bison, equine species such as horses, bovine species such as cow and steer, ovine species such as sheep, and porcine species such as pigs and boars), and domesticated mammals (e.g., cats, dogs, rabbits, and ferrets). Birds include, for example, chickens, turkeys, ostrich, geese, and ducks. Non-human animals can be any animals other than humans. For example, the non-human animal can be a non-human mammal, a rodent, a mouse, a rat, a hamster, a monkey, an agricultural mammal, a domestic mammal, a fish, or a bird.

The pluripotent cells in the above methods and compositions include any undifferentiated cells that possess the ability to develop into more than one differentiated cell type. For example, the pluripotent cells in the above methods and compositions can be embryonic stem (ES) cells or induced pluripotent stem (iPS) cells. ES cells include embryo-derived totipotent or pluripotent cells that are capable of contributing to any tissue of the developing embryo upon introduction into an embryo. Alternatively, they can be adult stem cells, or developmentally-restricted progenitor cells. The pluripotent cells can be from any animal. For example, the pluripotent cell can be a human ES cell, a non-human ES cell, a mammalian ES cell, a non-human mammalian ES cell, a rodent ES cell, a mouse ES cell, a rat ES cell, or a hamster ES cell.

For those mammals for which suitable genetically modifiable pluripotent cells are not readily available, other methods are employed to reprogram somatic cells into pluripotent cells, such as by introducing into somatic cells (e.g., fibroblasts) of a combination of pluripotency-inducing factors, including, but not limited to, Oct3/4, Sox2, KLF4, Myc, Nanog, LIN28, and Glis1.

A mouse pluripotent cell, totipotent cell, or host embryo can be from any strain of mouse including, for example, inbred strains, hybrid strains, and outbred strains. Examples of mouse strains include a 129 strain, a C57BL strain (e.g., a C57BL/6 strain), a mix of 129 and C57BL/6 (e.g., 50% 129 and 50% C57BL/6), a BALB/c strain, and a Swiss Webster strain. Examples of 129 strains include 129P1, 129P2, 129P3, 129X1, 129S1 (e.g., 129S1/SV, 129S1/ SvIm), 129S2, 129S4, 129S5, 12959/SvEvH, 129S6 (129/ SvEvTac), 129S7, 129S8, 129T1, and 129T2 (see, e.g., Festing et al. (1999) Revised nomenclature for strain 129 mice, Mammalian Genome 10:836). Examples of C57BL strains include C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/01a. Mice can be mixes of an aforementioned 129 strain (e.g., a 129S6 (129/SvEvTac) strain) and an aforementioned C57BL/6 strain, mixes of one or more aforementioned 129 strains, or mixes of one or more aforementioned C57BL strains. Mice can also be from a strain excluding 129 strains. For example, a mouse or mouse cell employed in the methods provided herein can be can be a mix of 129 and C57BL/6 strains, a mix of BALB/c and C57BL/6 strains, a mix of 129 and BALB/c strains, or a mix of BALB/c, C57BL/6, and 129 strains. For example, a mouse or mouse cell employed in the methods provided herein can be at least partially from a BALB/c strain (e.g., at least about 25%, at least about 50%, at least about 75% derived from a BALB/c strain, or about 25%, about 50%, about 75%, or about 100% derived from a BALB/c strain). In one example, the mice or mouse cells can have a strain comprising 50% BALB/c, 25% C57BL/6, and 25% 129. Alternatively, the mice or mouse cells can comprise a strain or strain combination that excludes BALB/c.

The Y chromosome in a mouse XY pluripotent cell can be from any strain. For example, the Y chromosome in the mouse XY pluripotent cell (e.g., mouse XY ES cell) can be from a 129 strain or a C57BL strain (e.g., a C57BL/6 strain). Alternatively, the Y chromosome can be from a BALB/c strain. An example of a mouse XY ES cell having a Y chromosome from a 129 strain is a VGF1 mouse ES cell. VGF1 (also known as F1H4) mouse ES cells were derived from hybrid embryos produced by crossing a female C57BL/6NTac mouse to a male 12956/SvEvTac mouse. Therefore, VGF1 ES cells contain a Y chromosome from 12956/SvEvTac mouse. See, e.g., Auerbach, W. et al. (2000) Biotechniques 29, 1024-1028, 1030, 1032, herein incorporated by reference in its entirety for all purposes. Alternatively, the Y chromosome in the mouse XY pluripotent cell is not from a 129 strain (e.g., is from a C57BL/6 strain). The VGB6 ES cell line was derived from a single male (XY) blastocyst embryo produced from the mating of a male and a female mouse of the C57BL/6NTac strain.

A rat pluripotent cell, totipotent cell, or host embryo can be from any rat strain, including, for example, inbred strains, hybrid strains, and outbred strains. Examples of rat strains include an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rat pluripotent cells, totipotent cells, or host embryos can also be obtained from a strain derived from a mix of two or more strains recited above. For example, the rat pluripotent cell, totipotent cell, or host embryo can be derived from a strain selected from a DA strain and an ACI strain. The ACI rat strain is characterized as having black agouti, with white belly and feet and an $RT1^{av1}$ haplotype. Such strains are available from a variety of sources including Harlan Laboratories. An example of a rat ES cell line from an ACI rat is the ACI.G1 rat ES cell. The Dark Agouti (DA) rat strain is characterized as having an agouti coat and an $RT1^{av1}$ haplotype. Such rats are available from a variety of sources including Charles River and Harlan Laboratories. Examples of a rat ES cell line from a DA rat and are the DA.2B rat ES cell line or the DA.2C rat ES cell line. Other examples of rat strains are provided, for example, in US 2014/0235933, US 2014/0310828, and US 2014/0309487, each of which is herein incorporated by reference in its entirety for all purposes.

In some methods and compositions, the animal is not from one or more of the following: *Akodon* spp., *Myopus* spp., *Microtus* spp., and *Talpa* spp. Likewise, in some methods and compositions, the animal is not any species of which a normal wild-type characteristic is XY female fertility.

III. Methods of Screening Compounds

Methods and compositions are provided for screening for compounds that have feminizing activity on an animal XY pluripotent or totipotent cell or clone (i.e., that increase the propensity of the cell or clone for producing fertile, phenotypically female XY animals in an F0 generation) when the cell or clone is cultured in the presence of the compound. The propensity of animal XY pluripotent or totipotent cell clones to produce fertile, phenotypically female XY animals in an F0 generation is inversely correlated with the expression or activity of Ddx3y, Uty, and Eif2s3y in those clones. Loss of expression of one or more of these genes in animal XY pluripotent or totipotent cells (e.g., XY ES cells) can predict which cell clones will produce XY female animals in an F0 generation: the more silencing of Ddx3y, Uty, and Eif2s3y that is observed, the higher the propensity of the XY ES cell clone to produce fertile, phenotypically female XY animals in an F0 generation (see, e.g., Example 3). Likewise, loss of activity or decreased expression and/or activity of one or more of these genes in animal XY pluripotent or totipotent cells (e.g., XY ES cells) can predict which cell clones will produce XY female animals in an F0 generation: the lower the expression of Ddx3y, Uty, and Eif2s3y that is observed, the higher the propensity of the XY ES cell clone to produce fertile, phenotypically female XY animals in an F0 generation (see, e.g., Example 3). In other words, expression and/or activity of one or more of these genes can be a surrogate marker for predicting XY female production.

This information can be used to screen for compounds that produce animal XY pluripotent or totipotent cells having a high propensity for producing fertile, phenotypically female XY animals in an F0 generation. For example, such a method can comprise culturing a first population and a second population of non-human animal XY pluripotent or totipotent cells in a medium comprising a base medium and supplements suitable for maintaining the pluripotency or totipotency of the cells, wherein the first population is cultured in the presence of a target compound and the second population is cultured in the absence of the target compound. The method can then further comprise assaying one or more of the non-human animal XY pluripotent or totipotent cells in each of the first and second populations for expression and/or activity of one or more of Ddx3y, Uty, and Eif2s3y, whereby feminizing activity is identified by a decrease in the expression and/or activity of the one or more of Ddx3y, Uty, and Eif2s3y in the one or more cells from the first population compared to the one or more cells from the second population. That is, the method can further comprise assaying one or more of the non-human animal XY pluripotent or totipotent cells in each of the first and second populations for expression and/or activity of one or more of Ddx3y, Uty, and Eif2s3y, and then selecting the target compound if the expression and/or activity of the one or more of Ddx3y, Uty, and Eif2s3y is decreased in the one or more cells from the first population compared to the one or more cells from the second population. The decrease in expression and/or activity can be of Ddx3y, of Uty, of Eif2s3y, of Ddx3y and Uty, of Ddx3y and Eif2s3y, of Uty and Eif2s3y, or of Ddx3y, Uty, and Eif2s3y.

Examples of compounds that can be screened include antibodies, antigen-binding proteins, site-specific DNA binding proteins (e.g., CRISPR-Cas complexes, CRISPRi libraries, CRISPRa libraries), polypeptides, beta-turn mimetics, polysaccharides, phospholipids, hormones, prostaglandins, steroids, aromatic compounds, heterocyclic compounds, benzodiazepines, oligomeric N-substituted glycines, and oligocarbamates. Large combinatorial libraries of the compounds can be constructed by the encoded synthetic libraries (ESL) method described in WO 1995/012608, WO 1993/006121, WO 1994/008051, WO 1995/035503, and WO 1995/030642, each of which is herein incorporated by reference in its entirety for all purposes. Peptide libraries can also be generated by phage display methods. See, e.g., U.S. Pat. No. 5,432,018, herein incorporated by reference in its entirety for all purposes. Use of libraries of guide RNAs for targeting CRISPR-Cas systems to different genes are disclosed, e.g., in WO 2014/204727, WO 2014/093701, WO 2015/065964, WO 2016/011080, Shalem et al. (2014) 343 (6166):84-87 (genome-scale CRISPR-Cas9 knockout (GeCKO) library), and Konermann et al. (2015) 517(7536): 583-588 (CRISPR/Cas9 Synergistic Activation Mediator (SAM) pooled library) each of which is herein incorporated by reference in its entirety for all purposes.

The first population of cells can be cultured in the presence of the target compound for any length of time. As an example, the first population of cells can be cultured in the presence of the target compound at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to assaying.

The medium can be a medium sufficient for maintaining the pluripotency or totipotency of the cells but without altering the cells' capacity to give rise to fertile female progeny. Alternatively, the medium can be a feminizing medium. Feminizing medium (e.g., a base medium and supplements suitable for maintaining animal XY pluripotent or totipotent cells in culture, wherein the base medium or the medium comprising the base medium and supplements has an osmolality from about 200 mOsm/kg to less than about 329 mOsm/kg) and methods for maintaining cells in such medium are disclosed elsewhere herein.

The feminizing activity of the target compound can be identified in a number of ways. For example, the feminizing activity can be identified by a lack of expression and/or activity of the one or more of Ddx3y, Uty, and Eif2s3y in the cells from the first population. Alternatively, the feminizing activity can be identified by a decrease in the expression and/or activity of all of Ddx3y, Uty, and Eif2s3y in the cells from the first population compared to the cells from the second population. Alternatively, the feminizing activity can be identified by a lack of expression and/or activity of all of Ddx3y, Uty, and Eif2s3y in the cells from the first population. Methods for assessing expression and/or activity are discussed in further detail below.

Some screening methods can further comprise selecting a donor non-human animal XY pluripotent or totipotent cell from the first population for producing a fertile, phenotypically female XY non-human animal in an F0 generation based on the expression and/or activity of the one or more of Ddx3y, Uty, and Eif2s3y, wherein the proportion of the fertile, phenotypically female XY non-human animals in the F0 generation is inversely related to the expression and/or activity of the one or more of Ddx3y, Uty, and Eif2s3y.

The donor animal XY pluripotent or totipotent cell can then be introduced into a host embryo, wherein the host embryo is capable of producing a fertile phenotypically female XY animal in an F0 generation. For example, the host embryo can be a pre-morula stage embryo, and the host embryo can be cultured to the blastocyst stage upon introduction of the donor animal XY pluripotent or totipotent cell. Animals, embryos, methods for introducing donor XY pluripotent or totipotent cells into embryos, and methods of producing F0 animals are disclosed elsewhere herein.

The animal XY pluripotent or totipotent cell can be maintained in the medium for various amounts of time prior to the assaying step and/or prior introduction into a host embryo. For example, the animal XY pluripotent or totipotent cell can be maintained in the feminizing medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to the assaying step and/or introduction into the host embryo. Alternatively, the animal XY pluripotent or totipotent cell can be maintained in the feminizing medium for no more than 1 day, 2 days, 3 days, 4 days, 5 days, 6 days, 7 days, 8 days, 9 days, 10 days, 11 days, 12 days, 13 days, 2 weeks, 3 weeks, or 4 weeks prior to the assaying step and/or introduction into the host embryo. In some methods, the XY pluripotent or totipotent cell is cultured or maintained in the feminizing medium until injection of the cell into an embryo. In other methods, the embryo into which the XY pluripotent or totipotent cell was injected is cultured or maintained in the feminizing medium until being transferred to a surrogate mother.

The donor cell can be selected after assaying one or more cells from the first population for expression and/or activity for one or more of Ddx3y, Uty, and Eif2s3y. The assaying step can comprise assaying the cell or clone itself and determining a level of expression and/or activity for one or more of Ddx3y, Uty, and Eif2s3y. Alternatively, the assaying step can comprise assaying several subclones derived from the clone and determining, for example, the percentage of subclones having reduced expression and/or activity or lacking expression and/or activity of one or more of Ddx3y, Uty, and Eif2s3y. Alternatively, the assaying step can comprise assaying several subclones derived from the clone and determining the comparative expression and/or activity of one or more of Ddx3y, Uty, and Eif2s3y among the subclones. Expression and/or activity of one or more of Ddx3y, Uty, and Eif2s3y can be decreased, or the expression and/or activity of all of Ddx3y, Uty, and Eif2s3y can be decreased. Alternatively, the donor animal XY pluripotent or totipotent cell lacks expression and/or activity of one or more of Ddx3y, Uty, and Eif2s3y or lacks expression and/or activity of all of Ddx3y, Uty, and Eif2s3y. For example, there can be a lack of detectable expression of all of Ddx3y, Uty, and Eif2s3y.

Expression can be assessed at the protein level or the mRNA level. The expression level of a polypeptide may be measured directly, for example, by assaying for the level of the polypeptide in the cell or organism (e.g., Western blot analysis, FACS analysis, ELISA), or indirectly, for example, by measuring the activity of the polypeptide. In other instances, reduced expression and/or activity of a gene can be measured using methods that include, for example, Southern blot analysis, DNA sequencing, PCR analysis, Northern blot analysis, quantitative RT-PCR analysis, Next Generation Sequencing (NGS), microarray analysis, or phenotypic analysis. For example, expression of a gene can be assessed by measuring mRNA levels by RT-PCR, RNA-seq, digital PCR, or any other suitable method for measure mRNA levels. As one example, RNA levels can be measured by RT-PCR relative to a control gene, such as B2m. In some cases, for example, the ΔCt between the control gene (e.g., B2m) and the target gene can be at least 2, at least 4, at least 6, or at least 8. Likewise, in some cases, there will be no detectable RNA for the target gene after 30, 31, 32, 33, 34, 35, 36, 37, 38, 39, or 40 cycles.

Optionally, when measuring expression levels of the mRNA or polypeptide, a control experiment can be done to confirm the presence of the Y chromosome. For example, a TAQMAN® copy number assay can be done to confirm the presence of one copy of the Y chromosome by using probes to different genomic sequences on the Y chromosome. Such assays are designed to measure copy number variation within the genome.

A decrease in expression or activity of a gene or the protein it encodes in a subject cell, embryo, or animal can include any statistically significant reduction in expression or activity levels when compared to an appropriate control cell, embryo, or animal or population of control cells, embryos, or animals. In general, the expression or activity is decreased if the expression or activity is statistically lower than the expression or activity in an appropriate control cell, embryo, or animal derived therefrom (e.g., an animal XY pluripotent cell) that has been cultured in an appropriate control medium that is not a feminizing medium, an animal XY pluripotent cell that historically produces entirely male mice, notwithstanding its being cultured in feminizing medium). Such a decrease includes a reduction of at least 1%, 5%, 10%, 20%, 30%, 40%, 50%, 60%, 70%, 80%, 90%, 95%, 99%, or greater relative to a control cell. Statistical significance means p≤0.05. A decrease in expression or activity can occur via any mechanism at any stage. For example, a decrease in expression could occur via events or regulation that occurs during transcription, post-transcription, during translation, or post-translation.

A "subject cell" is one that has been cultured in feminizing medium (e.g., low-osmolality medium) or is a cell which is descended from a cell cultured in feminizing medium. A "control" or "control cell" provides a reference point for measuring changes in phenotype of the subject cell. A control cell is preferably as closely matched as possible with the subject cell (for example, the respective cells can originate from the same cell line or the same clone or can have the same genotype) except it was either not cultured in feminizing medium or lacks the capability or has reduced capability to produce XY female mice notwithstanding its being cultured in feminizing medium. For example, the control cell may comprise: (a) a cell of the same genotype or that originates from the same cell line or clone as the subject cell but which has been cultured in an appropriate control medium that is not a feminizing medium (e.g., DMEM or another type of medium that is sufficient for maintaining pluripotency or totipotency of an animal XY pluripotent or totipotent cell but does not alter the cell by giving it the capacity to give rise to fertile female progeny); (b) an animal XY pluripotent or totipotent cell genetically identical to the subject cell or derived from the same cell line or clone but which is not genetically altered or exposed to conditions or stimuli that would give it the potential to generate fertile female XY animals; and (c) an animal XY pluripotent and totipotent cell that is cultured in feminizing medium (e.g., low-osmolality medium) but historically produces entirely male animals notwithstanding its being cultured in feminizing medium. For example, the control cell can be an animal XY pluripotent or totipotent cell that has been cultured in a medium that is sufficient for maintaining the pluripotency or totipotency of the cell but does not alter the cell's capacity to give rise to fertile female progeny. Optionally, the decreased expression and/or activity can be relative to a control non-human animal XY pluripotent or totipotent cell from the second population.

In some experiments, two or more of the cells or clones in the first population are assayed for expression and/or activity of one or more of Ddx3y, Uty, and Eif2s3y. The cell or clone with the lowest expression and/or activity of the one or more of Ddx3y, Uty, and Eif2s3y can then be selected to be a donor animal XY pluripotent or totipotent cell or clone, wherein the donor animal XY pluripotent or totipotent cell is capable of producing a fertile, phenotypically female XY animal in an F0 generation.

Selecting a donor animal XY pluripotent or totipotent cell having decreased expression and/or activity of one or more of Ddx3y, Uty, and Eif2s3y can result in higher percentages of F0 progeny that are phenotypically female XY animals, higher percentages of F0 progeny that are phenotypically female XY animals that are fertile, higher percentages of F0 XY progeny that are phenotypically female XY animals that are fertile, higher percentages of F0 XY females that are fertile, higher average numbers of lifetime litters for F0 XY females or fertile F0 XY females, and higher average litter sizes for F0 XY females or fertile F0 XY females. Such F0 progeny can be produced from the donor XY pluripotent or totipotent animal cells following introduction of the cells into a host embryo and gestation of the host embryo using the methods disclosed elsewhere herein.

The increase can be any statistically significant increase when compared to the appropriate control. For example, the increase can be at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, or 5-fold when compared to the appropriate control.

For example, the percentage of F0 progeny or F0 XY progeny that are phenotypically female XY animals can be increased by selecting a donor animal XY pluripotent or totipotent cell having decreased expression and/or activity of one or more of Ddx3y, Uty, and Eif2s3y. In some methods, the percentage of the F0 progeny or F0 XY progeny that are phenotypically female XY animals is higher for F0 progeny derived from donor XY pluripotent or totipotent animal cells having decreased expression and/or activity of one or more of Ddx3y, Uty, and Eif2s3y when compared to F0 progeny derived from XY pluripotent or totipotent animal cells having higher expression and/or activity of one or more of Ddx3y, Uty, and Eif2s3y.

The percentage of F0 progeny or F0 XY progeny that are fertile, phenotypically female XY animals can also be increased by selecting a donor animal XY pluripotent or totipotent cell having decreased expression and/or activity of one or more of Ddx3y, Uty, and Eif2s3y. In some methods, the percentage of the F0 progeny or F0 XY progeny that are fertile, phenotypically female XY animals is higher for F0 progeny derived from donor XY pluripotent or totipotent animal cells having decreased expression and/or activity of one or more of Ddx3y, Uty, and Eif2s3y when compared to F0 progeny derived from XY pluripotent or totipotent animal cells having higher expression and/or activity of one or more of Ddx3y, Uty, and Eif2s3y.

The percentage of F0 XY females that are fertile can also be increased by selecting a donor animal XY pluripotent or totipotent cell having decreased expression and/or activity of one or more of Ddx3y, Uty, and Eif2s3y. In some methods, the percentage of the F0 XY females that are fertile is higher for F0 XY progeny derived from donor XY pluripotent or totipotent animal cells having decreased expression and/or activity of one or more of Ddx3y, Uty, and Eif2s3y when compared to F0 XY progeny derived from XY pluripotent or totipotent animal cells having higher expression and/or activity of one or more of Ddx3y, Uty, and Eif2s3y.

The percentage of F0 XY females that are capable of producing normal numbers of litters and/or normal litter sizes (e.g., compared to wild type female animals) can also be increased by selecting a donor animal XY pluripotent or totipotent cell having decreased expression and/or activity of one or more of Ddx3y, Uty, and Eif2s3y. In some methods, the percentage of the F0 XY females that are capable of producing normal numbers of litters and/or normal litter sizes is higher for F0 XY progeny derived from donor XY pluripotent or totipotent animal cells having decreased expression and/or activity of one or more of Ddx3y, Uty, and Eif2s3y when compared to F0 XY progeny derived from XY pluripotent or totipotent animal cells having higher expression and/or activity of one or more of Ddx3y, Uty, and Eif2s3y.

The average litter size produced by F0 XY females or fertile F0 XY females can also be increased by selecting a donor animal XY pluripotent or totipotent cell having decreased expression and/or activity of one or more of Ddx3y, Uty, and Eif2s3y. In some methods, the average litter size produced by F0 XY females or fertile F0 XY females is higher for F0 XY females or fertile F0 XY females derived from donor XY pluripotent or totipotent animal cells having decreased expression and/or activity of one or more of Ddx3y, Uty, and Eif2s3y when compared to F0 XY females or fertile F0 XY females derived from XY pluripotent or totipotent animal cells having higher expression and/or activity of one or more of Ddx3y, Uty, and Eif2s3y.

The average number of lifetime litters produced by F0 XY females or fertile F0 XY females can also be increased by selecting a donor animal XY pluripotent or totipotent cell having decreased expression and/or activity of one or more of Ddx3y, Uty, and Eif2s3y. In some methods, the average number of lifetime litters produced by F0 XY females or fertile F0 XY females is higher for F0 XY females or fertile F0 XY females derived from donor XY pluripotent or totipotent animal cells having decreased expression and/or activity of one or more of Ddx3y, Uty, and Eif2s3y when compared to F0 XY females or fertile F0 XY females derived from XY pluripotent or totipotent animal cells having higher expression and/or activity of one or more of Ddx3y, Uty, and Eif2s3y.

The average number of lifetime offspring produced by F0 XY females or fertile F0 XY females can also be increased by selecting a donor animal XY pluripotent or totipotent cell having decreased expression and/or activity of one or more of Ddx3y, Uty, and Eif2s3y. In some methods, the average number of lifetime offspring produced by F0 XY females or fertile F0 XY females is higher for F0 XY females or fertile F0 XY females derived from donor XY pluripotent or totipotent animal cells having decreased expression and/or activity of one or more of Ddx3y, Uty, and Eif2s3y when compared to F0 XY females or fertile F0 XY females derived from XY pluripotent or totipotent animal cells having higher expression and/or activity of one or more of Ddx3y, Uty, and Eif2s3y.

V. Methods of Optimizing Concentrations of Components in Feminizing Media

Methods and compositions are provided for optimizing the concentration of a component in a feminizing medium for increased feminizing activity on an animal XY pluripotent or totipotent cell or clone (i.e., increased propensity of the cell or clone for producing fertile, phenotypically female XY animals in an F0 generation). The propensity of animal XY pluripotent or totipotent cell clones to produce fertile, phenotypically female XY animals in an F0 generation is inversely correlated with the expression or activity of Ddx3y, Uty, and Eif2s3y in those clones. Loss of expression of one or more of these genes in animal XY pluripotent or totipotent cells (e.g., XY ES cells) can predict which cell clones will produce XY female animals in an F0 generation: the more silencing of Ddx3y, Uty, and Eif2s3y that is observed, the higher the propensity of the XY ES cell clone to produce fertile, phenotypically female XY animals in an F0 generation (see, e.g., Example 3). Likewise, loss of activity or decreased expression and/or activity of one or more of these genes in animal XY pluripotent or totipotent cells (e.g., XY ES cells) can predict which cell clones will produce XY female animals in an F0 generation: the lower the expression of Ddx3y, Uty, and Eif2s3y that is observed, the higher the propensity of the XY ES cell clone to produce fertile, phenotypically female XY animals in an F0 generation (see, e.g., Example 3). In other words, expression and/or activity of one or more of these genes can be a surrogate marker for predicting XY female production.

This information can be used to screen for optimal concentrations of media components to have increased feminizing effects and produce animal XY pluripotent or totipotent cells having a high propensity for producing fertile, phenotypically female XY animals in an F0 generation. For example, such a method can comprise culturing a first population and a second population of non-human animal XY pluripotent or totipotent cells in a medium comprising a base medium and supplements suitable for maintaining the pluripotency or totipotency of the, wherein the first population is cultured in the presence of a first concentration of the target medium component and the second population is cultured in the presence of a second concentration of the target medium component that is different from the first concentration. The first concentration can be higher or lower than the second concentration. The method can then further comprise assaying one or more of the non-human animal XY pluripotent or totipotent cells in each of the first and second populations for expression and/or activity of one or more of Ddx3y, Uty, and Eif2s3y. The first concentration can then be selected if the expression and/or activity of the one or more of Ddx3y, Uty, and Eif2s3y is decreased in the one or more cells from the first population compared to the one or cells from the second population. The decrease in expression and/or activity can be of Ddx3y, of Uty, of Eif2s3y, of Ddx3y and Uty, of Ddx3y and Eif2s3y, of Uty and Eif2s3y, or of Ddx3y, Uty, and Eif2s3y.

Examples of media components whose concentrations can be altered include salts of an alkaline metal and a halide (e.g., sodium chloride), carbonic acid salts (e.g., sodium bicarbonate), glucose, fetal bovine serum (FBS), glutamine, antibiotic(s), penicillin and streptomycin (e.g., penstrep), pyruvate salts (e.g., sodium pyruvate), nonessential amino acids (e.g., MEM NEAA), 2-mercaptoethanol, and Leukemia Inhibitory Factor (LIF). Other media components whose concentrations can be altered are listed in Table 1. Typical media components are discussed in further detail elsewhere herein.

The first population of cells can be cultured in the presence of the target compound for any length of time. As an example, the first population of cells can be cultured in the presence of the target compound at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to assaying.

The medium can be a medium sufficient for maintaining the pluripotency or totipotency of the cells but without altering the cells' capacity to give rise to fertile female progeny. Alternatively, the medium can be a feminizing medium. Feminizing medium (e.g., a base medium and supplements suitable for maintaining animal XY pluripotent or totipotent cells in culture, wherein the base medium or medium comprising the base medium and supplements has an osmolality from about 200 mOsm/kg to less than about 329 mOsm/kg) and methods for maintaining cells in such medium are disclosed elsewhere herein.

The feminizing activity of the first concentration of the media component can be identified in a number of ways. For example, the first concentration can be selected if the cells from the first population lack of expression and/or activity of the one or more of Ddx3y, Uty, and Eif2s3y. Alternatively, the first concentration can be selected if the cells from the first population have decreased expression and/or activity of all of Ddx3y, Uty, and Eif2s3y compared to the cells from the second population. Alternatively, the first concentration can be selected if the cells from the first population lack expression and/or activity of all of Ddx3y, Uty, and Eif2s3y. Methods for assessing expression and/or activity are discussed in further detail below.

Some screening methods can further comprise selecting a donor non-human animal XY pluripotent or totipotent cell from the first population for producing a fertile, phenotypically female XY non-human animal in an F0 generation based on the expression and/or activity of the one or more of Ddx3y, Uty, and Eif2s3y, wherein the proportion of the fertile, phenotypically female XY non-human animals in the F0 generation is inversely related to the expression and/or activity of the one or more of Ddx3y, Uty, and Eif2s3y.

The donor animal XY pluripotent or totipotent cell can then be introduced into a host embryo, wherein the host embryo is capable of producing a fertile phenotypically female XY animal in an F0 generation. For example, the host embryo can be a pre-morula stage embryo, and the host embryo can be cultured to the blastocyst stage upon introduction of the donor animal XY pluripotent or totipotent cell. Animals, embryos, methods for introducing donor XY pluripotent or totipotent cells into embryos, and methods of producing F0 animals are disclosed elsewhere herein.

The animal XY pluripotent or totipotent cell can be maintained in the medium for various amounts of time prior to the assaying step and/or prior introduction into a host embryo. For example, the animal XY pluripotent or totipotent cell can be maintained in the feminizing medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to the assaying step and/or introduction into the host embryo. Alternatively, the animal XY pluripotent or totipotent cell can be maintained in the feminizing medium for no more than 1 day, 2 days, 3 days, 4 days, 5 days, 6 days, 7 days, 8 days, 9 days, 10 days, 11 days, 12 days, 13 days, 2 weeks, 3 weeks, or 4 weeks prior to the assaying step and/or introduction into the host embryo. In some methods, the XY pluripotent or totipotent cell is cultured or maintained in the feminizing medium until injection of the cell into an embryo. In other methods, the embryo into which the XY pluripotent or totipotent cell was injected is cultured or maintained in the feminizing medium until being transferred to a surrogate mother.

The donor cell can be selected after assaying one or more cells from the first population for expression or activity for one or more of Ddx3y, Uty, and Eif2s3y. The assaying step can comprise assaying the cell or clone itself and determining a level of expression or activity for one or more of Ddx3y, Uty, and Eif2s3y. Alternatively, the assaying step can comprise assaying several subclones derived from the clone and determining, for example, the percentage of subclones having reduced expression and/or activity or lacking expression and/or activity of one or more of Ddx3y, Uty, and Eif2s3y. Alternatively, the assaying step can comprise assaying several subclones derived from the clone and determining the comparative expression and/or activity of one or more of Ddx3y, Uty, and Eif2s3y among the subclones. Expression and/or activity of one or more of Ddx3y, Uty, and Eif2s3y can be decreased, or the expression and/or activity of all of Ddx3y, Uty, and Eif2s3y can be decreased. Alternatively, the donor animal XY pluripotent or totipotent cell lacks expression and/or activity of one or more of Ddx3y, Uty, and Eif2s3y or lacks expression and/or activity of all of Ddx3y, Uty, and Eif2s3y. For example, there can be a lack of detectable expression of all of Ddx3y, Uty, and Eif2s3y.

Expression can be assessed at the protein level or the mRNA level. The expression level of a polypeptide may be measured directly, for example, by assaying for the level of the polypeptide in the cell or organism (e.g., Western blot analysis, FACS analysis, ELISA), or indirectly, for example, by measuring the activity of the polypeptide. In other instances, reduced expression and/or activity of a gene can be measured using methods that include, for example, Southern blot analysis, DNA sequencing, PCR analysis, Northern blot analysis, quantitative RT-PCR analysis, Next Generation Sequencing (NGS), microarray analysis, or phenotypic analysis. For example, expression of a gene can be assessed by measuring mRNA levels by RT-PCR, RNA-seq, digital PCR, or any other suitable method for measure mRNA levels. As one example, RNA levels can be measured by RT-PCR relative to a control gene, such as B2m. In some cases, for example, the $\Delta$Ct between the control gene (e.g., B2m) and the target gene can be at least 2, at least 4, at least 6, or at least 8. Likewise, in some cases, there will be no detectable RNA for the target gene after 30, 31, 32, 33, 34, 35, 36, 37, 38, 39, or 40 cycles.

Optionally, when measuring expression levels of the mRNA or polypeptide, a control experiment can be done to confirm the presence of the Y chromosome. For example, a TAQMAN® copy number assay can be done to confirm the presence of one copy of the Y chromosome by using probes to different genomic sequences on the Y chromosome. Such assays are well known and are designed to measure copy number variation within the genome.

A decrease in expression or activity of a gene or the protein it encodes in a subject cell, embryo, or animal can include any statistically significant reduction in expression or activity levels when compared to an appropriate control cell, embryo, or animal or population of control cells, embryos, or animals. In general, the expression or activity is decreased if the expression or activity is statistically lower than the expression or activity in an appropriate control cell, embryo, or animal derived therefrom (e.g., an animal XY pluripotent cell) that has been cultured in an appropriate control medium that is not a feminizing medium, an animal XY pluripotent cell that historically produces entirely male mice, notwithstanding its being cultured in feminizing medium). Such a decrease includes a reduction of at least 1%, 5%, 10%, 20%, 30%, 40%, 50%, 60%, 70%, 80%, 90%, 95%, 99%, or greater relative to a control cell. Statistical significance means p≤0.05. A decrease in expression or activity can occur via any mechanism at any stage. For example, a decrease in expression could occur via events or regulation that occurs during transcription, post-transcription, during translation, or post-translation.

A "subject cell" is one that has been cultured in feminizing medium (e.g., low-osmolality medium) or is a cell which is descended from a cell cultured in feminizing medium. A "control" or "control cell" provides a reference point for measuring changes in phenotype of the subject cell. A control cell is preferably as closely matched as possible with the subject cell (for example, the respective cells can originate from the same cell line or the same clone or can have the same genotype) except it was either not cultured in feminizing medium or lacks the capability or has reduced capability to produce XY female mice notwithstanding its being cultured in feminizing medium. For example, the control cell may comprise: (a) a cell of the same genotype or that originates from the same cell line or clone as the subject cell but which has been cultured in an appropriate control medium that is not a feminizing medium (e.g., DMEM or another type of medium that is sufficient for maintaining pluripotency or totipotency of an animal XY pluripotent or totipotent cell but does not alter the cell by giving it the capacity to give rise to fertile female progeny); (b) an animal XY pluripotent or totipotent cell genetically identical to the subject cell or derived from the same cell line or clone but which is not genetically altered or exposed to conditions or stimuli that would give it the potential to generate fertile female XY animals; and (c) an animal XY pluripotent and totipotent cell that is cultured in feminizing medium (e.g., low-osmolality medium) but historically produces entirely male animals notwithstanding its being cultured in feminizing medium. For example, the control cell can be an animal XY pluripotent or totipotent cell that has been cultured in a medium that is sufficient for maintaining the pluripotency or totipotency of the cell but does not alter the cell's capacity to give rise to fertile female progeny. Optionally, the decreased expression and/or activity can be relative to a control non-human animal XY pluripotent or totipotent cell from the second population.

In some experiments, two or more of the cells or clones in the first population are assayed for expression and/or activity of one or more of Ddx3y, Uty, and Eif2s3y. The cell or clone with the lowest expression and/or activity of the one or more of Ddx3y, Uty, and Eif2s3y can then be selected to be a donor animal XY pluripotent or totipotent cell or clone, wherein the donor animal XY pluripotent or totipotent cell is capable of producing a fertile, phenotypically female XY animal in an F0 generation.

Selecting a donor animal XY pluripotent or totipotent cell having decreased expression and/or activity of one or more of Ddx3y, Uty, and Eif2s3y can result in higher percentages of F0 progeny that are phenotypically female XY animals, higher percentages of F0 progeny that are phenotypically female XY animals that are fertile, higher percentages of F0 XY progeny that are phenotypically female XY animals that are fertile, higher percentages of F0 XY females that are fertile, higher average numbers of lifetime litters for F0 XY females or fertile F0 XY females, and higher average litter sizes for F0 XY females or fertile F0 XY females. Such F0 progeny can be produced from the donor XY pluripotent or totipotent animal cells following introduction of the cells into a host embryo and gestation of the host embryo using the methods disclosed elsewhere herein.

The increase can be any statistically significant increase when compared to the appropriate control. For example, the increase can be at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, or 5-fold when compared to the appropriate control.

For example, the percentage of F0 progeny or F0 XY progeny that are phenotypically female XY animals can be increased by selecting a donor animal XY pluripotent or totipotent cell having decreased expression and/or activity of one or more of Ddx3y, Uty, and Eif2s3y. In some methods, the percentage of the F0 progeny or F0 XY progeny that are phenotypically female XY animals is higher for F0 progeny derived from donor XY pluripotent or totipotent animal cells having decreased expression and/or activity of one or more of Ddx3y, Uty, and Eif2s3y when compared to F0 progeny derived from XY pluripotent or totipotent animal cells having higher expression and/or activity of one or more of Ddx3y, Uty, and Eif2s3y.

The percentage of F0 progeny or F0 XY progeny that are fertile, phenotypically female XY animals can also be increased by selecting a donor animal XY pluripotent or totipotent cell having decreased expression and/or activity of one or more of Ddx3y, Uty, and Eif2s3y. In some methods, the percentage of the F0 progeny or F0 XY progeny that are fertile, phenotypically female XY animals is higher for F0 progeny derived from donor XY pluripotent or totipotent animal cells having decreased expression and/or activity of one or more of Ddx3y, Uty, and Eif2s3y when compared to F0 progeny derived from XY pluripotent or totipotent animal cells having higher expression and/or activity of one or more of Ddx3y, Uty, and Eif2s3y.

The percentage of F0 XY females that are fertile can also be increased by selecting a donor animal XY pluripotent or totipotent cell having decreased expression and/or activity of one or more of Ddx3y, Uty, and Eif2s3y. In some methods, the percentage of the F0 XY females that are fertile is higher for F0 XY progeny derived from donor XY pluripotent or totipotent animal cells having decreased expression and/or activity of one or more of Ddx3y, Uty, and Eif2s3y when compared to F0 XY progeny derived from XY pluripotent or totipotent animal cells having higher expression and/or activity of one or more of Ddx3y, Uty, and Eif2s3y.

The percentage of F0 XY females that are capable of producing normal numbers of litters and/or normal litter sizes (e.g., compared to wild type female animals) can also be increased by selecting a donor animal XY pluripotent or totipotent cell having decreased expression and/or activity of one or more of Ddx3y, Uty, and Eif2s3y. In some methods, the percentage of the F0 XY females that are capable of producing normal numbers of litters and/or normal litter sizes is higher for F0 XY progeny derived from donor XY pluripotent or totipotent animal cells having decreased expression and/or activity of one or more of Ddx3y, Uty, and Eif2s3y when compared to F0 XY progeny derived from XY pluripotent or totipotent animal cells having higher expression and/or activity of one or more of Ddx3y, Uty, and Eif2s3y.

The average litter size produced by F0 XY females or fertile F0 XY females can also be increased by selecting a donor animal XY pluripotent or totipotent cell having decreased expression and/or activity of one or more of Ddx3y, Uty, and Eif2s3y. In some methods, the average litter size produced by F0 XY females or fertile F0 XY females is higher for F0 XY females or fertile F0 XY females derived from donor XY pluripotent or totipotent animal cells having decreased expression and/or activity of one or more of Ddx3y, Uty, and Eif2s3y when compared to F0 XY females or fertile F0 XY females derived from XY pluripotent or totipotent animal cells having higher expression and/or activity of one or more of Ddx3y, Uty, and Eif2s3y.

The average number of lifetime litters produced by F0 XY females or fertile F0 XY females can also be increased by selecting a donor animal XY pluripotent or totipotent cell having decreased expression and/or activity of one or more of Ddx3y, Uty, and Eif2s3y. In some methods, the average number of lifetime litters produced by F0 XY females or fertile F0 XY females is higher for F0 XY females or fertile F0 XY females derived from donor XY pluripotent or totipotent animal cells having decreased expression and/or activity of one or more of Ddx3y, Uty, and Eif2s3y when compared to F0 XY females or fertile F0 XY females derived from XY pluripotent or totipotent animal cells having higher expression and/or activity of one or more of Ddx3y, Uty, and Eif2s3y.

The average number of lifetime offspring produced by F0 XY females or fertile F0 XY females can also be increased by selecting a donor animal XY pluripotent or totipotent cell having decreased expression and/or activity of one or more of Ddx3y, Uty, and Eif2s3y. In some methods, the average number of lifetime offspring produced by F0 XY females or fertile F0 XY females is higher for F0 XY females or fertile F0 XY females derived from donor XY pluripotent or totipotent animal cells having decreased expression and/or activity of one or more of Ddx3y, Uty, and Eif2s3y when compared to F0 XY females or fertile F0 XY females derived from XY pluripotent or totipotent animal cells having higher expression and/or activity of one or more of Ddx3y, Uty, and Eif2s3y.

V. Other Applications

Also provided are methods and compositions for silencing a region of the Y chromosome in an XY pluripotent or totipotent animal cell (or in vitro cell cultures, embryos, or animals derived therefrom) by maintaining an XY pluripotent or totipotent animal cell in a feminizing medium (e.g., a low-osmolality medium) as disclosed elsewhere herein and assaying the XY pluripotent or totipotent cell to identify silencing of the region of the Y chromosome. Such methods can find use, for example, in contexts in which a targeted modification would be used to reduce or eliminate expression of gene (e.g., a knockout to inhibit the activity of a protein encoded by the gene). Silencing through culturing with a feminizing medium requires much less time than generating specific targeted modifications and is thus a more efficient means to achieve the silencing.

Examples of feminizing media and their components and characteristics are disclosed elsewhere herein. Likewise, examples of the timing and length of time for culturing XY pluripotent or totipotent cells in feminizing media are disclosed elsewhere herein.

Culturing in the feminizing medium results in repression or silencing of Y chromosome genes. For example, a region of the Y chromosome can be silenced, such as all or part of the short arm of the Y chromosome. The silencing on the short arm of the Y chromosome can extend to the key regulator of the male sex determination pathway, the Sry gene, which fails to express sufficiently at the correct time from E11-E12 during mouse embryonic development, resulting in expression of the female sex determination program in the bipotential genital ridge (see Example 1 and FIG. 2A-D). Other genes such as Ddx3y and Eif2s3y can also fail to express (see Example 1 and FIGS. 3 and 4). From then on, the sex-reversed embryo can develop to birth (F0 generation) as a female and then grow into a normal, fertile female mouse despite its XY genotype. In some methods, the feminizing medium-induced Y chromosome silencing is not a permanent genetic change and does not persist into the F1 generation (i.e., not XY females are found among the F1 progeny of the F0 XY females).

Other regions of the Y chromosome that can be silenced by the feminizing medium in addition to, within, or including all or part of small arm of the Y chromosome are disclosed elsewhere herein. Silenced regions can also include the long arm (Yq), particularly other genes on the Y chromosome that are required for spermatogenesis. For example, the region can comprise all or part of the $Sxr^a$ region (e.g., a portion containing the Sry gene), and/or the region can comprise all or part of the $Sxr^b$ region (e.g., a portion containing the Zfy2 gene) of the mouse Y chromosome (see FIG. 1A) or a corresponding region of Y chromosomes from other species (e.g., the AZFa, AZFb, or AZFc regions of the human Y chromosome). For example, the region can comprise parts or all of both the $Sxr^a$ and $Sxr^b$ regions. The boundaries of the $Sxr^b$ region, for example, are Zfy1 and Zfy2 (see FIG. 1A and Mazeyrat et al. (1998) *Human Molecular Genetics* 7(11):1713-1724, incorporated by reference in its entirety for all purposes). Corresponding regions from other animal species include regions having one or more genes that are orthologous or homologous to genes in the region on the mouse Y chromosome. For example, the AZFa region of the human region corresponds with the $Sxr^b$ region of the mouse Y chromosome in that each region contains Uty, Dby (Ddx3y), and Dffry (Usp9y). See, e.g., Affara (2001) *Expert Rev. Mol. Med.*, Jan. 3, 2001: 1-16; Mazeyrat et al. (1998) *Human Molecular Genetics* 7(11); 1713-1724; and Sargent et al. (1999) *J. Med. Genet.* 36:370-377, each of which is incorporated by reference in its entirety for all purposes. The region can also comprise all or part of the Smy region or the Spy region (see FIG. 1A and Affara (2001) *Expert Rev. Mol. Med.*, Jan. 3, 2001: 1-16). Likewise, the region can comprise all or part of one or more of deletion interval 1, deletion interval 2, deletion interval 3, deletion interval 4, deletion interval 5, deletion interval 6, and deletion interval 7 of the mouse Y chromosome or corresponding regions of Y chromosomes from other animal species (see, e.g., FIG. 1A and Affara (2001) *Expert Rev. Mol. Med.*, Jan. 3, 2001: 1-16). For example, the region can comprise all or part of one or more of deletion interval 1, deletion interval 2, and deletion interval 3 of the mouse Y chromosome or corresponding regions of Y chromosomes from other animal species (see, e.g., FIG. 1A). In one example, the region can comprise deletion interval 2 and deletion interval 3, or part of deletion interval 2 and part of deletion interval 3.

The region can include one or more of the Rbmy cluster, H2al2y, Sry, Zfy2, Usp9y, Ddx3y, Uty, Tspy-ps, Eif2s3y, Kdm5d, Uba1y, or Zfy1. The region can be telomeric to the Rbmy cluster or can be centromeric or telomeric to H2al2y, Sry, Zfy2, Usp9y, Ddx3y, Uty, Tspy-ps, Eif2s3y, Kdm5d, Uba1y, or Zfy1. For example, the region can comprise a portion of the Y chromosome telomeric of Kdm5d or centromeric of Uspy9y, or the region can be telomeric of Zfy2, Sry, or the Rbmy cluster. The region can exclude one or more of the Rbmy cluster, H2al2y, Sry, Zfy2, Usp9y, Ddx3y, Uty, Tspy-ps, Eif2s3y, Kdm5d, Uba1y, or Zfy1. For example, the region can exclude one or more of the Rbmy cluster, Zfy2, and Sry. Likewise, the region can include a portion of the Y chromosome outside of one or more of the Rbmy cluster, H2al2y, Sry, Zfy2, Usp9y, Ddx3y, Uty, Tspy-ps, Eif2s3y, Kdm5d, Uba1y, or Zfy1. For example, the region can comprise a portion of the Y chromosome outside of one or more of the Rbmy cluster, Zfy2, and Sry.

The silencing can decrease the level and/or activity of a protein encoded by a gene located on the Y chromosome. For example, the level and/or activity of one or more of the proteins encoded by the Rbmy cluster, H2al2y, Sry, Zfy2, Usp9y, Ddx3y, Uty, Tspy-ps, Eif2s3y, Kdm5d, Uba1y, or Zfy1 can be decreased. Alternatively, the silencing can result in elimination of expression of a gene located on the Y chromosome (i.e., the gene is not expressed). In some methods, for example, one or more of one or more of the Rbmy cluster, H2al2y, Sry, Zfy2, Usp9y, Ddx3y, Uty, Tspy-ps, Eif2s3y, Kdm5d, Uba1y, or Zfy1 are not expressed upon silencing. In some methods, the level and/or activity of one or more of the proteins encoded by Ddx3y, Eif2s3y, Zfy2, and Sry is decreased, or one or more of Ddx3y, Eif2s3y, Zfy2, and Sry are not expressed.

A decrease in expression or activity in a subject cell, embryo, or animal can include any statistically significant reduction in expression or activity levels when compared to an appropriate control cell, embryo, or animal. In general, the expression or activity is decreased if the expression or activity is statistically lower than the expression or activity in an appropriate control cell, embryo, or animal derived therefrom (e.g., an animal XY pluripotent cell) that has been cultured in an appropriate control medium that is not a feminizing medium, an animal XY pluripotent cell that historically produces entirely male mice, notwithstanding its being cultured in feminizing medium). Such a decrease includes a reduction of at least 1%, 5%, 10%, 20%, 30%, 40%, 50%, 60%, 70%, 80%, 90%, 95%, 99% or greater relative to a control cell. Statistical significance means $p \leq 0.05$.

A "subject cell" is one that has been cultured in feminizing medium (e.g., low-osmolality medium) or is a cell which is descended from a cell cultured in feminizing medium. A "control" or "control cell" provides a reference point for measuring changes in phenotype of the subject cell. A control cell is preferably as closely matched as possible with the subject cell (for example, the respective cells can originate from the same cell line or the same clone or can have the same genotype) except it was either not cultured in feminizing medium or lacks the capability or has reduced capability to produce XY female mice notwithstanding its being cultured in feminizing medium. For example, the control cell may comprise: (a) a cell of the same genotype or that originates from the same cell line or clone as the subject cell but which has been cultured in an appropriate control medium that is not a feminizing medium (e.g., DMEM or another type of medium that is sufficient for maintaining pluripotency or totipotency of an animal XY pluripotent or totipotent cell but does not alter the cell by giving it the capacity to give rise to fertile female progeny); (b) an animal XY pluripotent or totipotent cell genetically identical to the subject cell or derived from the same cell line or clone but which is not genetically altered or exposed to conditions or stimuli that would give it the potential to generate fertile female XY animals; and (c) an animal XY pluripotent and totipotent cell that is cultured in feminizing medium (e.g., low-osmolality medium) but historically produces entirely male animals notwithstanding its being cultured in feminizing medium.

The decrease in expression or activity can occur via any mechanism at any stage. For example, a decrease in expression could occur via modifications made directly or indirectly to the region or via events or regulation that occurs during transcription, post-transcription, during translation, or post-translation.

Although an understanding of mechanism is not required for practice, altering chromatin and/or increasing levels of the phosphorylated form of histone variant γH2AX on the Y chromosome could contribute to the silencing. Phosphorylated histone γH2AX is known to be associated with transcriptional repression, and is associated with transcriptional repression of the X and Y chromosomes in the XY sex body during meiotic prophase. See, e.g., Alton et al. (2008) *Reproduction* 135:241-252.

The silencing can occur when the XY pluripotent or totipotent cell is being cultured, after the donor XY pluripotent or totipotent cell is introduced into a host embryo, or after the host embryo comprising the donor XY pluripotent or totipotent cell is introduced into a recipient female animal. The silencing can also occur during different stages of embryonic development or throughout embryonic development. In some cases, the silencing continues after birth. For example, after an oocyte is fertilized, some silencing can be maintained through the first two cell divisions. The sex reversal caused by the silencing can also be capable of being transmitted to F1 progeny. Some examples of periods in which the silencing occur include one or more of the following: (1) during embryonic development when the male sex determination program is engaged; (2) during embryonic development up to at least a developmental stage corresponding to E11-E12 in mice (e.g., developmental stages important for sex determination or sex reversal); (3) during embryonic development up to at least a development stage corresponding to E17-E19 in mice (e.g., developmental stages important for fertility in embryonic oocytes); (4) throughout the period of oogenesis; (5) during meiotic prophase in oocyte development, which initiates in the embryo just before birth; (6) after the oocyte is fertilized (e.g., during its first two cell divisions); or (7) in oocytes post-ovulation through the first two cell divisions post-fertilization.

Any means known in the art can be used for assaying a cell for silencing of the region of the Y chromosome. For example, genes within a silenced region may not be expressed (e.g., expression is eliminated or the cell lacks detectable expression of the gene). A gene is not expressed when transcription of the gene is not carried out or when there are no detectable levels of the products of a gene (e.g., mRNA or protein) by common techniques known in the art. The expression level of a polypeptide may be measured directly, for example, by assaying for the level of the polypeptide in the cell or organism (e.g., Western blot analysis, FACS analysis, ELISA), or indirectly, for example, by measuring the activity of the polypeptide. In other instances, reduced expression and/or activity of a gene can be measured using methods that include, for example, Southern blot analysis, DNA sequencing, PCR analysis, Northern blot analysis, quantitative RT-PCR analysis, Next Generation Sequencing (NGS), microarray analysis, or phenotypic analysis. Assaying can also comprise identifying which region, subregions, or genes on the Y chromosome are silenced.

All patent filings, websites, other publications, accession numbers and the like cited above or below are incorporated by reference in their entirety for all purposes to the same extent as if each individual item were specifically and individually indicated to be so incorporated by reference in its entirety for all purposes. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | DNA | mHPRT1 Probe |
| 2 | DNA | mHPRT1 Forward Primer |
| 3 | DNA | mHPRT1 Reverse Primer |
| 4 | DNA | mSox9 Probe |
| 5 | DNA | mSox9 Forward Primer |
| 6 | DNA | mSox9 Reverse Primer |
| 7 | DNA | mRspo1 Probe |
| 8 | DNA | mRspo1 Forward Primer |
| 9 | DNA | mRspo1 Reverse Primer |
| 10 | DNA | mDhh Probe |
| 11 | DNA | mDhh Forward Primer |
| 12 | DNA | mDhh Reverse Primer |
| 13 | DNA | mGata4 Probe |
| 14 | DNA | mGata4 Forward Primer |
| 15 | DNA | mGata4 Reverse Primer |
| 16 | DNA | mFgf9 Probe |
| 17 | DNA | mFgf9 Forward Primer |
| 18 | DNA | mFgf9 Reverse Primer |
| 19 | DNA | mSry Probe |
| 20 | DNA | mSry Forward Primer |
| 21 | DNA | mSry Reverse Primer |
| 22 | DNA | mSf1 Probe |
| 23 | DNA | mSf1 Forward Primer |
| 24 | DNA | mSf1 Reverse Primer |
| 25 | DNA | mWnt4 Probe |
| 26 | DNA | mWnt4 Forward Primer |
| 27 | DNA | mWnt4 Reverse Primer |
| 28 | DNA | mAmh Probe |
| 29 | DNA | mAmh Forward Primer |
| 30 | DNA | mAmh Reverse Primer |
| 31 | DNA | mNr0b1 Probe |
| 32 | DNA | mNr0b1 Forward Primer |
| 33 | DNA | mNr0b1 Reverse Primer |
| 34 | DNA | mFoxl2 Probe |
| 35 | DNA | mFoxl2 Forward Primer |
| 36 | DNA | mFoxl2 Reverse Primer |
| 37 | DNA | mDdx3y Probe |
| 38 | DNA | mDdx3y Forward Primer |
| 39 | DNA | mDdx3y Reverse Primer |
| 40 | DNA | mEif2s3y Probe |
| 41 | DNA | mEif2s3y Forward Primer |
| 42 | DNA | mEif2s3y Reverse Primer |
| 43 | DNA | Upstream Recognition Sequence for TALEN Targeting Sry |

TABLE 2-continued

Description of Sequences.

| SEQ ID NO | Type | Description |
|---|---|---|
| 44 | DNA | Downstream Recognition Sequence for TALEN Targeting Sry |
| 45 | DNA | X Chromosome Primer 1 |
| 46 | DNA | X Chromosome Primer 2 |
| 47 | DNA | X Chromosome Probe |
| 48 | DNA | Y Chromosome Primer 1 |
| 49 | DNA | Y Chromosome Primer 2 |
| 50 | DNA | Y Chromosome Probe |

EXAMPLES

Example 1. Generation of Fertile and Fecund F0 XY Female Mice from XY ES Cells

Materials and Methods

ES Cell Culture. All results described here were from experiments performed with VGF1, our C57BL6NTac/129S6SvEv F1 hybrid XY ES cell line (Poueymirou et al. (2007) *Nat. Biotechnol.* 25:91-99; Valenzuela et al. (2003) *Nat. Biotechnol.* 21:652-659). ES cells were cultured as previously described (Matise et al. (2000) Production of targeted embryonic stem cell clones. In: Joyner A L (ed) Gene targeting: a practical approach. Oxford University press, New York, pp 101-132). Custom-made high glucose DMEM media (LifeTech) with the $NaHCO_3$ concentrations indicated in Table 3 were supplemented with 0.1 mM nonessential amino acids, 1 mM sodium pyruvate, 0.1 mM 2-mercaptoethanol, 4 mM L-glutamine, 100 U/ml penicillin and 100 µg/ml streptomycin (Life Technologies), 15 FBS (Hyclone), and 2,000 U/ml leukemia inhibitory factor (LIF, Millipore). Osmolality of the media was measured with a Single Sample Osmometer (Advanced Instruments, Inc. model 3250). For electroporation, we mixed 1.5 µg of targeting vector DNA dissolved in 120 µl of electroporation buffer (Millipore) with $7.5 \times 10^6$ ES cells and transferred to a BTX multiwall electroporation plate (Harvard Apparatus). Following electroporation, cells were incubated on ice for 10 min before being plated on two 15 cm gelatinized dishes. Selection medium was added 48 h after electroporation and changed daily thereafter. Colonies were picked 10 days after electroporation and transferred into individual wells of a 96-well plate containing trypsin, after which cells were plated in gelatinized 96-well plates. Three days later, cells were trypsinized again and two-thirds of the content of each well was frozen and the remaining one-third transferred to a new plate for DNA extraction.

ES Cell Screening, Mouse Genotyping, and X and Y Chromosome Counting. We used the Loss-of-Allele method (Frendewey et al. (2000) *Methods Enzymol.* 476:295-307) to identify correctly targeted ES cell clones and to determine mouse allele genotypes. We determined X and Y chromosome counts by the following TAQMAN® quantitative PCR (qPCR) assays (Biosearch Technologies): for X, primers (5'-3') GGAGGGTAGCACGGGAAGAAG (SEQ ID NO: 45) and GCTGGCTACCCACTTGATTGG (SEQ ID NO: 46) and probe TCAAGCAGTCTCTCCCAGCTAAC-CTCCCT (SEQ ID NO: 47); and for Y, primers GATCAGCAAGCAGCTGGGAT (SEQ ID NO: 48) and CTCCTGGAAAAAGGGCCTTT (SEQ ID NO: 49) and probe CAGGTGGAAAAGCCTTACAGAAGCCGA (SEQ ID NO: 50). A qPCR assay for the albino mutation in the tyrosinase gene carried by the Swiss Webster strain and not present in the VGF1 ES cell genome quantified host embryo contribution. The limit of detection in this assay is approximately one albino allele in 2,000 haploid genome equivalents (Poueymirou et al. (2007) *Nat. Biotechnol.* 25:91-99). Dissected spleens were sent to the Van Andel Institute (Grand Rapids, Michigan) for spectral karyotyping (SKY).

Microinjection. On the day of injection, ES cells were trypsinized and resuspended in ES cell medium without LIF. Frozen 8-cell Swiss Webster embryos (Charles River Laboratories) were thawed and incubated in KSOM medium (Millipore) at 37° C. in 7.5% $CO_2$ for 90 min prior to microinjection. Injections of ES cells into 8-cell embryos were performed as previously described (Poueymirou et al. (2007) *Nat. Biotechnol.* 25:91-99). Following injections embryos were cultured overnight and transferred into pseudopregnant recipient female mice 2.5 days post coitus.

Results

To optimize the yield of VELOCIMICE® for both breeding and phenotyping studies, we tested a variety of ES cell culture media during gene-targeting experiments and prior to 8-cell embryo injection. One component we evaluated was the base medium known as Knockout™ DMEM (KO-DMEM, Life Technologies). Initially, it appeared that ES cells grown in media prepared with KO-DMEM performed poorly compared with cells maintained in media made with standard DMEM (Dulbecco's Modified Eagle's Medium) in that we obtained fewer male VELOCIMICE®. But we also observed a large increase in female VELOCIMICE®: 31% of the VELOCIMICE® produced from the injection of 78 clones derived from targeting experiments for 34 different genes were female (Table 3, KO-DMEM). A retrospective comparison of results recorded in our mouse production database for the injection of over 500 targeted ES cell clones grown in a conventional DMEM medium revealed that only 1% of all VELOCIMICE® were identified as female (Table 3, DMEM). The rare female VELOCIMICE® had not been bred and were not investigated further. Despite the high incidence of females from XY ES cell clones grown in the KO-DMEM medium, the 18% total yield of VELOCIMICE®, male and female, from this experiment was identical to our historical experience with clones derived in DMEM media (Table 3, KO-DMEM and DMEM).

ES cell clones grown in KO-DMEM produced female VELOCIMICE® in proportions that ranged from 0 to 60%. The propensity to produce female VELOCIMICE® was specific to each clone. Clones that did not produce females maintained this trait in repeated microinjections, while clones that gave rise to females tended to yield approximately the same proportion of females in repeat microinjection experiments. To see if we could alter the ability of a clone to produce female VELOCIMICE®, we performed media exchange experiments. ES cell clones from gene targeting experiments in which the ES cells were grown and maintained in either DMEM-based or KO-DMEM-based media for the entire targeting process—electroporation, selection of drug resistant colonies, screening for targeted mutations, expansion and cryopreservation—were thawed and grown in the opposite media for 3 days in preparation for microinjection into 8-cell embryos. After an overnight incubation in KSOM to allow the embryos to differentiate into blastocysts, they were transferred into surrogate mothers. We scored the proportion of XY females produced among the live born VELOCIMICE®.

TABLE 3

Effect of Media Formulation on Production of XY Female VELOCIMICE ®.

| Base Medium | Osmolality of Base Medium (mOsm/kg) | NaHCO₃ Conc. (mM) (mg/mL) | Clones Injected | Embryos Transferred | VELOCIMICE ® Produced | | | |
|---|---|---|---|---|---|---|---|---|
| | | | | | Males (%) | Females (%) | Total | % Efficiency[d] |
| KO-DMEM | 275[b] | N/A[a] | 78 | 4754 | 617 (69) | 277 (31) | 894 | 18 |
| DMEM | 340[b] | 44 mM 3.7 mg/mL | 553 | 21419 | 3792 (99) | 42 (1.1) | 3834 | 18 |
| mDMEM-1 | 290[c] | 44 mM 3.7 mg/mL | 6 | 250 | 33 (94) | 2 (5.7) | 35 | 14 |
| mDMEM-2 | 264[c] | 26 mM 2.2 mg/mL | 4 | 200 | 26 (72) | 10 (28) | 36 | 18 |
| mDMEM-3 | 292[c] | 18 mM 1.5 mg/mL | 4 | 200 | 35 (71) | 14 (29) | 49 | 24 |
| mDMEM-4 | 251[c] | 18 mM 1.5 mg/mL | 4 | 200 | 33 (66) | 17 (34) | 50 | 25 |

[a]Not available
[b]Average value as per supplier's certificate of analysis
[c]Measured values
[d]Ratio of VELOCIMICE ® produced to embryos transferred expressed as a percentage For the DMEM to KO-DMEM switch, we chose 11 clones from five different gene-targeting experiments performed in DMEM medium and thawed and grew them in either KO-DMEM or DMEM as a control. Approximately 400 embryos transferred from ES cells switched from DMEM to KO-DMEM produced 105 live born VELOCIMICE®, of which only 2 (1.9%) were female (Table 4, targeting in DMEM, thaw in KO-DMEM), similar to the proportion of females produced (2.4%) by the control embryos injected with ES cells maintained in DMEM (Table 4, targeting in DMEM, thaw in DMEM). For the reciprocal experiment, we selected three clones from a targeting experiment performed in KO-DMEM, and thawed and grew them in either or DMEM or KO-DMEM as a control. Three hundred embryos transferred from ES cells switched from KO-DMEM to DMEM produced 41 VELOCIMICE®, of which 8 (20%) were female (Table 4, targeting in KO-DMEM, thaw in DMEM), similar to the proportion of female VELOCIMICE® (18%) produced from the control embryos injected with ES cells maintained in KO-DMEM (Table 4, targeting in KO-DMEM, thaw in KO-DMEM).

sity to produce females. In both arms of the experiment, regardless of derivation in either DMEM or KO-DMEM, the clones exposed to KO-DMEM after thawing had a higher and similar efficiency of overall VELOCIMOUSE® production (27% and 28%) compared to those thawed in DMEM medium (10% and 14%).

Anatomically Normal Females Fully Derived from XY ES Cells. To eliminate chimerism as an explanation for the female VELOCIMOUSE® phenomenon, we confirmed that all females that were apparently fully ES cell-derived by coat color contribution were true VELOCIMICE® by qPCR assays on tail biopsies that showed no genetic contribution from the Swiss Webster 8-cell host embryo into which the ES cells were injected (Poueymirou et al. (2007) *Nat. Biotechnol.* 25:91-99). We knew that female VELOCIMICE® could be derived from XO ES cells, which produce exclusively female VELOCIMICE®, but this possibility was eliminated by qPCR chromosome counting assays that established that the female VELOCIMICE® (hereafter referred to as XY females) had one copy each of X and Y. The XY qPCR results were confirmed by SKY of

TABLE 4

Effect of Switching Media Formulation on Production of XY Female VELOCIMICE ®.

| Base Medium at Different Stages | | Clones Injected | Embryos Transferred | VELOCIMICE ® Produced | | | |
|---|---|---|---|---|---|---|---|
| Targeting[a] | Thaw and Growth for Injection | | | Males (%) | Females (%) | Total | % Efficiency[b] |
| DMEM | KO-DMEM | 11 | 388 | 103 (98) | 2 (1.9) | 105 | 27 |
| DMEM | DMEM | 11 | 413 | 41 (98) | 1 (2.4) | 42 | 10 |
| KO-DMEM | KO-DMEM | 3 | 300 | 69 (82) | 15 (18) | 84 | 28 |
| KO-DMEM | DMEM | 3 | 300 | 33 (80) | 8 (20) | 41 | 14 |

[a]Thaw of ES cells, growth, electroporation, drug selection, screening, expansion, and cryopreservation of targeted clones
[b]Ratio of VELOCIMICE ® produced to embryos transferred expressed as a percentage These results indicated that clones derived in a DMEM-based medium maintained a low frequency of female VELOCIMICE® production similar to our historical experience (Table 3, DMEM), and we could not increase this frequency by a brief exposure to KO-DMEM. Similarly, clones derived in KO-DMEM-based medium produced a higher frequency of female VELOCIMICE®, and a brief exposure to DMEM did not reduce the XY clones' propenspleen cells taken from five XY females, which also revealed a normal autosome count with no detectable translocations or deletions.

Examination of the abdominal cavities of fifteen XY females confirmed that the normal female anatomy exhibited by all XY females in their external genitalia extended to the internal organs. All demonstrated normal female reproductive organs, with no indication of hermaphrodism, ovotestes, or other indications of incomplete female sexual development. They possessed normal oviducts and well-vascularized uterine horns and appeared to have functional ovaries with a corpus hemorrhagicum that suggests an active ovulation process. In addition, we found that the XY females had body weights and serum chemistry profiles that fall within the range of values seen in wild type female mice derived by breeding.

To eliminate the possibility of tissue-specific host embryo chimerism in the female sexual organs, we performed qPCR assays for a Swiss Webster host embryo marker and for the X and Y chromosomes on tissues dissected from the fifteen XY females examined for normal anatomy. For all the mice, we found no host embryo contribution and one copy each of the X and Y chromosomes in all tissues, including ovary, oviduct, and uterus. We conclude that the XY females have a normal male karyotype, are fully derived from the injected XY ES cells, and display no detectable genetic contribution from the host embryo. They present an external and internal anatomy indistinguishable from normal female mice.

Sex-Reversed XY Females are Fertile and Fecund. To test the fertility of the XY females, we bred 119 female F0 VELOCIMICE® (50% C57BL/6N: 50% 129SvEvS6), derived from multiple independent XY gene-targeted ES cell clones, with wild-type C57BL/6NTac males. Sixty-three percent (75) of the XY females produced at least one litter. This level of fertility, although lower than the approximately 90% fertility we observe in production breeding for F1 generation (75% C57BL/6N: 25% 129SvEvS6) XX females derived from the same parental ES cell line, is unusually high compared with previously described cases of male to female sex reversal. To compare the fecundity of the XY females with XX females generated by normal breeding, we bred C57BL/6NTac males with 18 XY females or with 14 wild type XX F1 females. Over a nine-month period, we did not observe significant differences between the XY female mothers and the XX controls for three measures of fecundity—pups and litters produced per female, and litter size (Table 5).

TABLE 5

Breeding Results for XY Female VELOCIMICE ® Compared with XX Females.

| Female Type | Live Born Mice | | Litters | | |
|---|---|---|---|---|---|
| | Total | Per Female (Mean ± SD)[b] | Total | Per Female (Mean ± SD) | Litter Size (Mean ± SD) |
| F0 XY Females (n = 18) | 537 | 30 ± 15 | 84 | 4.7 ± 1.7 | 6.4 ± 2.8 |
| WT[a] F1 XX Females (n = 14) | 451 | 32 ± 23 | 70 | 5.0 ± 2.6 | 6.0 ± 3.1 |

[a]Wild type
[b]Standard deviation

The Male-to-Female Sex Reversal Trait is not Transmitted to the F1 Generation. To test for inheritance of the XY female trait, we quantified X and Y chromosome counts in 394 F1 progeny from matings between XY females and C57BL/6NTac males. We found that none of the phenotypically female progeny had an XY genotype, and all of the mice with at least one Y chromosome were phenotypically male. We did, however, observe twice as many males (260) as females (134) and aberrant sex chromosome counts in both male and female mice. Aberrant male karyotypes (XXY and XYY) have been reported in F1 progeny from the breeding of female chimeras produced by blastocyst injection of XY ES cells (Bronson et al. (1995) Proc. Natl. Acad. Sci. USA 92:3120-3123) and were associated with infertility. We also found that the XXY and XYY male F1 progeny of XY females were infertile, with very small testes that were either aspermic or had extremely low sperm counts.

Media Conditions that Promote the Generation of XY Females from XY ES Cells. ES cells grown in medium based on KO-DMEM had a much higher propensity to produce XY females after injection into 8-cell embryos than clones grown in a conventional DMEM medium (Table 3). The supplier's specifications indicate a difference in osmolality between these base media: approximately 275 mOsm/kg for KO-DMEM compared with approximately 340 mOsm/kg for DMEM. We therefore prepared modified versions of DMEM (mDMEM) with reduced measured osmolality by altering the concentrations of the salt and sugar components and then evaluated VELOCIMOUSE® production for targeted ES cells generated in the modified media (Table 3). In other experiments, different osmolalities, salt concentrations, and carbonate concentrations were tested for their effect on XY ES cells and F0 mice produced from those ES cells. Fertile F0 XY females were successfully produced at osmolalities between 218 and 322 mOsm/kg, at concentrations of a salt of an alkaline metal and halide (e.g., NaCl) of 3.0 to 6.4 mg/mL (~51.3 mM to ~109.5 mM), and at concentrations of a salt of a carbonic acid (e.g., $NaHCO_3$) of 1.5-3.7 mg/mL (~17.9 mM to ~44.0 mM) (Tables 6 and 7). For row 2 in Table 7 (DMEM), a typical osmolality of the base medium is from 337-341 or 340-341 mOsm/kg, and a typical osmolality for the complete medium (DMEM plus 15% FBS, pen/strep, non-essential amino acids, sodium pyruvate, beta-mercaptoethanol, L-glutamine, and LIF) is between 329-338 mOsm/kg. For row 1 in Table 7 (KO-DMEM), a typical osmolality of the base medium is between 271-278 mOsm/kg, and a typical osmolality for the complete medium (KO-DMEM base medium plus 15% FBS, pen/strep, non-essential amino acids, sodium pyruvate, beta-mercaptoethanol, L-glutamine, and LIF) is between 278-280 mOsm/kg. For row 4 in Table 7 (low NaCl base medium), a typical osmolality for the base medium is 200 mOsm/kg, and a typical osmolality for the complete medium is about 216 mOsm/kg.

The only component whose variation consistently correlated with changes in the production of XY females was sodium bicarbonate, regardless of the concentration of other salts, the measured osmolality or pH. The effect of sodium bicarbonate concentration is seen when comparing four of the modified media we tested. Use of a medium based on mDMEM-1 (Table 3), which had a sodium bicarbonate concentration equal to that of DMEM medium (44 mM), in gene targeting experiments produced ES cells that yielded a low proportion (5.7%) of XY females despite a measured osmolality that was reduced compared with DMEM medium. Lowering the sodium bicarbonate concentration below that of DMEM (26 mM for mDMEM-2 and 18 mM, for mDMEM-3 and -4) produced an average of 30% XY females (Table 3), similar to the proportion we observed with KO-DMEM. The mDMEM-4 medium had the lowest osmolality and produced both the highest proportion of XY females (34%) and the highest efficiency of total VELOCIMOUSE® production (25%). But low-osmolality did not always correlate with high frequency of XY females. The mDMEM-1 and -3 media had nearly identical osmolality but promoted very different proportions of XY females. In general, we observed a direct correlation between a medium's tendency to produce XY females and the yield of fully ES cell-derived F0 mice.

photransferase drug selection cassette. We produced F1 generation study cohorts of wild type (+/+), heterozygous (+/−), and homozygous knockout (−/−) mice by breeding F0

TABLE 6

Effect of Osmolality, Salt, and Carbonate on ES-Cell Derived Pups and F0 XY Females.

| Medium | Osmolality of Complete Medium (mOsm/kg) | NaCl (mg/mL) (mM) | NaHCO$_3$ (mg/mL) (mM) | Glucose (mg/mL) | ES-Derived Pups/Total Pups | ES-Derived Pups XY Male | ES-Derived Pups XY Female |
|---|---|---|---|---|---|---|---|
| DMEM | 329 | 6.4 mg/mL 110 mM | 3.7 mg/mL 44 mM | 4.5 | 13/58 (22.4%) | 13/13 | 0/13 (0%) |
| DMEM-LS/LC | 270 | 5.1 mg/mL 87 mM | 2.2 mg/mL 26 mM | 4.5 | 36/71 (50.7%) | 26/36 | 10/36 (27.8%) |
| DMEM-LS/LC/HG | 322 | 5.1 mg/mL 87 mM | 2.2 mg/mL 26 mM | 15.5 | 20/50 (40%) | 17/20 | 3/20 (15%) |
| DMEM-VLS/LC | 218 | 3.0 mg/mL 51 mM | 2.2 mg/mL 26 mM | 4.5 | 53/58 (91.4%) | 35/53 | 18/53 (34%) |
| DMEM-LS/VLC | 261 | 5.1 mg/mL 87 mM | 1.5 mg/mL 18 mM | 4.5 | 50/57 (87.7%) | 33/50 | 17/50 (34%) |
| DMEM-VLC | 294 | 6.4 mg/mL 110 mM | 1.5 mg/mL 18 mM | 4.5 | 49/68 (72.1%) | 35/49 | 14/49 (28/6%) |

TABLE 7

Effect of Osmolality, Salt, and Carbonate on ES-Cell Derived Pups and F0 XY Females.

| Base Medium | NaCl (mg/mL) (mM) | NaHCO$_3$ (mg/mL) (mM) | Osmolality of Complete Medium (mOsm/kg) | pH | # Clones Injected | # Embryos Transferred | Male VelociMice (%) | Female VelociMice (%) | % VelociMice/Embryo |
|---|---|---|---|---|---|---|---|---|---|
| KO-DMEM | 5.1 mg/mL (87 mM) | 2.2 mg/mL (26 mM) | 275 | 7.17 | 22 | 988 | 131 | 52 (28.4%) | 18.5 |
| DMEM | 6.4 mg/mL (110 mM) | 3.7 mg/mL (44 mM) | 332 | 7.38 | 32 | 1525 | 149 | 7 (4.5%) | 10.2 |
| KO-DMEM + glucose | 5.1 mg/mL (87 mM) | 2.2 mg/mL (26 mM) | 322 | | 4 | 200 | 17 | 3 (15.0%) | 10.0 |
| Low NaCl | 3.0 mg/mL (51 mM) | 2.2 mg/mL (26 mM) | 216 | 7.21 | 8 | 300 | 63 | 25 (28.4%) | 29.3 |
| Low NaHCO$_3$ | 5.1 mg/mL (87 mM) | 1.5 mg/mL (18 mM) | 261 | | 4 | 200 | 33 | 17 (34.0%) | 25.0 |
| High NaCl − Low NaHCO$_3$ | 6.4 mg/mL (110 mM) | 1.5 mg/mL (18 mM) | 294 | 6.99 | 4 | 200 | 35 | 14 (28.6%) | 24.5 |
| Low NaCl − Low NaHCO$_3$ | 3.0 mg/mL (51 mM) | 1.5 mg/mL (18 mM) | 203 | 6.98 | | | | | |
| KO-DMEM + NaHCO$_3$ | 5.1 mg/mL (87 mM) | 3.7 mg/mL (44 mM) | 288 | 7.40 | 4 | 100 | 20 | 0 (0%) | 20.0 |
| Low NaCl + NaHCO$_3$ | 3.0 mg/mL (51 mM) | 3.7 mg/mL (44 mM) | 238 | 7.41 | 4 | 100 | 17 | 2 (10.5%) | 19.0 |
| KO-DMEM in 5% CO$_2$ | 5.1 mg/mL (87 mM) | 2.2 mg/mL (26 mM) | 268 | 7.34 | 4 | 100 | 21 | 8 (27.6%) | 29.0 |
| Low NaCl in 5% CO$_2$ | 3.0 mg/mL (51 mM) | 2.2 mg/mL (26 mM) | 214 | 7.37 | 3 | 75 | 40 | 6 (13.0%) | 61.3 |

Phenotyping Mice Derived from Breeding Isogenic XY Male and Female VELOCIMICE®. As examples that illustrate the value of the fertile and fecund XY females, we compared the phenotypes of F1 generation knockout mice derived from the breeding of heterozygous isogenic XY male and female VELOCIMICE® with those of F2 generation knockout mice derived from conventional breeding for two genes: Ctsk, which encodes cathepsin K, a cysteine protease crucial for bone homeostasis; and Cldn7, which encodes claudin-7, a major component of tight junctions. For both, we replaced the entire coding region with a sequence encoding a beta-galactosidase reporter fused in-frame with the start codon followed by a neomycin phos- XY females with their clonal sibling XY male VELOCIMICE®. For the Cldn7 knockout we produced an additional conventional breeding control group by crossing male F0 VELOCIMICE® with C57BL/6NTac females to generate F1 heterozygous mice and then intercrossed these mice to produce F2 study cohorts.

Consistent with previous reports of Ctsk knockout mice, we found that the Ctsk$^{-/-}$ mice produced by XY female breeding were viable and fertile, but compared with their Ctsk$^{+/+}$ littermates they expressed a number of bone defects, including a significant increase in BMD and an increase in the retention of femur bone trabeculae in females. As expected from a previously reported Cldn7 knockout, the Cldn7$^{-/-}$ mice from both the conventional and XY female breeding schemes were runted and died a few days after birth. Among the live born mice, we observed a decreased number of homozygous mutant mice produced both by conventional breeding (Cldn7$^{+/+}$, 32; Cldn7$^{+/-}$, 74; Cldn7$^{-/-}$, 13; P=4.2×10$^{-7}$, $\chi^2$ test), and by XY female breeding (Cldn7$^{+/+}$, 54; Cldn7$^{+/-}$, 108; Cldn7$^{-/-}$, 24; P=9.2× 10$^{-4}$, $\chi^2$ test), indicating an incompletely penetrant embryonic lethality. Consistent with a kidney defect and identical to the published mutant mouse, the Cldn7$^{-/-}$ neonates from both the conventional and XY female breeding schemes failed to appropriately regulate plasma potassium ions. In addition to the matched growth and renal function phenotypes, we observed identical beta-galactosidase wholemount expression patterns in the major adult organs of heterozygotes from both the XY female and conventional breeding groups.

Discussion

Whether caused by incompatible genetic backgrounds (Eicher et al. (1982) *Science* 217:535-537; Taketo-Hosotani et al. (1989) *Development* 107:95-105) or mutations in genes required for sex determination (Bagheri-Fam et al. (2008) *Dev. Biol.* 314:71-83; Barrionuevo et al. (2006) *Biol. Reprod.* 74:195-201; Bogani et al. (2009) *PLoS Biol* 7:e1000196; Chaboissier et al. (2004) *Development* 131: 1891-1901; Colvin et al. (2001) *Cell* 104:875-889; Gierl et al. (2012) *Dev. Cell* 23:1032-1042; Hammes et al. (2001) *Cell* 106:319-329; Katoh-Fukui et al. (1998) *Nature* 393: 688-692; Meeks et al. (2003) *Nat. Genet.* 34:32-33; Tevosian et al. (2002) *Development* 129:4627-4634; Warr et al. (2012) *Dev. Cell* 23:1020-1031), male-to-female sex reversal in mice is nearly always accompanied by infertility. Some XY females carrying mutations in the primary male sex determination gene, Sry, are fertile but have small infrequent litters and short reproductive lifespans (Lovell-Badge and Robertson (1990) Development 109:635-646). Recently, a similarly low fertility and fecundity was reported for XY female mice carrying a 41 base pair (bp) deletion of Sry that was produced by directed targeting with a transcription activator-like effector nuclease (TALEN) (Wang et al. (2013) *Nat. Biotechnol.* 31:530-532). In another example of a TALEN-induced Sry mutation, a single XY female mouse carrying a 2 bp deletion was found to be sterile (Kato et al. (2013) *Sci. Rep.* 3:3136).

In marked contrast to these cases of impaired fertility, the XY female VELOCIMICE® produced from gene-targeted ES cells display an unprecedented high level of fertility and a normal fecundity that may appear to be counter to expectations. Besides the normal 20X gametes, an XY female could produce abnormal 20Y, 19O, and 21XY egg types, the latter two resulting from non-disjunction events in meiosis I that explain the XXY, XYY, and XO sex chromosome karyotypes in the F1 progeny of the XY females. It is therefore possible that XY females could have a reduced number of viable and functional eggs. In fact, the proportions of the various F1 sex chromosome karyotypes fit best (by $\chi^2$ analysis) with a model that assumes a 25-30% loss of the four types of viable fertilization progeny derived from the three abnormal gamete types. Such a loss would lead to only a 20% loss from all egg types, which would be unlikely to cause a fecundity difference we could discern in our nine-month breeding test.

The high fertility and fecundity of the XY females described here suggest a unique mechanism of male to female sex reversal. The lack of transmissibility of the XY female trait indicates that sex reversal is a transient event in which some cells in a gene-targeted ES cell clone acquire an epigenetic mark or some other physiological alternation that predestines them to favor the production of XY females. Whatever mark or change the ES cells have acquired, it appears to be fixed and stable. The propensity to produce XY females is peculiar to each gene-targeted XY ES cell clone. Each usually produces a reproducible proportion of XY females in repeat injection experiments, and individual clones cannot be 'feminized' or 'masculinized' by switching them to different culture conditions after the gene targeting process. A feature of the XY female phenomenon is that it affects only ES cells that have been maintained in a feminizing media through the entire process of gene targeting—thawing, growth, passage, electroporation, antibiotic selection, expansion, and freeze-down—suggesting that the stresses of the gene targeting process might occasionally induce an epigenetic mark that imparts a 'feminized' character on the XY ES cells.

We first observed XY females in significant numbers after we switched our basal medium from DMEM, which is hypertonic (>300 mOsmol/kg), to the isotonic (275-295 mOsmol/kg) KO-DMEM. Cells respond to osmotic stress by activating the MAP kinase pathway, and mutations in Map3k4 and Gadd45c, which are members of a MAP kinase pathway, or in the insulin pathway, which signals through MAP kinases, can result in reduced expression of Sry and failure to induce testis development in the indifferent genital ridge. Culturing ES cells in a hypertonic medium might stimulate the MAP kinase pathway and promote a physiological or epigenetic environment that reinforces male differentiation after the cells have expanded into the developing embryo. Conversely, culturing ES cells in tonic or slightly hypotonic media may dampen signaling through the MAP kinase pathway and thus mimic the effects of sex-reversing mutations.

Beyond its implications for understanding sex determination, the male to female sex reversal phenomenon we describe here has important practical consequences for the production of genetically modified mice. Because the XY females are both fertile and fecund, we could use F0 sibling intercrosses to produce F1 homozygous knockout mice whose phenotypes reproduced those generated by natural breeding schemes either in our laboratories or described in published reports. Even when mice carrying abnormal sex chromosome karyotypes are excluded, there remain sufficient normal F1 XX females and XY males for the assembly of study cohorts. Our culture method is faster and easier than generating fertile females from XO ES cell clones because there is no need to subclone and screen for the rare loss of the Y chromosome. Further explorations of the conditions that promote sex conversion and the molecular mechanisms responsible may enable the development of an improved method for the reliable, predictable, and efficient production of both male and female VELOCIMICE® from any targeted ES cell clone.

Example 2. Expression of Ddx3y (Dby), Eif2s3y, and Sry is Silenced or Decreased in Embryos Derived from XY ES Cells Cultured in Low-Osmolality Medium Embryos were dissected at developmental stage 11.5 days post coitum (dpc), their approximate stage determined using Theiler staging. As gestational ages vary widely within a litter, more precise staging of individual embryos was achieved by counting the number of tail somites (ts) from the posterior to the hind limb bud to the end of the tail. Using this technique, an embryo with 8 tail somites is 10.5 dpc, 18 tail somites is 11.5 dpc and 30 tail somites is 12.5 dpc (from Hacker, Capel, Goodfellow and Lovell-Badge, Devel 1995).

In B6 mice, Sry is reported to be detectable at approximately 13 ts, reaches a peak at approximately 17-18 ts and declines by at approximately 27 ts. Embryos with between 12-27 ts were taken from mice to capture the full time course of Sry. Genital ridges (containing the gonad and the adjacent mesonephros) were dissected from embryos at these stages, separated from the body wall and the metanephrous (developing kidney), and preserved in Trizol for RNA purification.

The sex determining gene on the Y chromosome (Sry) is responsible for initiating male sex determination in mammals. This gene is expressed in a limited population of cells in the gonad during a narrow window of development (approximately 11.5 dpc in the mouse). During this window, Sry initiates all changes necessary for the gonad to become a testis and the organism to acquire a male fate. However, if Sry expression is reduced during this window, or even expressed a few hours later, XY individuals develop ovaries, become female, and are considered sex reversed.

Figure 15:
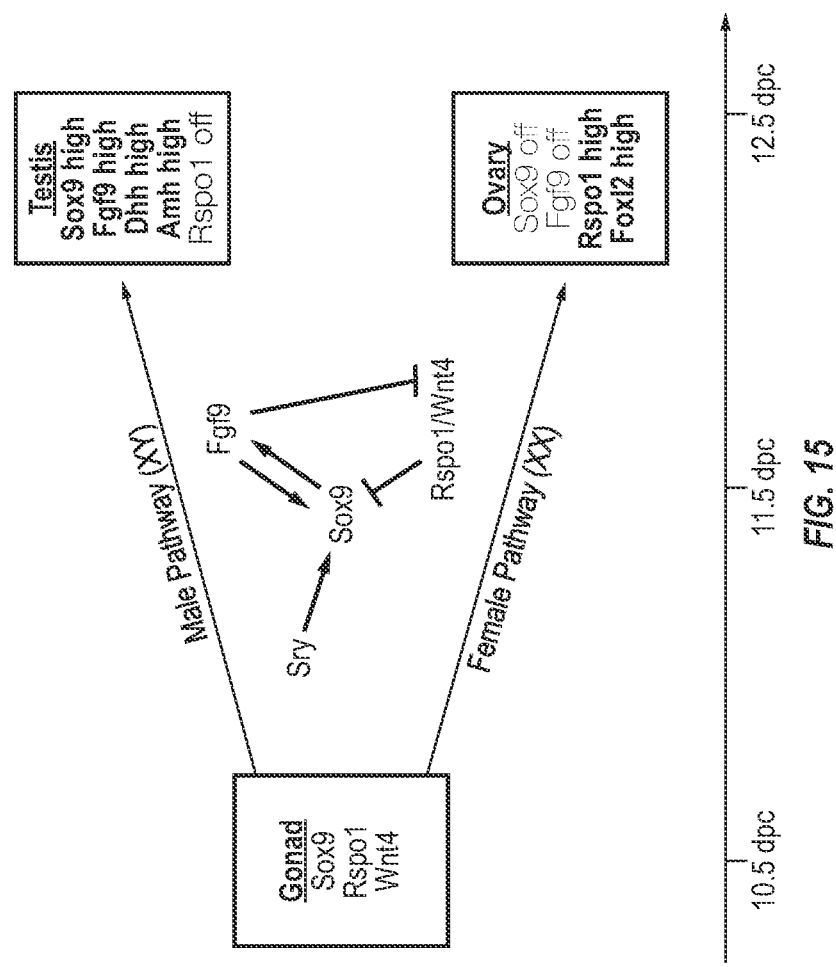
FIG. 15 shows an overview of sex determination signaling pathways in mice. During mouse embryogenesis, bipotential gonads arise from the genital ridges by 10.5 days post coitum (dpc). In somatic cells of XY genital ridges, Sry (sex-determining region on the chromosome Y) expression starts at 10.5 dpc, reaches a peak at 11.5 dpc and wanes by 12.5 dpc. Sox9 (SRY box containing gene 9) expression is upregulated a few hours later to induce differentiation of Sertoli cells. Sox9 expression peaks at 11.5-12.5 dpc, continues to be expressed postnatally and is supported by several positive-feedback loops (including FGF9 (fibroblast growth factor 9)), and SOX9 subsequently activates many male-specific genes, including Amh (anti-Müllerian hormone). At 12.5 dpc, testis cords have formed, and morphological differences between testis and ovary are evident. In the absence of SRY, genes such as Wnt4 (wingless-type MMTV integration site family, member 4), Rspo1 (R-spondin 1), and Fox12 (forkhead box L2) are expressed in a female-specific manner and induce ovarian development, as characterized by the expression of follistatin and many other ovary-specific genes.

To determine why some XY clones produce sex reversed mice, we used RT-PCR to determine the expression levels of markers of early sex determination in both males and females. In the male pathway, we looked at genes involved in the initiation of male sex determination: Sry, Sox9 (proposed to be the direct target of Sry; necessary for initiation and maintenance of testis development), genes involved in suppressing aspects of the female pathway (Fgf9), and genes that are good markers of early testis differentiation (Dhh and Amh). In the female pathway, we looked at genes that are active in very early female development (Fox12) and involved in suppressing aspects of the male pathway (Rspo1). See FIG. 15.

To prepare samples for RT-PCR, tissues were homogenized in TRIzol and chloroform was used for phase separation. The aqueous phase, containing total RNA, was purified using MagMAX™-96 for Microarrays Total RNA Isolation Kit (Ambion by Life Technologies, Cat #AM1839) according to manufacturer's specifications. Genomic DNA was removed using MagMAX™ Turbo™ DNase Buffer and TURBO DNase from the MagMAX kit listed above (Ambion by Life Technologies, Cat #AM1839). mRNA was reverse-transcribed into cDNA using SuperScript® VILO™ Master Mix (Invitrogen by Life Technologies, Cat #11755500). cDNA was amplified with the TAQMAN® Gene Expression Master Mix (Applied Biosystems by Life Technologies, Cat #4370074) using the ABI 7900HT Sequence Detection System (Applied Biosystems). The cycling conditions consisted of 10 minutes at 95° C. followed by 40 cycles of 95° C. for 3 seconds and 60° C. for 30 seconds. Hprt was used as the internal control gene to normalize any cDNA input differences. The reference sample was #1 that all the other samples are compared to in the delta delta CT comparative analysis method. All of the probes were labeled as 6FAM as the reporter and BHQ1 as the quencher. Sequences are shown in Table 8.

TABLE 8

RT-PCR Primers and Probes.

| Gene | Probe or Primer | Sequence (5' to 3') | SEQ ID NO |
| --- | --- | --- | --- |
| mHPRT1 | Probe | TGGGAGGCCATCACATTGTGGC | 1 |
| mHPRT1 | Forward | TGCTCGAGATGTCATGAAGGA | 2 |
| mHPRT1 | Reverse | CCAGCAGGTCAGCAAAGAAC | 3 |
| mSox9 | Probe | CGCTGACCATCAGAACTCCGGCT | 4 |
| mSox9 | Forward | ACCCGCTCGCAATACGACTA | 5 |
| mSox9 | Reverse | CCGGCTGCGTGACTGTAG | 6 |
| mRspo1 | Probe | TAGGACCTACCTGGGCACAGTGA | 7 |
| mRspo1 | Forward | CAACAGGGCCACTCACATCAG | 8 |
| mRspo1 | Reverse | GCACTGTACTCTTCCACAGGTATC | 9 |
| mDhh | Probe | ATCGGTCAAAGCTGATAACTCACTGGC | 10 |
| mDhh | Forward | AGTCCCGCAACCACATCCA | 11 |
| mDhh | Reverse | AGCGCACCGTGGCATTTCC | 12 |
| mGata4 | Probe | TGCAATGCCTGTGGCCTCTATCA | 13 |
| mGata4 | Forward | TGGGACGGGACACTACCT | 14 |
| mGata4 | Reverse | CGGTTGATGCCGTTCATCTTG | 15 |
| mFgf9 | Probe | AAACATGTGGACACCGGAAGGAGA | 16 |
| mFgf9 | Forward | CAACACCTACTCTTCCAACCTCTA | 17 |
| mFgf9 | Reverse | GGAGTCCCGTCCTTATTTAATGC | 18 |
| mSry | Probe | TTTACAGCCTGCAGTTGCCTCAACA | 19 |
| mSry | Forward | GGCTAAAGTGTCACAGAGGAGTG | 20 |

TABLE 8-continued

RT-PCR Primers and Probes.

| Gene | Probe or Primer | Sequence (5' to 3') | SEQ ID NO |
|---|---|---|---|
| mSry | Reverse | TCCAGTCTTGCCTGTATGTGATG | 21 |
| mSf1 | Probe | CTACCTCTGGGCCTGCCACCAC | 22 |
| mSf1 | Forward | TCCTGTCCCTGCATCTGTG | 23 |
| mSf1 | Reverse | GGAGCAGCAGGTCTTGGTG | 24 |
| mWnt4 | Probe | CAGTTCAAGCCACATACAGATGAGGACC | 25 |
| mWnt4 | Forward | CGCTGGTGCCTCGGAATG | 26 |
| mWnt4 | Reverse | CGGATGTCCTGCTCACAGAAG | 27 |
| mAmh | Probe | TCAACCAAGCAGAGAAGGTGCCA | 28 |
| mAmh | Forward | GCTCGGGCCTCATCTTAACC | 29 |
| mAmh | Reverse | GCGGGAATCAGAGCCAAATAGAAAG | 30 |
| mNr0b1 | Probe | TGCTCACTAGCGCTCAGCAAACG | 31 |
| mNr0b1 | Forward | AGGCAGGGCAGCATCTTATACAG | 32 |
| mNr0b1 | Reverse | CACTCGCCTCTGCGATGTG | 33 |
| mFox12 | Probe | TCACTCTGTCCGGCATCTACCA | 34 |
| mFox12 | Forward | CGAGAGCGCCGAGAAGAG | 35 |
| mFox12 | Reverse | GAACGGGAACTTGGCTATGATG | 36 |
| mDdx3y | Probe | TCAGCAGATTCGGGACTTAGAACGT | 37 |
| mDdx3y | Forward | GTGTATGGTGGTGCTGATACTGT | 38 |
| mDdx3y | Reverse | CGTCCTGGTGTGGCAACTAAC | 39 |
| mEif2s3y | Probe | AGCTGGTAATGAATCTTGTCCTCAACC | 40 |
| mEif2s3y | Forward | TGGATGCAGCTCTTCTGTTGA | 41 |
| mEif2s3y | Reverse | TGGCAGCCAGGTGTTCAG | 42 |

To normalize RT-PCR samples, we used a general housekeeping gene (Hprt) as well as genes that are specific to the genital ridge and expressed in equal levels in both sexes at these stages (Sf1 and Gata4).

Previous experiments indicated that two genes on the Y chromosome that are normally expressed in ES cells were down regulated in ES cells from sex-reversed lines (Ddx3y and Eif2s3y; see FIG. 1). These genes are on the short arm of the Y chromosome in the Sxr$^b$ region. Through deletion studies, this region is known to be critical for spermatogenesis but not involved in sex determination. Both of these genes are expressed in male gonads during this period of development but not in ovaries (affymetrix data from GUDMAP.org); thus, we used probes against these genes to show whether the process that gives rise to sex reversal effects expression of other genes the Y chromosome, beyond those involved in sex determination.

Two clones were used for this experiment: 1823CF11 historically produces only male VELOCIMICE® in the F0 generation, whereas 1823CE6 has produced 88% female XY VELOCIMICE® (sex reversed) in the F0 generation. Both clones were grown under identical conditions throughout their isolation and expansion in a medium based on KO-DMEM. Eleven litters of VELOCIMICE® were produced from each clone: 2 litters from each were allowed to go to term to verify the extent of sex reversal, leaving 9 litters from each clone for genital ridge collection (see Table 9). From the litters of each clone allowed to go to term so that offspring could be sexed, clone CF11 produced 11 XY male VELOCIMICE® and no XY female VELOCIMICE®, plus 2 male chimeras and 1 female chimera. Clone CE6 produced 2 XY male VELOCIMICE® and 6 XY female VELOCIMICE®, plus 3 male chimeras and 6 female chimeras.

Despite timing blastocyst injections and dissection start times for the same time of day for each clone, litters for the sex reversed CE6 clone were developmentally advanced in comparison to CF11 (see Table 10). For example, CF11 litters taken at 8:30 AM and 9:30 AM had somite ranges starting at 12-13 ts, while CE6 litters at this time had somite ranges of 16-20 ts. Overall, this represented approximately an 8 hour advancement of CE6 over CF11, and meant that the earliest stages of Sry expression is not measurable in this experiment in the CE6 line. However, the time of peak of Sry expression at 17-18 ts is still represented.

TABLE 9

Collection of Genital Ridge Samples.

|  | 1823CF11 | 1823CE6 |
|---|---|---|
| # Litters Pregnant | 11 | 11 |
| # Embryos | 71 | 68 |
| Tail Somite Range | 12-27 | 16-25 (no early ts) |

TABLE 10

Timing of Collection of Genital Ridge Samples and Stage of Development.

| Time | 1823CF11 | 1823CE6 |
|---|---|---|
| 8:00 | — | 2 litters 17-22 ts |
| 8:30 | 1 litter 12-16 ts | 1 litter 20-24 ts |
| 9:00 | — | 2 litters 16-20 ts |
| 9:30 | 2 litters 13-23 ts | — |
| 10:00 | — | 2 litters 20-24 ts |
| 11:00 | 2 litters 14-22 ts | — |
| 12:30 | — | 1 litter 21-23 ts |
| 1:00 | 1 litter 18-21 ts | — |
| 2:30 | — | 1 litter 18-25 ts |
| 3:00 | 1 litter 17-22 ts | — |
| 4:00 | 1 litter 22 ts | — |
| 5:00 | 1 litter 21-27 ts | — |

For controls, we also harvested genital ridges from the outbred strain CD1 during the window of sex determination (20ts). The XY samples from this outbred line should express high levels of Sry at this time and serve as a strongly positive control. The XX samples do not have the Y chromosome and are thus a negative control for Sry, genes on the Y chromosome, and other markers of the male pathway.

The VELOCIMOUSE® method of generating blastocysts largely produces mice derived entirely from the injected ES cells, but low numbers of host derived embryos and chimeras of both host and ES cell are still generated. To eliminate those samples from consideration, we used PCR to look for the presence of different alleles of tryosinase, a coat color gene that is mutated in the host blastocyst strain Swiss Webster (TyrMut) and functional in F1H4 ES cells (TyrWt). Samples were eliminated if they had TyrMut greater than or equal to 0.5, or levels of TyrWt less than or equal to 1.5 and TyrMut greater than 20% of TyrWt.

To normalize RT-PCR data to the amount of gonadal tissue in each sample, we examined the levels of the two genes expressed specifically in the gonads of both sexes: Sf1 and Gata4. Sf1 has a relatively constant expression in gonads relative to the housekeeping gene Hprt across the developmental stages we examined and was thus used as a normalizing gene in subsequent samples. Gata4 appears to have increased levels at early stages so was not used as a normalizing gene.

Figure 2:
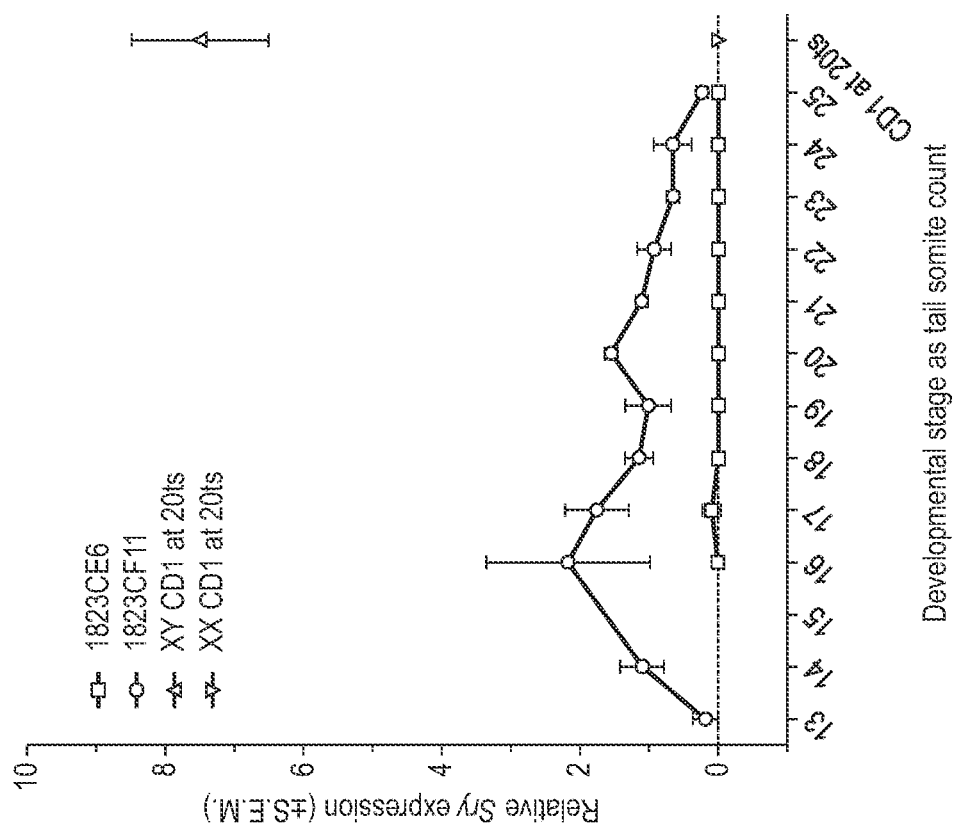
FIG. 2 shows Sry levels in genital ridges dissected from embryos derived from the 1823CE6 and 1823CF11 clones. The developmental stages of the embryos analyzed ranged from 13 to 25 tail somites (ts). CD1 XY embryos at 20 ts were used as a positive control, and CD1 XX embryos at 20 ts were used as a negative control. The x-axis shows the ts stage, and the y-axis shows Sry expression measured by TAQMAN® reverse transcription-coupled quantitative polymerase chain reaction (RT-qPCR) of mRNA normalized to that of the Sf1 reference gene. The same results were obtained when Hprt was used as the normalizing reference gene. The normalized expression values are plotted relative to one of the 1823CF11 ts 14 samples, whose value was arbitrarily set as 1.

As shown in FIG. 2, Sry expression is detectable in gonads from the CF11 line in the normal window of sex determination. Sry expression in FIG. 2 is shown relative to Sf1, a marker for somatic cells in the genital ridges of both sexes at this stage. Similar results were observed when Sry expression was normalized to Hprt expression (data not shown). CD1 XY and XX samples at 20 ts were used as controls (CD1 XY as a positive control for Sry expression, and CD1 XX as a negative control). As shown in FIG. 2, Sry expression becomes detectable starting at approximately 13 ts, reaches a peak at approximately 16-17 ts, and declines by approximately 25 ts. However, in gonads derived from the sex reversing CE6 clone, Sry expression is largely undetectable in during all stages of sex determination examined (16-25 ts). Most gonads from the CE6 clone did not have detectable CT values even after 40 cycles.

Figure 4:
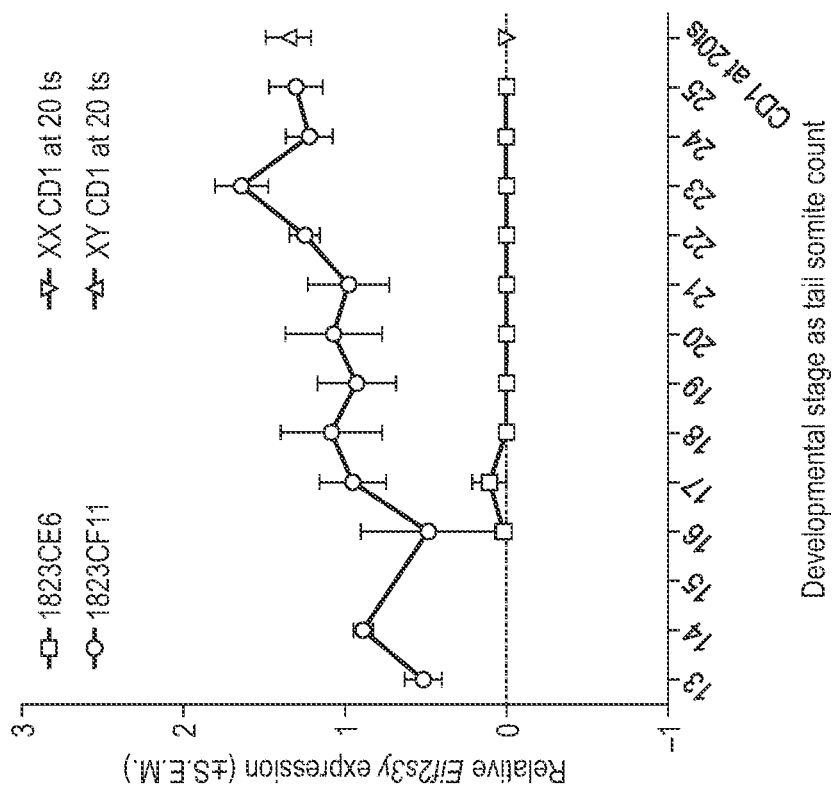
FIG. 4 shows relative Eif2s3y expression levels in the same genital ridge samples shown for Sry expression in FIG. 2 normalized and plotted in the same manner.
Figure 3:
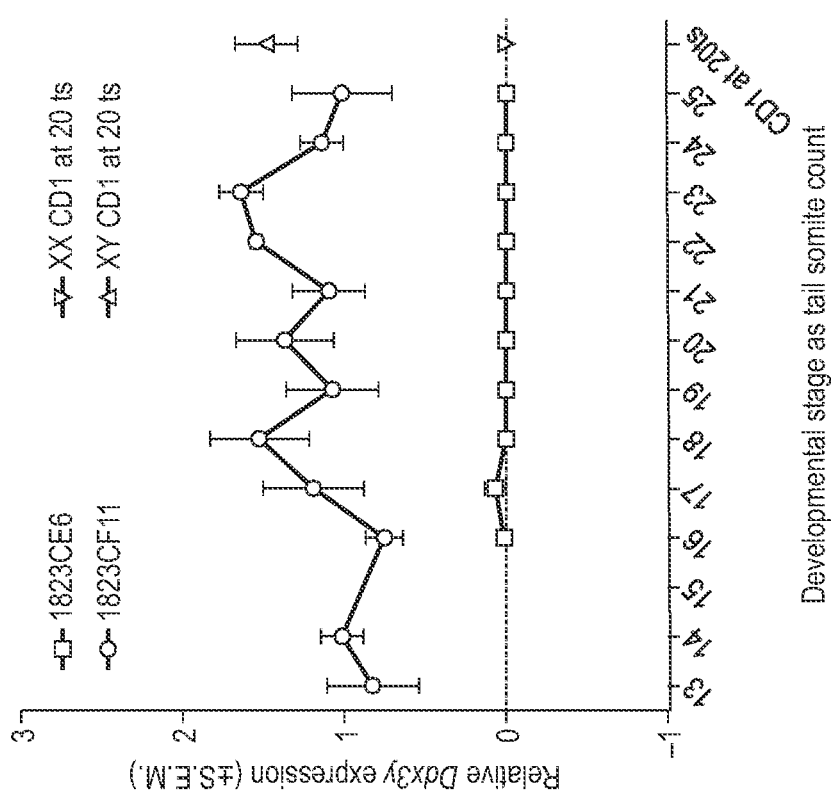
FIG. 3 shows relative Ddx3y expression levels in the same genital ridge samples shown for Sry expression in FIG. 2 normalized and plotted in the same manner.

The Y chromosome genes Ddx3y and Eif2s3y are expressed as expected in CF11 gonads at this stage but are largely undetectable in gonads from the sex reversed CE6 clone as shown in FIG. 3 and FIG. 4. FIG. 3 shows Ddx3y expression relative to Sf1 in CE6 and CF11. FIG. 4 shows Eif2s3y expression relative to Sf1 in CE6 and CF11. XY CD1 and XX CD1 were used as positive and negative controls, respectively (20 ts). Together with the data on Sry expression, these data indicate that three unrelated genes on the Y chromosome are strongly repressed in the sex reversed clone (CE6), suggesting large portions of the Y chromosome may be silenced in sex reversed clones.

Figure 5B:
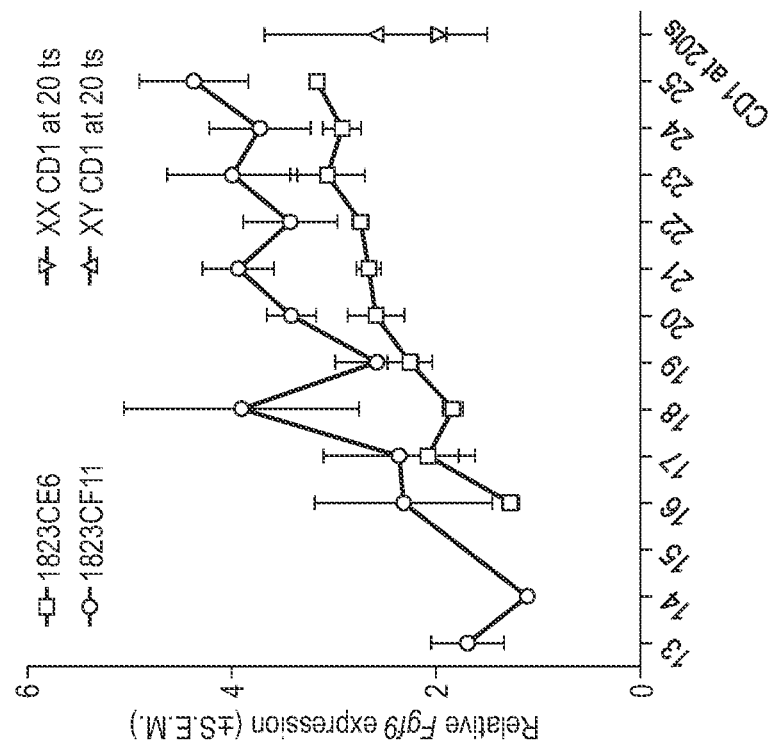
FIG. 5A-5D show relative expression levels of male sex-determining genes Sox9 (FIG. 5A), Fgf9 (FIG. 5B), mDhh (FIG. 5C), and Amh (FIG. 5D) in the same genital ridge samples shown for Sry expression in FIG. 2, normalized and plotted in the same manner.
Figure 5A:
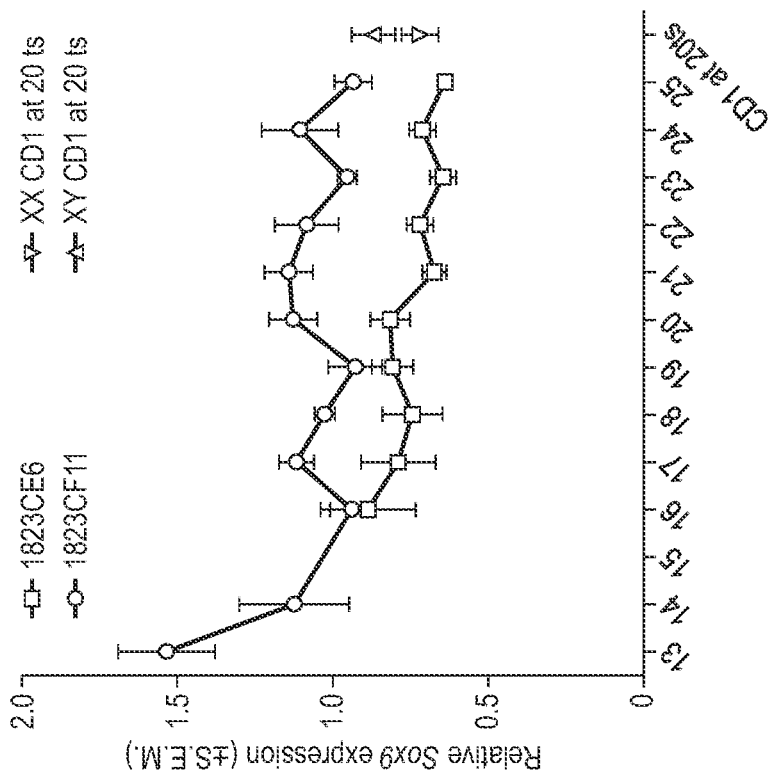
Figure 5D:
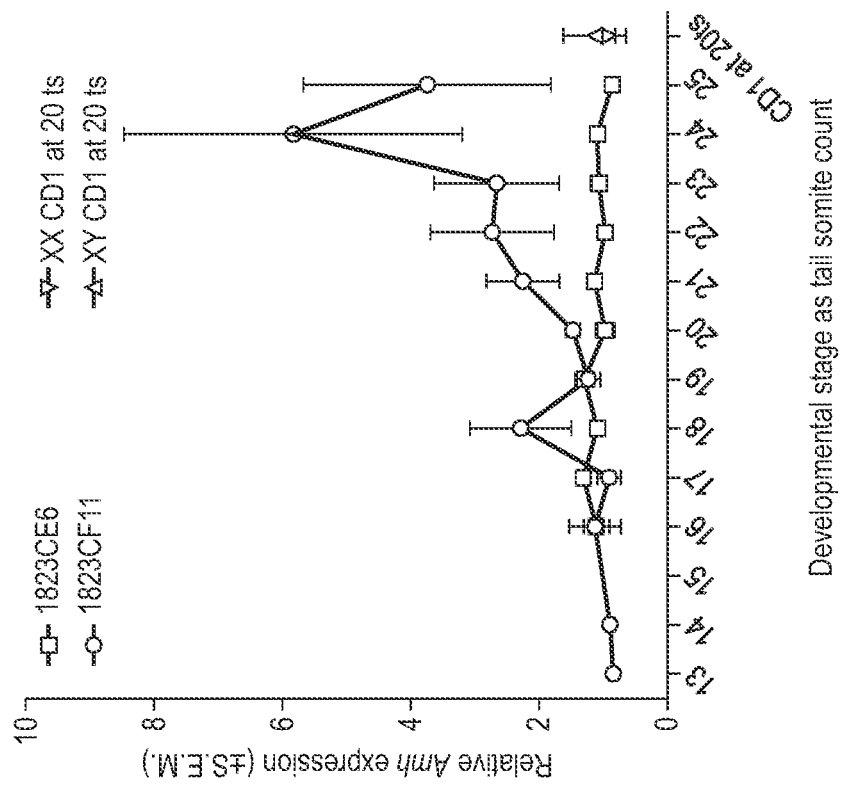
Figure 5C:
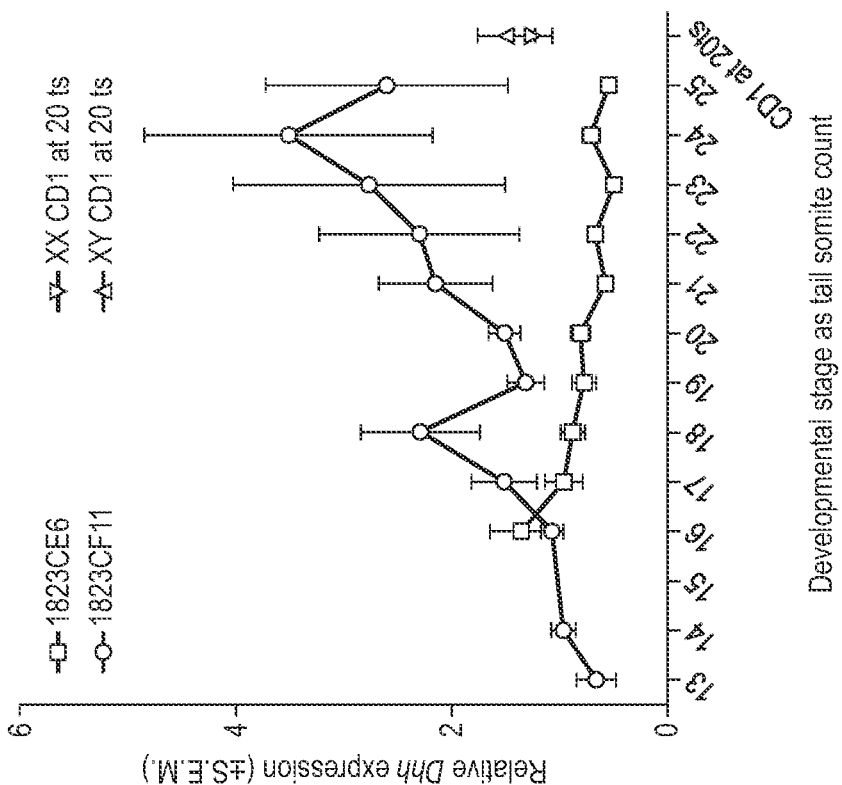

FIGS. 5A, 5B, 5C, and 5D show that markers of male sex determination and testis development downstream of Sry are decreased in gonads from the sex reversed CE6 clone when compared to the non-sex reversed CF11 clone. FIG. 5A shows Sox9 expression relative to Sf1, FIG. 5B shows Fgf9 expression relative to Sf1, FIG. 5C shows mDhh expression relative to Sf1, and FIG. 5D shows Amh expression relative to Sf1. XY CD1 and XX CD1 were used as positive and negative controls, respectively (20 ts).

Figures 6A, 6B:
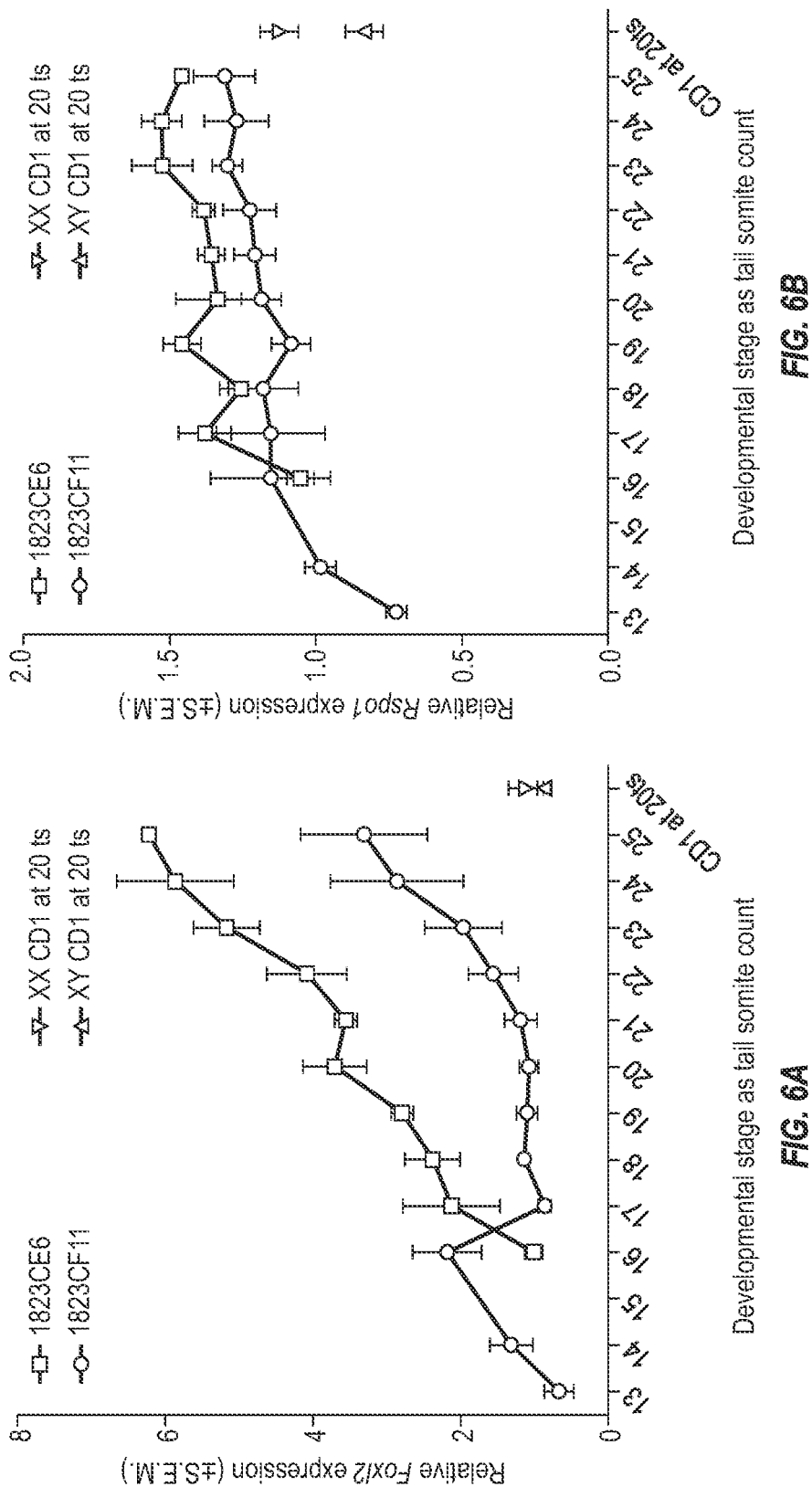
FIGS. 6A and 6B show relative expression levels of female sex-determining genes Fox12 (FIG. 6A) and Rspo1 (FIG. 6B) in the same genital ridge samples shown for Sry expression in FIG. 2, normalized and plotted in the same manner.

FIGS. 6A and 6B show markers of female sex determination and ovarian development in gonads from the sex reversed SE6 clone compared to the non-sex reversed CF11 clone. FIG. 6A shows Fox12 expression relative to Sf1, and FIG. 6B shows Rspo1 expression relative to Sf1. XY CD1 and XX CD1 were used as positive and negative controls, respectively (20 ts). Markers of female sex determination and ovarian development are generally initiated at stages somewhat later than these, however one of the earliest markers of ovarian development (Fox12) is strongly increased in gonads from the sex reversed CE6 clone. The ovarian marker Rspo1 is also up slightly in sex reversed samples. The small difference may simply be due to this stage being too early to detect most of ovarian-specific development.

Because clone 1823CE6 was later demonstrated to have lost its Y chromosome at some point in time, expression experiments were repeated as above using additional XY ES cell clones, including one moderate sex-reversing line and one strongly sex-reversing line in order to be sure that both still had the Y chromosome at all points in the experiment. The clones were grown under identical conditions throughout their isolation and expansion in a medium based on KO-DMEM. As explained in further detail below, these experiments confirmed that expression of Sry, Y chromosome genes, and male sex-determining genes is decreased in the XY ES cell sex-reversing lines, and tend to be more strongly repressed in lines that produce the highest frequency of sex reversal when compared to lines that produce less frequent sex reversal. In addition, these experiments demonstrated that Y chromosome genes are a good way of reporting on the sex reversal phenomenon because they are consistently repressed in sex-reversed lines during mouse development and in all organs tested after birth. In addition, in one XY ES cell line that never sex reverses, an unusually high level of most Y chromosome genes and male sex-determining genes was observed.

Figure 7:
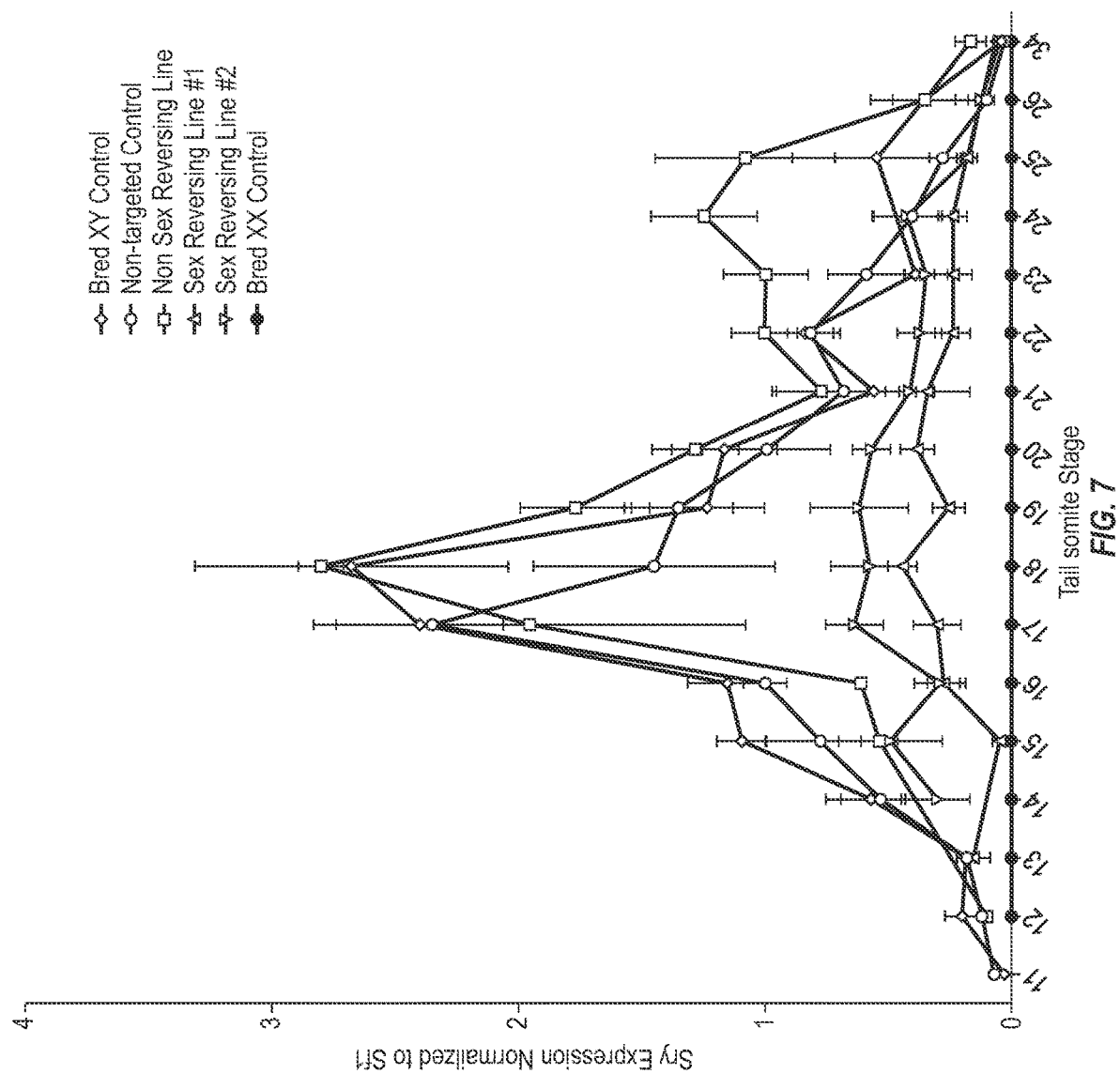
FIG. 7 shows relative expression levels of Sry in genital ridges dissected from embryos derived from two sex-reversing XY ES cell clones cultured in KO-DMEM. The developmental stages of the embryos analyzed ranged from 11 to 34 tail somites (ts). Three controls were used: XY mouse embryos generated via breeding; XY mouse embryos from non-targeted ES cells; and XY mouse embryos from a line that does not sex-reverse in KO-DMEM. The x-axis shows the ts stage, and the y-axis shows Sry expression measured by TAQMAN® reverse transcription-coupled quantitative polymerase chain reaction (RT-qPCR) of mRNA normalized to that of the Sf1 reference gene.

In FIG. 7, Sry expression was measured in gonads during sex determination. Three control lines were used: XY mouse embryos generated via breeding; XY mouse embryos from non-targeted XY ES cells; and XY mouse embryos from an XY ES cell line (1823-CF11) that does not sex reverse. These controls show the normal time course of Sry expression, with initiation around 14 ts, a peak at 17-18 ts, and loss by 26 ts. The two-sex reversing lines showed markedly less Sry expression during this critical period. Line #1 is strongly sex reversing line (averaging 86% XY females) and has less Sry expression over this time course than Line #2 (15069-CD1; 45% XY females). XX mouse embryos do not have any expression (due to the lack of a Y chromosome) and serve as a negative control.

Figure 8A:
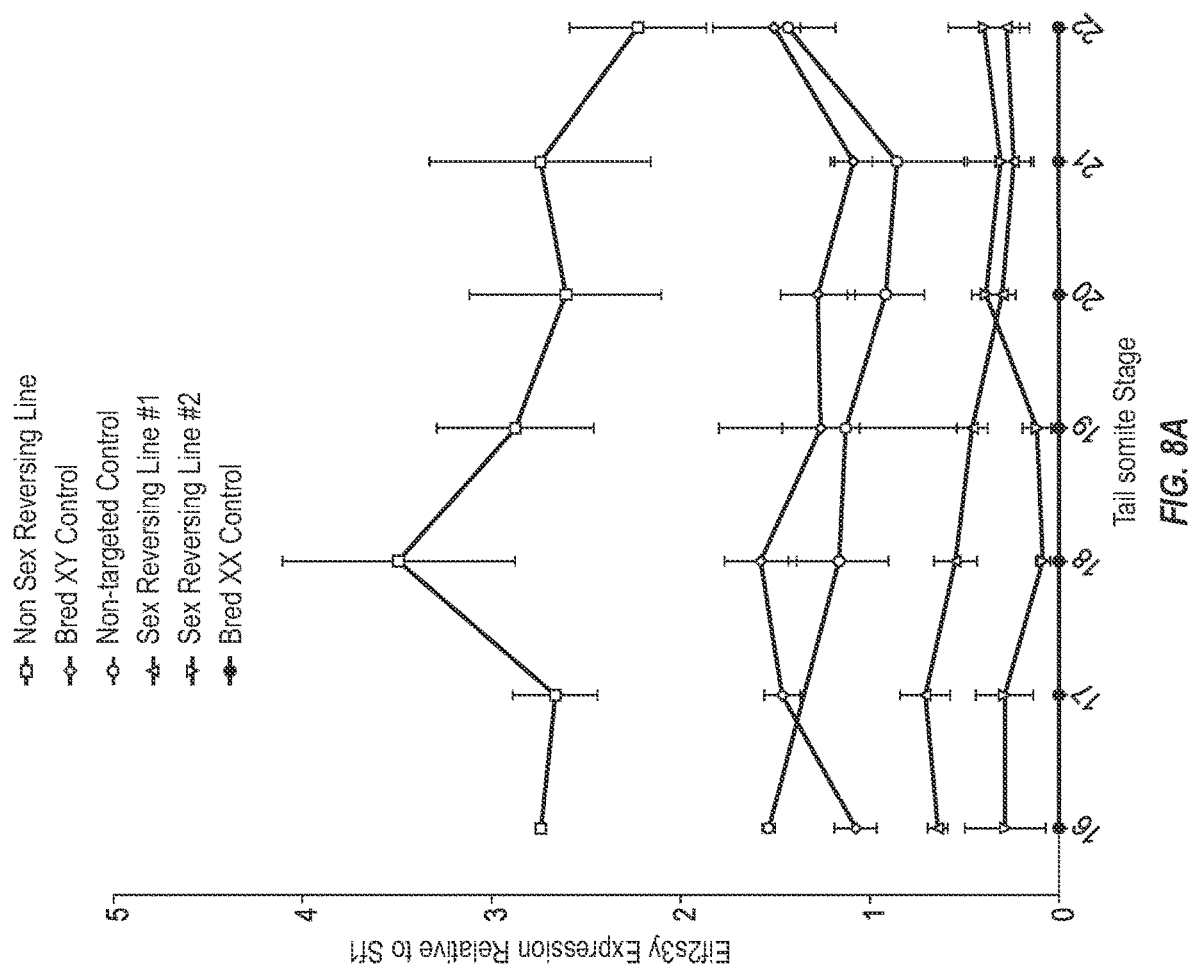
FIG. 8A-C show relative expression levels of Eif2s37 (FIG. 8A), Uty (FIG. 8B), and Ddx3y (FIG. 8C) in genital ridges dissected from embryos derived from two sex-reversing XY ES cell clones cultured in KO-DMEM. The developmental stages of the embryos analyzed ranged from 16 to 22 tail somites (ts). Three controls were used: XY mouse embryos generated via breeding; XY mouse embryos from non-targeted ES cells; and XY mouse embryos from a line that does not sex-reverse in KO-DMEM. The x-axis shows the ts stage, and the y-axis shows expression measured by TAQMAN® reverse transcription-coupled quantitative polymerase chain reaction (RT-qPCR) of mRNA normalized to that of the Sf1 reference gene.
Figure 8B:
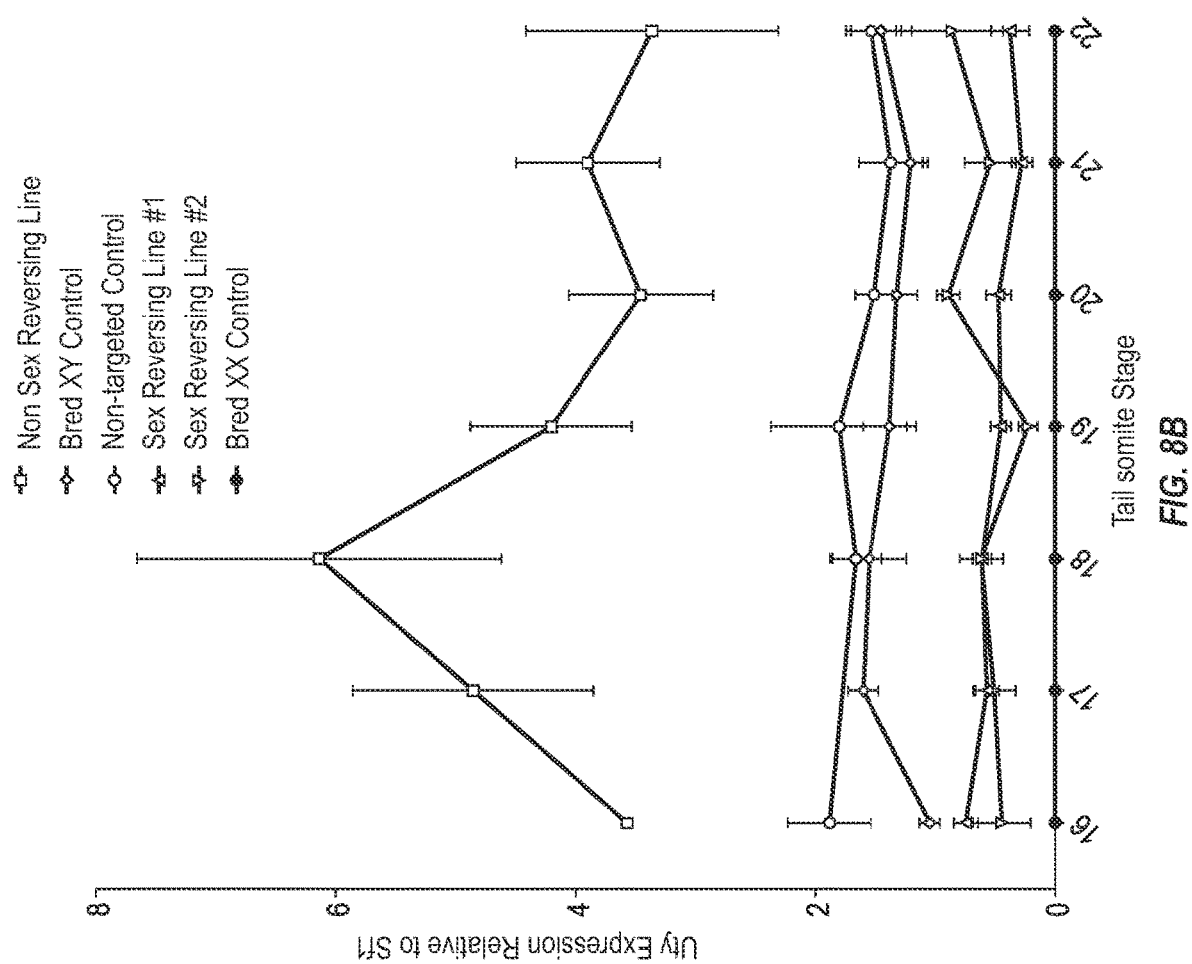
Figure 8C:
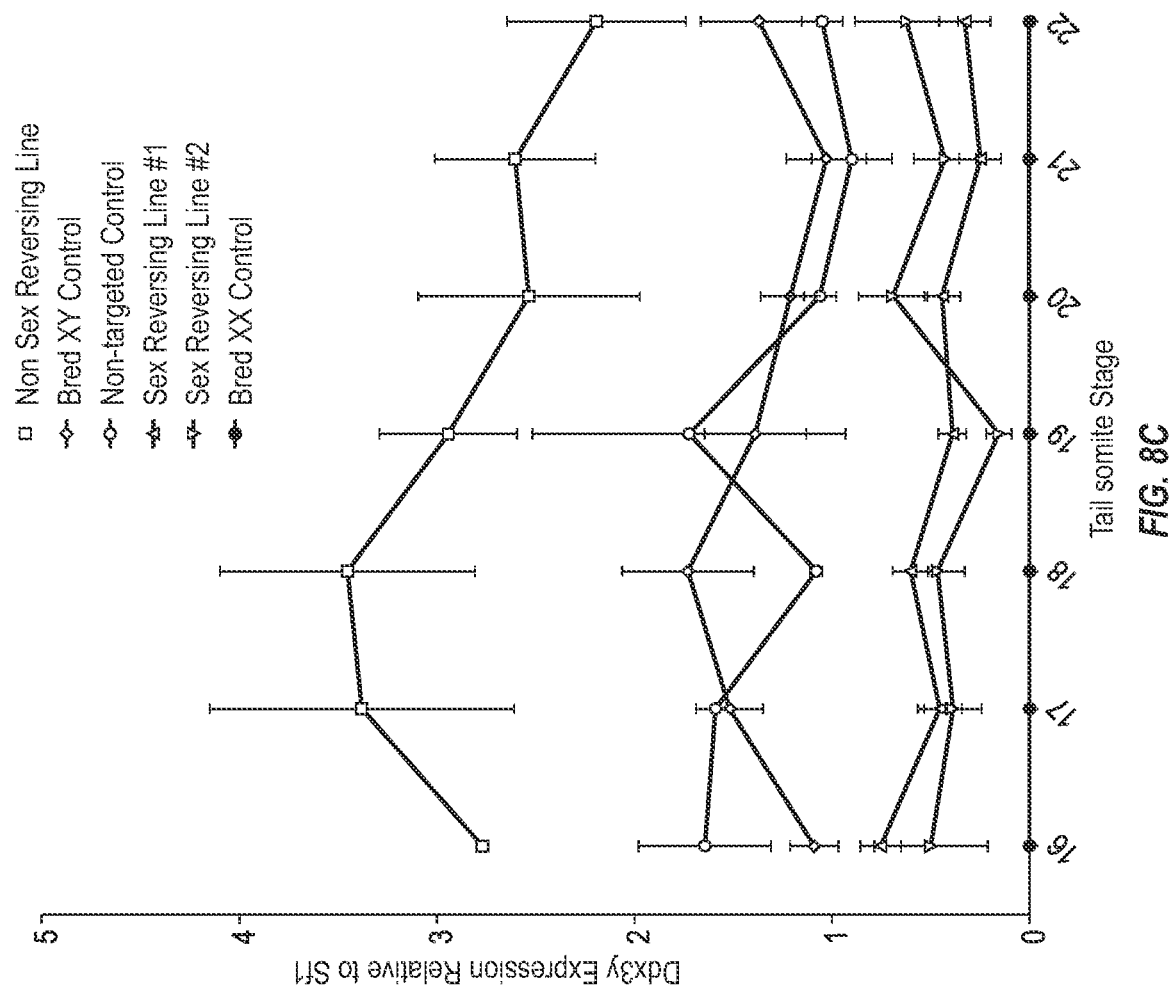
Figure 9:
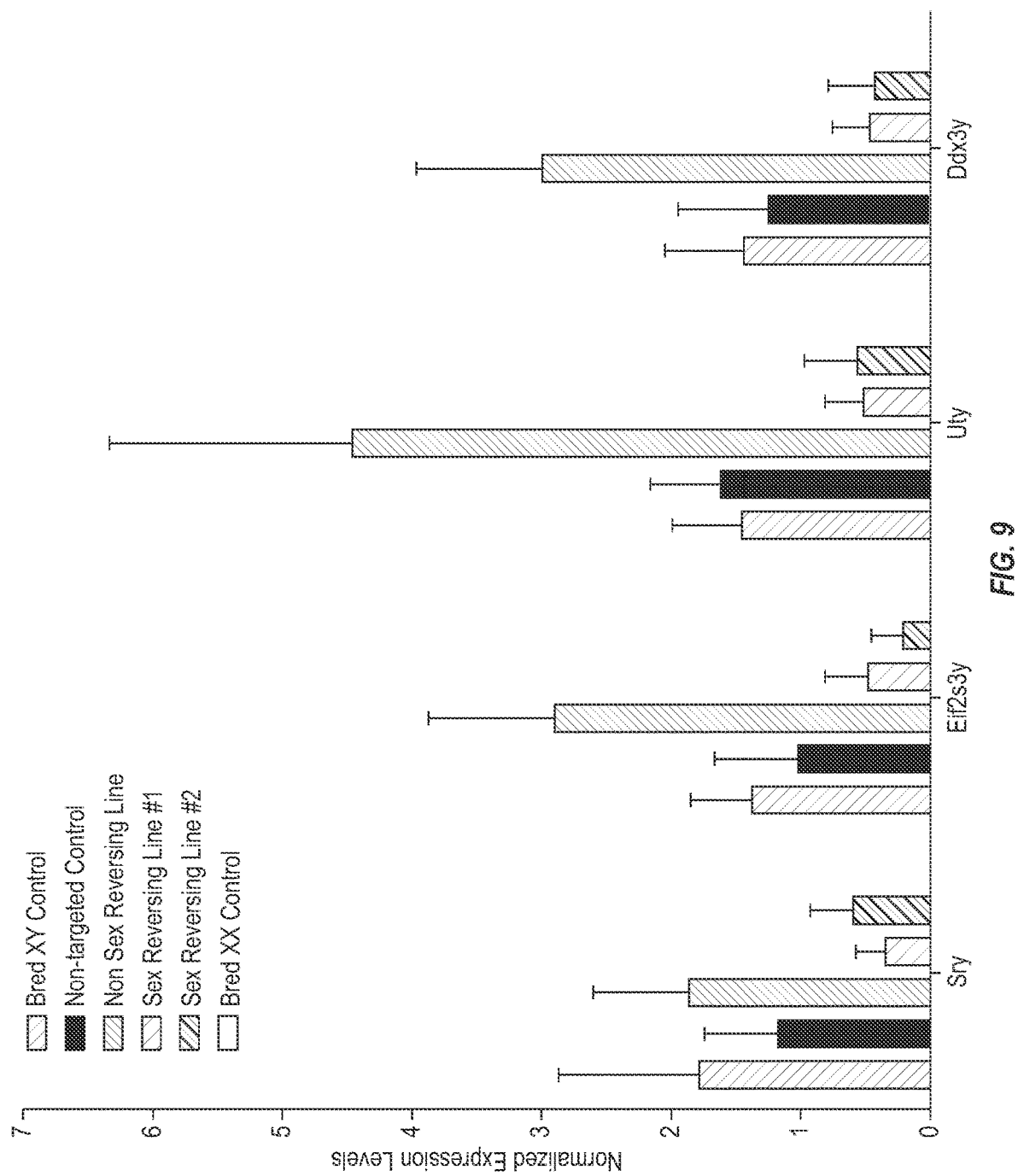
FIG. 9 shows relative expression of Sry, Eif2s3y, Uty, and Ddx3y in genital ridges dissected from embryos derived from two sex-reversing XY ES cell clones cultured in KO-DMEM. The normalized expression levels are averaged over the embryo developmental stages ranging from 17 to 20 tail somites (ts). Three controls were used: XY mouse embryos generated via breeding; XY mouse embryos from non-targeted ES cells; and XY mouse embryos from a line that does not sex-reverse. The x-axis shows the ts stage, and the y-axis shows expression measured by TAQMAN® reverse transcription-coupled quantitative polymerase chain reaction (RT-qPCR) of mRNA normalized to that of the Sf1 reference gene.

FIG. 8A-C shows expression levels of three genes on the Y chromosome in genital ridges during sex determination: Eif2s3y (FIG. 8A); Uty (FIG. 8B); and Ddx3y (FIG. 8C). All three showed strongest expression in mouse embryos generated from the non-sex-reversing XY ES cell line, moderate levels in controls (XY mouse embryos generated via breeding and XY mouse embryos from non-targeted XY ES cells) and the lowest levels in XY mouse embryos generated from the two sex-reversing XY ES cell lines, indicating that multiple genes on the Y chromosome are affected by this process beyond just Sry. FIG. 9 shows the same data is in FIGS. 7 and 8A-C, only compressed, showing the average of all 4 Y chromosome genes assayed in the embryonic genital ridge.

Figure 10A:
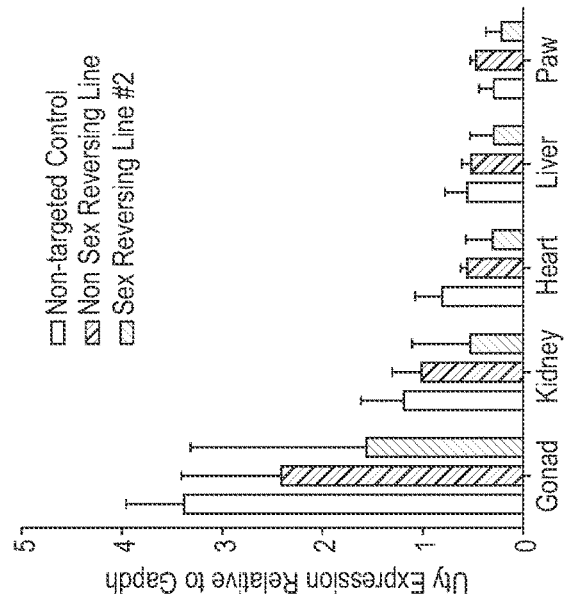
FIG. 10A-D show relative expression levels of Ddx3y (FIG. 10A), Uty (FIG. 10B), Eif2s3y (FIG. 10C), and Kdm5d (FIG. 10D) in various tissues one week after birth in mice derived from a sex-reversing XY ES cell clone cultured in KO-DMEM. Two controls were used: XY mouse embryos from non-targeted ES cells; and XY mouse embryos from a line that does not sex-reverse in KO-DMEM. The x-axis shows the tissue type, and the y-axis shows expression measured by TAQMAN® reverse transcription-coupled quantitative polymerase chain reaction (RT-qPCR) of mRNA normalized to that of the Gapdh reference gene.
Figure 10B:
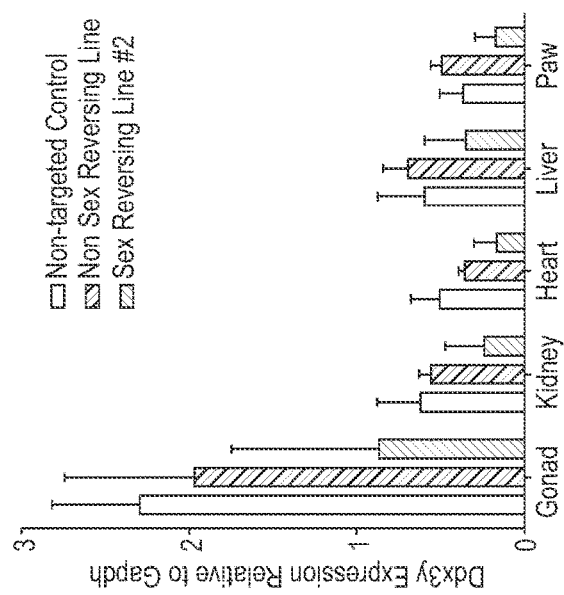
Figure 10C:
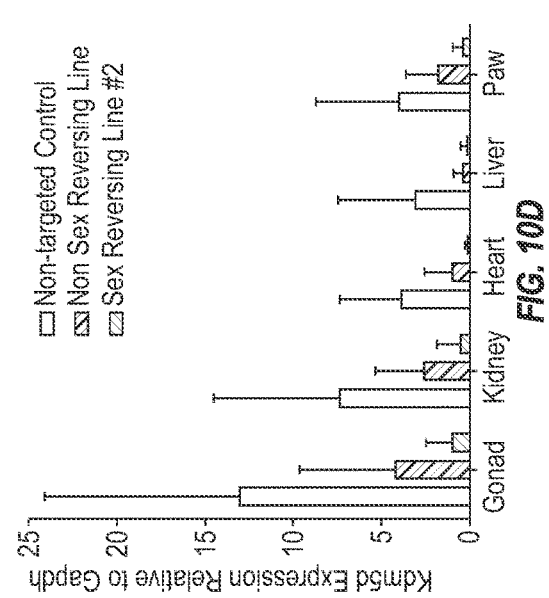
Figure 10D:
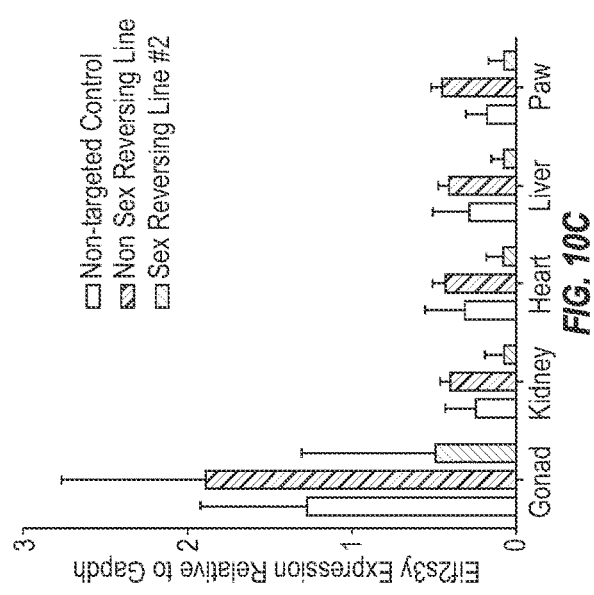

To determine whether expression of the Y chromosome genes is still repressed in mice generated from sex-reversing lines after birth, expression levels of Ddx3y (FIG. 10A); Uty (FIG. 10B); Eif2s3y (FIG. 10C), and Kdm5d (FIG. 10D) were determined in multiple organs one week after birth in mice generated from a non-targeted XY ES cell line, a non-sex-reversing XY ES cell line, and a sex-reversing line. Expression levels were tested in gonad, kidney, heart, liver, and paw. FIG. 10A-D show that Y chromosome genes are still repressed in mice generated from a sex-reversing line in multiple organs after birth, and expression levels of these genes are lower than levels in mice from non-targeted XY ES cells and in mice from an XY ES cell line that does not sex-reverse.

Figure 11B:
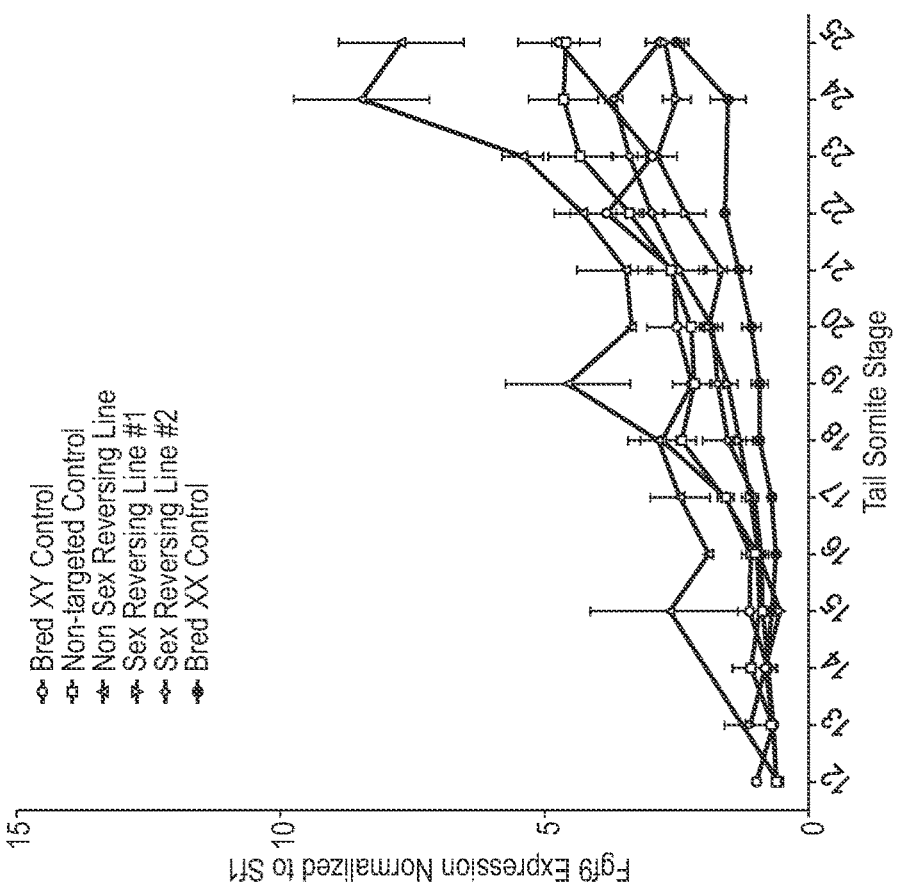
FIG. 11A-B show relative expression levels during the stages of sex determination of genes turned on during the earliest stages of male gonad development.
Figure 11A:
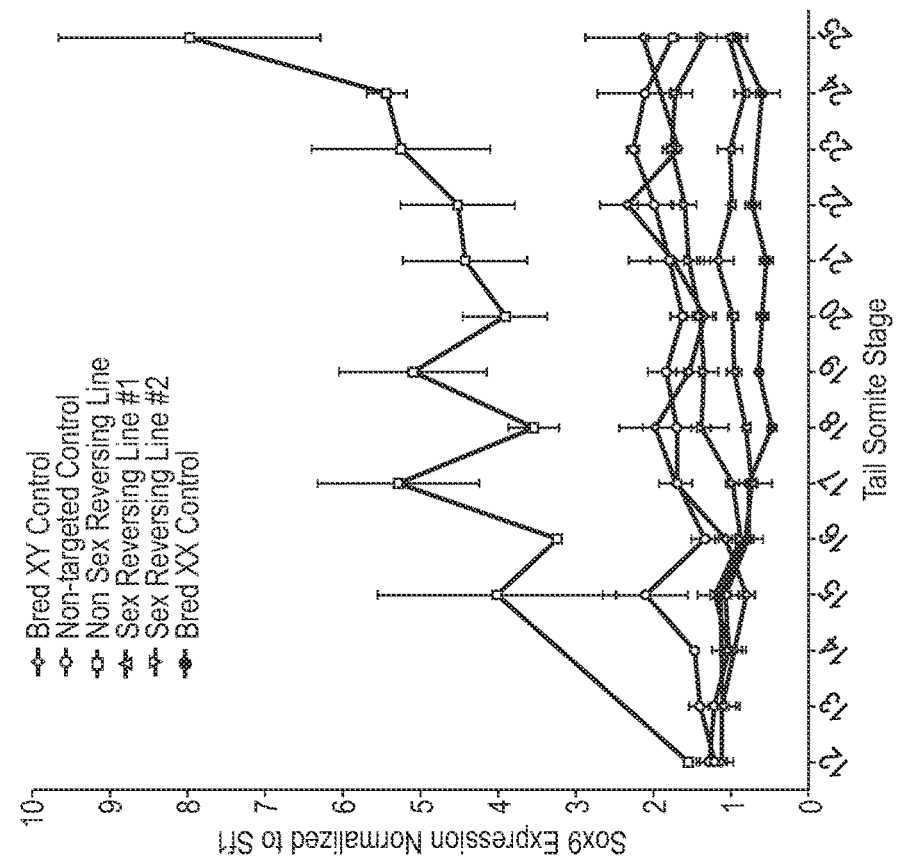

FIG. 11A (Sox9) and 11B (Fgf9) show that markers of male sex determination and testis development downstream of Sry are decreased in gonads from mouse embryos generated from the sex-reversing XY ES cell lines when compared to the non-sex reversing XY ES cell line, a non-targeted control XY ES cell line, and an XX mouse embryo generated by breeding. An XY mouse embryo generated by breeding was used as an additional control. Both Sox9 and Fgf9 are critical early genes in the male pathway, and both are upregulated around the peak of Sry expression (16-18 ts) in the gonad and is necessary for male testis development. Sox9 and Fgf9 levels are highest in gonads from a line that does not sex reverse, intermediate in controls (XY mouse embryos generated via breeding and mouse embryos from non-targeted XY ES cells) and lowest in XX mouse embryos generated via breeding. The XX mouse embryos were used to indicate the female level of expression for Sox9 and Fgf9 during this period. Expression levels in mouse embryos generated from the two sex-reversing lines fall between the XX and XY controls, with the more strongly reversing line #1 showing lower levels than #2 during the period of Sox9 induction.

Dhh and Amh are markers of testis development that are strongly and specifically unregulated during testis development and are not present during ovarian development. See FIG. 15. Both of these genes were expressed highest in gonads from male controls (XY mouse embryos from a line that does not sex reverse, XY mouse embryos generated via breeding, and XY mouse embryos from untargeted ES cells). Mice generated from the two sex-reversing lines had expression levels falling between the XX and XY bred controls, with the more strongly reversing line #1 showing lower, closer to female, levels than #2 (FIG. 12A (Dhh) and 12B (Amh)).

Figure 13:
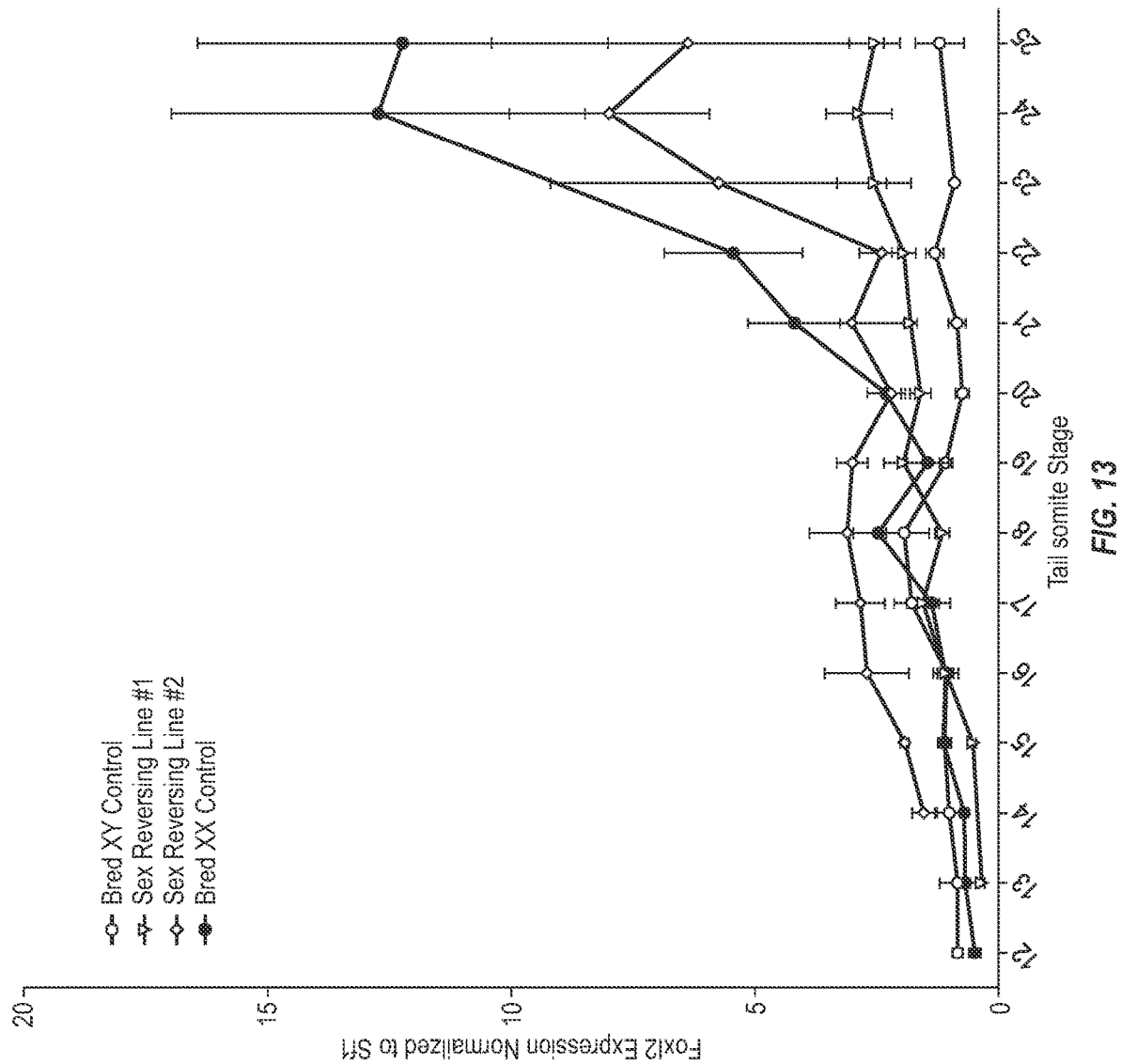
FIG. 13 shows relative expression levels during the stages of sex determination of a marker of female gonad development.

Fox12 is the earliest marker of female development and is strongly upregulated in female gonads between 21-23 ts. See FIG. 15. As shown in FIG. 13, expression levels of this gene in mice generated from the two sex-reversing XY ES cell lines fall between the XX and XY bred controls.

Example 3. Lack of or Decreased Ddx3y (Dby), Eif2s3y, and Uty Expression in XY ES Cell Clones Correlates with Production of Fertile XY F0 Female Mice from Those XY ES Cell Clones Table 11 shows the propensity of XY ES cell clones from gene targeting in the VGF1 ES cell line to produce female VELOCIMICE® following microinjection of the XY ES cell clones into 8-cell embryos. All clones were maintained and cultured in a medium based on KO-DMEM throughout the targeting and microinjection processes. From this sample of clones it is clear that the ability to produce XY female VELOCIMICE® is clone-specific and ranges from 0-60%. These results were reproducible in multiple microinjection experiments: clones that did not produce females maintained this trait in repeated microinjections, whereas clones that gave rise to females tended to yield approximately the same proportion of females in repeat microinjection experiments. The effects could not be reversed by re-growing clones in DMEM-based media. ES cell clones from gene targeting experiments in which the ES cells were grown and maintained in either DMEM-based or KO-DMEM-based media for the entire targeting process—electroporation, selection of drug resistant colonies, screening for targeted mutations, expansion, and cryopreservation—were thawed and grown in the opposite media for three days in preparation for microinjection into 8-cell embryos. Clones derived in a DMEM-based medium maintained a low frequency of female VELOCIMICE® production, and this could not be increased by a brief exposure to KO-DMEM. Likewise, clones derived in KO-DMEM-based medium produced a higher frequency of female VELOCIMICE®, and a brief exposure to DMEM did not reduce the XY clones' propensity to produce females.

TABLE 11

Clonal Variation in the Production of XY Female VELOCIMICE ® Derived from XY ES Cells Cultured in KO-DMEM.

| Clone Injected | Male VELOCIMICE ® | Female VELOCIMICE ® | Proportion of Females (%) |
|---|---|---|---|
| DG4 | 8 | 4 | 33 |
| EC2 | 3 | 1 | 25 |
| ED1 | 12 | 2 | 14 |

TABLE 11-continued

Clonal Variation in the Production of XY Female VELOCIMICE ® Derived from XY ES Cells Cultured in KO-DMEM.

| Clone Injected | Male VELOCIMICE ® | Female VELOCIMICE ® | Proportion of Females (%) |
|---|---|---|---|
| EH2 | 10 | 0 | 0 |
| EH3 | 6 | 0 | 0 |
| NB1 | 6 | 2 | 25 |
| ND1 | 8 | 4 | 33 |
| NF2 | 13 | 7 | 35 |
| NF3 | 12 | 6 | 33 |
| NG4 | 11 | 9 | 45 |
| NG5 | 4 | 6 | 60 |
| HN2 | 4 | 1 | 20 |

Gene expression profiles in feminized versus non-feminized gene-targeted XY ES cell clones were then compared (see Table 12). Four ES cell clones were used, and each was treated exactly the same. All four clones were derived from VGF1 cells grown in the same KO-DMEM-based medium throughout the entire process, including initial thawing, electroporation with the targeting vector, selection for drug resistant clones, and freeze down. Two of the clones produced no XY female VELOCIMICE® in multiple microinjections; two clones produced >50% XY female VELOCIMICE® in repeated microinjections. Expression levels for Y chromosome genes Ddx3y, Uty, and Eif2s3y were 10-20 times lower in feminized ES cells when compared to non-feminized ES cells. Two genes on chromosomes other than the Y chromosome (Col10a1 and Tm4sf1) were used as controls.

a sub-cloning experiment. Clones 985-AA8 and 1823-CF11 produced only male VELOCIMICE® in three separate microinjection experiments, whereas clones 15069-CD1, 4048-BC4, and 979-AC7 produced an average of between 30% and 50% XY female VELOCIMICE® in repeated microinjections (see Table 13). The ES cell clones were thawed from liquid nitrogen storage and subcloned into two replica 96-well plates, one of which was stored at −150° C. while the other was grown and passaged onto two other plates for DNA and RNA preparation. The DNA plate was used to screen for loss of the Y chromosome, while the RNA plate was used to examine expression of Eif2s3y, Uty, and Ddx3y by RT-qPCR. As shown in Table 13, the propensity of clones to produce XY female VELOCIMICE® was directly proportional to the percentage of subclones having no expression or decreased expression of Eif2s3y, Uty, and Ddx3y, indicating that loss of Y chromosome gene expression in subclones can predict the likelihood that a clone will produce XY female VELOCIMICE®: the greater proportion of subclones silenced for expression of Eif2s3y, Uty, and Ddx3y, the higher the propensity of the parental ES cell clone to produce XY female VELOCIMICE®.

TABLE 13

Lack of Expression of Eif2s3y, Uty, and Ddx3y in XY ES Cell Clones Correlates with and Predicts Production of Female VELOCIMICE ® from Those Clones

| Clone Injected | Male VELOCIMICE ® | Female VELOCIMICE ® | Proportion of Females (%) | Percent Subclones Lacking Expression of Eif2s3y, Uty, Ddx3y |
|---|---|---|---|---|
| 15069-CD1 | 17 | 16 | 48.5 | 65.6 |
|  | 2 | 2 | 60.0 |  |
| 4048-BC4 | 14 | 13 | 48.1 | 56.2 |
|  | 3 | 1 | 25.0 |  |
| 979-AC7 | 11 | 12 | 52.2 | 18.8 |
|  | 8 | 1 | 11.1 |  |
| 985-AA8 | 14 | 0 | 0.0 | 6.3 |
|  | 11 | 0 | 0.0 |  |
|  | 7 | 0 | 0.0 |  |
| 1823-CF11 | 7 | 0 | 0.0 | 4.2 |
|  | 4 | 0 | 0.0 |  |
|  | 8 | 0 | 0.0 |  |
|  | 11 | 0 | 0.0 |  |

TABLE 12

Comparison of Gene Expression in Feminized Versus Non-Feminized Gene Targeted XY ES Cell Clones.

| Gene | Ratio of Relative Expression in Female Clones vs. Male Clones | Chromosome |
|---|---|---|
| Col10a1 | 2.41 | 10 |
| Tm4sf1 | 1.76 | 3 |
| Ddx3y | 0.10 | Y |
| Uty | 0.07 | Y |
| Eif2s3y | 0.05 | Y |

Figure 14A:
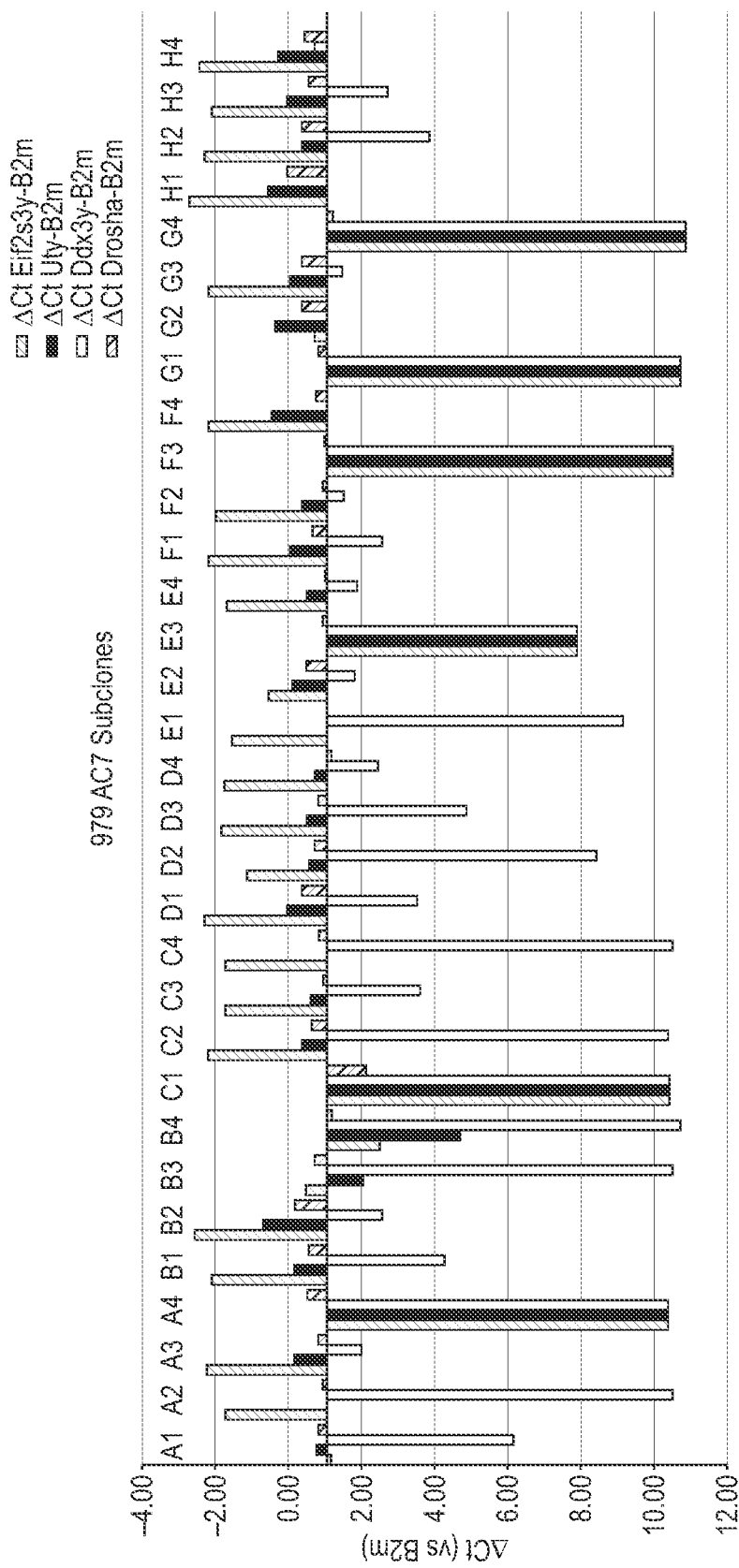
FIG. 14A-E show relative expression levels of Eif2s3y, Uty, and Ddx3y by RT-PCR in embryonic stem cell subclones from three parental F1H4 XY embryonic stem cell clones that produce both XY male and XY female mice (parental clones 979 AC7 (FIG. 14A), 4048 BC4 (FIG. 14B), and 15069 CD1 (FIG. 14C)) and from two parental F1H4 XY embryonic stem cell clones that produce only male mice (985 AA8 (FIG. 14D), and 1823 C11 (FIG. 14E)). Expression is relative to B2m. Drosha was used as a control.
Figure 14B:
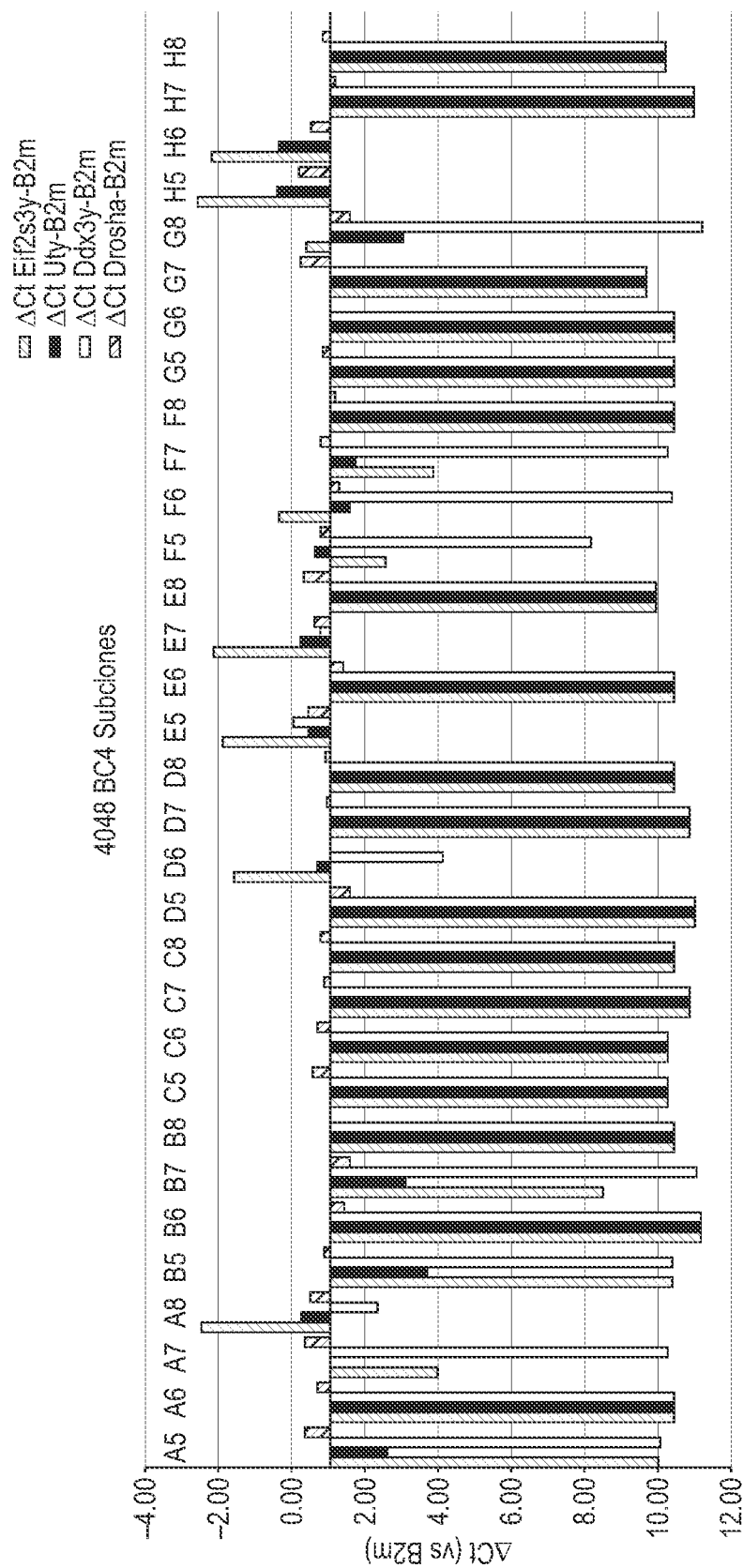
Figure 14C:
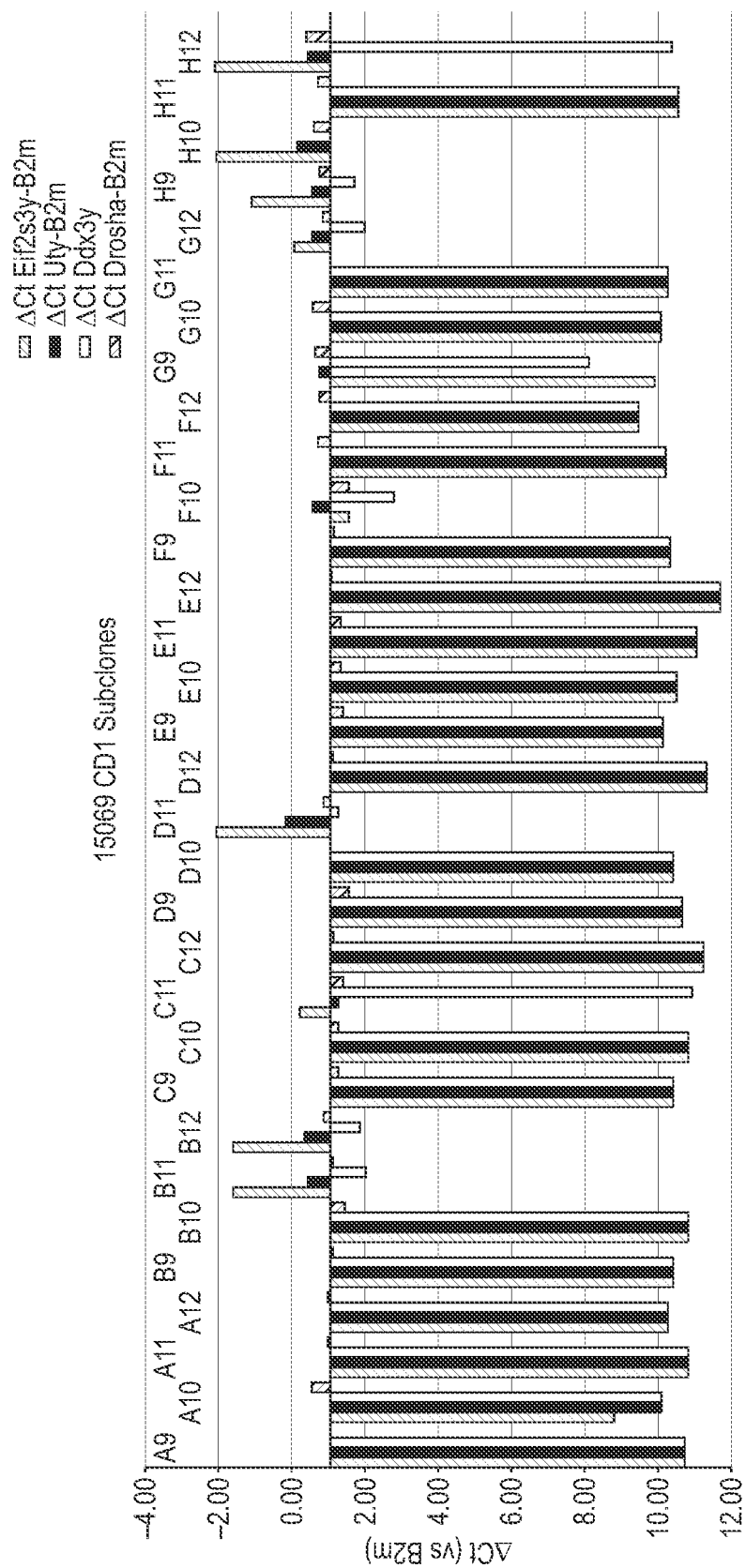

In another experiment, five gene-targeted ES cell clones derived identically in KO-DMEM medium were selected for To produce the data in the upper portion of Table 13, subclones from three parental XY ES cell lines that produce both female and male XY mice were submitted for RNA analysis of Eif2s3y, Uty, and Ddx3y gene expression. The three partially sex-reversing clones that were tested included 979-AC7, 4048-BC4, and 15069-CD1. Thirty-two subclones were tested for each, including subclones A1-A4, B1-B4, C1-C4, D1-D4, E1-E4, F1-F4, G1-G4, and H1-H4 for clone 979-AC7, subclones A5-A8, B5-B8, C5-C8, D5-D8, E5-E8, F5-F8, G5-G8, and H5-H8 for clone 4048-BC4, and subclones A9-A12, B9-B12, C9-C12, D9-D12, E9-E12, F9-F12, G9-G12, and H9-H12 for clone 15069-CD1. Expression of Drosha was used as a control, and expression of each gene was determined relative to B2m expression. The RT-PCR results are shown in the form of ΔCt (gene of interest—B2m) in FIGS. 14A-C. A negative ΔCt indicates a higher relative expression, and a positive ΔCt indicates a lower relative expression. As shown in FIG. 14A, in 6 out of the 32 subclones (18.8%) for clone 979-AC7, no expression was detected for Eif2s3y, Uty, or Ddx3y. As shown in FIG. 14B, in 18 out of the 32 subclones (56.2%) for clone 4048-BC4, no expression was detected for Eif2s3y, Uty, or Ddx3y. As shown in FIG. 14C, in 22 out of the 32 subclones for clone 15069-CD1, no expression was detected for Eif2s3y, Uty, or Ddx3y. However, subsequent analysis of the 32 subclones indicated that one of the 32 subclones—clone D9—had lost the Y chromosome, meaning that 21 of the 32 subclones (65.6%) for 15069 CD1 had the Y chromosome but had no detectable expression of Eif2s3y, Uty, or Ddx3y. Assessment of the presence of the Y chromosome was performed doing copy number assays with probes for two genes on the Y chromosome: Sry and Eif2s3y. All 32 subclones for clone 979-AC7, all 32 subclones for clone 4048-BC4, and 31/32 subclones for clone 15069-CD1 were confirmed by copy number assays to have one copy of the Y chromosome.

Figure 14D:
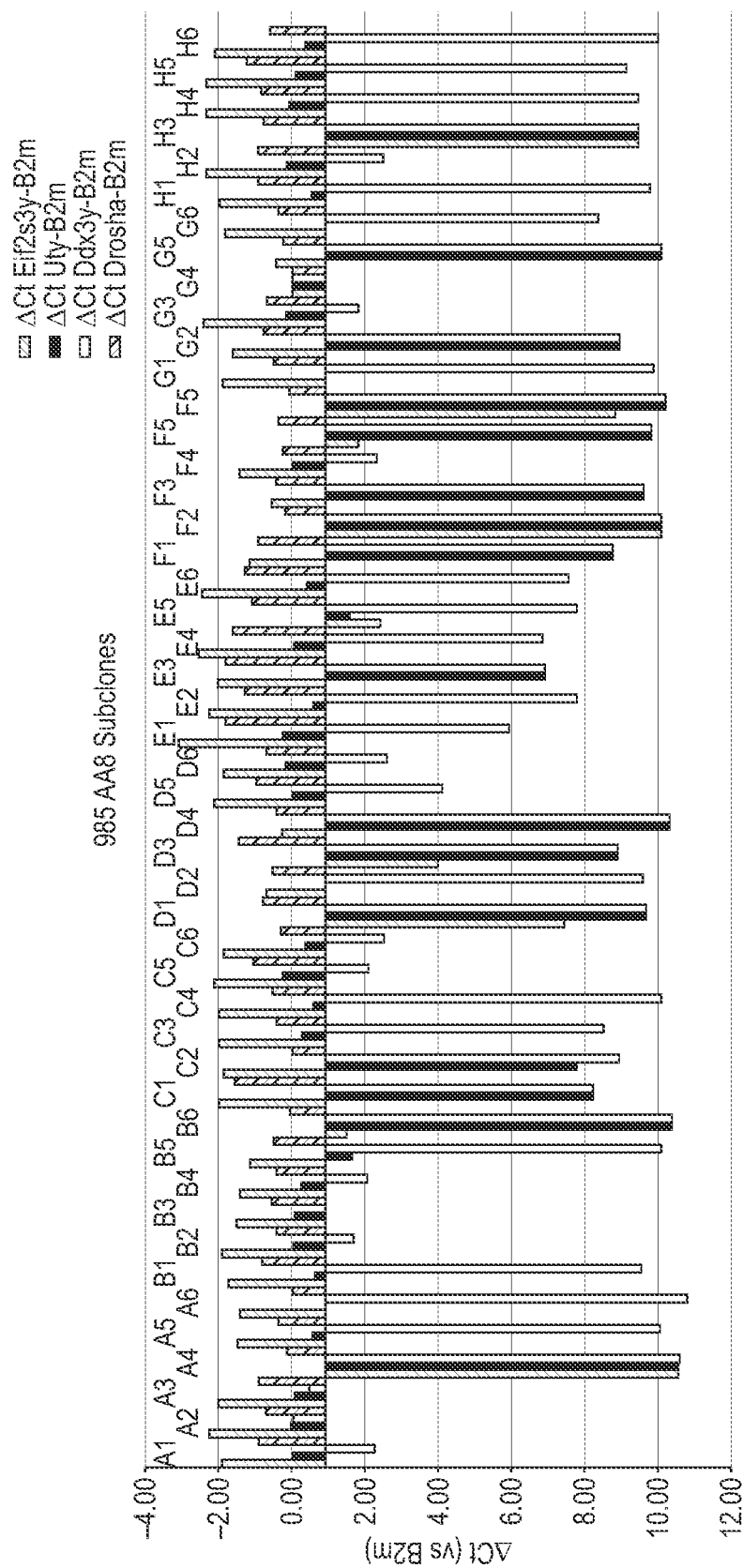
Figure 14E:
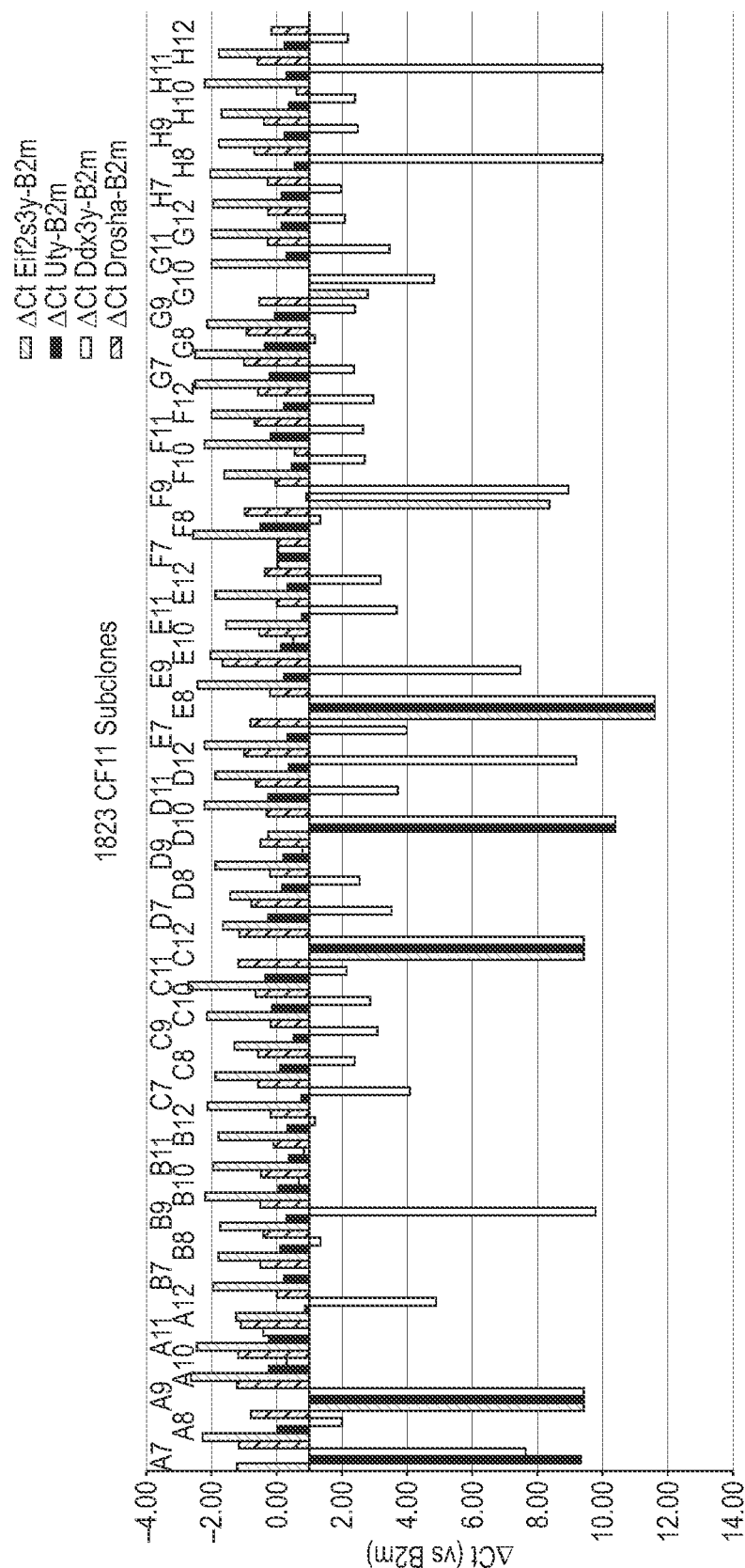

To produce the data in the lower portion of Table 13, subclones from two parental XY ES cell lines that produce only male XY mice were submitted for RNA analysis of Eif2s3y, Uty, and Ddx3y gene expression. The two clones that were tested included 985-AA8 and 1823-CF11. Forty-eight subclones were tested for each, including subclones A1-A6, B1-B6, C1-C6, D1-D6, E1-E6, F1-F6, G1-G6, and H1-H6 for clone 985-AA8, and subclones A7-A12, B7-B12, C7-C12, D7-D12, E7-E12, F7-F12, G7-G12, and H7-H12 for clone 1823-CF11. Expression of Drosha was used as a control, and expression of each gene was determined relative to B2m expression. The RT-PCR results are shown in the form of ΔCt (gene of interest—B2m) in FIGS. 14D-E. A negative ΔCt indicates a higher relative expression, and a positive ΔCt indicates a lower relative expression. As shown in FIG. 14D, in 3 out of the 48 subclones (6.25%; clones A4, F6, and H3) for clone 985-AA8, no expression was detected for Eif2s3y, Uty, or Ddx3y. Two other 985-AA8 subclones—D1 and F2—were shown to have lost the Y chromosome. As shown in FIG. 14E, in 2 out of the 48 subclones (4.16%; clones A9 and E8) for clone 1823-CF11, no expression was detected for Eif2s3y, Uty, or Ddx3y. One other 1823-CF11 subclone—C12—was shown to have lost the Y chromosome. Assessment of the presence of the Y chromosome was performed doing copy number assays with probes for one gene on the Y chromosome: Sry. Presence of one copy of the Y chromosome was confirmed by copy number assays in 46/48 subclones for 985 AA8 and 47/48 subclones for 1823 CF11.

Example 4. Increasing the Fertility of F0 XY Females with TALEN-Induced Mutations in the Y Chromosome Gene Sry Targeted deletions comprising a lacZ replacement allele for Sry were created with a large targeting vector (LTVEC) comprising an insertion cassette comprising lacZ fused in-frame with the Sry start codon and a neomycin resistance gene flanked by homology arms of 38 and 37 kb and based on a BAC from the bMQ library (129S7/SvEv Brd-Hprt b-m2). The LTVEC (see NIH KOMP project VG12778 LTVEC (available via internet on the World Wide Web (www) at the URL "velocigene.com/komp/detail/12778")) comprises in its homology arms all the known control elements for the expression of Sry. Its lacZ-encoded beta-galactosidase serves as a reporter for the tissue-specific and developmental stage-specific expression of the Sry gene. The allele created by correct targeting of the Sry gene with the targeting vector comprises a deletion of the Sry coding sequence and replacement with the insertion cassette. The targeting vector was used to target the Sry gene in both the VGB6 (a.k.a. B6A6) C57BL/6 and the VGF1 (a.k.a. F1H4) C57BL6/129 F1 hybrid ES cell lines. VGF1 (F1H4) mouse ES cells were derived from hybrid embryos produced by crossing a female C57BL/6NTac mouse to a male 12956/SvEvTac mouse. Therefore, VGF1 ES cells contain a Y chromosome from 12956/SvEvTac mouse. The female XY mice produced from the VGF1 cell line contain a Y chromosome derived from a 12956/SvEvTac mouse.

We obtained a TALEN designed to target part of the HMG box DNA binding motif coding sequence (upstream recognition sequence: 5'-TCCCGTGGTGAGAGGCAC-3' (SEQ ID NO: 43); downstream recognition sequence: 5'-TAT-TTTGCATGCTGGGAT-3' (SEQ ID NO: 44)) in the Sry gene. TALEN-1 was active in creating NHEJ mutations at the Sry locus in multiple experiments.

Deletion mutations, presumably the result of non-homologous end joining (NHEJ) repair of double strand DNA breaks, were created in the Sry gene by the action of a TALEN. Both VGB6 and VGF1 mouse ES cells were created with TALEN-induced mutations. Table 14 contains a list of all the clones and the sizes of the deletion mutations they carry and whether they have the lacZ-neo LTVEC insertion cassette at the Sry locus. Table 14 also includes the results of F0 generation VELOCIMICE® produced by microinjection of the Sry mutant ES cell clones into 8-cell embryos, and the breeding results of XY female VELOCIMICE® (sex-reversed females) with mutations in the Sry gene.

All of the VELOCIMICE® with Sry mutations derived from VGB6 ES cells were female, as expected for inactivation of Sry. As shown in Table 14, the Sry mutant female B6 VELOCIMICE® were sterile when test bred, which is in agreement with the literature on Sry mutations. Because of the sterility, LTVEC targeting (i.e., clones with correctly targeted Sry deletions and lacZ-neo insertions) was not formally confirmed by transmission of the mutant allele to F1 progeny. However, our data demonstrated very different results with the VGF1 clones.

Unlike VGB6 ES cells, which cannot be maintained in KO-DMEM-like low osmotic strength media and retain the ability to produce mice, VGF1 cells can be maintained in KO-DMEM-like low osmotic strength media. Thus, experiments were done to determine if VGF1 XY ES cells with mutations in Sry could be feminized by the medium (i.e., to determine if they, unlike the VGB6 Sry mutant XY ES cells, could produce some fertile XY Sry mutant females). First, the VGF1 ES cells were maintained, as usual, in our KO-DMEM-like low osmotic strength growth medium that is feminizing: some of the microinjected XY clones grown in this medium will produce fertile XY females even though they do not carry mutations. For example, clone TH4 (data not shown), has no Sry mutation but produced 2 female and 6 male VELOCIMICE®.

Six VGF1 ES cell clones with TALEN-induced small deletions ranging from 5 bp to over 1 kb were microinjected. LTVEC targeting (i.e., clones with correctly targeted Sry deletions and lacZ-neo insertions) was not observed in VGF1 ES cells grown in the KO-DMEM-like low osmotic strength growth medium. All produced female VELOCIMICE®, 32 of which were bred. Remarkably, all of the Sry mutant XY female VELOCIMICE® were fertile:

each produced at least one litter (Table 14). Many of the Sry mutant XY females produced multiple litters with normal litter sizes, while some of the XY females produced only one or two small litters. Out of 299 F1 mice from these breedings that have been genotyped, approximately half (146, 49%) are normal XY males or normal XX females. 174 (58%) of the F1 mice were phenotypic females, while 125 (42%) were phenotypic males. 26 of the females (15% of females, 8.6% of the total F1 generation) were XY females that inherited a mutant Sry allele. Because of meiotic nondisjunction events associated with XY oocytes, a number of aberrant genotypes—XXY, XYY, XO, XXYY—some of which included mutant Sry alleles were observed in the F1 progeny of Sry mutant XY female VELOCIMICE®.

Table 14 also reports the fertility results of XY Females derived from ES cells grown in conventional DMEM-based medium that had mutations of Sry. Unexpectedly, compared with the results for a similar experiment with ES cells grown in KO-DMEM-based medium, LTVEC targeting in DMEM-based medium produced clones with correctly targeted Sry deletions and lacZ-neo insertions (i.e., TALEN-assisted LTVEC targeted deletion-replacement). Nine out of ten $XY_{Sry(lacZ)}$ females derived from four targeted clones produced live born pups upon mating a 90% fertility rate.

To rescue the fertility of the VELOCIMICE® with Sry mutations derived from VGB6 XY ES cells or to increase the fertility or fecundity of the VELOCIMICE® with Sry mutations derived from VGF1 ES cells grown in conventional DMEM-based medium, additional regions of the Y chromosome are silenced in the XY ES cells. Such additional silencing can also increase the production of XY females. In one example, the Zfy2 gene is silenced by a targeted genetic modification generated with a nuclease (e.g., a ZFN, a TALEN, a meganuclease, or a CRISPR-Cas nuclease) and/or a targeting vector such as an LTVEC as described above for targeting the Sry gene.

Example 5. Expression of Y Chromosome Genes in ES Cells

To determine which Y chromosome genes are expressed in mouse embryonic stem (ES) cells and could be candidates for markers of sex-reversal, RNA-seq analysis was done on F1H4 ES cells. As shown in Table 15, Eif2s3y, Ddx3y, Erdr1, Kdm5d, Uty, Ubely1, Zfy1, Zfy2, Rbmy1a1, Sly, Usp9y, LOC100041346 have detectable levels of expression in F1H4 ES cells. Sry did not have detectable expression levels in F1H4 ES cells.

TABLE 14

Sry Targeting Results: TALEN + LTVEC

| Clone | ES Cell Line | Media | Allele Description | F0 XY Females | XY Females Bred | Fertile XY Females | Fertility Rate (%) |
|---|---|---|---|---|---|---|---|
| D-E11 | VGB6 | VGB6-Specific Medium | 303 bp deletion + 50 bp inversion | 1 | — | — | — |
| D-G5 | VGB6 | VGB6-Specific Medium | 627 bp deletion | 11 | 8 | 0 | 0 |
| E-D4 | VGB6 | VGB6-Specific Medium | lacZ-neo targeted (?) | 2 | — | — | — |
| E-G7 | VGB6 | VGB6-Specific Medium | lacZ-neo targeted (?) | 16 | 7 | 0 | 0 |
| T-B1 | VGF1 | KO-DMEM | 11 bp deletion | 2 | 2 | 2 | 100 |
| T-C2 | VGF1 | KO-DMEM | 5 bp deletion | 8 | 8 | 8 | 100 |
| U-A5 | VGF1 | KO-DMEM | 15 bp deletion | 4 | 4 | 4 | 100 |
| U-B5 | VGF1 | KO-DMEM | 1201 bp deletion | 4 | 4 | 4 | 100 |
| U-E12 | VGF1 | KO-DMEM | 9 bp deletion | 8 | 7 | 7 | 100 |
| W-E11 | VGF1 | KO-DMEM | >1.2 kb deletion | 7 | 7 | 7 | 100 |
| X-C4 | VGF1 | DMEM | lacZ-neo targeted | 5 | 3 | 3 | 100 |
| X-E10 | VGF1 | DMEM | lacZ-neo targeted | 1 | 1 | 1 | 100 |
| X-F3 | VGF1 | DMEM | lacZ-neo targeted | 5 | 3 | 3 | 100 |
| X-G3 | VGF1 | DMEM | lacZ-neo targeted | 9 | 3 | 2 | 67 |

TABLE 15

RNA-seq Data from F1H4 Embryonic Stem Cells.

| Gene | Chromosome | Strand | ES Cell Average Relative Expression |
|---|---|---|---|
| Eif2s3y | chrY | + | 28.28 |
| Ddx3y | chrY | − | 14.68 |
| Erdr1 | chrY | + | 9.47 |
| Kdm5d | chrY | + | 4.57 |
| Uty | chrY | − | 4.40 |
| Ube1y1 | chrY | + | 1.31 |
| Zfy1 | chrY | − | 1.25 |
| Zfy2 | chrY | − | 0.54 |
| Rbmy1a1 | chrY | + | 0.09 |
| Sly | chrY | + | 0.05 |
| Usp9y | chrY | − | 0.04 |
| LOC100041346 | chrY | + | 0.03 |
| Ssty1 | chrY | + | 0.00 |
| Sry | chrY | − | 0.00 |
| Tspy-ps | chrY | − | 0.00 |
| Ssty2 | chrY | + | 0.00 |
| Rbm31y | chrY | + | 0.00 |
| LOC380994 | chrY | − | 0.00 |
| LOC382133 | chrY | + | 0.00 |
| MGC107098 | chrY | − | 0.00 |
| LOC434960 | chrY | + | 0.00 |
| Gm6026 | chrY | + | 0.00 |
| LOC100039574 | chrY | − | 0.00 |
| LOC100039614 | chrY | + | 0.00 |
| LOC100039753 | chrY | − | 0.00 |
| LOC100039810 | chrY | − | 0.00 |
| LOC100040022 | chrY | − | 0.00 |
| LOC100040031 | chrY | + | 0.00 |
| LOC100040160 | chrY | − | 0.00 |
| LOC100040223 | chrY | + | 0.00 |
| LOC100040786 | chrY | − | 0.00 |
| LOC100040911 | chrY | − | 0.00 |
| LOC100041014 | chrY | − | 0.00 |
| LOC100041033 | chrY | − | 0.00 |
| LOC100041223 | chrY | + | 0.00 |
| LOC100041256 | chrY | − | 0.00 |
| LOC100041550 | chrY | + | 0.00 |
| LOC100042428 | chrY | + | 0.00 |
| Gm16501 | chrY | + | 0.00 |

We claim:

1. A method for selecting a donor mouse XY embryonic stem (ES) cell for producing a fertile, phenotypically female XY mouse, comprising:
   (a) culturing a population of mouse XY ES cells originating from the same cell line or the same clone or having the same genotype in a low-osmolality medium comprising a base medium and supplements suitable for maintaining the pluripotency of the mouse XY ES cells, wherein the base medium comprises sodium bicarbonate in a concentration of about 18 mM to about 26 mM, and wherein the low-osmolality medium has an osmolality of from about 216 mOsm/kg to about 322 mOsm/kg;
   (b) assaying at least two of the mouse XY ES cells in the population of mouse XY ES cells for mRNA expression of Ddx3y, Uty, and Eif2s3y; and
   (c) selecting the mouse XY ES cell having the lowest mRNA expression of Ddx3y, Uty, and Eif2s3y relative to the other assayed cells as a donor mouse XY ES cell for producing a fertile, phenotypically female XY mouse in an F0 generation,
   wherein the donor mouse XY ES cell has at least 90% decreased mRNA expression of Ddx3y, Uty, and Eif2s3y as compared to a control mouse XY ES cell cultured in a non-feminizing medium or that lacks the capability or has reduced capability to produce XY female mice notwithstanding its being cultured in the low osmolality medium.

2. The method of claim 1, wherein the donor mouse XY ES cell lacks mRNA expression of Ddx3y, Uty, and Eif2s3y.

3. The method of claim 1, wherein the mouse XY ES cells are cultured in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to assaying step (b).

4. The method of claim 1, wherein the donor mouse XY ES cell is a VGF1 mouse ES cell.

5. The method of claim 1, wherein the low-osmolality medium has one or more of the following properties:
   (I) the low-osmolality medium has an osmolality of from about 218 mOsm/kg to about 322 mOsm/kg;
   (II) the low-osmolality medium has an osmolality of 218 mOsm/kg;
   (III) the low-osmolality medium has a conductivity of about 11 mS/cm to about 13 mS/cm;
   (IV) the base medium comprises a salt of an alkaline metal and a halide in a concentration of about 50 mM to about 110 mM;
   (V) the base medium comprises sodium chloride in a concentration of about 50 mM to about 110 mM; and
   (VI) the base medium comprises sodium chloride in a concentration of 87±5 mM, and the low-osmolality medium has an osmolality of 261±26 mOsm/kg.

6. The method of claim 1, wherein the base medium comprises sodium chloride in a concentration of about 3 mg/mL and sodium bicarbonate in a concentration of about 2.2 mg/mL, and the low-osmolality medium has an osmolality of about 216 mOsm/kg.

7. The method of claim 1, wherein the donor mouse XY ES cell is from a C57BL/6 strain.

8. The method of claim 1, wherein the Y chromosome in the donor mouse XY ES cell is from a C57BL/6 strain, a 129 strain, or a BALB/c strain.

9. The method of claim 1, wherein the donor mouse XY ES cell is from a mix of a C57BL/6 strain and a 129 strain.

10. The method of claim 1, wherein the donor mouse XY ES cell comprises a targeted genetic modification in a target genomic locus.

11. The method of claim 10, wherein the targeted genetic modification comprises an insertion, a deletion, a knockout, a knockin, a point mutation, or a combination thereof.

12. The method of claim 1, further comprising:
    (d) introducing the donor mouse XY ES cell into a mouse host embryo;
    (e) introducing the mouse host embryo from step (d) into a recipient female mouse and gestating the mouse host embryo; and
    (f) obtaining F0 XY mouse progeny comprising a phenotypically female XY mouse, wherein upon attaining sexual maturity the F0 phenotypically female XY mouse is fertile and fecund.

13. The method of claim 12, further comprising:
    (g) breeding the F0 XY fertile female mouse to produce progeny.

14. The method of claim 13, wherein at least 5%, at least 10%, at least 20%, at least 30%, at least 40%, at least 50%, at least 60%, at least 70%, at least 80%, at least 90%, at least 95%, or all of the XY progeny produced in step (g) are phenotypically male and fertile.

15. The method of claim 13, wherein none of the XY progeny produced in step (g) are phenotypically female.

16. The method of claim 13, wherein the breeding comprises crossing the F0 XY fertile female mouse with a cohort F0 XY male mouse, wherein the F0 XY fertile female mouse and the F0 XY male mouse each is heterozygous for a genetic modification, and obtaining an F1 progeny mouse that is homozygous for the genetic modification.

17. The method of claim 12, wherein the host embryo is a pre-morula stage embryo, and step (d) further comprises culturing the host embryo to the blastocyst stage.

18. The method of claim 12, wherein the donor mouse XY ES cell is cultured in the low-osmolality medium for at least 1 day, 2 days, 3 days, 4 days, 5 days, 6 days, 7 days, 8 days, 9 days, 10 days, 11 days, 12 days, 13 days, 2 weeks, 3 weeks, or 4 weeks prior to introduction into the host embryo.

* * * * *

SEQUENCE LISTING

<160> NUMBER OF SEQ ID NOS: 50

<210> SEQ ID NO 1
<211> LENGTH: 22
<212> TYPE: DNA
<213> ORGANISM: Artificial Sequence
<220> FEATURE:
<223> OTHER INFORMATION: mHPRT1 Probe

<400> SEQUENCE: 1
tgggaggcca tcacattgtg gc                                                22

<210> SEQ ID NO 2
<211> LENGTH: 21
<212> TYPE: DNA
<213> ORGANISM: Artificial Sequence
<220> FEATURE:
<223> OTHER INFORMATION: mHPRT1 Forward Primer

<400> SEQUENCE: 2
tgctcgagat gtcatgaagg a                                                 21

<210> SEQ ID NO 3
<211> LENGTH: 20
<212> TYPE: DNA
<213> ORGANISM: Artificial Sequence
<220> FEATURE:
<223> OTHER INFORMATION: mHPRT1 Reverse Primer

<400> SEQUENCE: 3
ccagcaggtc agcaaagaac                                                   20

<210> SEQ ID NO 4
<211> LENGTH: 23
<212> TYPE: DNA
<213> ORGANISM: Artificial Sequence
<220> FEATURE:
<223> OTHER INFORMATION: mSox9 Probe

<400> SEQUENCE: 4
cgctgaccat cagaactccg gct                                               23

<210> SEQ ID NO 5
<211> LENGTH: 20
<212> TYPE: DNA
<213> ORGANISM: Artificial Sequence
<220> FEATURE:
<223> OTHER INFORMATION: mSox9 Forward Primer

<400> SEQUENCE: 5
acccgctcgc aatacgacta                                              20

<210> SEQ ID NO 6
<211> LENGTH: 18
<212> TYPE: DNA
<213> ORGANISM: Artificial Sequence
<220> FEATURE:
<223> OTHER INFORMATION: mSox9 Reverse Primer

<400> SEQUENCE: 6
ccggctgcgt gactgtag                                                18

<210> SEQ ID NO 7
<211> LENGTH: 23
<212> TYPE: DNA
<213> ORGANISM: Artificial Sequence
<220> FEATURE:
<223> OTHER INFORMATION: mRspo1 Probe

<400> SEQUENCE: 7
taggacctac ctgggcacag tga                                          23

<210> SEQ ID NO 8
<211> LENGTH: 21
<212> TYPE: DNA
<213> ORGANISM: Artificial Sequence
<220> FEATURE:
<223> OTHER INFORMATION: mRspo1 Forward Primer

<400> SEQUENCE: 8
caacagggcc actcacatca g                                            21

<210> SEQ ID NO 9
<211> LENGTH: 24
<212> TYPE: DNA
<213> ORGANISM: Artificial Sequence
<220> FEATURE:
<223> OTHER INFORMATION: mRspo1 Reverse Primer

<400> SEQUENCE: 9
gcactgtact cttccacagg tatc                                         24

<210> SEQ ID NO 10
<211> LENGTH: 27
<212> TYPE: DNA
<213> ORGANISM: Artificial Sequence
<220> FEATURE:
<223> OTHER INFORMATION: mDhh Probe

<400> SEQUENCE: 10
atcggtcaaa gctgataact cactggc                                      27

<210> SEQ ID NO 11
<211> LENGTH: 19
<212> TYPE: DNA
<213> ORGANISM: Artificial Sequence
<220> FEATURE:

```
<223> OTHER INFORMATION: mDhh Forward Primer

<400> SEQUENCE: 11
agtcccgcaa ccacatcca                                              19

<210> SEQ ID NO 12
<211> LENGTH: 19
<212> TYPE: DNA
<213> ORGANISM: Artificial Sequence
<220> FEATURE:
<223> OTHER INFORMATION: mDhh Reverse Primer

<400> SEQUENCE: 12
agcgcaccgt ggcatttcc                                              19

<210> SEQ ID NO 13
<211> LENGTH: 23
<212> TYPE: DNA
<213> ORGANISM: Artificial Sequence
<220> FEATURE:
<223> OTHER INFORMATION: mGata4 Probe

<400> SEQUENCE: 13
tgcaatgcct gtggcctcta tca                                         23

<210> SEQ ID NO 14
<211> LENGTH: 18
<212> TYPE: DNA
<213> ORGANISM: Artificial Sequence
<220> FEATURE:
<223> OTHER INFORMATION: mGata4 Forward Primer

<400> SEQUENCE: 14
tgggacggga cactacct                                               18

<210> SEQ ID NO 15
<211> LENGTH: 21
<212> TYPE: DNA
<213> ORGANISM: Artificial Sequence
<220> FEATURE:
<223> OTHER INFORMATION: mGata4 Reverse Primer

<400> SEQUENCE: 15
cggttgatgc cgttcatctt g                                           21

<210> SEQ ID NO 16
<211> LENGTH: 24
<212> TYPE: DNA
<213> ORGANISM: Artificial Sequence
<220> FEATURE:
<223> OTHER INFORMATION: mFgf9 Probe

<400> SEQUENCE: 16
aaacatgtgg acaccggaag gaga                                        24

<210> SEQ ID NO 17
<211> LENGTH: 24
<212> TYPE: DNA
<213> ORGANISM: Artificial Sequence
<220> FEATURE:
<223> OTHER INFORMATION: mFgf9 Forward Primer

<400> SEQUENCE: 17
caacacctac tcttccaacc tcta                                        24
```

```
<210> SEQ ID NO 18
<211> LENGTH: 23
<212> TYPE: DNA
<213> ORGANISM: Artificial Sequence
<220> FEATURE:
<223> OTHER INFORMATION: mFgf9 Reverse Primer

<400> SEQUENCE: 18
ggagtcccgt ccttatttaa tgc                                          23

<210> SEQ ID NO 19
<211> LENGTH: 25
<212> TYPE: DNA
<213> ORGANISM: Artificial Sequence
<220> FEATURE:
<223> OTHER INFORMATION: mSry Probe

<400> SEQUENCE: 19
tttacagcct gcagttgcct caaca                                        25

<210> SEQ ID NO 20
<211> LENGTH: 23
<212> TYPE: DNA
<213> ORGANISM: Artificial Sequence
<220> FEATURE:
<223> OTHER INFORMATION: mSry Forward Primer

<400> SEQUENCE: 20
ggctaaagtg tcacagagga gtg                                          23

<210> SEQ ID NO 21
<211> LENGTH: 23
<212> TYPE: DNA
<213> ORGANISM: Artificial Sequence
<220> FEATURE:
<223> OTHER INFORMATION: mSry Reverse Primer

<400> SEQUENCE: 21
tccagtcttg cctgtatgtg atg                                          23

<210> SEQ ID NO 22
<211> LENGTH: 22
<212> TYPE: DNA
<213> ORGANISM: Artificial Sequence
<220> FEATURE:
<223> OTHER INFORMATION: mSf1 Probe

<400> SEQUENCE: 22
ctacctctgg gcctgccacc ac                                           22

<210> SEQ ID NO 23
<211> LENGTH: 19
<212> TYPE: DNA
<213> ORGANISM: Artificial Sequence
<220> FEATURE:
<223> OTHER INFORMATION: mSf1 Forward Primer

<400> SEQUENCE: 23
tcctgtccct gcatctgtg                                               19

<210> SEQ ID NO 24
<211> LENGTH: 19
<212> TYPE: DNA
<213> ORGANISM: Artificial Sequence
<220> FEATURE:
<223> OTHER INFORMATION: mSf1 Reverse Primer
```

<400> SEQUENCE: 24
ggagcagcag gtcttggtg                                           19

<210> SEQ ID NO 25
<211> LENGTH: 28
<212> TYPE: DNA
<213> ORGANISM: Artificial Sequence
<220> FEATURE:
<223> OTHER INFORMATION: mWnt4 Probe

<400> SEQUENCE: 25
cagttcaagc cacatacaga tgaggacc                                 28

<210> SEQ ID NO 26
<211> LENGTH: 18
<212> TYPE: DNA
<213> ORGANISM: Artificial Sequence
<220> FEATURE:
<223> OTHER INFORMATION: mWnt4 Forward Primer

<400> SEQUENCE: 26
cgctggtgcc tcggaatg                                            18

<210> SEQ ID NO 27
<211> LENGTH: 21
<212> TYPE: DNA
<213> ORGANISM: Artificial Sequence
<220> FEATURE:
<223> OTHER INFORMATION: mWnt4 Reverse Primer

<400> SEQUENCE: 27
cggatgtcct gctcacagaa g                                        21

<210> SEQ ID NO 28
<211> LENGTH: 23
<212> TYPE: DNA
<213> ORGANISM: Artificial Sequence
<220> FEATURE:
<223> OTHER INFORMATION: mAmh Probe

<400> SEQUENCE: 28
tcaaccaagc agagaaggtg cca                                      23

<210> SEQ ID NO 29
<211> LENGTH: 20
<212> TYPE: DNA
<213> ORGANISM: Artificial Sequence
<220> FEATURE:
<223> OTHER INFORMATION: mAmh Forward Primer

<400> SEQUENCE: 29
gctcgggcct catcttaacc                                          20

<210> SEQ ID NO 30
<211> LENGTH: 25
<212> TYPE: DNA
<213> ORGANISM: Artificial Sequence
<220> FEATURE:
<223> OTHER INFORMATION: mAmh Reverse Primer

<400> SEQUENCE: 30
gcgggaatca gagccaaata gaaag                                    25

<210> SEQ ID NO 31
<211> LENGTH: 23

```
<212> TYPE: DNA
<213> ORGANISM: Artificial Sequence
<220> FEATURE:
<223> OTHER INFORMATION: mNr0b1 Probe

<400> SEQUENCE: 31
tgctcactag cgctcagcaa acg                                      23

<210> SEQ ID NO 32
<211> LENGTH: 23
<212> TYPE: DNA
<213> ORGANISM: Artificial Sequence
<220> FEATURE:
<223> OTHER INFORMATION: mNr0b1 Forward Primer

<400> SEQUENCE: 32
aggcagggca gcatcttata cag                                      23

<210> SEQ ID NO 33
<211> LENGTH: 19
<212> TYPE: DNA
<213> ORGANISM: Artificial Sequence
<220> FEATURE:
<223> OTHER INFORMATION: mNr0b1 Reverse Primer

<400> SEQUENCE: 33
cactcgcctc tgcgatgtg                                           19

<210> SEQ ID NO 34
<211> LENGTH: 22
<212> TYPE: DNA
<213> ORGANISM: Artificial Sequence
<220> FEATURE:
<223> OTHER INFORMATION: mFoxl2 Probe

<400> SEQUENCE: 34
tcactctgtc cggcatctac ca                                       22

<210> SEQ ID NO 35
<211> LENGTH: 18
<212> TYPE: DNA
<213> ORGANISM: Artificial Sequence
<220> FEATURE:
<223> OTHER INFORMATION: mFoxl2 Forward Primer

<400> SEQUENCE: 35
cgagagcgcc gagaagag                                            18

<210> SEQ ID NO 36
<211> LENGTH: 22
<212> TYPE: DNA
<213> ORGANISM: Artificial Sequence
<220> FEATURE:
<223> OTHER INFORMATION: mFoxl2 Reverse Primer

<400> SEQUENCE: 36
gaacgggaac ttggctatga tg                                       22

<210> SEQ ID NO 37
<211> LENGTH: 25
<212> TYPE: DNA
<213> ORGANISM: Artificial Sequence
<220> FEATURE:
<223> OTHER INFORMATION: mDdx3y Probe

<400> SEQUENCE: 37
```

-continued

```
tcagcagatt cgggacttag aacgt                                          25

<210> SEQ ID NO 38
<211> LENGTH: 23
<212> TYPE: DNA
<213> ORGANISM: Artificial Sequence
<220> FEATURE:
<223> OTHER INFORMATION: mDdx3y Forward Primer

<400> SEQUENCE: 38
gtgtatggtg gtgctgatac tgt                                            23

<210> SEQ ID NO 39
<211> LENGTH: 21
<212> TYPE: DNA
<213> ORGANISM: Artificial Sequence
<220> FEATURE:
<223> OTHER INFORMATION: mDdx3y Reverse Primer

<400> SEQUENCE: 39
cgtcctggtg tggcaactaa c                                              21

<210> SEQ ID NO 40
<211> LENGTH: 27
<212> TYPE: DNA
<213> ORGANISM: Artificial Sequence
<220> FEATURE:
<223> OTHER INFORMATION: mEif2s3y Probe

<400> SEQUENCE: 40
agctggtaat gaatcttgtc ctcaacc                                        27

<210> SEQ ID NO 41
<211> LENGTH: 21
<212> TYPE: DNA
<213> ORGANISM: Artificial Sequence
<220> FEATURE:
<223> OTHER INFORMATION: mEif2s3y Forward Primer

<400> SEQUENCE: 41
tggatgcagc tcttctgttg a                                              21

<210> SEQ ID NO 42
<211> LENGTH: 18
<212> TYPE: DNA
<213> ORGANISM: Artificial Sequence
<220> FEATURE:
<223> OTHER INFORMATION: mEif2s3y Reverse Primer

<400> SEQUENCE: 42
tggcagccag gtgttcag                                                  18

<210> SEQ ID NO 43
<211> LENGTH: 18
<212> TYPE: DNA
<213> ORGANISM: Artificial Sequence
<220> FEATURE:
<223> OTHER INFORMATION: Upstream Recognition Sequence for TALEN
      Targeting Sry

<400> SEQUENCE: 43
tcccgtggtg agaggcac                                                  18

<210> SEQ ID NO 44
<211> LENGTH: 18
<212> TYPE: DNA
```

```
<213> ORGANISM: Artificial Sequence
<220> FEATURE:
<223> OTHER INFORMATION: Downstream Recognition Sequence for TALEN
      Targeting Sry

<400> SEQUENCE: 44
tattttgcat gctgggat                                                     18

<210> SEQ ID NO 45
<211> LENGTH: 21
<212> TYPE: DNA
<213> ORGANISM: Artificial Sequence
<220> FEATURE:
<223> OTHER INFORMATION: X Chromosome Primer 1

<400> SEQUENCE: 45
ggagggtagc acgggaagaa g                                                 21

<210> SEQ ID NO 46
<211> LENGTH: 21
<212> TYPE: DNA
<213> ORGANISM: Artificial Sequence
<220> FEATURE:
<223> OTHER INFORMATION: X Chromosome Primer 2

<400> SEQUENCE: 46
gctggctacc cacttgattg g                                                 21

<210> SEQ ID NO 47
<211> LENGTH: 29
<212> TYPE: DNA
<213> ORGANISM: Artificial Sequence
<220> FEATURE:
<223> OTHER INFORMATION: X Chromosome Probe

<400> SEQUENCE: 47
tcaagcagtc tctcccagct aacctccct                                         29

<210> SEQ ID NO 48
<211> LENGTH: 20
<212> TYPE: DNA
<213> ORGANISM: Artificial Sequence
<220> FEATURE:
<223> OTHER INFORMATION: Y Chromosome Primer 1

<400> SEQUENCE: 48
gatcagcaag cagctgggat                                                   20

<210> SEQ ID NO 49
<211> LENGTH: 20
<212> TYPE: DNA
<213> ORGANISM: Artificial Sequence
<220> FEATURE:
<223> OTHER INFORMATION: Y Chromosome Primer 2

<400> SEQUENCE: 49
ctcctggaaa aagggccttt                                                   20

<210> SEQ ID NO 50
<211> LENGTH: 27
<212> TYPE: DNA
<213> ORGANISM: Artificial Sequence
```

```
<220> FEATURE:
<223> OTHER INFORMATION: Y Chromosome Probe

<400> SEQUENCE: 50
caggtggaaa agccttacag aagccga                                              27
```